United States Patent
Boddupalli et al.

(10) Patent No.: US 7,985,771 B2
(45) Date of Patent: *Jul. 26, 2011

(54) FURANONE DERIVATIVES

(75) Inventors: Sekhar Boddupalli, San Jose, CA (US);
Gail Walkinshaw, San Jose, CA (US);
Bing Wang, Cupertino, CA (US)

(73) Assignee: Monsanto Technology LLC, St. Louis, MO (US)

( * ) Notice: Subject to any disclaimer, the term of this patent is extended or adjusted under 35 U.S.C. 154(b) by 1252 days.

This patent is subject to a terminal disclaimer.

(21) Appl. No.: 10/630,170

(22) Filed: Jul. 30, 2003

(65) Prior Publication Data

US 2004/0029812 A1 Feb. 12, 2004

Related U.S. Application Data

(63) Continuation-in-part of application No. 10/354,474, filed on Jan. 30, 2003, now Pat. No. 6,667,330.

(60) Provisional application No. 60/353,939, filed on Jan. 31, 2002.

(51) Int. Cl.
*A01N 34/08* (2006.01)
*A01N 51/00* (2006.01)
*A01N 43/00* (2006.01)
*A01N 43/54* (2006.01)
*A01N 43/78* (2006.01)
*A01N 43/64* (2006.01)
*C07D 249/00* (2006.01)
*C07D 307/00* (2006.01)
*C07D 403/00* (2006.01)

(52) U.S. Cl. ........ 514/474; 514/156; 514/183; 514/256; 514/367; 514/383; 514/461; 514/473; 514/859; 514/863; 548/262.4; 549/313; 544/296

(58) Field of Classification Search .................. 514/367, 514/383, 473, 256, 156, 183, 474, 859, 863, 514/461; 548/156, 262.4; 549/313; 544/296
See application file for complete search history.

(56) References Cited

U.S. PATENT DOCUMENTS

| | | |
|---|---|---|
| 5,464,865 A | 11/1995 | Demers et al. |
| 6,136,832 A | 10/2000 | Hopper et al. |
| 6,297,274 B1 | 10/2001 | Cheng et al. |
| 6,858,216 B2 | 2/2005 | Schulze zur Wiesche et al. |
| 2003/0206933 A1 | 11/2003 | Schulze zur Wiesche et al. |

*Primary Examiner* — Michael G Hartley
*Assistant Examiner* — Leah Schlientz
(74) *Attorney, Agent, or Firm* — Senniger Powers LLP; Byron V. Olsen

(57) ABSTRACT

The invention relates to a method of treating with furanone derivatives and the pharmaceutically acceptable salts thereof, one or more conditions of the skin, in particular regulating skin condition, regulating signs of skin aging, treating a number of conditions such as contact dermatitis, skin irritation, rosacea, acne, psoriasis, and preventing and protecting skin tissue against age-related damage or damage resulting from insults such as harmful (UV) radiation or environmental pollution, stress and fatigue.

12 Claims, No Drawings

FURANONE DERIVATIVES

CROSS-REFERENCE TO RELATED APPLICATIONS

This application is a continuation-in-part of non-provisional application Ser. No. 10/354,474 filed on Jan. 30, 2003 now U.S. Pat. No. 6,667,330 claiming priority under 35 U.S.C. 119(e) to U.S. Provisional Application Ser. No. 60/353,939, filed Jan. 31, 2002, incorporated herein by reference in its entirety.

FIELD OF THE INVENTION

The present invention relates to furanone derivatives, particularly to derivatives having cytoprotective activity, especially certain 3-hydroxy-furan-2-one derivatives. The invention is also directed to formulations and methods for treating stroke, myocardial infarction and chronic heart failure, as well as other oxidative stress-related conditions that are typically responsive to cellular enzyme modulation. The invention is also directed to formulations and methods for treating neuroinflammation, cognitive disorders and neurodegenerative diseases such a Alzheimer's disease and senile dementia. This invention is also directed to methods for treating dermatological conditions.

BACKGROUND INFORMATION

The present invention deals with certain novel furanone derivatives, which are formed under proper conditions from a series of pyruvate derivatives described in our prior applications, U.S. Ser. Nos. 10/138,937 and 10/138,032.

Furanones are compounds having the following general structure.

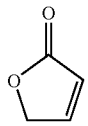

Furanone-derived compositions have been known in the art to have various utilities. For example, U.S. Pat. No. 6,296,889 describes the use of certain furanone compounds in conjunction with 1-nonen-3-one to provide dairy and coffee aroma flavor enhancement. Specific furanones (for example, 3,-(3,4-difluorophenyl)-4-(4-(methylsulfonyl)phenyl)-2-(5H)-furanone, 3-phenyl-4-(4-(methylsulfonyl)phenyl)-2-(5H)-furanone and 5,5-dimethyl-4-(4-(methylsulfonyl)phenyl)-3-(3-fluorophenyl)-5H-furan-2-one) have been shown to be cyclooxygenase-2 (COX-2) inhibitors useful in treating certain inflammatory conditions (U.S. Pat. Nos. 5,474,995, 6,239,173). The diversity of furanone derivative utilities is further illustrated by the discovery of certain halogenated furanones isolated from the Australian red seaweed *Delisea nulcha* as marine anti-fouling agents (U.S. Pat. No. 6,060,046) capable of preventing growth of various seaweeds, invertebrates and bacteria on marine structures. The furanone derivative 4-hydroxy-3-methanesulfonyl-2-methanesulfonylmethyl-5-oxo-2,5-dihydro-furan-2-carboxylic acid ethyl ester (CAS Registry No. 299923-61-8), is available for screening from the compound library of InterBioScreen Ltd. (Moscow, Russia-www.ibscreen.com), among other sources.

The synthesis of the compound 4-hydroxy-3-isobutyl-2-(3-methyl-butyryl)-5-oxo-2,5-dihydro-furan-2-carboxylic acid methyl ester has been described in Trogolo, C. et al *Annali di Chimica* 62(10), 674-92, (1972) and the synthesis of 4-hydroxy-5-oxo-2,3-dipentyl-2,5-dihydro-furan-2-carboxylic acid ethyl ester has been described in Hoffman, R. V. et al. *Journal of Organic Chemistry*, 62(8)2458-2465, (1997). The synthesis of certain furanonoes derivatives from hydroxy alkanoates is described in Stach, H., *Helvetica Chimica Acta* (1987), 70(2), 369-74.

Cerebral ischemia or "stroke" refers to the severe diminution or cessation of blood flow to all or part of the brain. Cerebral ischemia can occur as result of a number of causes or insults, including, but not limited to cerebrovascular occlusion, thromboembolytic insult, cardiac failure and hemorrhagic accident. It is now known that pharmacologic intervention, if provided within a reasonable interval of the initial insult, can significantly reduce cerebral tissue death following cerebral ischemia.

Alzheimer's Disease ("AD") is a progressive disease of the human central nervous system. It is manifested by dementia in the elderly, by disorientation, loss of memory, difficulty with language, calculation, or visual-spatial skills, and by psychiatric manifestations. It is associated with degenerating neurons in several regions of the brain. Alzheimer's Disease is reviewed by Price, D. L. et al. (*Clin. Neuropharm.* 14:S9-S14 (1991)); Pollwein, P. et al. (*Nucl. Acids Res.* 20:63-68 (1992)); Regland, B. et al. (*Med. Hypoth.* 38:11-19 (1992)) and Johnson, S. A. (In: *Review of Biological Research in Aging*, Vol. 4., Rothstein, M. (Ed.), Wiley-Liss, NY, 163-170 (1990)).

The present invention addresses the desire to provide the therapies for conditions characterized by oxidative stress and/or inflammation, and particularly, for providing neuroprotection in the event of cerebral ischemia; especially desired are agents that are effective even if first administered after a significant period of time (e.g., about 5 or more hours) following an ischemic insult. The present invention also addresses the desire to provide new therapies for conditions characterized by neuroinflammation, cognitive disorders, and/or neurodegenerative conditions such as Alzheimer's and senile dementia, as well as dermatological disorders or diseases.

SUMMARY OF THE INVENTION

The present invention is concerned with novel furanone derivatives that are particularly active in restoring or preserving metabolic integrity in oxidatively competent cells that have been subjected to oxygen deprivation. Such furanone derivatives are useful in the manufacture of pharmaceutical compositions for treating a number of conditions characterized by oxidative stress, and particularly, in providing neuroprotection in the event of cerebral ischemia, even when administered a significant time interval after an ischemic insult. In particular, the compositions of the present invention are useful in the treatment of stroke, as demonstrated by providing neuroprotection in a standard experimental model of focal cerebral ischemia. They are also useful in the treatment of neuroinflammation, cognitive disorders and neurodegenerative diseases such as neuropathy in cerebrovascular diseases, brain trauma, cerebral palsy, epilepsy, amyotrophic lateral sclerosis (ALS), Huntington's disease, mental diseases (e.g. psychosis, schizophrenia, depression), Parkinson's disease, Friedreich's disease, Down's syndrome, Creutzfeldt-Jakob syndrome, Alzheimer's disease, and senile dementia.

They are also useful in the treatment of myocardial ischemia (myocardial infarction), as well as other indications characterized by oxidative stress and/or inflammation, including, but not limited to, diabetes, renal disease, premenstrual syndrome, asthma, cardiopulmonary inflammatory disorders, chronic heart failure, rheumatoid arthritis, muscle fatigue, intermittent claudication and for the preservation of allograft tissue for transplantation.

The compounds of the present invention are useful for the treatment of dermatological conditions, particularly the compounds, formulation and methods of the present invention are useful in regulating skin condition, regulating signs of skin aging and in treating a number of conditions, including but not limited to contact dermatitis, skin irritation, rosacea, acne, psoriasis, and in the prevention and protection of skin tissue against age-related damage or damage resulting from insults such as harmful (UV) radiation or environmental pollution, stress and fatigue.

The present invention concerns the compounds represented by the formula:

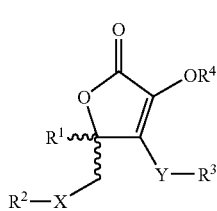

Formula I wherein:
  $R^1$ is: —C(O)OR'; —C(O)NR'R''; —CH$_2$OR'''; cyano; optionally substituted heterocyclyl; optionally substituted heterocyclyl-alkyl; optionally substituted heteroaryl, or optionally substituted heteroaralkyl;
  $R^2$ is: optionally substituted alkyl; optionally substituted cycloalkyl; optionally substituted aryl; optionally substituted aralkyl; optionally substituted heterocyclyl, optionally substituted heteroaryl; optionally substituted heteroaralkyl; an optionally substituted nucleoside; and optionally substituted amino acid; or an optionally substituted di-, tri- or tetra-peptide;
  $R^3$ is: optionally substituted alkyl; optionally substituted cycloalkyl; optionally substituted aryl; optionally substituted aralkyl; optionally substituted heterocyclyl, optionally substituted heteroaryl; optionally substituted heteroaralkyl; an optionally substituted nucleoside; an optionally substituted amino acid; or an optionally substituted di-, tri- or tetra-peptide;
  $R^4$ is: hydrogen; alkyl, alkylcarbonyl; (poly)alkoxyalkylene; or dialkoxyphosphoryloxy (or other moieties readily hydrolyzable to give an OH moiety);
  X is: lower alkylene; —N(R')—; —S—; —S(O)—; —S(O)$_2$—, or X taken together with $R^2$ is —P(O)(OR')$_2$;
  Y is: —N(R')—; —S—; —S(O)—; —S(O)$_2$—, or Y taken together with $R^3$ is —P(O)(OR')$_2$;
  or X—$R^2$ taken together with Y—$R^3$ form an optionally substituted aliphatic or aromatic ring,
  R' is: hydrogen; alkenyl; optionally substituted alkyl; optionally substituted cycloalkyl; phosphoryl; or optionally substituted aryl;
  R'' is: hydrogen, alkenyl, optionally substituted alkyl, or optionally substituted aryl;
  or R' and R'' together with the atom to which they are attached form a 5- to 7-membered aromatic, saturated or unsaturated ring, optionally incorporating one or more additional heteroatom chosen from N, O, or S, and optionally substituted with one or more substituents selected from the group consisting of optionally substituted lower alkyl, halo, cyano, alkylthio, lower alkoxy, carboxy, benzyl, and oxo; and
  R''' is: hydrogen; alkenyl; optionally substituted alkyl; optionally substituted cycloalkyl; acyl; phosphoryl; or optionally substituted aryl;
including single tautomers, single stereoisomers and mixtures of tautomers and/or stereoisomers, and the pharmaceutically acceptable salts thereof.

In one embodiment $R^4$ is hydrogen, ($C_1$ to $C_8$)alkyl, or ($C_1$ to $C_8$)alkylcarbonyl.

In another embodiment where $R^2$ and/or $R^3$ is a natural or substituted amino acid or peptide, $R^2$ and/or $R^3$ is selected from the group: Ala, Asn, Asp, Cys, Gln, Glu, Gly, Lys, Met, Ser and Thr, especially Ala, Asp, Cys, Glu and Gly. Further preferred are those compounds where $R^2$ and/or $R^3$ is a natural or substituted di- or tri-peptide, especially natural peptides.

In yet another embodiment, $R^2$ and/or $R^3$ is/are an optionally substituted heteroaryl or heteroaralkyl group, especially a nitrogen-containing optionally substituted heteroaryl, and particularly benzooxazole, benzoselenazol, and benzothiazole, or an optionally substituted heteroaralkyl group, particularly an optionally substituted furanyl-loweralkyl group.

In yet another embodiment, $R^2$ and/or $R^3$ is/are an optionally substituted alkyl or optionally substituted cycloalkyl.

In another embodiment, $R^2$ and/or $R^3$ is/are an optionally substituted aryl or optionally substituted aralkyl, preferably optionally substituted phenyl or benzyl.

Further preferred in each of the foregoing embodiments, $R^1$ is —C(O)OR', —CH$_2$OR''' or —C(O)NR'R''; and R', R'', and R''' are hydrogen or lower alkyl ($C_1$ to $C_8$), and especially R' is —C(O)OR', and R' is hydrogen or ($C_1$ to $C_8$)alkyl.

Presently preferred for the pharmaceutically acceptable salts of the invention are the TEA, TFA, HCl, HBr, MsOH, TsOH, AcOH, and Na salts of the furanone compounds of the present invention.

Further preferred in each of the foregoing embodiments are those compounds where X and Y are the same particularly —S—, —S(O)— or —S(O)$_2$—, preferably —S—; and especially those where —X—$R^2$ and —Y—$R^3$ are the same.

Another embodiment of the invention concerns compounds according to Formula I where X—$R^2$ and/or Y—$R^3$ is/are represented by the formula:

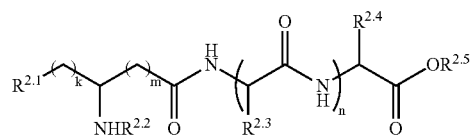

Formula II where:
  $R^{2.1}$ is: hydrogen, optionally substituted alkyl, optionally substituted aryl, —C(O)—O—$R^{2t}$, —S—, or —CH$_2$—S—;
  $R^{2.2}$ is: hydrogen, optionally substituted alkyl, optionally substituted aryl, optionally substituted aralkyl, or optionally substituted acyl (particularly including aliphatic, aromatic and cyclic
  $R^{2.3}$ is: hydrogen, optionally substituted lower alkyl, optionally substituted aralkyl, optionally substituted heteroaralkyl, or —CH$_2$—S— (selected independently, in each occurrence of R$^{2.3}$);

R$^{2.4}$ is: hydrogen, optionally substituted lower alkyl, optionally substituted aralkyl, optionally substituted heteroaralkyl, or —CH$_2$—S—;

R$^{2.5}$ is: hydrogen, optionally substituted alkyl, or optionally substituted aryl;

R$^{2'}$ is: hydrogen, optionally substituted alkyl, or optionally substituted aryl (selected independently, in each occurrence of R$^{2'}$);

k is: 0, 1 or 2;

m is: 0, 1 or 2; and n is: 0, 1, 2 or 3, at least one of R$^{2.1}$, R$^{2.3}$ and R$^{2.4}$ being —CH$_2$—S—.

Of the compounds where X—R$^2$ and/or Y—R$^3$ are represented by Formula II, preferred are those compounds the substituents of which are selected from the following groups:

R$^{2.1}$ is —C(O)—O—R$^{2'}$ where R$^{2'}$ is hydrogen or lower alkyl, especially ethyl;

R$^{2.2}$ is hydrogen;

R$^{2.3}$ is —CH$_2$—S—;

R$^{2.4}$ is hydrogen, optionally substituted lower alkyl, optionally substituted aralkyl, optionally substituted heteroaralkyl;

R$^{2.5}$ is hydrogen or lower alkyl, especially hydrogen; and/or k, m and n are respectively: 0,2,1; 1,0,1; or 2,0,1.

Another aspect of this invention concerns the compounds represented by the formula:

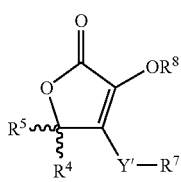

Formula III wherein:

R$^5$ is: —C(O)OR$^a$; —C(O)NR$^a$R$^b$; —CH$_2$OR$^d$; —C(O)R$^c$; cyano; optionally substituted heterocyclyl, or optionally substituted heteroaryl;

R$^6$ is hydrogen; —C(O)OR$^a$; —C(O)NR$^a$R$^b$; —CH$_2$OR$^d$; —C(O)R$^c$; cyano; optionally substituted alkyl; optionally substituted heterocyclyl; optionally substituted aryl; or optionally substituted heteroaryl;

or R$^5$ and R$^6$ with the atom to which they are attached form an optionally substituted ring;

R$^7$ is: optionally substituted alkyl; optionally substituted cycloalkyl; optionally substituted aryl; optionally substituted aralkyl; optionally substituted heterocyclyl; optionally substituted heteroaryl; optionally substituted heteroaralkyl; an optionally substituted nucleoside; an optionally substituted amino acid; or an optionally substituted di-, tri- or tetra-peptide; with the proviso that when R$^6$ is alkyl, then R$^7$ is optionally substituted heterocyclyl, optionally substituted heteroaryl, or optionally substituted heteroaralkyl.

or R$^5$ and R$^7$ with the atoms to which they are attached form an optionally substituted heterocyclic ring;

R$^8$ is: hydrogen; alkyl, alkylcarbonyl; (poly)alkoxyalkylene; or dialkoxyphosphoryloxy;

Y' is: —N(R$^a$)—; —S—; —S(O)—; or —S(O)$_2$—;

R$^a$ is: hydrogen; alkenyl; optionally substituted alkyl; optionally substituted cycloalkyl; or optionally substituted aryl;

R$^b$ is: hydrogen; alkenyl; optionally substituted alkyl; alkyl ether; or optionally substituted aryl;

or R$^a$ and R$^b$ together with the atom to which they are attached form a 5- to 7-membered aromatic, saturated or unsaturated ring, optionally incorporating one more additional heteroatom chosen from N, O, or S, and optionally substituted with one or more substituents selected from the group consisting of optionally substituted lower alkyl, halo cyano alkylthio, lower alkoxy, carboxy, benzyl, and oxo;

R$^c$ is optionally substituted alkyl or optionally substituted aryl; and

R$^d$ is hydrogen; alkenyl; optionally substituted alkyl; acyl, optionally substituted cycloalkyl; or optionally substituted aryl;

including single tautomers, single stereoisomers and mixtures of tautomers and/or stereoisomers, and the pharmaceutically acceptable salts thereof.

In another embodiment, R$^7$ is an optionally substituted heteroaryl group, especially a nitrogen-containing optionally substituted heteroaryl, and particularly selected from the group: imidazole; pyrazole; triazole; thiadiazole; oxadiazole; benzoimidazole; benzooxazole; benzoselenazole and benzothiazole.

In another embodiment R$^5$ is —C(O)OR$^a$ or —C(O)R$^c$; R$^a$ is hydrogen, (C$_1$-C$_8$)alkyl, or (C$_3$-C$_8$)cycloalkyl; and R$^c$ is lower alkyl or aryl.

In another embodiment R$^5$ is heteroaryl and R$^6$ is hydrogen.

In another preferred embodiment R$^6$ is hydrogen or —C(O)OR$^a$; and R$^a$ is hydrogen or lower alkyl (C$_1$ to C$_8$).

In another preferred embodiment R$^5$ and R$^6$ form a ring, particularly a pyrimidine-2,4,6-trione ring or a cyclohexanone ring.

In another preferred embodiment R$^5$ and R$^7$ form a ring, particularly when R$^7$ is benzoimidazole, the ring is 3-methylthiomorpholin-3-ol and the compound formed is 1,4-dihydro-4-methyl-3a,4-dihydro-3-oxa-10-thia-4a,9-diaza-cyclopenta[b]fluoren-2-one.

In another preferred embodiment R$^8$ is hydrogen.

Further preferred in each of the foregoing embodiments are those compounds where R$^5$ is —C(O)OR$^a$ or —C(O)R$^c$, R$^6$ is hydrogen, and Y' is —S—.

In another aspect the invention relates to compounds of Formula I or Formula III forming a complex with a metal, especially when said metal is selected form divalent copper, manganese, or zinc, particularly wherein said metals are selected from Cu$^{2+}$Cl$_2$, Mn$^{2+}$Cl$_2$, and Zn$^{2+}$Cl$_2$.

In another aspect, the invention relates to a pharmaceutical composition containing a therapeutically effective amount of a compound of Formula I or Formula III, or a pharmaceutically acceptable salt thereof admixed with at least one pharmaceutically acceptable excipient. Particularly preferred are those pharmaceutical compositions wherein the compound of Formula I or Formula III is selected from the preferred compounds.

In still another aspect, the invention relates to a method of treating stroke and/or other oxidative stress-related conditions that are responsive to cellular enzyme modulation such as cerebral ischemia, myocardial infarction and chronic heart failure (especially stroke/cerebral ischemia) in a mammal by administering to a mammal in need of such treatment a therapeutically effective amount of a compound of Formula I or Formula III or a pharmaceutically acceptable salt thereof.

Particularly preferred are those methods of treatment and uses in the manufacture of pharmaceutical compositions thereof, wherein the compound of Formula I or Formula III is selected from the preferred compounds, and especially from the compounds selected from:

3-(Benzothiazol-2-ylsulfanyl)-2-(benzothiazol-2-ylsulfanylmethyl)-4-hydroxy-5-oxo-2,5-dihydro-furan-2-carboxylic acid (2-hydroxy-ethyl)-amide;

3-(2,4-Dichloro-benzylsulfanyl)-2-(2,4-dichloro-benzylsulfanylmethyl)-4-hydroxy-5-oxo-2,5-dihydro-furan-2-carboxylic acid ethyl ester;

3-(5-Amino-[1,3,4]thiadiazol-2-ylsulfanyl)-2-(5-amino-[1,3,4]thiadiazol-2-ylsulfanylmethyl)-4-hydroxy-5-oxo-2,5-dihydro-furan-2-carboxylic acid;

4-(2,2-Dimethyl-propionyloxy)-3-(furan-2-ylmethylsulfanyl)-2-(furan-2-ylmethylsulfanylmethyl)-5-oxo-2,5-dihydro-furan-2-carboxylic acid ethyl ester;

3-(Benzothiazol-2-ylsulfanyl)-2-(benzothiazol-2-ylsulfanylmethyl)-4-hydroxy-5-oxo-2,5-dihydro-furan-2-carboxylic acid ethyl ester;

3-(Benzooxazol-2-ylsulfanyl)-2-(benzooxazol-2-ylsulfanylmethyl)-4-hydroxy-5-oxo-2,5-dihydro-furan-2-carboxylic acid ethyl ester;

3-(1H-Benzoimidazol-2-ylsulfanyl)-2-(1H-benzoimidazol-2-ylsulfanylmethyl)-4-hydroxy-5-oxo-dihydro-furan-2-carboxylic acid;

4-Hydroxy-5-oxo-3-(pyrrolidine-1-carbothioylsulfanyl)-2-(pyrrolidine-1-carbothioylsulfanylmethyl)-2,5-dihydro-furan-2-carboxylic acid ethyl ester;

3-Cyclohexylsulfanyl-2-cyclohexylsulfanylmethyl-4-hydroxy-5-oxo-2,5-dihydro-furan-2-carboxylic acid ethyl ester;

4-Hydroxy-5-oxo-3-(pyridin-4-ylsulfanyl)-2-(pyridin-4-ylsulfanylmethyl)-2,5-dihydro-furan-2-carboxylic acid ethyl ester;

4-Hydroxy-5-oxo-3-(5-phenyl-[1,3,4]oxadiazol-2-ylsulfanyl)-2-(5-phenyl-[1,3,4]oxadiazol-2-ylsulfanymethyl)-2,5-dihydro-furan-2-carboxylic acid ethyl ester; and 3-(1H-Benzoimidazol-2-ylsulfanyl)-2-(1H-benzoimidazol-2-ylsulfanylmethyl)-4-hydroxy-5-oxo-2,5-dihydro-furan-2-carboxylic acid ethyl ester.

In a preferred embodiment the invention relates to methods of treating a condition selected from stroke, cerebral ischemia, retinal ischemia, post-surgical cognitive dysfunctions, peripheral neuropathy/neuropathic pain, spinal cord injury, head injury and surgical trauma.

In another preferred embodiment the invention relates to methods of treating a condition involving inflammatory or autoimmune components, especially diseases including but not limited to diabetes, renal disease, premenstrual syndrome, asthma, rheumatoid arthritis, osteoarthritis, muscle fatigue, irritable bowel syndrome, inflammatory bowel disease, and intermittent claudication. Particularly preferred are those methods of treatment and uses in the manufacture of pharmaceutical compositions therefore, wherein the compound is selected from the preferred compounds, and especially from the compounds selected from;

3-(Benzothiazol-2-ylsulfanyl)-2-(benzothiazol-2-ylsulfanylmethyl)-4-hydroxy-5-oxo-2,5-dihydro-furan-2-carboxylic acid ethyl ester;

4-Hydroxy-5-oxo-3-(5-phenyl-2H-[1,2,4]triazol-3-ylsulfanyl)-2-(5-phenyl-2H-[1,2,4]triazol-3-ylsulfanylmethyl)-2,5-dihydro-furan-2-carboxylic acid ethyl ester;

4-(1H-Benzoimidazol-2-ylsulfanyl)-5-(1H-benzoimidazol-2-ylsulfanylmethyl)-3-hydroxy-5-hydroxymethyl-5H-furan-2-one;

4-Hydroxy-5-oxo-3-(4-trifluoromethyl-pyrimidin-2-ylsulfanyl)-2-(4-trifluoromethyl-pyrimidin-2-ylsulfanylmethyl)-2,5-dihydro-furan-2-carboxylic acid ethyl ester;

4-Hydroxy-5-oxo-3-(pyrimidin-2-ylsulfanyl)-2-(pyrimidin-2-ylsulfanylmethyl)-2,5-dihydro-furan-2-carboxylic acid ethyl ester;

4-Hydroxy-5-oxo-3-(2-sulfo-ethylsulfanyl)-2-(2-sulfo-ethylsulfanylmethyl)-2,5-dihydro-furan-2-carboxylic acid ethyl ester;

4-Hydroxy-5-oxo-3-(7-trifluoromethyl-quinolin-4-ylsulfanyl)-2-(7-trifluoromethyl-quinolin-4-ylsulfanylmethyl)-2,5-dihydro-furan-2-carboxylic acid ethyl ester;

3-(Benzoselenazol-2-ylsulfanyl)-2-(benzoselenazol-2-ylsulfanylmethyl)-4-hydroxy-5-oxo-2,5-dihydro-furan-2-carboxylic acid ethyl ester;

4-Hydroxy-5-oxo-3-(5-sulfonic acid-1H-benzoimidazol-2-ylsulfanyl)-2-(5-sulfonic acid-1H-benzoimidazol-2-ylsulfanylmethyl)-2,5-dihydro-furan-2-carboxylic acid ethyl ester;

3-(1H-Benzoimidazol-2-ylsulfanyl)-2-(1H-benzoimidazol-2-ylsulfanylmethyl)-4-hydroxy-5-oxo-2,5-dihydro-furan-2-carboxylic acid;

4-Hydroxy-5-oxo-3-(pyrrolidine-1-carbothioylsulfanyl)-2-(pyrrolidine-1-carbothioylsulfanylmethyl)-2,5-dihydro-furan-2-carboxylic acid ethyl ester;

3-Cyclohexylsulfanyl-2-cyclohexylsulfanylmethyl-4-hydroxy-5-oxo-2,5-dihydro-furan-2-carboxylic acid ethyl ester;

3-(2-Dimethylamino-ethylsulfanyl)-2-(2-dimethylamino-ethylsulfanylmethyl)-4-hydroxy-5-oxo-2,5-dihydro-furan-2-carboxylic acid ethyl ester, hydrochloride salt;

4-Hydroxy-5-oxo-3-(pyridin-4-ylsulfanyl)-2-(pyridin-4-ylsulfanylmethyl)-2,5-dihydro-furan-2-carboxylic acid ethyl ester;

5,8-Dichloro-3-hydroxy-2-oxo-2H-1-oxa-4,9-dithia-benzo[f]azulene-10a-carboxylic acid ethyl ester;

3-(5-Chloro-benzothiazol-2-ylsulfanyl)-2-(5-chloro-benzothiazol-2-ylsulfanylmethyl)-4-hydroxy-5-oxo-2,5-dihydro-furan-2-carboxylic acid ethyl ester; and 3-(5-Amino-[1,3,4]thiadiazol-2-ylsulfanyl)-2-(5-amino-[1,3,4]thiadiazol-2-ylsulfanylmethyl)-4-hydroxy-5-oxo-2,5-dihydro-furan-2-carboxylic acid ethyl ester;

In still another aspect, the invention relates to a method of treating neuroinflammation, cognitive disorders, and/or neurodegenerative disorders in a mammal by administering to a mammal in need of such treatment a therapeutically effective amount of a compound of Formula I or Formula III, or a pharmaceutically acceptable salt thereof. Particularly preferred are those methods of treatment and uses in the manufacture of pharmaceutical and/or cosmetic compositions thereof, wherein the compound of Formula I or Formula III is selected from the preferred compounds, and especially from the compounds selected from:

3-(2-Chloro-6-fluoro-benzylsulfanyl)-2-(2-chloro-6-fluoro-benzylsulfanylmethyl)-4-hydroxy-5-oxo-2,5-dihydro-furan-2-carboxylic acid ethyl ester;

4-Hydroxy-3-(5-methoxy-benzothiazol-2-ylsulfanyl)-2-(5-methoxy-benzothiazol-2-ylsulfanylmethyl)-5-oxo-2,5-dihydro-furan-2-carboxylic acid ethyl ester;

2-(Benzothiazole-2-sulfinylmethyl)-3-(benzothiazol-2-ylsulfanyl)-4-hydroxy-5-oxo-2,5-dihydro-furan-2-carboxylic acid ethyl ester;

4-Hydroxy-3-(6-nitro-benzothiazol-2-ylsulfanyl)-2-(6-nitro-benzothiazol-2-ylsulfanylmethyl)-5-oxo-2,5-dihydro-furan-2-carboxylic acid ethyl ester;

4-Hydroxy-3-[4-(2-methoxycarbonyl-vinyl)-phenylsulfa-
nyl]-2-[4-(2-methoxycarbonyl-vinyl)-phenylsulfanylm-
ethyl]-5-oxo-2,5-dihydro-furan-2-carboxylic acid ethyl
ester;
4-(2,2-Dimethyl-propionyloxy)-3-(furan-2-ylmethylsulfa-
nyl)-2-(furan-2-ylmethylsulfanylmethyl)-5-oxo-2,5-dihy-
dro-furan-2-carboxylic acid ethyl ester;
4-Hydroxy-3-(4-methoxy-benzylsulfanyl)-2-(4-methoxy-
benzylsulfanylmethyl)-5-oxo-2,5-dihydro-furan-2-car-
boxylic acid ethyl ester;
2-(1H-Benzoimidazol-2-ylsulfanylmethyl)-4-ethoxy-3-(1-
ethyl-1H-benzoimidazol-2-ylsulfanyl)-5-oxo-2,5-dihy-
dro-furan-2-carboxylic acid ethyl ester;
3-(Benzothiazol-2-ylsulfanyl)-2-(benzothiazol-2-ylsulfanyl-
methyl)-4-hydroxy-5-oxo-2,5-dihydro-furan-2-carboxy-
lic acid ethyl ester;
4-Hydroxy-5-oxo-3-(4-trifluoromethyl-pyrimidin-2-ylsulfa-
nyl)-2-(4-trifluoromethyl-pyrimidin-2-ylsulfanylmethyl)-
2,5-dihydro-furan-2-carboxylic acid ethyl ester;
4-Hydroxy-3-(4-methyl-pyrimidin-2-ylsulfanyl)-2-(4-me-
thyl-pyrimidin-2-ylsulfanylmethyl)-5-oxo-2,5-dihydro-
furan-2-carboxylic acid ethyl ester;
4-Hydroxy-5-oxo-3-(pyrimidin-2-ylsulfanyl)-2-(pyrimidin-
2-ylsulfanylmethyl)-2,5-dihydro-furan-2-carboxylic acid
ethyl ester; and
3-(Benzoselenazol-2-ylsulfanyl)-2-(benzoselenazol-2-ylsul-
fanylmethyl)-4-hydroxy-5-oxo-2,5-dihydro-furan-2-car-
boxylic acid ethyl ester.

Another group of diseases characterized by oxidative stress fall within the group dermatologic conditions, including, but not limited to prevention and protecting skin tissue against age-related damage or damage resulting from insults such as harmful ultraviolet (UV) radiation, stress and fatigue, and in the treatment of contact dermatitis, skin irritation, skin pigmentation, psoriasis, rosacea, or acne. In a method for regulating skin condition, regulating the signs of skin aging or for treating contact dermatitis, skin irritation, acne, rosacea, psoriasis, age-related damage or damage resulting from harmful (UV) radiation or environmental pollution, stress or fatigue, the invention entails topically administering to a mammal in need of such treatment a therapeutically effective amount of a compound of Formula I, Formula II, or Formula III or a pharmaceutically acceptable salt thereof. Particularly preferred are those methods of treatment and uses in the manufacture of pharmaceutical compositions therefore, wherein the compound is selected from the preferred compounds, and especially from the compounds selected R-3-[2-(4-Amino-4-carboxy-butyrylamino)-2-(carboxym-
ethyl-carbamoyl)-ethylsulfanyl]-2-[2-(4-amino-4-car-
boxy-butyrylamino)-2-(carboxymethyl-carbamoyl)ethyl-
sulfanylmethyl]-4-hydroxy-5-oxo-2,5-dihydro-furan-2-
carboxylic acid ethyl ester;
3-(5-Chloro-benzothiazol-2-ylsulfanyl)-2-(5-chloro-ben-
zothiazol-2-ylsulfanylmethyl)-4-hydroxy-5-oxo-2,5-di-
hydro-furan-2-carboxylic acid ethyl ester;
3-Cyclohexylsulfanyl-2-cyclohexylsulfanylmethyl-4-hy-
droxy-5-oxo-2,5-dihydro-furan-2-carboxylic acid ethyl
ester;
4-Hydroxy-5-oxo-3-(pyrrolidine-1-carbothioylsulfanyl)-2-
(pyrrolidine-1-carbothioylsulfanylmethyl)-2,5-dihydro-
furan-2-carboxylic acid ethyl ester;
3-(Benzoselenazol-2-ylsulfanyl)-2-(benzoselenazol-2-ylsul-
fanylmethyl)-4-hydroxy-5-oxo-2,5-dihydro-furan-2-car-
boxylic acid ethyl ester;
4-Hydroxy-5-oxo-3-(7-trifluoromethyl-quinolin-4-ylsulfa-
nyl)-2-(7-trifluoromethyl-quinolin-4-ylsulfanylmethyl)-
2,5-dihydro-furan-2-carboxylic acid ethyl ester;
4-Hydroxy-5-oxo-3-(2-sulfo-ethylsulfanyl)-2-(2-sulfo-eth-
ylsulfanylmethyl)-2,5-dihydro-furan-2-carboxylic acid
ethyl ester;
4-Hydroxy-5-oxo-3-(4-trifluoromethyl-pyrimidin-2-ylsulfa-
nyl)-2-(4-trifluoromethyl-pyrimidin-2-ylsulfanylmethyl)-
2,5-dihydro-furan-2-carboxylic acid ethyl ester;
4-Hydroxy-5-oxo-3-(1-oxy-pyridin-2-ylsulfanyl)-2-(1-oxy-
pyridin-2-ylsulfanylmethyl)-2,5-furan-2-carboxylic acid
ethyl ester;
3-(Benzothiazol-2-ylsulfanyl)-2-(benzothiazol-2-ylsulfanyl-
methyl)-4-hydroxy-5-oxo-2,5-dihydro-furan-2-carboxy-
lic acid ethyl ester;
3-(2-Chloro-phenylsulfanyl)-2-(2-chloro-phenylsulfanylm-
ethyl)-4-hydroxy-5-oxo-2,5-dihydro-furan-2-carboxylic
acid ethyl ester;
3-Hexylsulfanyl-2-hexylsulfanylmethyl-4-hydroxy-5-oxo-
2,5-dihydro-furan-2-carboxylic acid ethyl ester;
4-Hydroxy-5-oxo-3-(1-phenyl-1H-tetrazol-5-ylsulfanyl)-2-
(1-phenyl-1H-tetrazol-5-ylsulfanylmethyl)-2,5-dihydro-
furan-2-carboxylic acid ethyl ester;
4-Hydroxy-3-(naphthalen-2-ylsulfanyl)-2-(naphthalen-2-yl-
sulfanylmethyl)-5-oxo-2,5-dihydro-furan-2-carboxylic
acid ethyl ester;
4-Hydroxy-5-oxo-3-(4-phenyl-thiazol-2-ylsulfanyl)-2-(4-
phenyl-thiazol-2-ylsulfanylmethyl)-2,5-dihydro-furan-2-
carboxylic acid ethyl ester;
4-(5-sulfo-1H-benzoimidazol-2-ylsulfanyl)-5-(5-sulfo-1H-
benzoimidazol-2-ylsulfanylmethyl)-3-hydroxy-5-hy-
droxymethyl-5H-furan-2-one;
3-(Furan-2-ylmethylsulfanyl)-2-(furan-2-ylmethylsulfanyl-
methyl)-4-isobutyryloxy-5-oxo-2,5-dihydro-furan-2-car-
boxylic acid ethyl ester;
4-Hydroxy-3-[4-(2-methoxycarbonyl-vinyl)-phenylsulfa-
nyl]-2-[4-(2-methoxycarbonyl-vinyl)-phenylsulfanylm-
ethyl]-5-oxo-2,5-dihydro-furan-2-carboxylic acid ethyl
ester;
4-Hydroxy-3-(6-nitro-benzothiazol-2-ylsulfanyl)-2-(6-ni-
tro-benzothiazol-2-ylsulfanylmethyl)-5-oxo-2,5-dihydro-
furan-2-carboxylic acid ethyl ester;
2-(Benzothiazole-2-sulfinylmethyl)-3-(benzothiazol-2-yl-
sulfanyl)-4-hydroxy-5-oxo-2,5-dihydro-furan-2-carboxy-
lic acid ethyl ester;
3-(2,4-Dichloro-benzylsulfanyl)-2-(2,4-dichloro-benzylsul-
fanylmethyl)-4-hydroxy-5-oxo-2,5-dihydro-furan-2-car-
boxylic acid ethyl ester;
4-Hydroxy-3-(5-methoxy-benzothiazol-2-ylsulfanyl)-2-(5-
methoxy-benzothiazol-2-ylsulfanylmethyl)-5-oxo-2,5-di-
hydro-furan-2-carboxylic acid ethyl ester;
3-(2-Chloro-6-fluoro-benzylsulfanyl)-2-(2-chloro-6-fluoro-
benzylsulfanylmethyl)-4-hydroxy-5-oxo-2,5-dihydro-fu-
ran-2-carboxylic acid ethyl ester;
Dimethylamino-acetic acid 3-(1H-benzoimidazol-2-ylsulfa-
nyl)-2-(1H-benzoimidazol-2-ylsulfanylmethyl)-4-hy-
droxy-5-oxo-2,5-dihydro-furan-2-ylmethyl ester;
3-(2-Chloro-4-fluoro-phenylsulfanyl)-2-(2-chloro-4-fluoro-
phenylsulfanylmethyl)-4-hydroxy-5-oxo-2,5-dihydro-fu-
ran-2-carboxylic acid ethyl ester;
3-(Benzothiazol-2-ylsulfanyl)-2-(benzothiazol-2-ylsulfanyl-
methyl)-4-hydroxy-5-oxo-2,5-dihydro-furan-2-carboxy-
lic acid;
2-(Furan-2-ylmethanesulfinylmethyl)-3-(furan-2-yl-
methanesulfonyl)-4-hydroxy-5-oxo-2,5-dihydro-furan-2-
carboxylic acid ethyl ester;
3-(furan-2-ylmethanesulfinyl)-2-(furan-2-ylmethanesulfi-
nylmethyl)-4-hydroxy-5-oxo-2,5-dihydro-furan-2-car-
boxylic acid ethyl ester;

4-(2,2-dimethyl-propionyloxy)-3-ethoxycarbonylmethylsulfanyl-2-ethoxycarbonylmethylsulfanylmethyl-5-oxo-2,5-dihydro-furan-2-carboxylic acid ethyl ester;

3-(2-Dimethylamino-ethylsulfanyl)-2-(2-dimethylaminoethylsulfanylmethyl)-4-hydroxy-5-oxo-2,5-dihydro-furan-2-carboxylic acid;

3-(5,6-Dichloro-1H-benzoimidazol-2-ylsulfanyl)-2-(5,6-dichloro-1H-benzoimidazol-2-ylsulfanylmethyl)-4-hydroxy-5-oxo-2,5-dihydro-furan-2-carboxylic acid ethyl ester;

3-Benzylsulfanyl-2-benzylsulfanylmethyl-4-hydroxy-5-oxo-2,5-dihydro-furan-2-carboxylic acid ethyl ester;

4-(1H-Benzoimidazol-2-ylsulfanyl)-3-hydroxy-1-oxa-7,9-diaza-spiro[4.5]dec-3-ene-2,6,8,10-tetraone;

3-(Benzothiazol-2-ylsulfanyl)-2-(benzothiazol-2-ylsulfanylmethyl)-4-hydroxy-5-oxo-2,5-dihydro-furan-2-carboxylic acid isopropyl ester;

4-Acetoxy-3-(furan-2-ylmethylsulfanyl)-2-(furan-2-ylmethylsulfanylmethyl)-5-oxo-2,5-dihydro-furan-2-carboxylic acid ethyl ester;

4-Ethoxy-3-(1-ethyl-1H-benzoimidazol-2-ylsulfanyl)-2-(1-ethyl-1H-benzoimidazol-2-ylsulfanylmethyl)-5-oxo-2,5-dihydro-furan-2-carboxylic acid ethyl ester;

2-(1H-Benzoimidazol-2-ylsulfanylmethyl)-4-ethoxy-3-(1-ethyl-1H-benzoimidazol-2-ylsulfanyl)-5-oxo-2,5-dihydro-furan-2-carboxylic acid ethyl ester;

4-Acetoxy-3-benzylsulfanyl-2-benzylsulfanylmethyl-5-oxo-2,5-dihydro-furan-2-carboxylic acid ethyl ester;

4-Hydroxy-3-(1-methyl-1H-benzoimidazol-2-ylsulfanyl)-2-(1-methyl-1H-benzoimidazol-2-ylsulfanylmethyl)-5-oxo-2,5-dihydro-furan-2-carboxylic acid ethyl ester;

3-(1H-Benzoimidazol-2-ylsulfanyl)-4-hydroxy-5-oxo-2,5-dihydro-furan-2-carboxylic acid ethyl ester;

4-Hydroxy-3-(5-methyl-1H-benzoimidazol-2-ylsulfanyl)-5-oxo-2,5-dihydro-furan-2-carboxylic acid 2-isopropyl-5-methyl-cyclohexyl ester;

Di-[2-(4-Hydroxy-5-oxo-2-carboxylic acid methyl ester)]-disulfide; and 3-(4-Fluoro-benzylsulfanyl)-4-hydroxy-5-oxo-5H-furan-2,2-dicarboxylic acid diethyl ester.

In certain embodiments of the invention the dermatologic composition for the treatment of a dermatological condition additionally comprises an additional benefit agent, selected from sunscreens, retinoid and derivatives thereof, antioxidants, hydroxyacids, botanical extracts, salicylic acid, benzoylperoxide, antibiotics, antiandrogens, anti-inflammatory agents, vitamins, tocopherol ($\alpha$-, $\beta$-, $\gamma$-, $\delta$-) and esters thereof, corticosteroid and mixtures thereof.

Certain embodiments of the invention provide novel and preferred combinations of substituent groups pendant from the formulae of the different inventions.

In yet another aspect, the invention relates to a method of promoting a product by directing a user to apply to the skin a pharmaceutical or cosmetic composition incorporating a compound of any of Formula I, II or III, or a pharmaceutically acceptable salt thereof, for regulating skin condition, regulating the signs of skin aging, or for treating contact dermatitis, skin irritation, rosacea, acne, psoriasis, age-related damage or damage resulting from harmful (UV) radiation or environmental pollution, stress of fatigue. The invention also entails a product including instructions directing the user to apply a composition of the invention to the skin for regulating skin condition, regulating signs of skin aging, or for treating contact dermatitis, skin irritation, rosacea, acne, psoriasis, age-related damage or damage resulting from harmful (UN) radiation or environmental pollution, stress or fatigue, where the composition incorporates a compound of any of Formula I, II, or III or a pharmaceutically or cosmetic acceptable salt thereof.

Excluded from the compositions of matter (but, e.g., not from the methods of use and pharmaceutical formulations) of the present invention is the compound 4-hydroxy-3-methanesulfonyl-2-methanesulfonylmethyl-5-oxo-2,5-dihydro-furan-2-carboxylic acid ethyl ester.

DETAILED DESCRIPTION OF THE INVENTION

Definitions

As used in the present specification, the following words and phrases are generally intended to have the meanings as set forth below, except to the extent that the context in which they are used indicates otherwise.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined below. It will be understood by those skilled in the art with respect to any group containing one or more substituents that such groups are not intended to introduce any substitution or substitution patterns that are sterically impractical and/or synthetically non-feasible.

Certain compound, reactant, or reaction parameter abbreviations are defined as follows:

"DCM" refers to dichloromethane or methylene chloride

"DMF" refers to N, N-dimethyl formamide

"Eq." refers to equivalent.

"MeOH" refers to methanol.

"TFA" refers to trifluoroacetic acid.

The term "acyl" refers to the groups —C(O)—H, —C(O)-(optionally substituted alkyl), —C(O)-(optionally substituted cycloalkyl), —C(O)-(optionally substituted alkenyl), —C(O)-(optionally substituted cycloalkenyl), —C(O)-(optionally substituted aryl), —C(O)-(optionally substituted heteroaryl) and —C(O)-(optionally substituted heterocyclyl).

The term "acyloxy" refers to the moiety —O-acyl, including, for example, —O—C(O)-alkyl.

The term "alkoxy" refers to the groups —O-alkyl, —O-alkenyl, —O-cycloalkyl, —O-cycloalkenyl, and —O-alkynyl. Preferred alkoxy groups are —O-alkyl and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups —O-(substituted alkyl), —O-(substituted alkenyl), —O-(substituted cycloalkyl), —O-(substituted cycloalkenyl), —O-(substituted alkynyl) and —O-(optionally substituted alkylene)-alkoxy.

The term "alkyl" refers to a monoradical branched or unbranched saturated hydrocarbon chain preferably having from about 1 to 20 carbon atoms, more preferably about 1 to 10 carbon atoms, and even more preferably about 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to an alkyl group in which 1 or more (up to about 5, preferably up to about 3) hydrogen atoms is replaced by a substituent independently selected from the group: =O, =S, acyl, acyloxy, optionally substituted alkoxy, optionally substituted amino, azido, carboxyl, (optionally cycloalkyl, optionally substituted cycloalkenyl, halogen, hydroxyl, nitro, sulfanyl, sulfinyl, sulfanyl, and sulfonic acid. One of the preferred optional substituents for alkyl is hydroxy, exemplified by hydroxyalkyl groups, such as 2-hydroxyethyl, 3-hydroxypropyl, 3-hydroxybutyl, 4-hydroxybutyl, and the like; dihydroxyalkyl groups (glycols), such as 2,3-dihydroxypropyl, 3,4-dihydroxybutyl, 2,4-dihydroxybutyl, and the like; and those compounds known as polyethylene glycols, polypropylene glycols and polybutylene glycols, and the like The term "alkylene" refers to a diradical derived from the above-defined monoradical, alkyl. This term is exemplified by groups such as methylene (—$CH_2$—), ethylene (—$CH_2CH_2$—), the propylene isomers [e.g., —$CH_2CH_2CH_2$— and —$CH(CH_3)CH_2$—] and the like.

The term "substituted alkylene" refers to a diradical derived from the above-defined monoradical, substituted alkyl. Examples of substituted alkylenes are chloromethylene (—CH(Cl)—), aminoethylene (—$CH(NH_2)CH_2$—), methylaminoethylene (—$CH(NHMe)CH_2$—), 2-carboxypropylene isomers (—$CH_2CH(CO_2H)CH_2$—), ethoxyethylene (—$CH_2CH_2O$—$CH_2CH_2$—), ethyl(N-methyl)aminoethylene (—$CH_2CH_2N(CH_3)CH_2CH_2$—), 1-ethoxy-2-(2-ethoxyethoxy)ethylene —$CH_2CH_2O$—$CH_2CH_2$—$OCH_2CH_2$—$OCH_2CH_2$—), and the like.

The term "amino" refers to the group —$NH_2$.

The term "substituted amino" refers to the group —NHR or —NRR where each R is independently selected from the group: optionally substituted alkyl, optionally substituted cycloalkyl, optionally substituted alkenyl, optionally substituted cycloalkenyl, optionally substituted alkynyl, optionally substituted aryl, optionally substituted heteroaryl, optionally substituted heterocyclyl, acyl, optionally substituted alkoxy, carboxy and alkoxycarbonyl.

The term "amino acid" or "natural amino acid" refers to any of the twenty (20) common amino acids as generally accepted in the peptide art and represent L-amino acids unless otherwise designated (with the exception of achiral amino acids such as glycine).

The term "substituted amino acid" refers to an amino acid containing one or more additional chemical moieties that are not normally a part of the amino acid. Such substitutions can be introduced by a targeted derivatizing agent that is capable of reacting with selected side chains or terminal residues and via other art-accepted methods. For example, cysteinyl residues most commonly are reacted with .alpha.-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole. Carboxyl side groups (aspartyl or glutamyl) are selectively modified by reaction with carbodiimides (R'—N—C—N—R') such as 1-cyclohexyl-3-(2-morpholinyl-(4-ethyl) carbodiimide or 1-ethyl-3 (4 azonia 4,4-dimethylpentyl) carbodiimide. Furthermore, aspartyl and glutamyl residues are converted to asparaginyl and glutaminyl residues by reaction with ammonium ions. Glutaminyl and asparaginyl residues are frequently deamidated to the corresponding glutamyl and aspartyl residues. Alternatively, these residues are deamidated under mildly acidic conditions. Other modifications include hydroxylation of proline and lysine, phosphorylation of hydroxyl groups of seryl or theonyl residues, methylation of the .alpha.-amino groups of lysine, arginine, and histidine side chains (see, e.g., T. E. Creighton, Proteins: Structure and Molecule Properties, W. H. Freeman & Co., San Francisco, pp. 79-86 (1983)), acetylation of the N-terminal amine, and, in some instances, amidation of the C-terminal carboxyl groups.

The term "aromatic" refers to a cyclic or polycyclic moiety having a conjugated unsaturated (4n+2) π electron system (where n is a positive integer), sometimes referred to as a delocalized π electron system.

The term "aryl" refers to an aromatic cyclic hydrocarbon group of from 6 to 20 carbon atoms having a single ring (e.g., phenyl) or multiple condensed (fused) rings (e.g., naphthyl or anthryl). Preferred aryls include phenyl, naphthyl and the like.

The term "substituted aryl" refers to an aryl group as defined above, which unless otherwise constrained by the definition for the aryl substituent, is substituted with from 1 to 5 substituents, and preferably 1 to 3 substituents, independently selected from the group consisting of: =O, =S, acyl, acyloxy, optionally substituted alkenyl, optionally substituted alkoxy, optionally substituted alkyl (such as tri-halomethyl), optionally substituted alkynyl, optionally substituted amino, optionally substituted aryl, optionally substituted aryloxy, azido, carboxyl, (optionally substituted alkoxy)carbonyl, (optionally substituted amino)carbonyl, cyano, optionally substituted cycloalkenyl, halogen, optionally substituted heteroaryl, optionally substituted heteroaryloxy, optionally substituted heterocyclyl, optionally substituted heterocyclooxy, hydroxyl, nitro, sulfanyl, sulfinyl, sulfanyl, and sulfonic acid. Preferred aryl substituents include alkyl, alkenyl, alkoxy, halo, cyano, nitro, trihalomethyl, carboxyalkenyl, and sulfinyl.

The term "aryloxy" refers to the group —O-aryl.

The term "substituted aryloxy" refers to the group —O-(substituted aryl).

The term "aralkyl" refers to the moiety "-alkylene-aryl" each having the meaning as defined herein. Such aralkyl groups are exemplified by benzyl, phenethyl, 3-naphthylpropyl and the like.

The term "substituted aralkyl" refers to the moiety "-(optionally substituted alkylene)-(optionally substituted aryl)", each having the meaning as defined herein, where at least one of the aryl or alkylene groups is substituted, e.g., 4-(N-methyl-pyrrolyl)pentylene.

The term "carbonyl" refers to the di-radical "—C(=O)—", which is also illustrated as "—C(O)—".

The term "(optionally substituted alkoxy)carbonyl" refers to the groups: —C(O)O-(optionally substituted alkyl), —C(O)O-(optionally substituted cycloalkyl), —C(O)O-(optionally substituted alkenyl), and —C(O)O-(optionally substituted alkynyl). These moieties are also referred to as esters.

The term "(optionally substituted amino)carbonyl" refers to the group —C(O)-(optionally substituted amino). This moiety is also referred to as a primary, secondary or tertiary carboxamide.

The term "(optionally substituted amino)carbonyloxy" refers to the group —O—C(O)-(optionally substituted amino).

The term "carboxy" or "carboxyl" refers to the moiety "—C(O)OH", which is also illustrated as "—COOH".

The term "cognitive disorders" refers to disorders generally characterized by symptoms of forgetfulness, confusion, memory loss, impairment in attention and memory, behavioral and relation disorders, abulia, lack of interest, affective disturbances, and/or, in some cases poor personal care. These symptoms may arise as a result of the general aging process and/or, from organic brain disease, cerebrovascular disease, head injury, or developmental or genetic defects. Cognitive disorders include Alzheimer's disease, senile dementia, anxiety, HIV-related dementia, diabetic neuropathies; depression; Parkinson's disease; drug dependency; substance abuse; consciousness disorders, sleeping disorders, disorders of the circadian rhythm, mood disorders, epilepsy; Down's syndrome; Huntington's chorea or disease; stress-related somatic disorders; Pick's disease, Friedreich's ataxia, Creutzfeldt-Jacob disease; disorders associated with panic, phobia or stress.

The term "compound of Formula I or Formula III" is intended to encompass the furanone derivatives of the invention as disclosed, and/or the pharmaceutically acceptable salts of such compounds or metal complexes thereof. In addition, the compounds of this invention include the keto and enol tautomers, individual stereochemical isomers (arising from the selection of substituent groups) and mixtures of tautomers and/or isomers.

The term "cosmetics" includes make-up, foundation, and skin care products. The term "make-up" refers to products that leave color on the face, including foundations, blacks and browns, i.e., mascara, concealers, eye liners, brow colors, eye shadows, blushers, lip colors, and so forth. The term "foundation" refers to liquid, creme, mousse, pancake, compact, concealer or like products that even out the overall coloring of the skin. Foundation is typically manufactured to work better over moisturized and/or oiled skin. The term "skin care products" refers to products used to treat or otherwise care for, moisturize, improve, or clean the skin. Products contemplated by the phrase "skin care products" include, but are not limited to, adhesives, bandages, toothpaste, anhydrous occlusive moisturizers, antiperspirants, deodorants, powder laundry detergent, fabric softener towels, occlusive drug delivery patches, nail polish, powders, tissues, wipes, solid emulsion compact, anhydrous hair conditioners medicated shampoos, scalp treatments and the like.

The term "dermatologically-acceptable," as used herein, means that the compositions or components thereof so-described are suitable for use in contact with human skin without undue toxicity, incompatibility, instability, allergic response, or the like.

The term "cycloalkyl" refers to non-aromatic cyclic hydrocarbon groups of having about 3 to 40 (preferably about 4 to 15) carbon atoms having a single ring or multiple condensed rings. Such cycloalkyl groups include, by way of example, single ring structures such as cyclopropyl, cyclobutyl, The term "cycloalkyl" refers to non-aromatic cyclic hydrocarbon groups of having about 3 to 40 (preferably about 4 to 15) carbon atoms having a single ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to a cycloalkyl group substituted with from 1 to 5 substituents, and preferably 1 to 3 substituents, independently selected from the group consisting of: =O, =S, acyl, acyloxy, optionally substituted alkenyl, optionally substituted alkoxy, optionally substituted alkyl (such as tri-halomethyl), optionally substituted alkynyl, optionally substituted amino, optionally substituted aryl, optionally substituted aryloxy, azido, carboxyl, (optionally substituted alkoxy)carbonyl, (optionally substituted amino)carbonyl, cyano, optionally substituted cycloalkyl, optionally substituted cycloalkenyl, halogen, optionally substituted heteroaryl, optionally substituted heteroaryloxy, optionally substituted heterocyclyl, optionally substituted heterocyclooxy, hydroxyl, nitro, sulfanyl, sulfinyl, sulfanyl, and sulfonic acid. A cycloalkyl ring substituted with an alkyl group is also referred as "alkylcycloalkyl".

The term "halo" or "halogen" refers to fluoro, chloro, bromo and iodo.

The term "heteroaryl" refers to an aromatic cyclic hydrocarbon group having about 1 to 40 (preferably from about 3 to 15) carbon atoms and about 1 to 10 hetero atoms (preferably about 1 to 4 heteroatoms, selected from nitrogen, sulfur, selenium, phosphorus, and/or oxygen) within at least one ring. Such heteroaryl groups can have a single ring (e.g., pyridyl or furyl) or multiple condensed rings (e.g., indolizinyl or benzothienyl. Preferred heteroaryls include pyridyl, pyrryl and furyl. Other preferred heteroaryls include imidazole, triazole, tetrazole, thiadiazole, oxodiazole, pyrazole, benzoimidazole, benzooxazole, benzoselenazole, and benzothiazole.

The term "substituted heteroaryl" refers to a heteroaryl group as defined above, which unless otherwise constrained by the definition for the heteroaryl substituent, is substituted with from 1 to 5 substituents, and preferably 1 to 3 substituents, independently selected from the group consisting of: =O, =S, acyl, acyloxy, optionally substituted alkenyl, optionally substituted alkoxy, optionally substituted substituted aryl, optionally substituted aryloxy, azido, carboxyl, (optionally substituted alkoxy)carbonyl, (optionally substituted amino)carbonyl, cyano, optionally substituted cycloalkyl, optionally substituted cycloalkenyl, halogen, optionally substituted heteroaryl, optionally substituted heteroaryloxy, optionally substituted heterocyclyl, optionally substituted heterocyclooxy, hydroxyl, nitro, sulfanyl, sulfinyl, sulfanyl, and sulfonic acid.

The term "heteroaralkyl" refers to the moiety "-alkylene-heteroaryl" each having the meaning as defined herein.

The term "substituted heteroaralkyl" refers to the moiety "-(optionally substituted alkylene)-(optionally substituted heteroaryl)", each having the meaning as defined herein.

The term "heteroaryloxy" refers to the group —O-heteroaryl.

The terms "heterocycle", "heterocyclic" and "heterocyclyl" refer to a monoradical, saturated or unsaturated, non-aromatic cyclic hydrocarbon group having about 1 to 40 (preferably from about 3 to 15) carbon atoms and about 1 to 10 hetero atoms (preferably about 1 to 4 heteroatoms, selected from nitrogen, sulfur, phosphorus, and/or oxygen) within the ring. Such heterocyclic groups can have a single ring or multiple condensed rings. Preferred heterocyclics include morpholino, piperidinyl, and the like.

"Regulating skin condition" includes prophylactically regulating and/or therapeutically regulating skin condition, including visible and/or tactile discontinuities in skin such as, but not limited to, regulating visible and/or tactile discontinuities in the texture of skin, reducing post-inflammatory hyperpigmentation, regulating non-melanin discoloration of skin, regulating moisturization and barrier properties of skin, atrophy, regulating the elasticity of skin, reducing oily skin, regulating cellulite in skin, regulating pruritus in skin, and promoting wound healing in skin. As used herein, prophylactically regulating skin condition includes delaying, minimizing and/or preventing visible and/or tactile discontinuities in skin. As used herein, therapeutically regulating skin condition includes ameliorating, e.g., diminishing, minimizing and/or effacing, discontinuities in skin. Regulating skin condition involves improving skin appearance and/or feel.

"Regulating the signs of skin aging" includes prophylactically regulating and/or therapeutically regulating one or more of such signs (similarly, regulating a given sign of skin aging, e.g., lines, wrinkles or pores, includes prophylactically regulating and/or therapeutically regulating that sign). As used herein, prophylactically regulating such signs includes delaying, minimizing and/or preventing signs of skin aging. As used herein, therapeutically regulating such signs includes ameliorating, e.g., diminishing, minimizing and/or effacing signs of skin aging.

"Signs of skin aging" include, but are not limited to, all outward visibly and tactilely perceptible manifestations as well as any other macro or micro effects due to skin aging. Such signs may be induced or caused by intrinsic factors or extrinsic factors, e.g., chronological aging and/or environmental damage (e.g., sunlight, UV, smoke, ozone, pollutants, stress, etc.). These signs may result from wrinkles, including both fine superficial wrinkles and coarse deep wrinkles, skin lines, facial frown lines, expression lines, rhytides, dermatoheliosis, photodamage, premature skin aging, crevices, bumps, pits, large pores (e.g., associated with adnexal structures such as sweat gland ducts, sebaceous glands, or hair follicles), "orange-peel" skin appearance, dryness, scaliness, flakiness and/or other forms of skin unevenness or roughness; blemishes such as acne, pimples, breakouts; excess skin oil problems such as over production of sebum, oiliness, facial shine, foundation breakthrough; abnormal desquamation (or hair follicles), "orange-peel" skin appearance, dryness, scaliness, flakiness and/or other forms of skin flakiness, keratoses, hyperkeratinization; inadequate skin moisturization (or hydration) such as caused by skin barrier damage, environmental dryness; loss of skin elasticity (loss and/or inactivation of functional skin elastin) such as elastosis, sagging (including puffiness in the eye area and jowls), loss of skin firmness, loss of skin tightness, loss of skin recoil from deformation; non-melanin skin discoloration such as undereye circles, blotching (e.g., uneven red coloration due to, e.g., rosacea), sallowness (pale color), discoloration caused by telangiectasia or spider vessels; melanin-related hyperpigmented (or unevenly pigmented) skin regions such as age spots (liver spots, brown spots) and freckles; post-inflammatory hyperpigmentation such as that which occurs following an inflammatory event (e.g., as an such as, but not limited to, that associated with aging or steroid use; other histological or microscopic alterations in skin components such as ground substance (e.g., hyaluronic acid, glycosaminoglycans, etc.), collagen breakdown and structural alterations or abnormalities (e.g., changes in the stratum corneum, dermis, epidermis, the skin vascular system such as telangiectasia or spider vessels); tissue responses to insult such as itch or pruritus; and alterations to underlying tissues (e.g., subcutaneous fat, cellulite, muscles, trabeculae, septae, and the like), especially those proximate to the skin.

The terms "substituted heterocycle", "substituted heterocyclic" and "substituted heterocyclyl" refer to a heterocyclyl group as defined above, which unless otherwise constrained by the definition for the heterocycle, is substituted with from 1 to 5 substituents, and preferably 1 to 3 substituents, independently selected from the group consisting of: =O, =S, acyl, acyloxy, optionally substituted alkenyl, optionally substituted alkoxy, optionally substituted alkyl (such as tri-halomethyl), optionally substituted alkynyl, optionally substituted amino, optionally substituted aryl, optionally substituted aryloxy, azido, carboxyl, (optionally substituted alkoxy)carbonyl, (optionally substituted amino)carbonyl, cyano, optionally substituted cycloalkyl, optionally substituted cycloalkenyl, halogen, optionally substituted heteroaryl, optionally substituted heteroaryloxy, optionally substituted heterocyclyl, optionally substituted heterocyclooxy, hydroxyl, nitro, sulfanyl, sulfinyl, sulfanyl and sulfonic acid.

The term "heterocycloalkyl" refers to the moiety "-alkylene-heterocycle" each having the meaning as defined herein.

The term "substituted heterocycloalkyl" refers to the moiety "-(optionally substituted alkylene)-(optionally substituted heterocycle)", each having the meaning as defined herein.

The term "heterocyclooxy" refers to the group —O-heterocycle.

The term "inflammation", "inflammatory conditions", or "inflammation conditions" includes but is not limited to muscle fatigue, osteoarthritis, rheumatoid arthritis, inflammatory bowel syndrome or disorder, skin inflammation, such as atopic dermatitis, contact dermatitis, allergic dermatitis, xerosis, eczema, rosacea, seborrhea, psoriasis, atherosclerosis, thermal and radiation burns, acne, oily skin, harmful UV damage, keratinization abnormalities, skin irritation including retinoid induced irritation, hirsutism, alopecia, dyspigmentation, inflammation due to wounds, scarring or stretch marks, loss of elasticity, skin atrophy and gingivitis.

The term "ischemia" refers to deficiency of blood to an organ or tissue due to functional constriction or actual obstruction of a blood vessel. Cerebral ischemia, also known as stroke, usually results from the interruption or reduction of blood and oxygen to the blood vessels of the brain; more rarely this may be the result of an hemorrhage. Signs of stroke include paralysis, slurred speech, general confusion, impairment of gait, cortical sensory loss over toes, foot and leg, and urinary incontinence, to name just a few. Many types of heart disease including cardiac arrhythmias or diseases due to cardiac structural abnormalities may produce cerebral emboli. Atrial fibrillation from any cause, including rheumatic valvular disease, may result in emboli being produced which can migrate into the arteries of the brain. Emboli formation and migration can occur as a result of atherosclerotic cardiovascular disease and myocardial infarction. Emboli formation is also a definite risk for intracardiac surgery and prosthetic valve replacement. Heart bypass surgery and angioplasty can result in the formation of microemboli which can migrate into the arteries of the brain and cause a series of occlusions in a number of arteries, resulting in mental impairment. Cerebral embolism is also the principal complication in the transplant of artificial hearts. Furthermore, the overall risk of stroke after any type of general surgery is 0.2 to 1 percent. The vegetations of acute and subacute bacterial endocarditis can give rise to emboli which can occlude a major intracranial artery. Populations at risk of ischemia include but are not limited to patients scheduled for coronary arterial bypass graft surgery (CABG), patients at risk for postoperative complications, patients with subarachnoid hemorrhage (SAH), patients with a first or second ischemic stroke, patients with acute ischemic stroke, patients undergoing cardiopulmonary resuscitation (CPR), patients with temporary lobectomy, patients with dominant hemisphere resection, patients receiving prophylactic brain radiation, patients with closed head trauma with neurological loss, patients with microvascular multi-infarct dementia, patients with homozygous and heterozygous MELAS (Mitochondrial myopathy, encephalopathy, lactacidosis, stroke); patients with atherosclerotic or progressive supranuclear palsy disease, patients with symptomatic and asymptomatic Huntington's disease, patients with neonatal asphyxia, patients with meningitis or encephalitis, patients with post herpetic neuropathy, patients with intermittent claudication, patients with spinal cord injury, patients with Huntington's disease, Amyotrophic Lateral Sclerosis (ALS) or Friedreich's ataxia, patients with diabetic neuropathy or patients with a disease associated with a hypercoagulable state secondary to systemic disease, carcinoma, vasoconstriction (including reversible cerebral vasoconstriction, e.g. migraine, trauma, idiopathy), or venous conditions (including dehydration, pulmonary embolism, pericranial infection, postpartum and postoperative states and system cancer).

The term "neurodegenerative disorders" refers to disorders characterized by a loss of neurons and may or may not include an inflammatory process. Neurodegenerative disorders include stroke, head trauma, cerebral hypoxia, spinal cord injury, senile dementia, Alzheimer's disease, amyotrophic lateral sclerosis (ALS), cerebral amyloid angiopathy, HIV-related dementia, Parkinson's disease, Huntington's disease, prion diseases, myasthenia gravis, Down's syndrome, Creutzfeldt-Jakob disease, diabetic neuropathy, neuropathic pain, encephalitis, meningitis, and Duchenne's muscular dystrophy.

The term "neuroinflammation" or "neuroinflammatory diseases, disorders or conditions" refers to diseases, disorders or conditions characterized by large numbers of reactive microglia in postmortem brain samples, indicative of an active inflammatory process (McGeer E. G. and McGeer P. L., "Neurodegeneration and the immune system". Calne D. B., ed. Neurodegenerative Diseases, 1994:277-300). Neuroinflammation refers to inflammation which occurs in response to brain injury or autoimmune disorders, and has been shown to cause destruction of healthy neuronal and/or cerebral tissue. Neuroinflammation relates to mechanisms implicated in a broad range of acute and chronic neurodegenerative disorders, including stroke, head trauma, cerebral amyloid angiopathy, HIV-related dementia, Huntington's disease, prion diseases, meningitis, myelin degradation, Down's syndrome, post-ischemic brain injury, encephalopathy, Parkinson's disease, senile dementia, Alzheimer's disease, amyotrophic lateral sclerosis, multiple sclerosis and certain disorders involving the peripheral nervous system, such as myasthenia gravis and Duchenne's muscular dystrophy.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "pharmaceutically acceptable salt" refers to salts which retain the biological effectiveness and properties of the compounds of this invention and which are not biologically or otherwise undesirable. In many cases, the compounds of this invention are capable of forming acid and/or base salts by virtue of the presence of amino and/or carboxyl groups or groups similar thereto. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "sulfanyl" refers to the groups: —S-(optionally substituted alkyl), —S-(optionally substituted aryl), —S-(optionally substituted heteroaryl), —S-(optionally substituted heterocyclyl). Preferred sulfanyl groups include, by way of example, methylsulfanyl (—SCH$_3$), n-(iso-propylsulfanyl) (—SCH(CH$_3$)$_2$) and the like.

The term "sulfinyl" refers to the groups: —S(O)-(optionally substituted alkyl), —S(O)-optionally substituted aryl), —S(O)-(optionally substituted heteroaryl), —S(O)-(optionally substituted heterocyclyl).

The term "sulfonyl" refers to the groups: —S(O$_2$)-(optionally substituted alkyl), —S(O$_2$)-optionally substituted aryl), —S(O$_2$)-(optionally substituted heteroaryl), —S(O$_2$)-(optionally substituted heterocyclyl).

The term "sulfonic acid" refers to the group: —S(O$_2$)—OH.

The term "tautomers" refers to compounds whose structures differ markedly in arrangement of atoms, but which exist in easy and rapid equilibrium. The most common kind of tautomerism involves structures that differ in the point of attachment of hydrogen. As is well-known in the art, the 3-hydroxy-5H-furan-2-one group in compounds such as the compounds of this invention can be in tautomeric equilibrium with the dihydrofuran 2,3-dione group:

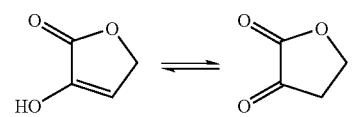

For convenience, all the compounds of this invention are shown as having the 3-hydroxy-5H-furan-2-one form, but it is to be understood that compounds of both tautomeric forms are intended to be within the scope of the invention.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the particular compound of Formula I or Formula III chosen, the dosing regimen to be followed, timing of administration, the manner of administration and the like, all of which can readily be determined by one of ordinary skill in the art.

The term "treatment" or "treating" means any treatment of a disease or disorder in a mammal, including:

preventing or protecting against the disease or disorder, that is, causing the clinical symptoms not to develop;

inhibiting the disease or disorder, that is, arresting or suppressing the development of clinical symptoms; and/or relieving the disease or disorder that is, causing the regression of clinical symptoms.

It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" as defined herein. The term "protection," as used herein, is meant to include "prophylaxis."

The term "effective amount" means a dosage sufficient to provide treatment for the disorder or disease state being treated. This will vary depending on the patient, the disease and the treatment being effected.

Nomenclature

The compounds of the present invention are named and numbered as described below, for example, with reference to Formulae Ia, Ib, Ic, and Id.

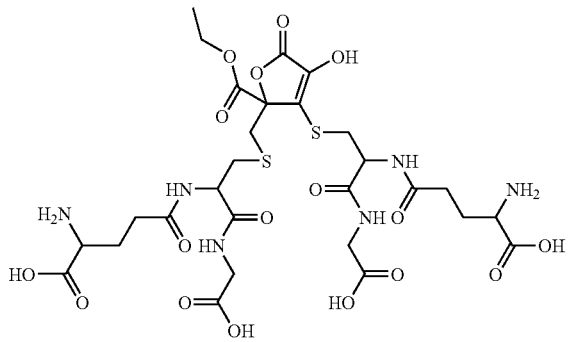

Formula Ib

Formula Ib represents the compound of Formula I where $R^1$ is —C(O)OR' and R' is ethyl; $R^2$ and $R^3$ are each a 2-amino-4-[1-(carboxymethyl-carbamoyl)-ethylcarbamoyl]-butyric acid; $R^4$ is hydrogen; X is sulfur and Y is sulfur. The compound is shown without specifying stereo configuration. The compound of Formula Ib can be named: 3-[2-(4-amino-4-carboxy-butyryl amino)-2-(carboxymethyl-carbamoyl)-ethylsulfanyl]-2-[2-(4-amino-4-carboxy-butyrylamino)-2-(carboxymethyl-carbamoyl)-ethylsulfanylmethyl]-4-hydroxy-5-oxo-2,5-dihydro-furan-2-carboxylic acid. The analogous compound corresponding to Formula Ib where X and Y are each —S(O)$_2$— can be named: 3-[2-(4-amino-4-carboxy-butyryl amino)-2-(carboxymethyl-carbamoyl)-ethanesulfonyl]-2-[2-(4-amino-4-carboxy-butyrylamino)-2-(carboxymethyl-carbamoyl)-ethanesulfonylmethyl]-4-hydroxy-5-oxo-2,5-dihydro-furan-2-carboxylic acid.

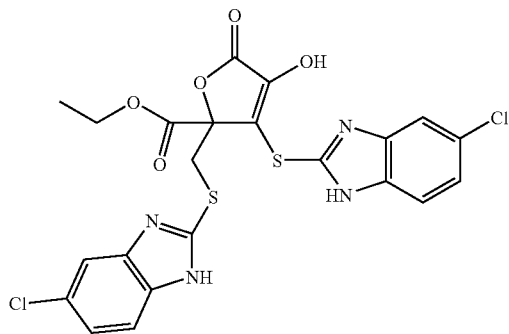

Formula Ia

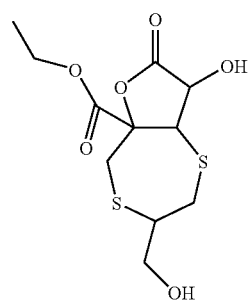

Formula Ic

Formula Ia represents the compound according to Formula I where $R^1$ is —C(O)OR' and R' is ethyl; $R^2$ and $R^3$ are each 1H-benzoimidazol-2-yl; $R^4$ is hydrogen; X is sulfur and Y is sulfur. The compound is shown without specifying stereo configuration. The compound of Formula Ia can be named: 3-(5-chloro-1H-benzoimidazol-2-ylsulfanyl)-2-(5-chloro-1H-benzoimidazol-2-ylsulfanylmethyl)-4-hydroxy-5-oxo-2,5-dihydro-furan-2-carboxylic acid ethyl ester.

Formula Ic represents the compound of Formula I where $R^1$ is —C(O)OR' and R' is ethyl; $R^4$ is hydrogen; X and Y are sulfur and X—$R^2$ taken together with Y—$R^3$ form a hydroxymethyl substituted aliphatic ring. The compound of Formula Ic can be named: 3-hydroxy-6-hydroxymethyl-2-oxo-5,6-dihydro-2H-1-oxa-4,7-dithia-azulene-8a-carboxylic acid ethyl ester

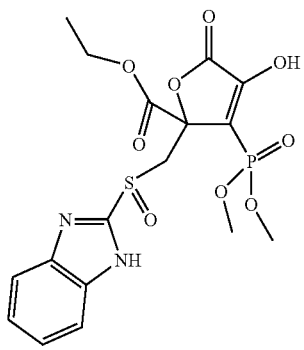

Formula Id

Formula Id represents the compound according to Formula I where $R^1$ is —C(O)OR' and R' is ethyl; $R^2$ is 1H-benzoimidazole, Y taken together with $R^3$ is —P(O)(OR')$_2$ where R' is methyl; $R^4$ is hydrogen; and X is —S(O)—. The compound of Formula Id can be named: 2-(1H-benzoimidazole-2-sulfinyl-methyl)-3-(dimethoxy-phosphoryl)-4-hydroxy-5-oxo-2,5-dihydro-furan-2-carboxylic acid ethyl ester.

In general, the nomenclature used in this Application was generated using version 2.1 of the AUTONOM® naming package within the ChemOffice® version 6.0 suite of programs by CambridgeSoft Corp (Cambridge, Mass.).

Synthesis of the Compounds of the Invention

Synthetic Reaction Parameters

The terms "solvent", "inert organic solvent" or "inert solvent" mean a solvent inert under the conditions of the reaction being described in conjunction therewith. Solvents employed in synthesis of the compounds of the invention include, for example, methanol, acetone, water, acetonitrile, 1,4-dioxane, dimethylformamide ("DMF"), benzene, toluene, tetrahydrofuran ("THF"), chloroform, methylene chloride (or dichloromethane), diethyl ether, pyridine and the like, as well as mixtures thereof. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Unless specified to the contrary, the reactions described herein take place at atmospheric pressure within a temperature range from 0° C. to 110° C. (preferably from 0° C. to 25° C.; most preferably at "room" or "ambient" temperature, e.g., 20° C.). Further, unless otherwise specified, the reaction times and conditions are intended to be approximate, e.g., taking place at about atmospheric pressure within a temperature range of about 0° C. to about 110° C. (preferably from about 0° C. to about 25° C.; most preferably at about "room" or "ambient" temperature, e.g., approximately 20° C.) over a period of about 1 to about 10 hours (preferably about 5 hours). Parameters given in the Examples are intended to be specific, not approximate.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, asymmetric synthetic approaches and other equivalent separation or isolation procedures can, of course, also be used.

Brief Description of Reaction Schemes

Reaction Scheme 1 illustrates the synthesis of the compounds of Formula I via an aldol addition between pyruvate derivatives, followed by an intramolecular cyclization reaction in the presence of a base.

Reaction Scheme 2 illustrates synthesis of the compounds of Formula I where X—$R^2$ taken together with Y—$R^3$ form an optionally substituted aliphatic or aromatic ring (where X and Y are —S—).

Reaction Scheme 3 illustrates synthesis of the compounds of Formula III via a base catalyzed condensation between a pyruvate derivative and a carbonyl component of another molecule.

Starting Materials

The compound ethyl-3-bromopyruvate is commercially available, e.g., from Aldrich Chemical Company, Milwaukee, Wis. Other reactants, are likewise commercially available or may be readily prepared by those skilled in the art using commonly employed methodology.

The starting materials employed in Reaction Scheme 1, Formulae 101 and 102, are prepared as described in co-pending U.S. application Ser. No. 10/138,937 and 10/138,032, by contacting a halopyruvate (preferably ethyl-3-bromopyruvate) with a precursor of the formula $R^2$—X—H or $R^3$—Y—H, where $R^2$ and $R^3$ have the meanings previously described, and where X and Y are —N(R')— or —S—. Such starting materials include:

an aryl, aralkyl, heteroaryl or heteroaralkyl compound,
a nucleoside, amino acid, di-, tri- or tetra-peptide,
an aryl-amine, -thiol, -sulfane, -sulfone,
an aralkyl-amine, -thiol, -sulfane, -sulfone,
a heteroaryl-amine, -thiol, -sulfane, -sulfone, or
a heteroaralkyl-amine, -thiol, -sulfane, -sulfone, and are contacted in an appropriate solvent (such as methanol, acetone, water, acetonitrile, 1,4-dioxane or DMF), optionally in the presence of an organic base (such as a tertiary amine or imidazole). The reaction takes place at a temperature from 0° C. to 110° C. (preferably 0° C. to 25° C.) for 30 minutes to 15 hours (preferably 3-5 hours), followed by removal of the solvent(s), isolation and purification to give the corresponding product of Formulae 101 or 102. Additional isolation and purification steps well known to those skilled in the art may be performed, e.g., to provide single stereo isomers and/or tautomers. Where X taken together with $R^2$ or Y taken together with $R^3$ is —P(O)(OR')$_2$ a phosphite precursor (typically a trialkylphosphite) is contacted with the halopryuvate.

Reaction Scheme 1

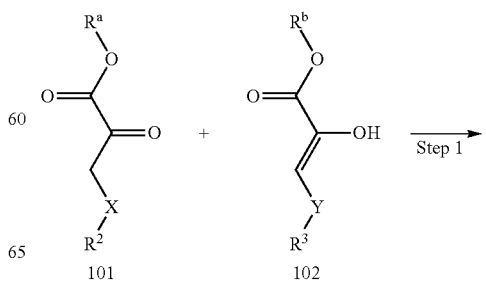

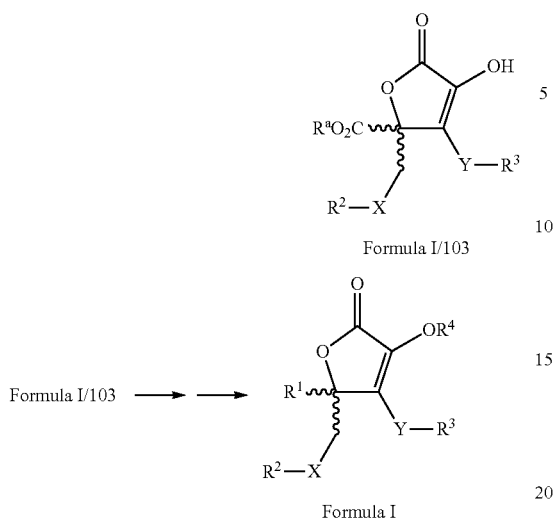

Formula I/103

Formula I/103 →→

Formula I

As illustrated in Reaction Scheme 1, Step 1, an aldol addition between two tautomeric pyruvate derivatives of Formulae 101 and 102 (where $R^a$ and $R^b$ are lower alkyl, preferably ethyl) gives the corresponding cyclized furanone derivative of Formula I/103. In the synthesis of many of the compounds of Formula I, the groups $X$—$R^2$ and $Y$—$R^3$ will be the same the pyruvate derivative(s) of Formulae 101 and 102, which will be employed as a single reactant (without regard to tautomeric form). Aldol addition between pyruvate derivatives of Formulae 101 and 102 where $R^2$ and $R^3$ contain chiral centers, produces diastereomers. When $R^2$ and $R^3$ are achiral, it produces a racemic mixture and the resulting compound has only one chiral center at the 5-position of the furanone.

In each instance, the product(s) of Reaction Scheme 1, Step 1 will fall within the scope of the compounds of the present invention according to Formula I, where $R^1$ is —C(O)OR' (R' being a lower alkyl group corresponding to $R^a$ or $R^b$) and $R^4$ is hydrogen. The compounds of Formula I where $R^1$ is —C(O)OR' (R' being other than lower alkyl), —C(O)NR'R" or —CH$_2$OR''', or where $R^4$ is other than hydrogen, can be prepared as illustrated after Step 1 in Reaction Scheme 1, (for example, by conversion of $R^1$ lower alkyl ester to another ester, amide, free acid, alcohol or like moiety) employing reactants and conditions well known to those skilled in organic synthesis.

Reaction Scheme 2
The compounds fo Formula I where X-R2 taken together with Y-R3 form an optionally substituted aliphatic or aromatic ring (where X and Y are the same, such as -S-) are synthesized, for example, as illustrated below with regard to Reaction Scheme 2.

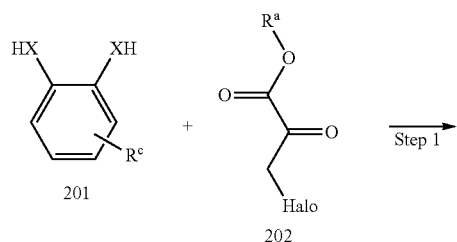

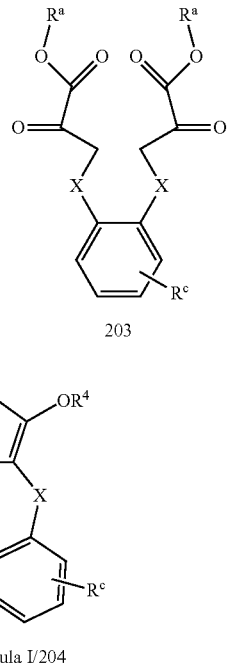

Formula I/204

As illustrated in Reaction Scheme 2, Step 1, an optionally substituted di-thiol of Formula 201 [where $R^c$ is optionally one or more substituents selected from lower alkyl, hydroxy (lower alkyl), sulfonic acid (lower alkyl), —C(O)OR', or represents an optionally substituted aliphatic or aromatic ring] and a halopyruvate of Formula 202 are reacted to give the corresponding di-thiol-bridged di-pyruvate compound of Formula 203.

As illustrated in Reaction Scheme 2, Step 2, a compound of Formula 203 is cyclized to the corresponding compound of Formula I/204 under aldol addition conditions similar to those employed in Step 1 of Reaction Scheme 1.

Reaction Scheme 3

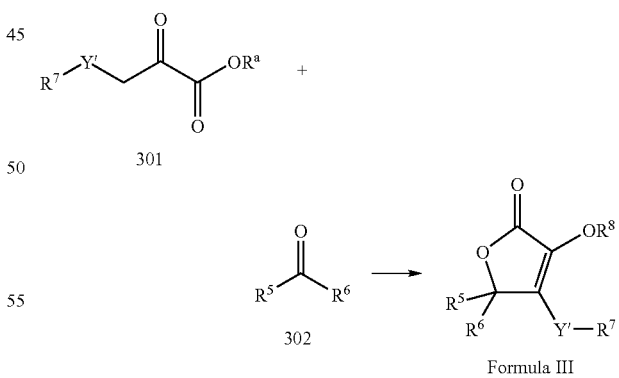

Formula III

As illustrated in Reaction Scheme 3, a base catalyzed condensation between the pyruvate of Formula 301 wherein $R^a$ is a lower alkyl group, preferably ethyl, and the carbonyl component of Formula 302 wherein $R^a$, $R^5$, $R^6$ and $R^7$ are as described herein, can give the corresponding cyclized furanone derivative of Formula III, wherein $R^6$ is hydrogen. The compounds of Formula III where $R^8$ is other than hydrogen, can be prepared by ways well known in the art, for example, compounds wherein $R^8$ is alkyl carbonyl can be prepared by acetylation of the alcohol group in the presence of a base.

Preferred Processes and Last Steps

The preferred process for generating compounds of Formula I or III is as exemplified for the syntheses of Examples 1-34. This process involves preparation of pyruvate derivatives and the subsequent aldol addition and cyclization between two pyruvate derivatives. The preparation of pyruvate precursors has already been exemplified in the previous Applications U.S. Ser. Nos. 10/138,937 and 10/138,032. In this invention, the preferred process for the preparation of compounds of Formula I is the aldol addition and the subsequent cyclization between the tautomers, namely the enol and keto forms, of pyruvate derivatives in the presence of a base.

Thus, in one preferred aspect, the pyruvate derivatives are treated with a base.

In another preferred aspect, the cyclized furanone diastereoisomers are separated using reverse phase chromatography method if the pyruvate precursors containing chiral center(s).

In yet another preferred aspect, the cyclized furanone racemic mixture is separated using chiral column chromatography method if the pyruvate precursors containing achiral centers.

In still another preferred aspect, the stereoisomers are converted into different pharmaceutically acceptable salts either from one salt to another or from a salt-free entity as exemplified in Examples.

A compound of Formula I or Formula III is contacted with a pharmaceutically acceptable acid to form the corresponding acid addition salt.

A pharmaceutically acceptable acid addition salt of Formula I or Formula III is contacted with a base to form the corresponding free base of Formula I or Formula III.

Preferred Compounds

The compounds of Formula I and of Formula III encompass the furanone derivatives of the invention as disclosed, and/or the pharmaceutically acceptable salts of such compounds. In addition, the compounds of this invention include the individual stereochemical isomers or tautomers and mixtures thereof, arising from the selection of substituent groups.

Preferred for the compounds, pharmaceutical formulations, methods of manufacture and use of the present invention are the following combinations and permutations of substituent groups of Formula I (sub-grouped, respectively, in increasing order of preference):
1. X is the same as Y:
   a. Especially where X and Y are —S— or —S(O)—, preferably —S—.
      i. Preferably where $R^4$ is hydrogen.
      ii. Preferably where $R^1$ is —C(O)OR' and R' is hydrogen or lower alkyl.
      iii. Preferably where $R^2$ is the same as $R^3$.
         Particularly where $R^2$ and $R^3$ are selected from optionally substituted alkyl, optionally substituted heteroaryl, optionally substituted heteroaralkyl, an optionally substituted amino acid or an optionally substituted di-, tri- or tetra-peptide, and especially as further described as preferred below.
2. $R^1$ is —C(O)OR'; —CH$_2$OR''' or —C(O)NR'R'' where R', R'' and R''' are hydrogen or lower alkyl
   a. Preferably $R^1$ is —C(O)OR', where R' is hydrogen or lower alkyl
      i. Especially where $R^4$ is hydrogen.
      ii. Especially where $R^2$ is the same as $R^3$
         1. Particularly where $R^2$ and $R^3$ are selected from optionally substituted alkyl, optionally substituted cycloalkyl, optionally substituted aryl, optionally substituted aralkyl, optionally substituted heteroaryl, optionally substituted heteroaralkyl, an optionally substituted amino acid or an optionally substituted di-, tri- or tetra-peptide, and especially as further described as preferred below.
3. $R^4$ is hydrogen.
4. $R^2$ is the same as $R^3$:
   a. Especially where $R^2$ and $R^3$ are selected from optionally substituted alkyl, optionally substituted cycloalkyl, optionally substituted aryl, optionally substituted aralkyl, optionally substituted heteroaryl, optionally substituted heteroaralkyl, an optionally substituted amino acid or an optionally substituted di-, tri- or tetra-peptide.
      i. Preferably where $R^2$ and $R^3$ are optionally substituted heteroaryl, optionally substituted heteroaralkyl, optionally substituted aryl or optionally substituted aralkyl.
         Particularly where optionally substituted heteroaryl or optionally substituted heteroaralkyl is selected from: optionally substituted 4-pyridinyl, optionally substituted 2-pyridinyl, optionally substituted 1H-benzoimidazol-2-yl, optionally substituted-1H-benzothiazol-2-yl, optionally substituted benzooxazole-2-yl; optionally substituted benselenazol-2-yl; optionally substituted 1H-[1,2,4]triazol-3-yl, optionally substituted 2H-[1,2,4]triazol-3-yl, optionally substituted 4H-[1,2,4]triazol-3-yl, optionally substituted [1,3,4]oxadiazol-2-yl, optionally substituted [1,2,4]thiadiazol-5-yl, optionally substituted [1,3,5]thiadiazol-2-yl optionally substituted 4,5-dihydro-thiazol-2-yl, optionally substituted 1H-pyrazolo[3,4-d]pyrimidin-6-yl, optionally substituted 1H-imidazol-2-yl, optionally substituted quinolyn-4-yl, optionally substituted pyrimidin-4-yl, optionally substituted pyrimidin-2-yl, optionally substituted 2H-chromen-7-yl, optionally substituted furan-2-yl-lower alkyl, and optionally substituted 3,4-dihydro-quinazolin-2-yl, and wherein the substitutents are selected from ($C_1$-$C_8$)alkyl, ($C_1$-$C_8$)alkenyl, halogen, haloalkyl, acyl, sulfonic acid, sulfonyl, amino, mono- or di-substituted amino, aryl, carboxy, carboxyvinyl, ester, amide, hydroxy, and alkoxy.
         a. More preferably where optionally substituted heteroaryl or heteroaralkyl is selected from optionally substituted benzyl; optionally substituted 1-H-benzoimidazol-2-yl; optionally substituted benzothiazol-2yl; optionally substituted benzooxazol-2-yl; optionally substituted benzosenlenazol-2-yl; optionally substituted furan-2-yl-lower alkyl; optionally substituted thiazol-2-yl; optionally substituted 1H-imidazol-2-yl; optionally substituted pyridine-2-yl; optionally substituted pyrimidin-2-yl; optionally substituted quinolinin-4-yl; optionally substituted [1,3,4]oxadiazol-2-yl; optionally substituted 2H-[1,2,4]-triazol-3-yl; and optionally substituted [1,3,4]thiadiazole-2-yl; and wherein the substituents are selected from ($C_1$-$C_8$)alkyl, ($C_1$-$C_8$)alkenyl, halogen, haloalkyl, acyl, sulfonic acid, sulfonyl, amino, mono- or di-substituted amino, aryl, carboxy, carboxyvinyl, ester, amide, hydroxy, and alkoxy.
  b. Most preferably 1-H-benzoimidazol-2-yl; benzothiazol-2-yl; 5-methoxy-benzothiazol-2-yl; 6-nitro-benzothiazol-2-yl; benzooxazol-2-yl; 5-amino-[1,3,4]thiadiazol-2-yl; furan-2-ylmethyl; pyridin-4-yl; 5-phenyl-[1,3,4]oxadiazol-2-yl; pyrrolidine-1-carbothioyl; 4-(2-methoxycarbonyl-vinyl)-phenyl; 4-trifluoromethyl-pyrimidin-2-yl; 4-methyl-pyrimidin-2-yl; and pyrimidin-2-yl.
  Especially wherein $R^1$ is —C(O)OR', R' is selected from hydrogen and $(C_1\text{-}C_8)$alkyl; and $R^4$ is hydrogen.
  Especially wherein $R^1$ is —$CH_2OR'''$; R''' is selected from hydrogen and $(C_1\text{-}C_8)$alkyl; and $R^4$ is hydrogen.
  Especially wherein $R^1$ is —C(O)NR'R''; R' and R'' are selected from hydrogen, $(C_1\text{-}C_8)$alkyl and hydroxy$(C_1\text{-}C_8)$alkyl; and $R^4$ is hydrogen.
  ii. Preferably where $R^2$ and $R^3$ are optionally substituted di-, tri- or tetra-peptides. Particularly (4-amino-4-carboxyburyrylamino-2-(carboxymethyl-carbamoyl)-ethyl.
  iii. Preferably where $R^2$ and $R^3$ are optionally substituted alkyl or optionally substituted cycloalkyl.
    Particularly $R^2$ and $R^3$ are selected from $(C_3\text{-}C_8)$cycloalkyl, butyl, 2-acetylamino-2-methoxycarbonyl-ethyl, 3-(2-carboxy-pyrrolidin-1-yl)-2-methyl-3-oxo-propyl, 2-carboxy-2-isobutyrylamino-ethyl, 2-methoxycarbonyl-ethyl, 3-ethoxycarbonylmethyl; methoxycarbonylmethyl, carboxymethyl-carbamoyl-ethyl, dimethylthiocarbamoyl, isobutyl, 2-hydroxy-1-methyl-propyl, 2,3-dihydroxy-propyl, and allyl.
  iv. Preferably where $R^2$ and $R^3$ are optionally substituted aryl or optionally substituted aralkyl,
    1. Particularly where optionally substituted aryl or optionally substituted aralkyl are selected from optionally substituted phenyl, optionally substituted naphthyl or optionally substituted benzyl.
      a. More preferably where optionally substituted aryl or optionally substituted aralkyl are selected from: 4-methoxy-benzyl; 2,4-dichloro-benzyl; 2-chloro-6-fluoro-benzyl; 4-fluoro-benzyl; benzyl; 2-chloro-phenyl; and 2-chloro-4-fluoro-phenyl.
5. X—$R^2$ taken together with Y—$R^3$ forms an optionally substituted aliphatic or aromatic ring.
  a. Especially an optionally substituted dithia-cyclohexene, optionally substituted dithia-cycloheptene, 7,8-dihydro-6H-5,9-dithia-benzocycloheptene,
    i. Particularly 1,4-dichloro-7,8-dihydro-6H-5,9-dithia-benzocycloheptene, 2,3-dimethyl-[1,4]dithiepane, or [1,3]dithiane-2-thione.
6. Metal complex where the metal is selected from divalent copper, manganese and zinc
  a. Especially where the metal is selected from $Cu^{2+}Cl_2$, $Mn^{2+}Cl_2$, and $Zn^{2+}Cl_2$,
    i. Particularly with a compound of Formula I wherein $XR^2$ and $YR^3$ are both benzoimidazol-2-ylsulfanyl.
Of the compounds where X—$R^2$ and/or Y—$R^3$ are represented by Formula II, preferred are those compounds the substituents of which are selected from the following groups:
$R^{2.1}$ is —C(O)—O—R' where R' is hydrogen or lower alkyl, especially ethyl;

$R^{2.2}$ is hydrogen;
$R^{2.3}$ is —$CH_2$—S—;
$R^{2.4}$ is hydrogen, optionally substituted lower alkyl, optionally substituted aralkyl, optionally substituted heteroaralkyl;
$R^{2.5}$ is hydrogen or lower alkyl, especially hydrogen; and/or
k, m and n are respectively: 0,2,1; 1,0,1; or 2,0,1.
Also preferred for the compounds, pharmaceutical formulations, methods of manufacture and use of the present invention are the following combinations and permutations of substituent groups of Formula III (sub-grouped, respectively, in increasing order of preference):
1. Y' is —S—, —S(O)— or —$S(O)_2$—; especially where Y' is —S—.
  i. Preferably where $R^7$ is selected from optionally substituted phenyl, optionally substituted naphthalenyl, optionally substituted benzyl, optionally substituted 1-H-benzoimidazol2-yl, optionally substituted benzothiazole-2yl, optionally substituted benzooxazole-2-yl, optionally substituted furan-2-yl-lower alkyl, optionally substituted thiazol-2-yl, optionally substituted 1H-imidazol-2-yl, optionally substituted pyridine-2-yl, optionally substituted pyrimidin-2-yl, optionally substituted quinolinin-4-yl; optionally substituted [1,3,4]oxadiaazol-2-yl, optionally substituted 2H[1,2,4]-triazol-3-yl.
    a. more preferably where $R^7$ is selected from benzyl; 4-fluorobenzyl; 1-H-benzoimidazol-2-yl; 5-methyl-1-H-benzoimidazol2-yl; benzothiazole-2yl; 5-chloro-benzothiazole-2yl; and 4-phenyl-thiazol-2-yl.
  ii. Preferably where $R^8$ is hydrogen
  iii. Preferably where $R^5$ is —$C(O)OR^a$ or —$C(O)R^c$, $R^a$ is selected from hydrogen, $(C_1\text{-}C_5)$alkyl, and $(C_1\text{-}C_8)$alkyl-$(C_3\text{-}C_8)$cycloalkyl, and $R^c$ is selected from hydrogen, $(C_1\text{-}C_8)$alkyl, and aryl,
    a. More preferably where $R^6$ is hydrogen or —$C(O)OR^a$ and $R^a$ is selected from hydrogen and $(C_1\text{-}C_5)$alkyl.
  iv. Preferably where $R^5$ is —$C(O)R^c$, and $R^c$ is selected from hydrogen, $(C_1\text{-}C_8)$alkyl, and aryl, and $R^6$ is hydrogen.
2. $R^5$ is —$C(O)OR^a$ or —$C(O)R^c$, $R^a$ is selected from hydrogen, $(C_1\text{-}C_8)$alkyl, and $(C_1\text{-}C_8)$alkyl-$(C_3\text{-}C_8)$cycloalkyl, and $R^c$ is selected from hydrogen, $(C_1\text{-}C_8)$alkyl, and aryl.
  i. Especially where $R^8$ is hydrogen.
  ii. Especially where $R^7$ is selected from optionally substituted phenyl, optionally substituted naphthalenyl, optionally substituted benzyl, optionally substituted 1-H-benzoimidazol2-yl, optionally substituted benzothiazole-2yl, optionally substituted benzooxazole-2-yl, optionally substituted furan-2-yl-lower alkyl, optionally substituted thiazol-2-yl, optionally substituted 1H-imidazol-2-yl, optionally substituted pyridine-2-yl, optionally substituted pyrimidin-2-yl, optionally substituted quinolinin-4-yl; optionally substituted [1,3,4]oxadiaazol-2-yl, optionally substituted 2H-[1,2,4]-triazol-3-yl.
    a. Preferably where $R^7$ is selected from benzyl; 4-fluorobenzyl; 1-H-benzoimidazol-2-yl; 5-methyl-1-H-benzoimidazol2-yl; benzothiazole-2yl; 5-chloro-benzothiazole-2yl; and 4-phenyl-thiazol-2-yl.
3. $R^5$ and $R^6$ taken together with the atom to which they are attached form a ring optionally incorporating one or more additional heteroatoms chosen from N, O or S and optionally substituted with one or more substitutents selected from the group consisting of optionally substituted lower alkyl, halo, carboxy, and oxo;
  a. Especially a pyrimidine 2,4,6-trione ring or a cyclohexanone ring.
4. $R^5$ and $R^7$ together with the atoms to which they are attached form a ring optionally incorporating one or more additional heteroatoms chosen from N, O or S and optionally substituted with one or more substituents selected from the group consisting of optionally substituted lower alkyl, halo, carboxy and oxo;
  a. Especially a 3-methyl-thiomorpholin-3-ol ring and the compound formed is 1,4-dihydro-4-methyl-3a,4-dihydro-3-oxa-10-thia-4a,9-diaza-cyclopenta[b]fluoren-2-one.

The preferred compounds include the following, as well as their stereoisomer, tautomers, salts, and mixtures thereof:

4-(Benzothiazol-2-ylsulfanyl)-3-hydroxy-1-oxa-spiro[4.5]dec-3-ene-2,6-dione;
Methanesulfonic acid 3-(1H-benzoimidazol-2-ylsulfanyl)-2-(1H-benzoimidazol-2-ylsulfanylmethyl)-4-hydroxy-5-oxo-2,5-dihydro-furan-2-ylmethyl ester;
3-(Benzothiazol-2-ylsulfanyl)-4-hydroxy-5-oxo-5H-furan-2,2-dicarboxylic acid diethyl ester;
3-(5-Chloro-benzothiazol-2-ylsulfanyl)-4-hydroxy-5-oxo-5H-furan-2,2-dicarboxylic acid diethyl ester;
3-[9-(3,4-Dihydroxy-5-hydroxymethyl-tetrahydro-furan-2-yl)-2-methyl-9H-purin-6-ylsulfanyl]-2-[9-(3,4-dihydroxy-5-hydroxymethyl-tetrahydro-furan-2-yl)-2-methyl-9H-purin-6-ylsulfanylmethyl]-4-hydroxy-5-oxo-2,5-dihydro-furan-2-carboxylic acid ethyl ester;
4-Hydroxy-3-(2-methyl-propane-1-sulfonyl)-2-(2-methyl-propane-1-sulfonylmethyl)-5-oxo-2,5-dihydro-furan-2-carboxylic acid ethyl ester;
4-Hydroxy-5-oxo-3-(9H-purin-6-ylsulfanyl)-2-(9H-purin-6-ylsulfanylmethyl)-2,5-dihydro-furan-2-carboxylic acid methyl ester;
4-Hydroxy-5-oxo-3-(5-phenyl-2H-[1,2,4]triazol-3-ylsulfanyl)-2-(5-phenyl-2H-[1,2,4]triazol-3-ylsulfanylmethyl)-2,5-dihydro-furan-2-carboxylic acid ethyl ester;
4-Hydroxy-2-methyl-3-(5-methyl-1H-benzoimidazol-2-ylsulfanyl)-5-oxo-2,5-dihydro-furan-2-carboxylic acid ethyl ester;
4-(1H-Benzoimidazol-2-ylsulfanyl)-5-(1H-benzoimidazol-2-ylsulfanylmethyl)-3-hydroxy-5-(4-methyl-piperazine-1-carbonyl)-5H-furan-2-one;
4-Hydroxy-5-oxo-3-(3-sulfo-propylsulfanyl)-2-(3-sulfo-propylsulfanylmethyl)-2,5-dihydro-furan-2-carboxylic acid ethyl ester;
4-Hydroxy-5-oxo-3-(2-sulfo-ethylsulfanyl)-2-(2-sulfo-ethylsulfanylmethyl)-2,5-dihydro-furan-2-carboxylic acid ethyl ester;
3-(2-Dimethylamino-ethylsulfanyl)-2-(2-dimethylamino-ethylsulfanylmethyl)-4-hydroxy-5-oxo-2,5-dihydro-furan-2-carboxylic acid ethyl ester, as hydrochloric acid salt; and
3-[3-(2-Carboxy-pyrrolidin-1-yl)-2-methyl-3-oxo-propylsulfanyl]-2-[3-(2-carboxy-pyrrolidin-1-yl)-2-methyl-3-oxo-propylsulfanylmethyl]-4-hydroxy-5-oxo-2,5-dihydro-furan-2-carboxylic acid ethyl ester.

The more preferred compounds include the following, as well as their stereoisomers, tautomers, salts, and mixtures thereof:

4-(1H-Benzoimidazol-2-ylsulfanyl)-3-hydroxy-5-thiazol-2-yl-5H-furan-2-one;
4-(1H-Benzoimidazol-2-ylsulfanyl)-3-hydroxy-1-oxa-7,9-diaza-spiro[4.5]dec-3-ene-2,6,8,10-tetraone;
Phosphoric acid mono-[3-(benzothiazol-2-ylsulfanyl)-2-(benzothiazol-2-ylsulfanylmethyl)-4-hydroxy-5-oxo-2,5-dihydro-furan-2-ylmethyl]ester;
4-(Benzothiazol-2-ylsulfanyl)-3-hydroxy-1-oxa-7,9-diaza-spiro[4.5]dec-3-ene-2,6,8,10-tetraone;
2-(Furan-2-ylmethanesulfinylmethyl)-3-(furan-2-ylmethylsulfanyl)-4-hydroxy-5-oxo-2,5-dihydro-furan-2-carboxylic acid ethyl ester;
4-Hydroxy-5-oxo-3-(4-phenyl-thiazol-2-ylsulfanyl)-2,5-dihydro-furan-2-carboxylic acid;
3-[(4-(2-Carboxy-vinyl)-phenylsulfanyl]-2-[4-(2-carboxy-vinyl)-phenylsulfanylmethyl]-4-hydroxy-5-oxo-2,5-dihydro-furan-2-carboxylic acid ethyl ester;
Di-[2-(4-Hydroxy-5-oxo-2-carboxylic acid methyl ester)]-disulfide;
4-(5-sulfo-1H-benzoimidazol-2-ylsulfanyl)-5-(5-sulfo-1H-benzoimidazol-2-ylsulfanylmethyl)-3-hydroxy-5-hydroxymethyl-5H-furan-2-one;
3-(1H-Benzoimidazol-2-ylsulfanyl)-4-hydroxy-5-oxo-2,5-dihydro-furan-2-carboxylic acid ethyl ester;
4-Hydroxy-5-oxo-3-(9H-purin-6-ylsulfanyl)-2-(9H-purin-6-ylsulfanylmethyl)-2,5-dihydro-furan-2-carboxylic acid ethyl ester;
4-Hydroxy-3-(5-methyl-1H-benzoimidazol-2-ylsulfanyl)-2-(5-methyl-1H-benzoimidazol-2-ylsulfanylmethyl)-5-oxo-2,5-dihydro-furan-2-carboxylic acid ethyl ester;
3-Hexylsulfanyl-2-hexylsulfanylmethyl-4-hydroxy-5-oxo-2,5-dihydro-furan-2-carboxylic acid ethyl ester;
4-(1H-Benzoimidazol-2-ylsulfanyl)-5-(1H-benzoimidazol-2-ylsulfanylmethyl)-3-hydroxy-5-hydroxymethyl-5H-furan-2-one;
4-Hydroxy-3-(1H-imidazol-2-ylsulfanyl)-2-(1H-imidazol-2-ylsulfanylmethyl)-5-oxo-2,5-dihydro-furan-2-carboxylic acid ethyl ester;
4-Hydroxy-5-oxo-3-(7-trifluoromethyl-quinolin-4-ylsulfanyl)-2-(7-trifluoromethyl-quinolin-4-ylsulfanylmethyl)-2,5-dihydro-furan-2-carboxylic acid ethyl ester;
3-(2-Diethylamino-ethylsulfanyl)-2-(2-diethylamino-ethylsulfanylmethyl)-4-hydroxy-5-oxo-2,5-dihydro-furan-2-carboxylic acid ethyl ester;
4-Hydroxy-5-oxo-3-(5-sulfo-1H-benzoimidazol-2-ylsulfanyl)-2-(5-sulfo-1H-benzoimidazol-2-ylsulfanylmethyl)-2,5-dihydro-furan-2-carboxylic acid ethyl ester;
4-Hydroxy-5-oxo-3-(pyrrolidine-1-carbothioylsulfanyl)-2-(pyrrolidine-1-carbothioylsulfanylmethyl)-2,5-dihydro-furan-2-carboxylic acid ethyl ester;
3-(1H-Benzoimidazol-2-ylsulfanyl)-2-(1H-benzoimidazol-2-ylsulfanylmethyl)-4-hydroxy-5-oxo-2,5-dihydro-furan-2-carboxylic acid methyl ester;
4-Hydroxy-3-(2-methoxycarbonyl-ethylsulfanyl)-2-(2-methoxycarbonyl-ethylsulfanylmethyl)-5-oxo-2,5-dihydro-furan-2-carboxylic acid ethyl ester;
4-Hydroxy-3-methoxycarbonylmethylsulfanyl-2-methoxycarbonylmethylsulfanylmethyl-5-oxo-2,5-dihydro-furan-2-carboxylic acid ethyl ester;
4-Hydroxy-3-(5-methoxy-1H-benzoimidazol-2-ylsulfanyl)-2-(5-methoxy-1H-benzoimidazol-2-ylsulfanylmethyl)-5-oxo-2,5-dihydro-furan-2-carboxylic acid ethyl ester;
4-Hydroxy-3-(5-nitro-1H-benzoimidazol-2-ylsulfanyl)-2-(5-nitro-1H-benzoimidazol-2-ylsulfanylmethyl)-5-oxo-2,5-dihydro-furan-2-carboxylic acid ethyl ester; and
4-Hydroxy-5-oxo-3-p-tolylsulfanyl-2-p-tolylsulfanylmethyl-2,5-dihydro-furan-2-carboxylic acid ethyl ester.

The most preferred compounds include the following as well as their stereoisomers, tautomers, salts, and mixtures thereof:

4-(1H-Benzoimidazol-2-ylsulfanyl)-5-(1H-benzoimidazol-2-ylsulfanylmethyl)-3-hydroxy-5-thiazol-2-yl-5H-furan-2-one;

3-(Benzothiazol-2-ylsulfanyl)-2-(benzothiazol-2-ylsulfanylmethyl)-4-hydroxy-5-oxo-2,5-dihydro-furan-2-carboxylic acid (2-hydroxy-ethyl)-amide;

4-(Benzothiazol-2-ylsulfanyl)-5-benzoyl-3-hydroxy-5H-furan-2-one;

3-(Benzothiazol-2-ylsulfanyl)-2-(benzothiazol-2-ylsulfanylmethyl)-4-hydroxy-5-oxo-2,5-dihydro-furan-2-carboxylic acid;

Dimethylamino-acetic acid 3-(benzothiazol-2-ylsulfanyl)-2-(benzothiazol-2-ylsulfanylmethyl)-4-hydroxy-5-oxo-2,5-dihydro-furan-2-ylmethyl ester;

4-(5-Chloro-benzothiazol-2-ylsulfanyl)-5-(5-chloro-benzothiazol-2-ylsulfanylmethyl)-3-hydroxy-5-hydroxymethyl-5H-furan-2-one;

4-(Benzothiazol-2-ylsulfanyl)-5-(benzothiazol-2-ylsulfanylmethyl)-3-hydroxy-5-hydroxymethyl-5H-furan-2-one;

3-(5,6-Dichloro-1H-benzoimidazol-2-ylsulfanyl)-2-(5,6-dichloro-1H-benzoimidazol-2-ylsulfanylmethyl)-4-hydroxy-5-oxo-2,5-dihydro-furan-2-carboxylic acid ethyl ester;

3-(1H-Benzoimidazol-2-ylsulfanyl)-4-hydroxy-5-oxo-5H-furan-2,2-dicarboxylic acid diethyl ester;

4-(Furan-2-ylmethylsulfanyl)-5-(furan-2-ylmethylsulfanylmethyl)-3-hydroxy-5-hydroxymethyl-5H-furan-2-one;

5-Acetyl-4-(benzothiazol-2-ylsulfanyl)-3-hydroxy-5H-furan-2-one;

2-(Furan-2-ylmethanesulfinylmethyl)-3-(furan-2-ylmethanesulfonyl)-4-hydroxy-5-oxo-2,5-dihydro-furan-2-carboxylic acid ethyl ester;

3-(Furan-2-ylmethanesulfonyl)-2-(furan-2-ylmethanesulfonylmethyl)-4-hydroxy-5-oxo-2,5-dihydro-furan-2-carboxylic acid ethyl ester;

3-Benzylsulfanyl-4-hydroxy-5-oxo-2,5-dihydro-furan-2-carboxylic acid ethyl ester;

4-Hydroxy-3-methylsulfanyl-2-methylsulfanylmethyl-5-oxo-2,5-dihydro-furan-2-carboxylic acid ethyl ester;

3-(5-Amino-[1,3,4]thiadiazol-2-ylsulfanyl)-2-(5-amino-[1,3,4]thiadiazol-2-ylsulfanylmethyl)-4-hydroxy-5-oxo-2,5-dihydro-furan-2-carboxylic acid;

3-(Benzothiazol-2-ylsulfanyl)-4-hydroxy-5-oxo-2,5-dihydro-furan-2-carboxylic acid;

3-Hydroxy-5,6-dimethyl-2-oxo-5,6-dihydro-2H-1-oxa-4,7-dithia-azulene-8a-carboxylic acid ethyl ester;

4-Hydroxy-3-(5-methyl-1H-benzoimidazol-2-ylsulfanyl)-5-oxo-2,5-dihydro-furan-2-carboxylic acid 2-isopropyl-5-methyl-cyclohexyl ester;

3-(2-Dimethylamino-ethylsulfanyl)-2-(2-dimethylamino-ethylsulfanylmethyl)-4-hydroxy-5-oxo-2,5-dihydro-furan-2-carboxylic acid;

3-(Furan-2-ylmethylsulfanyl)-2-(furan-2-ylmethylsulfanylmethyl)-4-hydroxy-5-oxo-2,5-dihydro-furan-2-carboxylic acid ethyl ester;

4-Hydroxy-3-(1-methyl-1H-imidazol-2-ylsulfanyl)-2-(1-methyl-1H-imidazol-2-ylsulfanylmethyl)-5-oxo-2,5-dihydro-furan-2-carboxylic acid ethyl ester;

3-Cyclopentylsulfanyl-2-cyclopentylsulfanylmethyl-4-hydroxy-5-oxo-2,5-dihydro-furan-2-carboxylic acid ethyl ester;

4-Hydroxy-3-isobutylsulfanyl-2-isobutylsulfanylmethyl-5-oxo-2,5-dihydro-furan-2-carboxylic acid ethyl ester;

4-Hydroxy-3-(naphthalen-2-ylsulfanyl)-2-(naphthalen-2-ylsulfanylmethyl)-5-oxo-2,5-dihydro-furan-2-carboxylic acid ethyl ester;

4-Hydroxy-5-oxo-3-(1-phenyl-1H-tetrazol-5-ylsulfanyl)-2-(1-phenyl-1H-tetrazol-5-ylsulfanylmethyl)-2,5-dihydro-furan-2-carboxylic acid ethyl ester;

4-Hydroxy-5-oxo-3-(thiazol-2-ylsulfanyl)-2-(thiazol-2-ylsulfanylmethyl)-2,5-dihydro-furan-2-carboxylic acid ethyl ester;

3-(2-Chloro-phenylsulfanyl)-2-(2-chloro-phenylsulfanylmethyl)-4-hydroxy-5-oxo-2,5-dihydro-furan-2-carboxylic acid ethyl ester;

3-(Benzooxazol-2-ylsulfanyl)-2-(benzooxazol-2-ylsulfanylmethyl)-4-hydroxy-5-oxo-2,5-dihydro-furan-2-carboxylic acid ethyl ester;

3-(1H-Benzoimidazol-2-ylsulfanyl)-2-(1H-benzoimidazol-2-ylsulfanylmethyl)-4-hydroxy-5-oxo-2,5-dihydro-furan-2-carboxylic acid;

4-Hydroxy-5-oxo-3-(pyridin-4-ylsulfanyl)-2-(pyridin-4-ylsulfanylmethyl)-2,5-dihydro-furan-2-carboxylic acid ethyl ester;

5,8-Dichloro-3-hydroxy-2-oxo-2H-1-oxa-4,9-dithia-benzo[f]azulene-10a-carboxylic acid ethyl ester;

3-(5-Chloro-benzothiazol-2-ylsulfanyl)-2-(5-chloro-benzothiazol-2-ylsulfanylmethyl)-4-hydroxy-5-oxo-2,5-dihydro-furan-2-carboxylic acid ethyl ester;

4-Hydroxy-5-oxo-3-(5-phenyl-[1,3,4]oxadiazol-2-ylsulfanyl)-2-(5-phenyl-[1,3,4]oxadiazol-2-ylsulfanylmethyl)-2,5-dihydro-furan-2-carboxylic acid ethyl ester;

3-(5-Amino-2H-[1,2,4]triazol-3-ylsulfanyl)-2-(5-amino-2H-[1,2,4]triazol-3-ylsulfanylmethyl)-4-hydroxy-5-oxo-2,5-dihydro-furan-2-carboxylic acid ethyl ester;

3-(3-Amino-[1,2,4]thiadiazol-5-ylsulfanyl)-2-(3-amino-[1,2,4]thiadiazol-5-ylsulfanylmethyl)-4-hydroxy-5-oxo-2,5-dihydro-furan-2-carboxylic acid ethyl ester;

3-[2-(4-Amino-4-carboxy-butyrylamino)-2-(carboxymethyl-carbamoyl)-ethanesulfonyl]-2-[2-(4-amino-4-carboxy-butyrylamino)-2-(carboxymethyl-carbamoyl)-ethanesulfonylmethyl]-4-hydroxy-5-oxo-2,5-dihydro-furan-2-carboxylic acid ethyl ester;

R-3-[2-(4-Amino-4-carboxy-butyrylamino)-2-(carboxymethyl-carbamoyl)-ethylsulfanyl]-2-[2-(4-amino-4-carboxy-butyrylamino)-2-(carboxymethyl-carbamoyl) ethylsulfanylmethyl]-4-hydroxy-5-oxo-2,5-dihydro-furan-2-carboxylic acid ethyl ester;

S-3-[2-(4-Amino-4-carboxy-butyrylamino)-2-(carboxymethyl-carbamoyl)-ethylsulfanyl]-2-[2-(4-amino-4-carboxy-butyrylamino)-2-(carboxymethyl-carbamoyl) ethylsulfanylmethyl]-4-hydroxy-5-oxo-2,5-dihydro-furan-2-carboxylic acid;

R-3-[2-(4-Amino-4-carboxy-butyrylamino)-2-(carboxymethyl-carbamoyl)-ethylsulfanyl]-2-[2-(4-amino-4-carboxy-butyrylamino)-2-(carboxymethyl-carbamoyl) ethylsulfanylmethyl]-4-hydroxy-5-oxo-2,5-dihydro-furan-2-carboxylic acid;

3-(2-Acetylamino-2-methoxycarbonyl-ethylsulfanyl)-2-(2-acetylamino-2-methoxycarbonyl-ethylsulfanylmethyl)-4-hydroxy-5-oxo-2,5-dihydro-furan-2-carboxylic acid ethyl ester;

3-(1H-Benzoimidazol-2-ylsulfanyl)-2-(1H-benzoimidazol-2-ylsulfanylmethyl)-4-hydroxy-5-oxo-2,5-dihydro-furan-2-carboxylic acid ethyl ester;

(S)-3-(1H-Benzoimidazol-2-ylsulfanyl)-2-(1H-benzoimidazol-2-ylsulfanylmethyl)-4-hydroxy-5-oxo-2,5-dihydro-furan-2-carboxylic acid ethyl ester; and (R)-(3-(1H-Benzoimidazol-2-ylsulfanyl)-2-(1H-benzoimidazol-2-ylsulfanylmethyl)-4-hydroxy-5-oxo-2,5-dihydro-furan-2-carboxylic acid ethyl ester.

Other most preferred compounds include the following as well as their stereoisomers, tautomers, salts, and mixtures thereof:

3-(2-Chloro-4-fluoro-phenylsulfanyl)-2-(2-chloro-4-fluoro-phenylsulfanylmethyl)-4-hydroxy-5-oxo-2,5-dihydro-furan-2-carboxylic acid ethyl ester;

3-(4-Fluoro-benzylsulfanyl)-4-hydroxy-5-oxo-5H-furan-2,2-dicarboxylic acid diethyl ester;

4-(Benzooxazol-2-ylsulfanyl)-5-(benzooxazol-2-ylsulfanylmethyl)-3-hydroxy-5-hydroxymethyl-5H-furan-2-one;

3-(2-Chloro-6-fluoro-benzylsulfanyl)-2-(2-chloro-6-fluoro-benzylsulfanylmethyl)-4-hydroxy-5-2,5-dihydro-furan-2-carboxylic acid ethyl ester;

4-Hydroxy-3-(5-methoxy-benzothiazol-2-ylsulfanyl)-2-(5-methoxy-benzothiazol-2-ylsulfanylmethyl)-5-oxo-2,5-dihydro-furan-2-carboxylic acid ethyl ester;

3-(2,4-Dichloro-benzylsulfanyl)-2-(2,4-dichloro-benzylsulfanylmethyl)-4-hydroxy-5-oxo-2,5-dihydro-furan-2-carboxylic acid ethyl ester;

2-(Benzothiazole-2-sulfinylmethyl)-3-(benzothiazol-2-ylsulfanyl)-4-hydroxy-5-oxo-2,5-dihydro-furan-2-carboxylic acid ethyl ester;

4-Hydroxy-3-(6-nitro-benzothiazol-2-ylsulfanyl)-2-(6-nitro-benzothiazol-2-ylsulfanylmethyl)-5-2,5-dihydro-furan-2-carboxylic acid ethyl ester;

3-(Furan-2-ylmethanesulfinyl)-2-(furan-2-ylmethanesulfinylmethyl)-4-hydroxy-5-oxo-2,5-dihydro-furan-2-carboxylic acid ethyl ester;

3-(Benzooxazol-2-ylsulfanyl)-2-(benzothiazol-2-ylsulfanylmethyl)-4-hydroxy-5-oxo-2,5-dihydro-furan-2-carboxylic acid methyl ester;

4-Hydroxy-3-[4-(2-methoxycarbonyl-vinyl)-phenylsulfanyl]-2-[4-(2-methoxycarbonyl-vinyl)-phenylsulfanylmethyl]-5-oxo-2,5-dihydro-furan-2-carboxylic acid ethyl ester;

3-(Furan-2-ylmethylsulfanyl)-2-(furan-2-ylmethylsulfanylmethyl)-4-isobutyryloxy-5-oxo-2,5-dihydro-furan-2-carboxylic acid ethyl ester;

4-(2,2-Dimethyl-propionyloxy)-3-(furan-2-ylmethylsulfanyl)-2-(furan-2-ylmethylsulfanylmethyl)-5-oxo-2,5-dihydro-furan-2-carboxylic acid ethyl ester;

4-(2,2-Dimethyl-propionyloxy)-3-ethoxycarbonylmethylsulfanyl-2-ethoxycarbonylmethylsulfanylmethyl-5-oxo-2,5-dihydro-furan-2-carboxylic acid ethyl ester;

4-Hydroxy-5-oxo-3-(4-phenyl-thiazol-2-ylsulfanyl)-2-(4-phenyl-thiazol-2-ylsulfanylmethyl)-2,5-dihydro-furan-2-carboxylic acid ethyl ester;

3-(Furan-2-ylmethylsulfanyl)-2-(furan-2-ylmethylsulfanylmethyl)-4-hydroxy-5-oxo-2,5-dihydro-furan-2-carboxylic acid ethyl ester;

3-Butylsulfanyl-2-butylsulfanylmethyl-4-hydroxy-5-oxo-2,5-dihydro-furan-2-carboxylic acid ethyl ester;

4-Hydroxy-3-(4-methoxy-benzylsulfanyl)-2-(4-methoxy-benzylsulfanylmethyl)-5-oxo-2,5-dihydro-furan-2-carboxylic acid ethyl ester;

3-Benzylsulfanyl-2-benzylsulfanylmethyl-4-hydroxy-5-oxo-2,5-dihydro-furan-2-carboxylic acid ethyl ester;

4-Hydroxy-3-(4-methoxy-phenylsulfanyl)-2-(4-methoxy-phenylsulfanylmethyl)-5-oxo-2,5-dihydro-furan-2-carboxylic acid ethyl ester;

2-(1H-Benzoimidazol-2-ylsulfanylmethyl)-4-ethoxy-3-(1-ethyl-1H-benzoimidazol-2-ylsulfanyl)-5-oxo-2,5-dihydro-furan-2-carboxylic acid ethyl ester;

3-(Benzothiazol-2-ylsulfanyl)-2-(benzothiazol-2-ylsulfanylmethyl)-4-hydroxy-5-oxo-2,5-dihydro-furan-2-carboxylic acid ethyl ester;

4-Hydroxy-5-oxo-3-(1-oxy-pyridin-2-ylsulfanyl)-2-(1-oxy-pyridin-2-ylsulfanylmethyl)-2,5-dihydro-furan-2-carboxylic acid ethyl ester;

4-Hydroxy-5-oxo-3-(4-trifluoromethyl-pyrimidin-2-ylsulfanyl)-2-(4-trifluoromethyl-pyrimidin-2-ylsulfanylmethyl)-2,5-dihydro-furan-2-carboxylic acid ethyl ester;

4-Hydroxy-3-(4-methyl-pyrimidin-2-ylsulfanyl)-2-(4-methyl-pyrimidin-2-ylsulfanylmethyl)-5-oxo-2,5-dihydro-furan-2-carboxylic acid ethyl ester;

4-Hydroxy-5-oxo-3-(pyrimidin-2-ylsulfanyl)-2-(pyrimidin-2-ylsulfanylmethyl)-2,5-dihydro-furan-2-carboxylic acid ethyl ester;

3-(Benzoselenazol-2-ylsulfanyl)-2-(benzoselenazol-2-ylsulfanylmethyl)-4-hydroxy-5-oxo-2,5-dihydro-furan-2-carboxylic acid ethyl ester; and 3-Cyclohexylsulfanyl-2-cyclohexylsulfanylmethyl-4-hydroxy-5-oxo-2,5-dihydro-furan-2-carboxylic acid ethyl ester.

Another preferred sub-group of compounds (including single tautomers, single steroisomers and mixtures of tautomers and/or stereoisomers, and the pharmaceutically or cosmetically acceptable salts) employed as compound for use in cosmetic compositions of the present invention is:

3-(5-Chloro-benzothiazol-2-ylsulfanyl)-2-(5-chloro-benzothiazol-2-ylsulfanylmethyl)-4-hydroxy-5-oxo-2,5-dihydro-furan-2-carboxylic acid ethyl ester;

3-Cyclohexylsulfanyl-2-cyclohexylsulfanylmethyl-4-hydroxy-5-oxo-2,5-dihydro-furan-2-carboxylic acid ethyl ester 3-(Benzoselenazol-2-ylsulfanyl)-2-(benzoselenazol-2-ylsulfanylmethyl)-4-hydroxy-5-oxo-2,5-dihydro-furan-2-carboxylic acid ethyl ester 3-(Benzothiazol-2-ylsulfanyl)-2-(benzothiazol-2-ylsulfanylmethyl)-4-hydroxy-5-oxo-2,5-dihydro-furan-2-carboxylic acid ethyl ester 3-(2-Chloro-phenylsulfanyl)-2-(2-chloro-phenylsulfanylmethyl)-4-hydroxy-5-oxo-2,5-dihydro-furan-2-carboxylic acid ethyl ester 3-Hexylsulfanyl-2-hexylsulfanylmethyl-4-hydroxy-5-oxo-2,5-dihydro-furan-2-carboxylic acid ethyl ester 4-Hydroxy-3-(naphthalen-2-ylsulfanyl)-2-(naphthalen-2-ylsulfanylmethyl)-5-oxo-2,5-dihydro-furan-2-carboxylic acid ethyl ester 4-Hydroxy-5-oxo-3-(4-phenyl-thiazol-2-ylsulfanyl)-2-(4-phenyl-thiazol-2-ylsulfanylmethyl)-2,5-dihydro-furan-2-carboxylic acid ethyl ester 3-(Furan-2-ylmethylsulfanyl)-2-(furan-2-ylmethylsulfanylmethyl)-4-isobutyryloxy-5-oxo-2,5-dihydro-furan-2-carboxylic acid ethyl ester 3-(2,4-Dichloro-benzylsulfanyl)-2-(2,4-dichloro-benzylsulfanylmethyl)-4-hydroxy-5-oxo-2,5-dihydro-furan-2-carboxylic acid ethyl ester 3-(2-chloro-4-fluoro-phenylsulfanyl)-2-(2-chloro-4-fluoro-phenylsulfanylmethyl)-4-hydroxy-5-oxo-2,5-dihydro-furan-2-carboxylic acid ethyl ester 3-(furan-2-ylmethanesulfinyl)-2-(furan-2-ylmethanesulfinylmethyl)-4-hydroxy-5-oxo-2,5-dihydro-furan-2-carboxylic acid ethyl ester;

4-(2,2-dimethyl-propionyloxy)-3-ethoxycarbonylmethylsulfanyl-2-ethoxycarbonylmethylsulfanylmethyl-5-oxo-2,5-dihydro-furan-2-carboxylic acid ethyl ester;

3-(1H-Benzoimidazol-2-ylsulfanyl)-4-hydroxy-5-oxo-2,5-dihydro-furan-2-carboxylic acid ethyl ester;

4-Hydroxy-3-(5-methyl-1H-benzoimidazol-2-ylsulfanyl)-5-oxo-2,5-dihydro-furan-2-carboxylic acid 2-isopropyl-5-methyl-cyclohexyl ester;

Di-[2-(4-Hydroxy-5-oxo-2-carboxylic acid methyl ester)]-disulfide;

3-(4-Fluoro-benzylsulfanyl)-4-hydroxy-5-oxo-5H-furan-2,2-dicarboxylic acid diethyl ester;

4-(1H-Benzoimidazol-2-ylsulfanyl)-3-hydroxy-1-oxa-7,9-diaza-spiro[4.5]dec-3-ene-2,6,8,10-tetraone;

3-(Benzothiazol-2-ylsulfanyl)-2-(benzothiazol-2-ylsulfanylmethyl)-4-hydroxy-5-oxo-2,5-dihydro-furan-2-carboxylic acid isopropyl ester; and 4-Hydroxy-3-(1-methyl-1H-benzoimidazol-2-ylsulfanyl)-2-(1-methyl-1H-benzoimidazol-2-ylsulfanylmethyl)-5-oxo-2,5-dihydro-furan-2-carboxylic acid ethyl ester.

Utility, Testing and Administration

General Utility

Compounds of the present invention are useful in treating a number of disorders, particularly those characterized by oxidative stress and/or inflammation. In particular, compounds of the present invention can be used in the treatment of cerebral ischemia ("stroke" most often caused by thrombosis, vasoconstriction and embolism), myocardial ischemia (including chronic stable angina, angina pectoris, unstable angina and Prinzmetal's angina, silent ischemia, reinfarction, reocclusion, restenosis, myocardial infarction and other forms of heart disease), diabetes, renal disease, pre-menstrual syndrome, asthma, cardiopulmonary inflammatory disorders, chronic heart failure, rheumatoid arthritis, muscle fatigue, irritable bowel syndrome, inflammatory bowel disease, intermittent claudication and for the preservation of allograft tissue for transplantation. Compounds of the present invention are also useful in treating conditions falling with the group of dermatologic conditions, in particular prevention and protecting skin tissue against age-related damage or damage resulting from insults such as harmful ultraviolet (UV) radiation, stress and fatigue, and in the treatment of contact dermatitis, skin irritation, skin pigmentation, rosacea, psoriasis, or acne. Compounds of the present invention are also useful in treating a number of disorders associated with neuroinflammation, cognition, and neurodegeneration, particularly Friedreich's ataxia, epilepsy, Parkinson's disease, Alzheimer's disease, and senile dementia.

Without subscribing to a particular theory or mechanism of action, compounds of the invention may target certain enzymes known as "oxidoreductases" that function widely across a variety of physiological processes. In particular, oxidoreductases catalyze reactions in which two molecules interact so that one molecule is oxidized and the other is reduced, with a molecule of water entering the reaction. Some of the most important oxidoreductases include, dehydrogenases (including ubiquinone), reductases, peroxidases, nitric acid synthases, cholesterol oxidases, acyl-coenzyme A dehydrogenases and reductases, hydroxylases, and the like. These enzymes play roles in such essential processes as digestion, signal transduction, maintenance of ionic homeostasis, and the like. Alterations in oxidoreductases are thought to account for as many as 3% of all known human genetic diseases. In addition to the diseases and disorders listed above, abnormalities in oxidoreductase activity may underly such disorders as congestive heart failure, respiratory chain defects (e.g., abnormalities associated with enzymes of the respiratory chain), glycogen storage disease, rheumatoid arthritis, amyotrophic lateral sclerosis (ALS), chronic alcohol liver damage (CALD), Refsum's disease (hereditary neuropathy), Crohn's disease, Eales Disease (pervasculitis), prion diseases, Huntington's Disease, cataracts, multiple sclerosis, acute respiratory distress syndrome (ARDS), Zellweger Syndrome (peroxisomal biogenesis), polycystic ovary syndrome, Alpers Syndrome (encephalopathy), steatosis/steatohepatitis, metabolic syndrome, diabetes, asthma, Fanconi anemia, retinopathy, age-related macular degeneration (AMD), pre-eclampsia, cholestatic liver disease, end-stage renal disease, Creutzfeldt-Jakob Disease (CJD), and sickle cell disease.

The compounds, formulations and methods of the present invention are useful in treating a number of dermatological condition, including, but not limited to prevention and protecting skin tissue against age-related damage or damage resulting from insults such as harmful ultraviolet (UV), radiation, stress and fatigue. Such compounds, formulations and methods are likewise useful, e.g. in treating contact dermatitis, skin irritation, rosacea, acne and psoriasis (including scalp psoriasis), and re amenable to topical application for hair care and treatments of the scalp, for example by incorporation in medicated shampoos, anhydrous hair conditioners and the like.

For example, exposure to sunlight can pose a number of hazards to the skin. The major short-term hazard of prolonged exposure to sunlight is erythema, i.e., sunburn, which primarily results from UVB radiation having a wavelength of from about 290 nm to about 320 nm. Over the long term, however, such prolonged exposure can often cause malignant changes in the skin surface to occur. Epidemiologic studies demonstrate a strong relationship between sunlight exposure and human skin cancer. Another long-term hazard of ultraviolet radiation is premature aging of the skin, which is primarily caused by UVA radiation having a wavelength of from about 320 nm to about 400 nm. This condition is characterized by wrinkling and pigment changes of the skin, along with other physical changes such as cracking, telangiectasis, solar dermatoses, ecchymoses, and loss of elasticity. Individuals, particularly those having light-skin who burn easily and tan poorly, who have had a great deal sun exposure in childhood can show the following gross cutaneous alterations in later adult life: wrinkling, leatheriness, yellowing, looseness, roughness, dryness, mottling (hyperpigmentation) and various premalignant growths (often subclinical). These cumulative effects of sunlight are often referred to as "photoaging". Although the anatomical degradation of the skin is most advanced in the elderly, the destructive effects of excessive sun exposure are already evident by the second decade. Serious microscopic alterations of the epidermis and dermis occur decades before these become clinically visible. Wrinkling, yellowing, leatheriness and loss of elasticity are very late changes.

Other skin conditions that may benefit from the methods of the present invention include, but are not limited to, diaper rash, a common form of contact dermatitis and irritation occurring in infants, as well as adults, who wear diapers. U.S. Pat. No. 6,211,186, incorporated herein by reference, describes possible etiologies and methods of treating this condition. It is generally thought that one or more fecal and lipolytic enzymes, as well as ammonia, bacteria, urine pH, overhydration and *Candida albicans* may be involved in the onset of skin irritation and inflammation associated with diaper rash. It is also likely that physiological responses of the skin to the irritants, such as production of cytokines by keratinocytes, contribute to the ensuing appearance of erythema, papules, scaling and ulceration characteristic of the condition. In addition, compositions and methods of the present invention may be useful in treating acne, a skin condition characterized by a profound inflammatory component.

The compositions of the present invention are also useful for regulating skin condition, including visible and/or tactile discontinuities in skin (especially the skin surface; such discontinuities are generally undesired). Such discontinuities may be induced or caused by internal and/or external factors, and include the signs of skin aging described herein.

The compositions of the present invention are useful for regulating signs of skin aging, especially visible and/or tactile discontinuities in skin texture associated with aging. It is to be understood that the present invention is not to be limited to regulation of the "signs of skin aging" that arise due to the above-mentioned mechanisms associated with skin aging, but is intended to include regulation of such signs irrespective of their mechanism of origin.

Testing

This section describes how compositions incorporating compositions of the present invention are selected, using in vitro and/or in vivo animal models, for example, and used as therapeutic interventions in the exemplary indications, i.e., stroke, chronic heart failure, myocardial infarction, and Alzheimer's disease.

Insults to the brain that disrupt its blood supply, as in ischemia, or its oxygen supply, as in hypoxia (low oxygen) or anoxia (no oxygen), rapidly cause neuronal imbalance leading to cell death (Flynn, C. J., et al., 1989, in G. Siegel et al., (Eds), *Basic Neurochemistry*, Raven Press, NY). Investigations into the cellular and molecular mechanisms that lead to neuronal damage and inflammation associated with various types of brain ischemia can be carried out using in vitro model systems, such as primary cell cultures, that retain the metabolic characteristics of neurons in vivo. The use of such cell-based models has led to advances in identification of biochemical mechanisms leading to neuronal death in conditions such as anoxia, hypoglycemia, excitotoxicity, and exposure to reactive oxygen species. Neuronal cell lines such as the pheochromocytoma cell line, PC12, are also useful models for studying the effects of oxidative stress on the structure and function of neuron-specific proteins that are expressed in the cell lines. As many neuronal cell lines do not express all the properties of genuine neurons, primary neuronal cultures are now widely used as in vitro models in which to discern the processes that occur in intact brain.

In vitro models of ischemia approximate oxygen and glucose deprivation that mimic in vivo conditions, for example, by placing neuronal cultures into large anaerobic or hypoxic chambers and exchanging culture medium with de-oxygenated and defined ionic composition media. The toxic overstimulation of neuronal glutamate receptors, especially N-methyl-D-aspartate (NMDA) receptors, contributes to hypoxic-ischemic neuronal injury (Choi, D. M., 1988, *Neuron* 1: 623-634), ischemic induction of reactive oxygen species (ROS) (Watson, B. D., et al., 1988, *Ann NY Acad Sci.*, 59: 269-281), excessive calcium influx (Grotta, J. C., 1988, *Stroke* 19: 447-454), arachidonic acid increase (Siesjo, B. K., 1981, *J. Cereb. Blood Flow Metab.* 1: 155-186) and DNA damage (MacManus, J. P., et al., 1993, *Neurosci. Lett.*, 164: 89-92), each causing a cascade of neurodegeneration.

Primary embryonic hippocampal neuronal cells are widely recognized as useful in models of neuronal function. The hippocampus is a source of a relatively homogenous population of neurons with well-characterized properties typical of central nervous system (CNS) neurons in general. Pyramidal neurons, the principal cell type in the hippocampus, have been estimated to account for 85% to 90% of the total neuronal population (Banker and Goslin, 1998, *Culturing Nerve Cells*, 2nd edition. The MIT Press, Cambridge, Mass.). The hippocampus also exhibits a remarkable capacity for activity-dependent changes in synaptic function, such as long-term potentiation (Hawkins R D, Kandel E R, Siegelbaum S A. (1993) Learning to modulate transmitter release: themes and variations in synaptic plasticity [review], *Ann. Rev Neurosci.* 16:625-665.).

In experiments carried out in support of the present invention according to methods detailed in the Examples, anoxia/ischemia was induced in primary cultures of hippocampal neuronal cells, and compounds were tested for their ability to prevent cell death. Certain compounds found to have activity in such in vitro assays are then further tested in one or more animal models of cerebral ischemia ("stroke"), such as the middle cerebral artery occlusion (MCAO) model in rats.

Briefly, primary cultures of hippocampal neurons are used to test compounds for activity in neuronal protection. Hippocampal cultures are typically prepared from 18- to 19-day fetal rats. At this age, the generation of pyramidal neurons, which begins in the rat at about E15, is essentially complete. The brain tissue at this stage is relatively easy to dissociate, the meninges are removed readily, and the number of glial cells still is relatively modest (Park L C, Calingasan N Y, Uchida K, Zhang H, Gibson G E. (2000). Metabolic impairment elicits brain cell type-selective changes in oxidative stress and cell death in culture. *J Neurochem* 74(1): 114-124).

In order to evaluate the activity of compounds of the present invention, a test compound is assessed for its ability to protect cells against one or more standard stressors, including hypoxia, as detailed in the Examples. In general, desirable therapeutic compound candidates are effective in this model at concentrations less than about 1 mM and even more preferably, less than about 100 µM. By effective, it is meant that such compounds protect at least 20%, preferably 30%, more preferably 40% and even more preferably 50% or more of the cells tested from stressor-induced death. By way of example, compounds that are effective in providing protection over a concentration a range of about 1 to 1000 µM would be expected to provide neuroprotection in vivo. Since precise values may vary depending upon the specific conditions under which the neuroprotective cell assay is carried out, it is the intent of the present disclosure to provide the foregoing criteria as guidance in the form of a benchmark against which to compare subsequently tested compounds, rather than to provide absolute concentrations at which the compounds of the present invention are considered to be effective. Typically, compounds that are found to be neuroprotective in such in vitro cell systems are then further tested in an in vivo animal model of neuroprotection, such as the rat middle cerebral artery occlusion model described below, or other appropriate models such as are well known in the art.

Cerebral ischemic insults are modeled in animals by occluding vessels to, or within, the cranium (Molinari, G. F., 1986, in H. J. M. Barnett, et al., (Eds) *Stroke: Pathophysiology, Diagnosis and Management*, Vol. 1, Churchill Livingstone, N.Y.). The rat middle cerebral artery occlusion (MCAO) model is one of the most widely used techniques to induce transient focal cerebral ischemia approximating cerebral ischemic damage in humans, e.g., those who suffer from a stroke. The middle cerebral artery used as the ischemic trigger in this model is the most affected vessel in human stroke. The model also entails a period of reperfusion, which typically occurs in human stroke victims. MCAO involving a two-hour occlusion has been found to produce the maximum size of cortical infarction obtainable without increased mortality at twenty-four hours.

Briefly, a nylon filament is implanted into the right carotid artery of the rat. To effect occlusion, the rat is anesthetized, and the filament is advanced into the internal carotid artery 18-20 mm from the point of bifurcation of internal and external arteries and a suture is tightly ligated around the filament for a period of two hours. Two hours post occlusion, animals are re-anesthetized, and the filament is removed, to allow reperfusion for the remainder of the experiment. Test drugs can be administered any time during this process—before, during or after occlusion, and can be administered by one or more of a variety of means, including but not limited to intracerebroventricular (ICV) infusion, intravenous (IV) infusion, intraperitoneal (IP) administration, as well as enteral administration (e.g., gavage). Animals are maintained normothermic during the experiment, as described in the Examples. At a pre-determined time following occlusion and reperfusion, animals are sacrificed and their brains are removed and processed for assessment of damage as measured by infarct volume. In general, compounds are considered to have activity in this model, if they provide a significant reduction in total infarct volume at a dose that is less than about 10 mg/kg, preferably less than 1 mg/kg, more preferably less than 100 µg/kg and even more preferably less than about 1 µg/kg, when administered ICV or IV. By significant reduction of total infarct volume is meant a reduction of at least 20%, preferably at least 30%, more preferably at least 40%, and even more preferably about 50%, compared to control values.

Further validation of efficacy in neuroprotection can be assessed in functional tests, such as the grip strength test or the rotorod test. Animals treated with compounds that show neuroprotection maintain their pre-MCAO grip strength values after MCAO, as compared to untreated animals, which showed a significant reduction in grip strength, indicating loss of sensorimotor function. Likewise, animals treated with compounds that show neuroprotection also maintained their pre-MCAO rotorod activity scores after MCAO, as compared to untreated animals, which showed a significant reduction in rotorod scores, indicating loss of sensorimotor function at higher brain levels.

Similarly, primary cultures of myocytes can be used to test compounds in vitro for ability to provide protection against heart damage, resulting for example from myocardial ischemia or congestive heart failure. Preparation of myocardiocytes from neonatal rats is described in the Examples. Such cells are typically used to study molecular models of myocardial ischemia (Webster, K A, Discher, D J & Bishopric, N H. 1995. J. Mol. Cell Cardiol. 27:453-458; Camilleri, L, Moins, N, Papon, J, Maublant, J, Bailly, P, de Riberolles, C & Veyre, A. 1997. Cell Biol. & Toxicol. 13:435-444; Bielawska, A E, Shapiro, J P, Jiang, L, Melkonyan, H S, Piot, C, Wolfe, C L, Tomei, L D, Hannun, Y A & Umansky, S R. 1997. Am. J. Pathol. 151:1257-1263) and are therefore accepted as indicative of myoprotective activity. Exemplary stressor assays for this purpose are provided in the Examples. For example, cardiomyocytes in culture exhibit contractile ("beating") activity; each cardiomyocyte contraction is associated with a rise in intracellular calcium termed "calcium". These calcium transients can be measured using Fluo-4, a fluorescent dye which exhibits large fluorescence intensity increases upon the binding of calcium. This assay is cell-based and tests the ability of potential cytoprotectant molecules to guard against ischemic damage and allow the cells to maintain their contractile function.

Further validation of compounds can be carried out in a whole organ assay, such as the isolated heart (Langendorff) model of cardiac function. Similarly, compounds can be further validated in additional animal models of disease (e.g., diabetes, renal failure, asthma, muscle fatigue, inflammation), such as are well known in the art.

Further validation of neuroantiinflammatory activity of compounds can be assessed in vitro by the inhibition of IL-1.beta. release from a microglial cell line.

Interleukin-1 (IL-1) is a proinflammatory cytokine that exists in two separate forms that share 30% sequence homology (alpha and beta). Constitutive expression of IL-1 is low in the brain but levels of both forms of this cytokine increase dramatically after injury. There is substantial evidence that IL-1 is an important mediator of neurodegeneration induced by cerebral ischemia (Touzani O et al, J Neuroimmunol 100: 203-215,1999). Both IL-1 forms are rapidly induced in experimental models of stroke and administration of recombinant IL-1beta enhances ischemic injury (see Hill J K. et al. Brain Res 820:45-54, 1999, Hillhouse E W et al. Neurosci Lett 249:177-179, 1998, Loddick S A et al J Cereb Blood Flow Metab 16:932-940, 1996, Stroemer R P et al., J Cereb Blood Flow Metab 18:833-839, 1998). Conversely, blocking IL-1 actions with a receptor antagonist or a neutralizing antibody markedly reduces neuronal death and inflammation in models of ischemic damage (see Betz A L, J Cereb Blood Flow Metab 15:547-551, 1995, Relton J K, Brain Res Bull 29:243-246, 1992, Yamasaki Y et al, Stroke 26:676-680, 1995). Furthermore, mice with decreased IL-1.beta. production (caspase-1 knockouts) are significantly protected from ischemic injury (Schielke G P, et al. J Cereb Blood Flow Metab 18:180-185, 1998) and IL-1.alpha. and .beta. double knockouts exhibit dramatically reduced ischemic infarct volumes compared with wild-type mice (87% reduction in cortex) (Boutin H et al., J Neurosci 21:5528-5534, 2001).

In addition to a role in ischemic damage, IL-1 elevation has been associated with many neurodegenerative diseases. There is increasing evidence for a role of IL-1 in Alzheimer's Disease (AD) (Mrak R E et al. Neurobiol Aging 22(6):903-908, 2001). Elevated levels of IL-1.beta. have been shown to surround amyloid plaques in the disease and recent genetic studies have indicated that a polymorphism in IL-1.alpha. is linked to an increased risk of AD (3-6 fold increase) (Griffin W S et al., J Leukoc Biol 72(2):233-238, 2002). This polymorphism has also been correlated with rate of cognitive decline in AD patients (Murphy G M et al., Neurology, 56(11) 1595-1597, 2001). The risk of AD is increased even further when the polymorphism in IL-1.alpha. is found in combination with another polymorphism in IL-1.beta. (see Griffin W S, supra), providing convincing evidence that these cytokines play an important role in the pathology of the disease.

This assay measures the release of IL-1.beta. from a mouse microglial cell line following an inflammatory challenge with LPS and interferon-gamma. The ability of test articles to inhibit microglial cell activation and IL-1beta release is determined by co-incubation of the test article with the inflammatory challenge. Cytokine release is measured using a mouse IL-1.beta. ELISA and cell toxicity is determined using Cell Tracker Green (a fluorescent dye that measures cell viability).

Further in-vitro evaluation of anti-inflammatory activity can be determined by the well characterized E-selectin (ELAM) production assay, which measures activity of test compounds in reducing expression of ELAM in activated endothelial cells. Briefly, endothelial cells are created by adding known activators such as lipopolysaccharides, TNF or IL-1β alone or in some combination. Activated cells produce ELAM, which can be measured using, for example, an E-selectin monoclonal antibody based Elisa assay. In studies carried out in support of the present invention, ELAM production was decreased as described in Example 45.

In vivo evaluation of anti-inflammatory activity can be determined by well characterized assays measuring Carrageenan-Induced Paw Edema and by Mouse Ear Inflammatory Response to Topical Arachidonic Acid. (Gabor, M., Mouse Ear Inflammation Models and their Pharmacological Applications, 2000). Carrageenan-Induced Paw Edema is a model of inflammation, which causes time-dependent edema formation following carrageenan administration into the intraplantar surface of a rat paw. The application of arachidonic acid (AA) to the ears of mice produces immediate vasodilatation and erythema, followed by the abrupt development of edema, which is maximal at 40 to 60 min. The onset of edema coincides with the extravasations of protein and leukocytes. After one hour the edema wanes rapidly and the inflammatory cells leave the tissue so that at 6 hours the ears have returned to near normal. These assays, as described in Examples 42 and 43 respectively, measure a test compound's ability to treat these inflammatory processes via systemic and topical routes of administration.

Cytoprotective activity for skin can be evaluated in cell culture using the Epiderm Skin Model (EPI-100) from the Mattek Corporation of Ashland, Mass. Cell cultures of neonatal foreskin are cultured in accordance with the manufacturer's directions, and are assayed for percent cellular viability by measuring the amount of 3-(4,5-dimethylthiazol-2-yl)-2,5-diphenyltetrazolium bromide (MTT) dye taken up by the cells, as described in Example 44.

Administration

The compounds of Formula I or III are administered at a therapeutically effective dosage, e.g., a dosage sufficient to provide treatment for the disease states previously described. Administration of the compounds of the invention or the pharmaceutically acceptable salts thereof can be via any of the accepted modes of administration for agents that serve similar utilities.

While human dosage levels have yet to be optimized for the compounds of the invention, generally, a daily dose is from about 0.01 to 2.0 mg/kg of body weight, preferably about 0.1 to 1.5 mg/kg of body weight, and most preferably about 0.3 to 1.0 mg/kg of body weight. Thus, for administration to a 70 kg person, the dosage range would be about 0.7 to 140 mg per day, preferably about 7.0 to 105 mg per day, and most preferably about 21 to 70 mg per day. The amount of active compound administered will, of course, be dependent on the subject and disease state being treated, the severity of the affliction, the manner and schedule of administration and the judgment of the prescribing physician.

The compositions of the present invention are suitable for providing protection against the harmful effects of ultraviolet radiation, preferably in personal care products. More preferably, the compositions of the present invention are suitable for use as sunscreens to provide protection to human skin from the harmful effects of UV radiation, which include, but are not limited to, sunburn and premature aging of the skin. The present invention therefore also further relates to methods of protecting human skin from the harmful effects of UV radiation. Such methods generally involve attenuating or reducing the amount of UV radiation that reaches the skin's surface. In the case of the present invention, the methods of treatment for the harmful effects of ultraviolet radiation also include administration of a composition of the invention after the exposure to UV radiation has already taken place. To protect the skin from UV radiation, a safe and effective (photoprotective) amount of the composition is topically applied to the skin. "Topical application" refers to application of the present compositions by spreading, spraying, etc. onto the surface of the skin. The exact amount applied may vary depending on the level of UV protection desired. From about 0.5 mg of composition per square centimeter of skin to about 25 mg of composition per square centimeter of skin are typically applied.

Compounds and methods of the invention may be employed in any skin care application where decreased inflammatory response is desirable. For example, compounds and compositions of the invention may be incorporated into leave-on and rinse-off acne preparations, facial milks and conditioners, shower gels, foaming and non-foaming facial cleansers, cosmetics, hand and body lotions, leave-on moisturizers, cosmetic and cleaning wipes, salves for poison ivy, chicken pox, or pruritis, or the like. Generally, for dermal applications, topical administration is preferred; however, systemic administration, as described elsewhere herein, is also possible.

Compositions of the present invention may also be used in cosmetic compositions. Cosmetic compositions of the present invention are ideally suited for use in treating the skin and lips, especially in the form of a lipstick or lip balm for applying to the lips a permanent or semi-permanent color, ideally with a gloss or luster finish. The cosmetic compositions can also be used in treating the skin and/or lips with a skin care agent for protection against exposure to adverse weather, including the wind and rain, dry and/or hot environments, environmental pollutants (e.g., ozone, smoke, and the like), or exposure to excessive doses of sunlight. The compositions are also useful in providing sun protection, moisturizing and/or conditioning for the hair and skin, improved skin feel, regulating skin texture, reducing fine lines and wrinkles, reducing oily shine on hair or skin, skin lightening and reducing skin or hair odor. The cosmetic compositions can accordingly be applied to the skin and/or lips in the traditional manner with or without a conventional holder or applicator to provide a decorative and/or protective film thereto.

In employing the compounds of this invention for treatment of the above conditions, any pharmaceutically acceptable mode of administration can be used. The compounds of Formula I or III can be administered either alone or in combination with other pharmaceutically acceptable excipients, including solid, semi-solid, liquid or aerosol dosage forms, such as, for example, tablets, capsules, powders, liquids, suspensions, suppositories, aerosols or the like. The compounds of Formula I can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages. The compositions will typically include a conventional pharmaceutical carrier or excipient and a compound of Formula I or III or a pharmaceutically acceptable salt thereof. In addition, these compositions may include other medicinal agents, pharmaceutical agents, carriers, adjuvants, and the like, including, but not limited to anticoagulants, blood clot dissolvers, permeability enhancers and slow release formulations.

Generally, depending on the intended mode of administration, the pharmaceutically acceptable composition will contain about 0.1% to 90%, preferably about 0.5% to 50%, by weight of a compound or salt of Formula I or III, the remainder being suitable pharmaceutical excipients, carriers, etc.

One preferred manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions take the form of solutions, suspensions, tablets, dispersible tablets, pills, capsules, powders, sustained release formulations and the like.

Preferably the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound in an amount effective to alleviate the symptoms of the subject being treated.

Dosage forms or compositions containing active ingredient in the range of 0.005% to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum and the like. Such compositions take the form of solutions, suspensions, tablets, capsules, powders, sustained release formulations and the like. Such compositions may contain 0.01%-95% active ingredient, preferably 0.1-50%.

For a solid dosage form, the solution or suspension, in for example propylene carbonate, vegetable oils or triglycerides, is preferably encapsulated in a gelatin capsule. Such diester solutions, and the preparation and encapsulation thereof, are disclosed in U.S. Pat. Nos. 4,328,245; 4,409,239; and 4,410,545. For a liquid dosage form, the solution, e.g. in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active compound or salt in vegetable oils, glycols, triglycerides, propylene glycol esters (e.g. propylene carbonate) and the like, and encapsulating these solutions or suspensions in hard or soft gelatin capsule shells.

Other useful formulations include those set forth in U.S. Pat. Nos. Re. 28,819 and 4,358,603.

The formulation can be administered in a single unit dosage form for continuous treatment or in a single unit dosage form ad libitum when relief of symptoms is specifically required. For example, the formulation may be administered as a bolus or as a continuous intravenous infusion after onset of symptoms of stroke, myocardial infarction or chronic heart failure.

Another preferred manner of administration is the topical administration. "Topical administration" refers to application of the present compositions by spreading, spraying, etc. onto the surface of the skin. The typical amount applied may vary from about 0.1 mg of composition per square centimeter of skin to about 25 mg of composition per square centimeter of skin. The compounds of the present invention may be formulated for topical administration to the epidermis as ointments, creams or lotions or as transdermal patch. Formulations suitable for topical administration in the mouth include lozenges, pastilles and mouthwashes.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

A more recently devised approach for parenteral administration employs the implantation of a slow-release or sustained-release system, such that a constant level of dosage is maintained. See, e.g., U.S. Pat. No. 3,710,795. The percentage of active compound contained in such parenteral compositions is highly dependent on the specific nature thereof, as well as the activity of the compound and the needs of the subject. However, percentages of active ingredient of 0.01% to 10% in solution are employable, and will be higher if the composition is a solid which will be subsequently diluted to the above percentages. Preferably the composition will comprise 0.2-2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, preferably less than 10 microns.

EXAMPLES

The following preparations and examples are given to enable those skilled in the art to more clearly understand and to practice the present invention. They should not be considered as limiting the scope of the invention, but merely as being illustrative and representative thereof.

General Characterization Methods

As reported in the following examples, Nuclear Magnetic Resonance (NMR) spectra were recorded on a Bruker DTX 300 spectrometer using, in most cases, tetramethyl silane (TMS) as the internal reference. Mass spectra were obtained on an Agilent 1100 LC/MSD instrument using either electrospray ionization (positive or negative mode) (ESI) or atmospheric pressure chemical ionization (positive or negative mode) (APCI).

Example 1

Preparation of 3-(1H-Benzoimidazol-2-ylsulfanyl)-2-(1H-benzoimidazol-2-ylsulfanylmethyl)-4-hydroxy-5-oxo-2,5-dihydro-furan-2-carboxylic acid ethyl ester

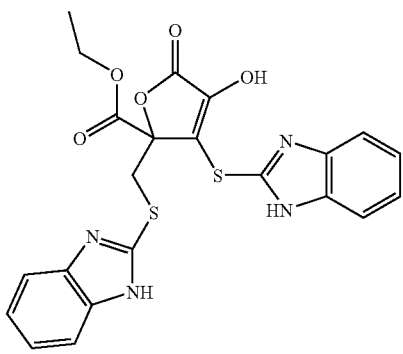

A solution of 2-mercaptobenzimidaole (4.0 g) and ethyl bromopyruvate (4 mL) in ethanol (40 mL) and acetone (50 mL) was stirred at 20° C. for 16 hours under argon. The white solid formed was filtered to give 4.5 g of pyruvate adduct, which was used directly for the next step without further purification. The mother liquid was concentrated and allowed to form a second crop of white solid. After filtration, it gave 4.17 g of the same intermediate. The first crop of the pyruvate adduct (4.5 g) was dissolved in methylene chloride and treated with aqueous sodium bicarbonate solution until the pH reached 7. Methylene chloride phase was separated, dried, and concentrated to about 20 mL in volume. To this solution was added 4-dimethylaminepyridine (700 mg) followed by stirring at 20° C. under argon. Column chromatography purification (100 g of silica gel, using gradient methylene chloride-ethanol mixture as the eluents) gave the title furanone product (500 mg), along with a mixture of the product and 4-dimethylaminepyridine (2.78 g). $^1$H-NMR (300 MHz, $d_6$-DMSO/$d_6$-acetone) δ (ppm) 7.50-7.45 (m, 2H), 7.40-7.35 (m, 2H), 7.25-7.15 (m, 2H), 7.10-7.00 (m, 2H), 4.37 (s, 2H), 4.01 (q, J=7.1 Hz, 2H), 1.13 (t, J=7.1 Hz, 3H). $^{13}$C-NMR (75 MHz, $d_6$-DMSO) δ (ppm) 166.8, 266.4, 149.9, 148.9, 146.4, 139.3, 122.6, 122.0, 114.7, 112.4, 85.2, 63.0, 13.9. MS (API-ESI) m/z 242, 483 (M+H$^+$).

Example 2

Preparation of 3-(3-Amino-[1,2,4]thiadiazol-5-ylsulfanyl)-2-(3-amino-[1,2,4]thiadiazol-5-ylsulfanylmethyl)-4-hydroxy-5-oxo-2,5-dihydro-furan-2-carboxylic acid ethyl ester

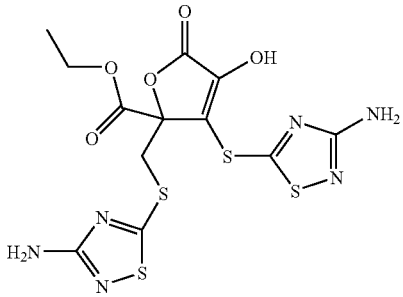

2A. Preparation of the Trimethylamine Salt.

A suspension of 5-amino-1,3,4-thiadiazole-2-thiol (665 mg, 5 mmol) and ethyl bromopyruvate (0.65 mL, 5.16 mmol) in ethanol (15 mL) was stirred at 20° C. under argon for 1 hour. To this solution was added a trimethylamine water solution (2 mL) to adjust pH to neutral, and it was then allowed to stir for additional 16 hours. A trimethylamine salt of the title furanone product (820 mg) was isolated after filtration. $^1$H-NMR (300 MHz, $d_3$-MeOD/$D_2$O) δ (ppm) 4.05-3.70 (m, 4H), 2.91 (s, 9H), 1.15 (t, J=7.2 Hz, 3H). MS (API-ESI) m/z 225 ((M+2H)/2, 15), 449 (M+H$^+$).

2B. Preparation of the Salt-free Furanone.

A suspension of 5-amino-1,3,4-thiadiazole-2-thiol (665 mg, 5 mmol) and ethyl bromopyruvate (0.65 mL, 5.16 mmol) in ethanol (15 mL) was stirred at 20° C. under argon for 1 hour. The pH of the solution was adjusted to about 7.5 using sodium bicarbonate aqueous solution. After 16 hours stirring at 20° C., the precipitate that formed was separated by filtration. Upon drying, the title salt-free furanone product was obtained as a solid (590 mg). $^1$H-NMR (300 MHz, $D_2$O) δ (ppm) 4.05-3.80 (m, 4H), 1.09 (t, J=7.2 Hz, 3H). MS (API-ESI) m/z 225, 449 (M+H$^+$).

Example 3

Preparation of 3-(5-Amino-2H-[1,2,4]triazol-3-ylsulfanyl)-2-(5-amino-2H-[1,2,4]triazol-3ylsulfanylmethyl)-4-hydroxy-5-oxo-2,5-dihydro-furan-2-carboxylic acid ethyl ester

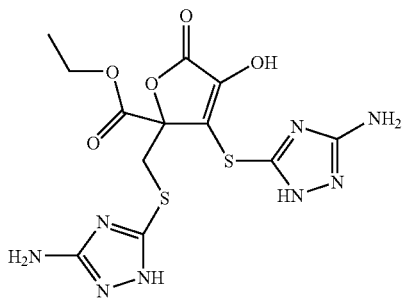

A suspension of 3-amino-5-mercapto-1,2,4-triazole (580 mg, 5 mmol) and ethyl bromopyruvate (0.65 mL, 5.16 mmol) in ethanol (15 mL) was stirred at 20° C. under argon for 2 hours. The pH of the solution was adjusted to about 7.5 using sodium bicarbonate aqueous solution. After evaporation to dryness, the residue was extracted with hot ethanol. Upon cooling, the ethanol solution was filtered and the filtrate was evaporated to dryness, giving the title furanone product (650 mg) as a light brown powder. $^1$H-NMR (300 MHz, $D_2$O) δ (ppM) 4.00-3.60 (m, 4H), 1.01 (t, J=7.2 Hz, 3H). MS (API-ESI) m/z 208, 415 (M+H$^+$).

Example 4

Preparation of 4-Hydroxy-3-(5-nitro-1H-benzoimidazol-2-ylsulfanyl)-2-(5-nitro-1H-benzoimidazol-2-ylsulfanylmethyl)-5-oxo-2,5-dihydro-furan-2-carboxylic acid ethyl ester

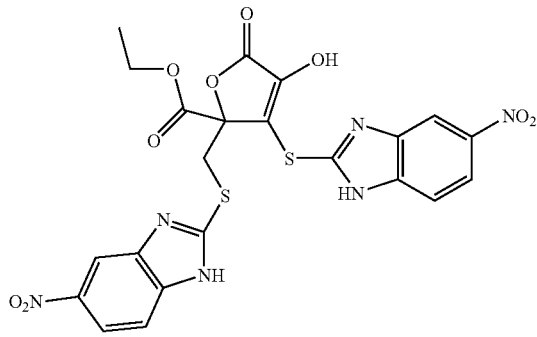

A solution of 3-mercapto-5-nitrobenzimidazole (975 mg, 5 mmol) and ethyl bromopyruvate (0.65 mL, 5.16 mmol) in acetone (10 mL) and ethanol (12 mL) was stirred at 20° C. under argon for 3 hours. The pH of the solution was adjusted to about 7.2 using sodium bicarbonate aqueous solution. After evaporation to dryness, the residue was dissolved in ethyl acetate (150 mL) and extracted with water (2×10 mL). The second portion of the water phase (10 mL) was freeze-dried, which gave the title furanone product (646 mg) as a brown powder. $^1$H-NMR (300 MHz, $d_6$-acetone) δ (ppm) 8.12 (s, 2H), 7.90-7.80 (m, 2H), 7.45-7.30 (m, 2H), 4.42 (d, J=14.4 Hz, 1H), 4.25-4.10 (m, 3H), 1.11 (t, J=7.2 Hz, 3H). MS (API-ESI) m/z 573 (M+H$^+$).

Example 5

Preparation of 4-Hydroxy-5-oxo-3-(5-phenyl-[1,3,4]oxadiazol-2-ylsulfanyl)-2-(5-phenyl-[1,3,4]oxadiazol-2-ylsulfanylmethyl)-2,5-dihydro-furan-2-carboxylic acid ethyl ester

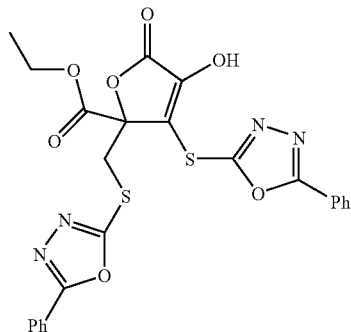

A solution of 5-phenyl-1,3,4-oxadiazole-2-thiol (891 mg, 5.0 mmol) and ethyl bromopyruvate (0.65 mL, 5.16 mmol) in acetonitrile (100 mL) was stirred at 20° C. under argon for 3 hours. Diisopropyl ethylamine (0.5 mL) was added to the solution and it was then allowed to stir for 3 additional hours. After the removal of solvents, the residue was dissolved in ethanol (5 mL). The pH of the solution was subsequently adjusted to about 7.2 using sodium bicarbonate aqueous solution. After evaporation to dryness, the residue was dissolved in ethyl acetate (150 mL) and extracted with water (2×10 mL). The second portion of the water phase (10 mL) was freeze-dried. Further column chromatography purification (silica gel, methylene chloride-ethanol from 95:5 to 80:20) gave the title furanone product (80 mg). $^1$H-NMR (300 MHz, CDCl$_3$) δ (ppm) 7.84 (d, J=7.3 Hz, 1H), 7.75 (d, J=7.3 Hz, 1H), 7.50-7.20 (m, 6H), 4.07 (d, J=14.1 Hz, 1H), 4.00-3.85 (m, 3H), 1.02 (t, J=7.1 Hz, 3H). MS (API-ESI) m/z 539 (m+H$^+$).

Example 6

Preparation of 3-(5-Chloro-benzothiazol-2-ylsulfanyl)-2-(5-chloro-benzothiazol-2-ylsulfanylmethyl)-4-hydroxy-5-oxo-2,5-dihydro-furan-2-carboxylic acid ethyl ester

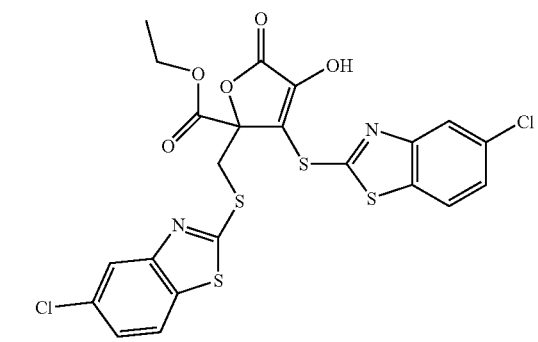

A solution of 5-chloro-2-mercaptobenzothiazole (1.01 g, 5 mmol) and ethyl bromopyruvate (0.65 mL, 5.16 mmol) in acetonitrile (100 mL) was stirred at 20° C. under argon for 3 hours. The precipitates were filtered off and washed with acetonitrile. Drying under vacuum, afforded the corresponding pyruvate adduct (1.68 g) as a solid. A portion of this intermediate (200 mg) was dissolved in ethanol (5 mL). The pH of the solution was adjusted to about 7.2 using sodium bicarbonate aqueous solution. After evaporation to dryness, the residue was purified using column chromatography method (silica gel, methylene chloride-ethanol from 95:5 to 80:20) gave the title furanone product (72 mg). $^1$H-NMR (300 MHz, CDCl$_3$) δ (ppm) 7.84 (d, J=8.3 Hz, 1H), 7.78 (d, J=2.0 Hz, 1H), 7.76 (d, J=8.5 Hz, 1H), 7.70 (d, J=2.1 Hz, 1H), 7.30 (dd, J=2.1 Hz, J=8.5 Hz, 1H), 7.21 (dd, J=2.1 Hz, 8.5 Hz, 1H), 4.63 (d, J=14.1 Hz, 1H), 4.21 (d, J=14.1 Hz, 1H), 4.10-3.85 (m, 2H), 1.00 (t, J=7.1 Hz, 3H) ppm. MS (API-ESI) m/z 233 (100), 585 (M+H$^+$).

Example 7

Preparation of 4-Hydroxy-3-(5-methoxy-1H-benzoimidazol-2-ylsulfanyl)-2-(5-methoxy-1H-benzoimidazol-2-ylsulfanylmethyl)-5-oxo-2,5-dihydrofuran-2-carboxylic acid ethyl ester

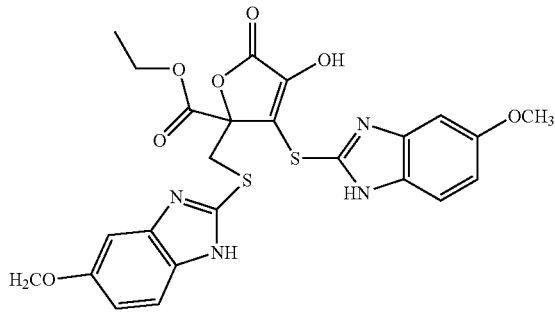

A solution of 5-methoxy-2-benzimidazole thiol (901 mg, 5 mmol) and ethyl bromopyruvate (0.65 mL, 5.16 mmol) in ethanol (10 mL) and acetone (20 mL) was stirred at 20° C. under argon for 3 hours. The precipitates were filtered off and washed with ethyl acetate. Drying under vacuum afforded the corresponding pyruvate adduct intermediate (1.20 g) as a solid. A portion of the intermediate (300 mg) was dissolved in ethanol (5 mL). The pH of the solution was adjusted to about 7.2 using sodium bicarbonate aqueous solution. After evaporation to dryness, the residue was dissolved in ethyl acetate and washed with water. After drying over anhydrous magnesium sulfate, the organic phase was evaporated to dryness, to give the title furanone product (240 mg). $^1$H-NMR (300 MHz, $d_6$-DMSO/$d_6$-acetone) δ (ppm) 7.37 (d, J=8.8 Hz, 1H), 7.29 (d, J=8.7 Hz, 1H), 6.98 (d, J=2.4 Hz, 1H), 6.89 (d, J=2.4 Hz, 1H), 6.81 (dd, J=2.4 Hz, J=8.8 Hz, 1H), 6.69 (dd, J=2.4 Hz, J=8.7 Hz, 1H), 4.31 (d, J=14.3 Hz, 1H), 4.25 (d, J=14.3 Hz, 1H), 4.10-4.00 (m, 2H), 3.79 (s, 3H), 3.77 (s, 3H), 1.09 (t, J=7.1 Hz, 3H). MS (API-ESI) m/z 272, 543 (M+H$^+$).

Example 8

Preparation of 4-Hydroxy-5-oxo-3-p-tolylsulfanyl-2-p-tolylsulfanylmethyl-2,5-dihydro-furan-2-carboxylic acid ethyl ester

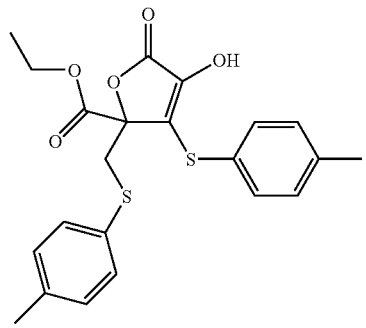

To a solution of 4-methyl benzenethiol (248 mg, 2 mmol) in DCM (10 mL) was added ethyl bromopyruvate (431 mg, 2.0 mmol, in 2 mL AcCN) dropwise with vigorous stirring. Upon completion of the addition, the reaction was stirred for another 30 min. The mixture was then washed with water (2×5 mL) and dried over Na$_2$SO$_4$. After solvent evaporation, the residue was chromatographed to afford a pyruvate adduct intermediate (1:1 mixture of enol and keto form) as a pale yellow oil (310 mg, 65%). $^1$H-NMR (300 MHz, CD$_3$OD) δ (ppm) 7.37-7.27 (m, 2H), 7.17-7.09 (m, 2H), 6.55 (s, 0.22H), 4.37-4.20 (m, 2H), 3.89 (s, 0.72H), 2.34-2.30 (m, 3H), 1.44-1.26 (m, 3H). MS-ESI (2M+H$^+$) m/z 477.

To the solution of the intermediate (102 mg, 0.43 mmol) in DCM (5 mL) was added 3 drops of TEA (in 0.2 mL of DCM). The reaction was monitored using MS. Upon the completion of the reaction (3 h), the reaction mixture was diluted with EtOAc (30 mL) and washed with aqueous HCl solution (0.1M, 10 mL). After solvent evaporation, the residue was chromatographed to give the title furanone product as a pale yellow oil (53 mg, 58%). $^1$H-NMR (300 MHz, CD$_3$OD) δ (ppm) 7.33-7.29 (m, 4H), 7.11-7.08 (m, 2H), 4.40 (s, 1H), 4.05-3.98 (m, 2H), 3.70-3.58 (m, 2H), 2.32 (s, 3H), 2.31 (s, 3H), 1.17 (t, J=7.2 Hz, 3H). $^{13}$CNMR (75 MHz) δ (ppm) 167.5, 166.9, 138.8, 137.5, 132.3, 132.1, 131.6, 130.0, 129.9, 129.8, 125.7, 86.6, 62.9, 41.0, 21.2, 21.1, 13.8.

Example 9

Preparation of 3-(2-Acetylamino-2-methoxycarbonyl-ethylsulfanyl)-2-(2-acetylamino-2-methoxycarbonyl-ethylsulfanylmethyl)-4-hydroxy-5-oxo-2,5-dihydro-furan-2-carboxylic acid ethyl ester

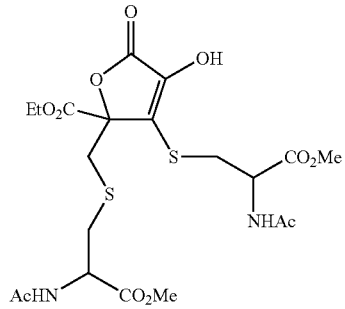

To a solution of 2-acetylamino-3-mercapto-propionic acid methyl ester (177 mg, 1 mmol) in acetonitrile (5 mL) at room temperature with stirring was added ethyl bromopyruvate (215 mg, 1.0 mmol, in 1.0 mL AcCN) dropwise. The reaction was monitored using MS. Upon completion, the reaction was quenched by adding 30 mL of EtOAc. After solvent evaporation, the residue was chromatographed using DCM/MeOH (8:1) as the eluents to afford the corresponding pyruvate adduct as a yellow oil containing both enol and keto forms (151 mg, 52%). $^1$H-NMR (300 MHz, CD$_3$OD) δ (ppm) 6.18 (s, 0.2H), 4.85-4.72 (m, 1H), 4.33-4.19 (m, 2H), 3.71 (s, 3H), 3.59-3.57 (m, 0.8H), 3.25-2.81 (m, 2H), 2.02-1.98 (m, 3H), 1.35-1.23 (m, 3H). $^{13}$C-NMR (75 MHz) δ (ppm) 185.9, 171.0, 170.3, 170.2, 130.1, 162.6, 160.7, 138.0, 111.6, 62.9, 62.1, 52.7, 52.5, 51.7, 51.5, 40.5, 37.1, 35.7, 34.1, 22.9, 14.2, 13.9. MS-ESI (M+H$^+$) m/z 292.

To a solution of the pyruvate adduct (85 mg) in AcCN (3 mL) was added 5 drops of Na$_2$CO$_3$ (2.0 M). The resulting suspension was stirred for 3 h until MS indicated the completion of the condensation. The reaction was quenched by adding EtOAc (20 mL) and the mixture was then dried over Na$_2$SO$_4$. After solvent evaporation, the residue was chromatographed (DCM/MeOH, 6:1) to give the title furanone product as a pale yellow oil (42 mg, 53%). $^1$H-NMR (300 MHz, CD$_3$OD) δ (ppm) 4.86-4.75 (m, 2H), 4.29-4.21 (m, 2H), 3.76 (s, 3H), 3.75 (s, 3H), 3.65-3.06 (m, 6H), 2.07 (s, 3H), 2.04 (s, 3H), 1.32-1.24 (m, 3H). $^{13}$C-NMR (75 MHz) δ (ppm) 171.4, 171.3, 171.0, 170.7, 167.6, 147.3, 128.4, 87.0, 63.1, 53.0, 52.84, 52.75, 52.8, 52.1, 37.7, 35.7, 34.9, 33.7, 22.97, 22.91, 13.98. MS-ESI (M+H$^+$) m/z 537.

Example 10

Preparation of 3-[2-(4-Amino-4-carboxy-butyryl amino)-2-(carboxymethyl-carbamoyl)-ethylsulfanyl]-2-[2-[2-(4-amino-4-carboxy-butyrylamino)-2-(carboxymethyl-carbamoyl)-ethylsulfanylmethyl]-4-hydroxy-5-oxo-2,5-dihydro-furan-2-carboxylic acid, a TFA salt of the Diastereoisomer Mixture

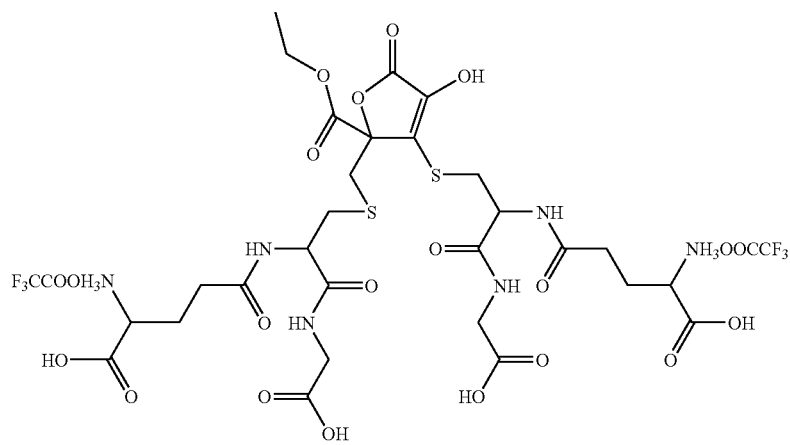

To a solution of 1-glutathione (2-amino-4-[1-(carboxymethyl-carbamoyl)-2-mercapto-ethylcarbamoyl]-butyric acid) (8.14 g, 26.5 mmol) in water (50 mL) and methanol (10 mL) (degassed and purged with nitrogen) was added bromo-3-ethylpyruvate (5.17 g, 26.5 mmol) at room temperature. Upon the addition of bromo-3-ethylpyruvate, the cloudy suspension turned to yellowish translucent almost instantly. After stirring for 2 hours at room temperature, the mixture was concentrated on a rotary evaporator under the reduced pressure. The solution was then washed with methylene chloride thoroughly. The organic layer was discarded. The aqueous layer was evaporated to dryness under reduced pressure. After freeze-drying under high vacuum for 48 hours, a yellowish solid was obtained as the pyruvate-glutathione adduct (13.0 g, 98.0%). NMR data indicate that there exist two tautomeric forms of the product, namely the keto form, 2-amino-4-[1-(carboxymethyl-carbamoyl)-2-(2-carboxy-2-oxo-ethylsulfanyl)-ethylcarbamoyl]-butyric acid ethyl ester, and the enol form, 3-[2-(4-amino-4-carboxy-butyrylamino)-2-(carboxymethyl-carbamoyl)-ethylsulfanyl]-2-hydroxy-acrylic acid ethyl ester. $^1$H-NMR (D$_3$COD, 300 MHz) δ (ppm): 1.17 (t, 3H), 1.93 (m, 2H), 2.11 (m, 2H), 2.75-3.28 (m, 2H), 2.29 (ss, 1.6H), 3.93 (s, 2H), 4.09 (m, 1H), 4.25 (q, 2H), 4.83 (m, 1H), 6.43 (s, 0.4H). $^{13}$C-NMR (D$_3$COD, 75 MHz) δ (ppm): 14.1, 26.6, 32.1, 35.6, 40.0, 41.4, 53.2, 54.6, 62.1, 62.7, 100.0, 113.4, 139.7, 163.4, 170.8, 172.3, and 174.1. MS (ESI) m/z: 422 (M+H$^+$).

The pyruvate-glutathione adduct (1.0 g, 1.99 mmol) was dissolved in water (10 mL) and the pH of the solution was adjusted to 7.4 using 1.0 M aq. sodium hydroxide solution. After the disappearance of the starting reactant (monitored by LC/MS), the mixture was adjusted to pH 3.0 using 10% TFA in water. The solution was passed through Bio gel P2 column using water as the eluent to separate the product from sodium salts of HBr and TFA. The fractions containing the product were pooled, concentrated under reduced pressure at 30° C. and finally lyophilized to obtain 0.8 g of the product as a pale yellow solid, which was found to be about 85% pure by LC. This crude product was further purified using reverse phase medium pressure liquid chromatography (MPLC) using water and acetonitrile as the gradient (5 to 15% CH$_3$CN, 50 min; 15% AcCN, 50-70 min.). The fractions containing the desired furanone were pooled, concentrated under reduced pressure at 30° C. and then lyophilized to obtain the title product as a white solid (0.7 g, 77%). $^1$H-NMR (300 MHz, D$_2$O) δ (ppm) 4.62-4.50 (m, 2H), 4.31-4.22 (m, 2H), 4.09-4.03 (m, 2H), 3.98 (brs, 4H), 3.82-3.68 (m, 1H), 3.48-3.42 (m, 1H), 3.33-2.87 (m, 4H), 2.58-2.52 (m, 4H), 2.26-2.16 (m, 4H), 1.25 (m, 3H). $^{19}$F-NMR (282 MHz, no reference) δ (ppm) −76.1. MS (ESI) m/z: 797(M+H$^+$, 40), 399 (M+2H$^+$, 100).

Example 11

Preparation of 3-[2-(4-Amino-4-carboxy-butyryl amino)-2-(carboxymethyl-carbamoyl)-ethylsulfanyl]-2-[2-(4-amino-4-carboxy-butyrylamino)-2-(carboxymethyl-carbamoyl)-ethylsulfanylmethyl]-4-hydroxy-5-oxo-2,5-dihydro-furan-2-carboxylic acid, a Salt-Free Diastereoisomer Mixture

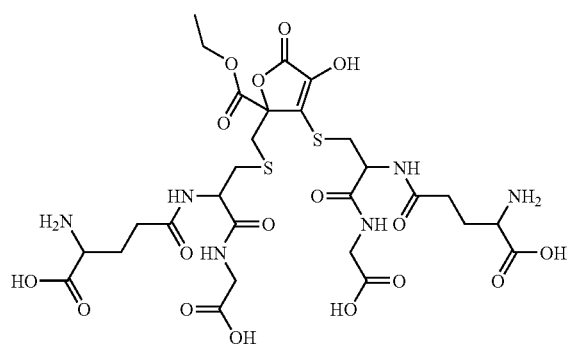

The TFA salt of diastereoisomer mixture prepared in Example 10 (1 g, 0.976 mmol) was dissolved in water (5 mL) to which was added 2 equivalents of aq. 1 N NaOH (1.95 mL, 1.95 mmol) at ambient temperature and the solution was agitated for 10 minutes. The mixture was then purified by reverse phase HPLC using water and acetonitrile as the eluent (5 to 15% CH$_3$CN, 50 min; 15% CH$_3$CN, 50-70 min.). The fractions containing the desired furanone were pooled, concentrated under vacuum at 30° C. and finally freeze-dried to obtain the title, salt-free product as a white solid. $^{19}$F NMR indicated that substantially all (>99.5%, based on the relative peak intensity before and after purification) of the original TFA salt has been converted to salt-free form. $^1$HNMR (300 MHz, D$_2$O) δ (ppm) 4.61-4.51 (m, 2H), 4.32-4.23 (m, 2H), 3.93 (brs, 4H), 3.82-3.63 (m, 3H), 3.48-3.41 (dd, J=5.3 Hz, 1H), 3.32-3.05 (m, 3H), 2.97-2.88 (m, 1H), 2.57-2.45 (m, 4H), 2.18-2.11 (m, 4H), 1.26 (m, 3H). MS-ESI (M+H$^+$) m/z 797.

Example 12

Preparation of 3-[2-(4-Amino-4-carboxy-butyryl amino)-2-(carboxymethyl-carbamoyl)-ethylsulfanyl]-2-[2-(4-amino-4-carboxy-butyrylamino)-2-(carboxymethyl-carbamoyl)-ethylsulfanylmethyl]-4-hydroxy-5-oxo-2,5-dihydro-furan-2-carboxylic acid, an HCl Salt of the Diastereoisomer Mixture

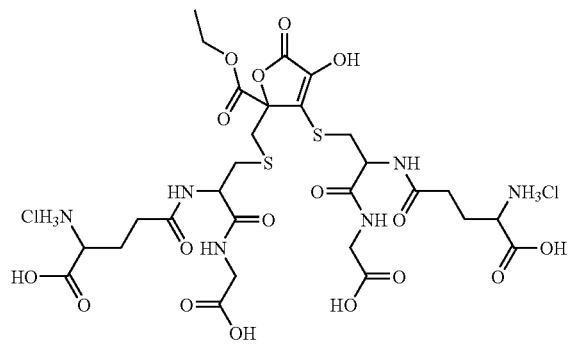

To a solution of the TFA salt of the diastereoisomer mixture prepared in Example 10 (60 mg, 0.0586 mmol) in deionized water (10 mL) at 0° C. (ice bath) was added dropwise a HCl solution (2.15 mL, 0.129 mmol, 0.06 M, 2.2 eq). The mixture was stirred for 20 min at 0° C. and then freeze-dried to afford a white sticky solid (48.2 mg). $^{19}$F NMR indicated that substantially all (>99%, based on the relative peak intensity before and after HCl treatment) of the original TFA salt has been converted to the HCl salt. $^1$H-NMR (300 MHz, D$_2$O) δ (ppm) 4.50-4.38 (m, 2H), 4.19-4.11 (m, 2H), 3.98-3.91 (m, 2H), 3.86-3.85 (m, 4H), 3.71-3.55 (m, 1H), 3.33 (dd, J=15.0, 5.0 Hz, 1H), 3.20-2.80 (m, 4H), 2.48-2.41 (m, 4H), 2.14-2.05 (m, 4H), 1.16-1.11 (m, 3H). MS-ESI (M+H$^+$) m/z 797.

Example 13

Preparation of 3-[2-(4-Amino-4-carboxy-butyryl amino)-2-(carboxymethyl-carbamoyl)-ethylsulfanyl]-2-[2-(4-amino-4-carboxy-butyrylamino)-2-(carboxymethyl-carbamoyl)-ethylsulfanylmethyl]-4-hydroxy-5-oxo-2,5-dihydro-furan-2-carboxylic acid, an HBr Salt of the Diastereoisomer Mixture

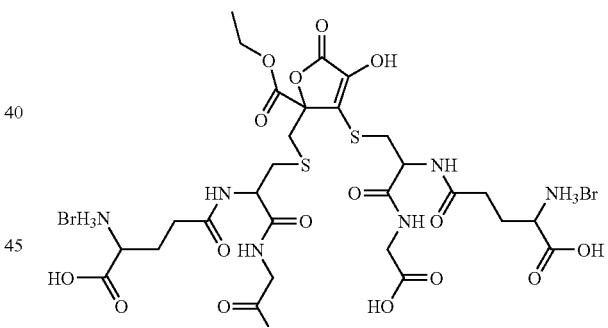

The HBr salt of the diastereoisomer mixture was prepared as a pale yellow sticky solid, substituting HBr for HCl in the same procedure described in Example 12. $^1$H-NMR (300 MHz, D$_2$O) δ (ppm) 4.48-4.36 (m, 2H), 4.17-4.09 (m, 2H), 3.98-3.92 (m, 2H), 3.84 (brs, 4H), 3.68-3.55 (m, 1H), 3.32 (dd, J=15.0, 5.0 Hz, 1H), 3.19-2.2.76 (m, 4H), 2.44-2.40 (m, 4H), 2.12-2.03 (m, 4H), 1.16-1.12 (m, 3H). MS-ESI (M+H$^+$) m/z 797.

Example 14

Preparation of 3-[2-(4-Amino-4-carboxy-butyryl amino)-2-(carboxymethyl-carbamoyl)-ethylsulfanyl]-2-[2-(4-amino-4-carboxy-butyrylamino)-2-(carboxymethyl-carbamoyl)-ethylsulfanylmethyl]-4-hydroxy-5-oxo-2,5-dihydro-furan-2-carboxylic acid, a MsOH Salt of the Diastereoisomer Mixture

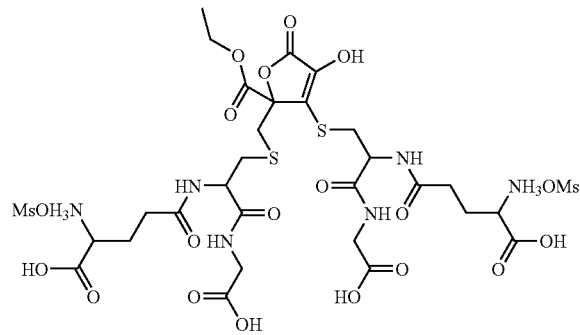

To a solution of salt-free diastereoisomer mixture prepared in Example 11 (60 mg, 0.0753 mmol) in deionized water (10 mL) at 0° C. (ice bath) was added, dropwise, a 0.1 M aqueous methyl sulfonic acid solution (1.51 mL, 0.151 mmol, 2 eq). The mixture was stirred for 20 min at 0° C. and then freeze-dried to afford the title furanone salt as a fluffy white solid (61.5 mg). $^1$H-NMR (300 MHz, D$_2$O) δ (ppm) 4.48-4.38 (m, 2H), 4.19-4.13 (m, 2H), 3.80-3.79 (m, 4H), 3.68-3.51 (m, 3H), 3.37-3.30 (m, 1H), 3.23-2.80 (m, 5H), 2.67-2.66 (m, 6H), 2.43-2.37 (m, 4H), 2.06-1.98 (m, 4H), 1.15 (m, 3H).

Example 15

Preparation of 3-[2-(4-Amino-4-carboxy-butyryl amino)-2-(carboxymethyl-carbamoyl)-ethylsulfanyl]-2-[2-(4-amino-4-carboxy-butyrylamino)-2-(carboxymethyl-carbamoyl)-ethylsulfanylmethyl]-4-hydroxy-5-oxo-2,5-dihydro-furan-2-carboxylic acid, a TsOH Salt of the Diastereoisomer Mixture

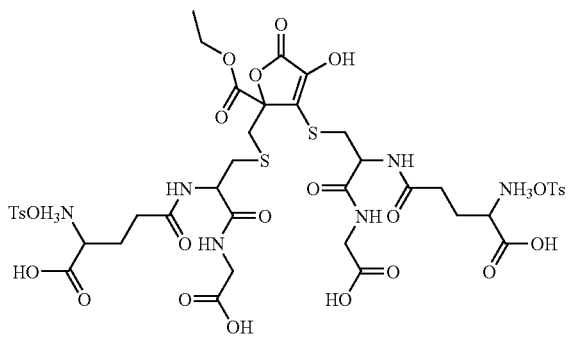

The TsOH salt of the diastereoisomer mixture was prepared according to the procedure described in Example 14 by treating the salt-free mixture with 2 eq of dilute aq. TsOH. The title furanone salt was obtained as a white fluffy solid. $^1$H-NMR (300 MHz, D$_2$O) δ (ppm) 7.55 (d, J=7.0 Hz, 4H), 7.22 (d, J=7.0 Hz, 4H), 4.48-4.38 (m, 2H), 4.19-4.12 (m, 2H), 3.81-3.80 (m, 4H), 3.70-3.51 (m, 3H), 3.37-2.76 (m, 6H), 2.43-2.36 (m, 4H), 2.25 (brs, 6H), 2.06-1.99 (m, 4H), 1.15 (m, 3H).

Example 16

Preparation of 3-[2-(4-Amino-4-carboxy-butyryl amino)-2-(carboxymethyl-carbamoyl)-ethylsulfanyl]-2-[2-(4-amino-4-carboxy-butyrylamino)-2-(carboxymethyl-carbamoyl)-ethylsulfanylmethyl]-4-hydroxy-5-oxo-2,5-dihydro-furan-2-carboxylic acid, an AcOH Salt of the Diastereoisomer Mixture

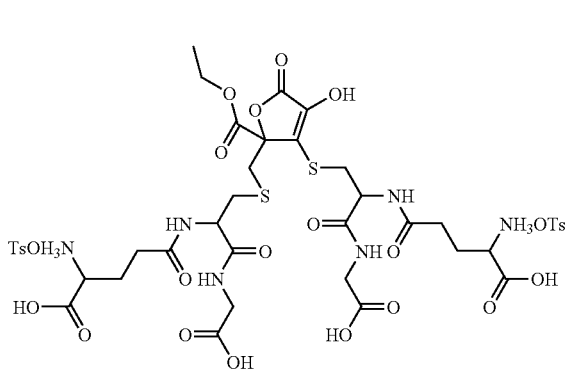

The acetic acid salt of the diastereoisomer mixture was prepared according to the procedure described in Example 14 by treating the salt-free mixture with 2 eq of dilute aq. AcOH. The title furanone salt was obtained as a white fluffy solid. $^1$H-NMR (300 MHz, D$_2$O) δ (ppm) 4.47-4.37 (m, 2H), 4.19-4.13 (m, 2H), 3.83-3.82 (m, 4H), 3.71-3.53 (m, 3H), 3.37-2.76 (m, 6H), 2.43-2.36 (m, 4H), 2.20-2.00 (m, 4H), 1.94-1.93 (m, 6H), 1.15 (m, 3H).

Example 17

Preparation of 3-[2-(4-Amino-4-carboxy-butyryl amino)-2-(carboxymethyl-carbamoyl)-ethylsulfanyl]-2-[2-(4-amino-4-carboxy-butyrylamino)-2-(carboxymethyl-carbamoyl)-ethylsulfanylmethy]-4-hydroxy-5-oxo-2,5-dihydro-furan-2-carboxylic acid, a Bis-triethylamine Salt of the Diastereoisomer Mixture

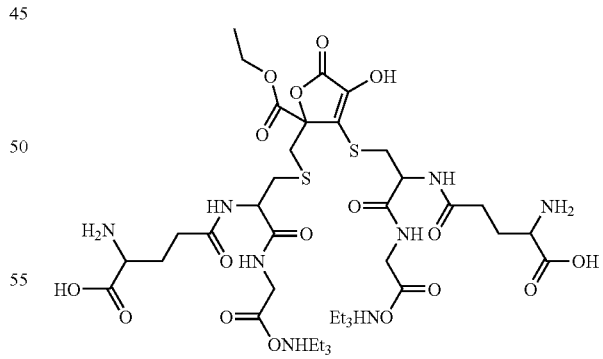

The triethylamine salt of the diastereoisomer mixture was prepared according to the procedure described in Example 14 by the treatment of the salt-free mixture with 2 eq. of dilute aq. TEA. The title furanone salt was obtained as a white solid. $^1$H-NMR (300 MHz, D$_2$O) δ (ppm) 4.46-4.36 (m, 2H), 4.20-4.11 (m, 2H), 3.69-3.63 (m, 6H), 3.46-3.14 (m, 3H), 3.06 (q, J=7.3 Hz, 12H), 3.14-2.74 (m, 3H), 2.42-2.37 (m, 4H), 2.06-2.01 (m, 4H), 1.16-1.11 (m, 21H).

Example 18

Preparation of 3-[2-(4-Amino-4-carboxy-butyryl amino)-2-(carboxymethyl-carbamoyl)-ethylsulfanyl]-2-[2-(4-amino-4-carboxy-butyrylamino)-2-(carboxymethyl-carbamoyl)-ethylsulfanylmethyl]-4-hydroxy-5-oxo-2,5-dihydro-furan-2-carboxylic acid, a Tetra-triethylamine Salt of the Diastereoisomer Mixture

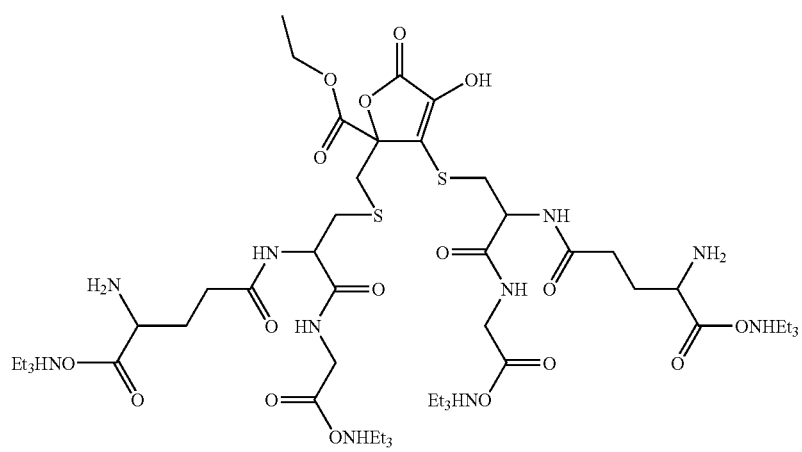

The triethylamine salt of the diatereoisomer mixture was prepared according to the procedure described in Example 14 by the treatment of the salt-free mixture with 4 eq. of dilute aq. TEA. The title furanone salt was obtained as a white solid. $^1$H-NMR (300 MHz, D$_2$O) δ (ppm) 4.56-4.38 (m, 2H), 4.26-4.17 (m, 2H), 3.73-3.71 (m, 4H), 3.65-3.58 (m, 2H), 3.44-3.23 (m, 2H), 3.15 (q, J=7.3 Hz, 24H), 3.19-2.83 (m, 4H), 2.50-2.41 (m, 4H), 2.31-2.00 (m, 4H), 1.26-1.21 (m, 39H).

Example 19

Preparation of 3-[2-(4-Amino-4-carboxy-butyryl amino)-2-(carboxymethyl-carbamoyl)-ethylsulfanyl]-2-[2-(4-amino-4-carboxy-butyrylamino)-2-(carboxymethyl-carbamoyl)-ethylsulfanylmethyl]-4-hydroxy-5-oxo-2,5-dihydro-furan-2-carboxylic acid, a Sodium Salt of the Diastereoisomer Mixture

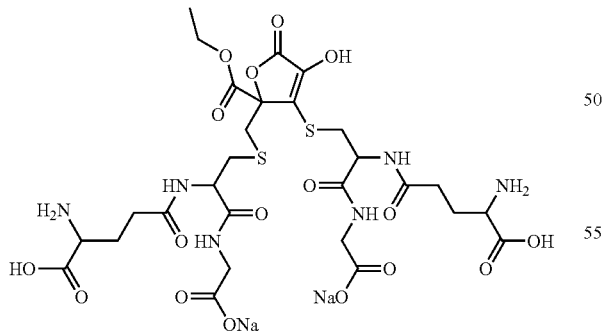

The sodium salt of the diatereoisomer mixture was prepared according to the procedure described in Example 14 by the treatment of the salt free twin mixture with 2 eq of dilute NaOH solution (0.05M). The title furanone salt was obtained as a white solid. $^1$H-NMR (300 MHz, CD$_3$OD) δ (ppm) 4.48-4.36 (m, 2H), 4.22-4.10 (m, 2H), 3.72-3.59 (m, 6H), 3.36-2.97 (m, 5H), 2.84-2.75 (m, 1H), 2.46-2.33 (m, 4H), 2.07-1.99 (m, 4H), 1.18-1.12 (m, 3H).

Example 20

Separation of 3-[2-(4-Amino-4-carboxy-butyryl amino)-2-(carboxymethyl-carbamoyl)-ethylsulfanyl]-2-[2-(4-amino-4-carboxy-butyrylamino)-2-(carboxymethyl-carbamoyl)-ethylsulfanylmethyl]-4-hydroxy-5-oxo-2,5-dihydro-furan-2-carboxylic acid Diasteroisomers, a TFA Salt Isomer #1

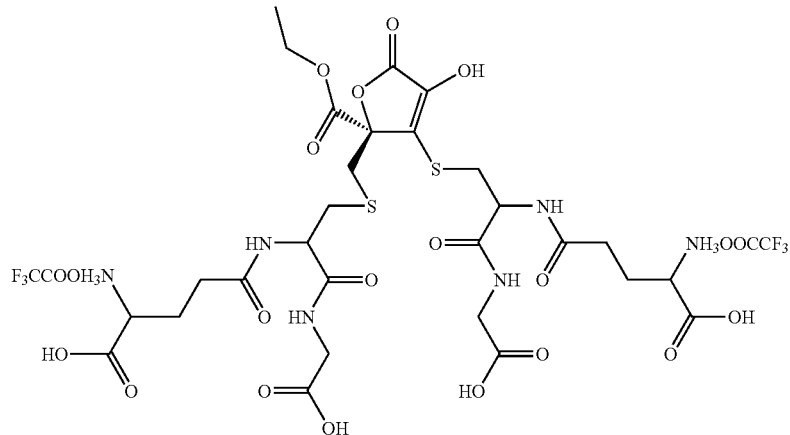

Isomer #2

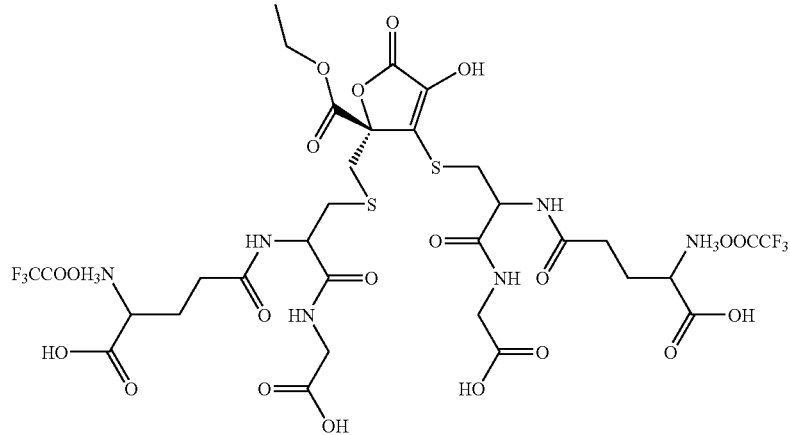

The two single diastereoisomers were separated from the mixture whose preparation was described in Example 10. The separation was achieved by preparative HPLC using water and acetonitrile gradient elution, each containing 0.1% TFA (2 to 18% AcCN for 25 min and then 18% AcCN for 25-30 min).

For isomer #1: $^1$H-NMR (300 MHz, D$_2$O) δ (ppm) 4.49 (dd, J=8.5, 5.1 Hz, 2H), 4.41 (dd, J=8.5, 5.1 Hz, 2H), 4.19-4.11 (m, 2H), 3.95-3.89 (m, 2H), 3.86 (brs, 4H), 3.60 (dd, J=14.2, 5.2 Hz, 1H), 3.35-3.14 (m, 3H), 3.04-2.97 (dd, J=14.2, 5.2 Hz, 1H), 2.83-2.76 (dd, J=14.1, 8.7 Hz, 1H), 2.48-2.41 (m, 4H), 2.13-2.05 (m, 4H), 1.14 (t, J=7.2 Hz, 3H). $^{13}$C-NMR (75 MHz, D$_2$O) δ (ppm) 174.6, 174.4, 173.15, 173.13, 172.8, 172.2, 172.1, 172.05, 168.5, 167.8, 142.2, 125.9, 87.2, 64.7, 53.9, 53.5, 52.6, 41.4, 37.2, 34.8, 31.9, 31.3, 31.2, 25.8, 13.5. MS-ESI m/z 797 (M+H$^+$, 40), 399 (M+2H$^+$, 100). $^{19}$F NMR (282 MHz, no reference) δ −76.2.

For isomer #2: $^1$H-NMR (300 MHz, D$_2$O) δ (ppm) 4.56-4.46 (m, 2H), 4.30-4.19 (m, 2H), 3.98-3.70 (m, 8H), 3.48-3.40 (m, 1H), 3.27-2.80 (m, 4H), 2.55-2.40 (m, 4H), 2.20-2.10 (m, 4H), 1.25 (t, J=6.9 Hz, 3H). $^{13}$C-NMR (75 MHz, D$_2$O) δ (ppm) 174.5, 173.1, 173.0, 172.6, 172.2, 171.9, 171.8, 168. 167.6, 142.2, 125.8, 87.3, 64.7, 53.7, 53.4, 52.6, 41.3, 37.6, 34.8, 32.0, 31.3, 31.2, 25.8, 25.7, 13.4. MS-ESI m/z 797(M+H$^+$, 40), 399 (M+2H$^+$, 100).

Example 21

Preparation of 3-[2-(4-Amino-4-carboxy-butyryl amino)-2-(carboxymethyl-carbamoyl)-ethylsulfanyl]-2-[2-(4-amino-4-carboxy-butyrylamino)-2-(carboxymethyl-carbamoyl)-ethylsulfanylmethyl]-4-hydroxy-5-oxo-2,5-dihydro-furan-2-carboxylic acid Diasteroisomer, an HBr Salt

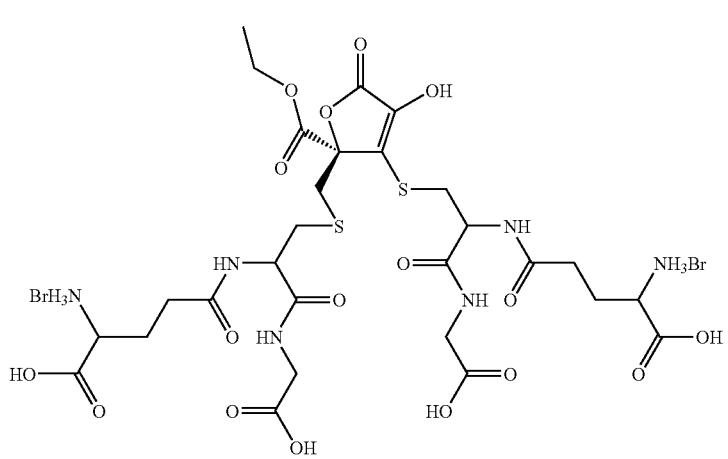

Isomer #1

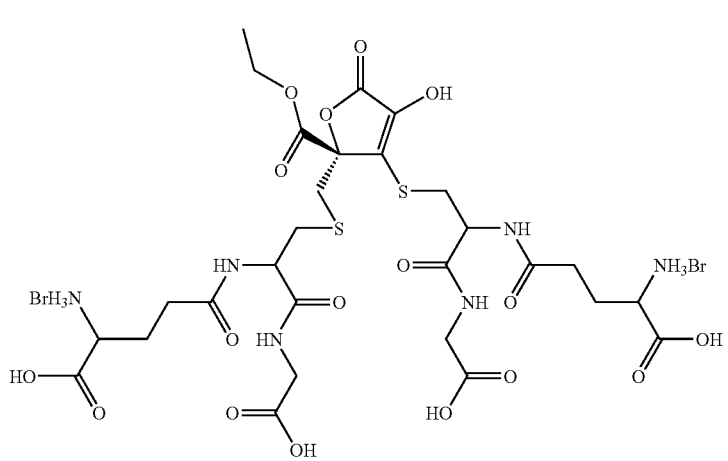

Isomer #2

By following the procedures described in Examples 13 and 20, the HBr salts of both isomer #1 and isomer #2_were prepared (as yellow sticky solids).

For isomer #1: $^1$H-NMR (300 MHz, D$_2$O) δ (ppm) 4.46 (dd, J=8.5, 5.1 Hz, 2H), 4.39 (dd, J=8.5, 5.1 Hz, 2H), 4.16-4.08 (m, 2H), 3.98-3.92 (m, 2H), 3.85 (brs, 4H), 3.58 (dd, J=14.2, 5.2 Hz, 1H), 3.34-3.11 (m, 3H), 3.01-2.95 (dd, J=14.2, 5.2 Hz, 1H), 2.81-2.73 (dd, J=14.2, 8.7 Hz, 1H), 2.45=2.40 (m, 4H), 2.10-2.05 (m, 4H), 1.14 (t, J=7.1 Hz, 3H). MS-ESI (M+H$^+$) m/z 797.

For isomer #2: $^1$HNMR (300 MHz, D$_2$O) δ (ppm) 4.46-4.39 (m, 2H), 4.19-4.12 (m, 2H), 4.16-4.08 (m, 2H), 3.98-3.93 (m, 2H), 3.86-3.85 (m, 4H), 3.67 (dd, J=14.2, 4.2 Hz, 1H), 3.37-2.80 (m, 5H), 2.48-2.42 (m, 4H), 2.14-2.04 (m, 4H), 1.14 (t, J=7.1 Hz, 3H). MS-ESI (M+H$^+$) m/z 797.

Example 22

Preparation of 3-[2-(4-Amino-4-carboxy-butyryl amino)-2-(carboxymethyl-carbamoyl)-ethylsulfanyl]-2-[2-(4-amino-4-carboxy-butyrylamino)-2-(carboxymethyl-carbamoyl)-ethylsulfanylmethyl]-4-hydroxy-5-oxo-2,5-dihydro-furan-2-carboxylic acid Diasteroisomer, an HCl Salt

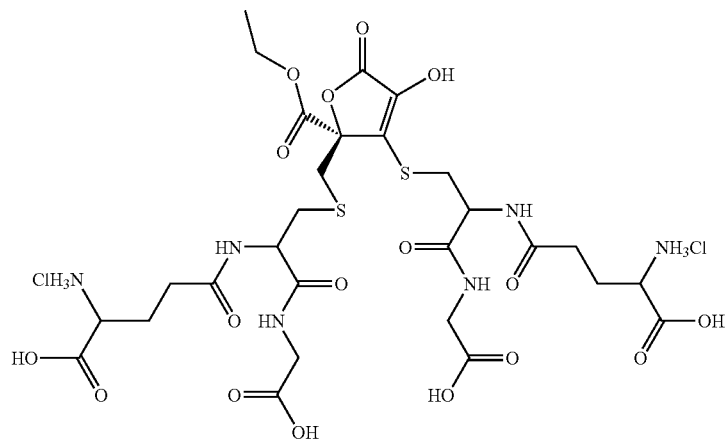

Isomer #1

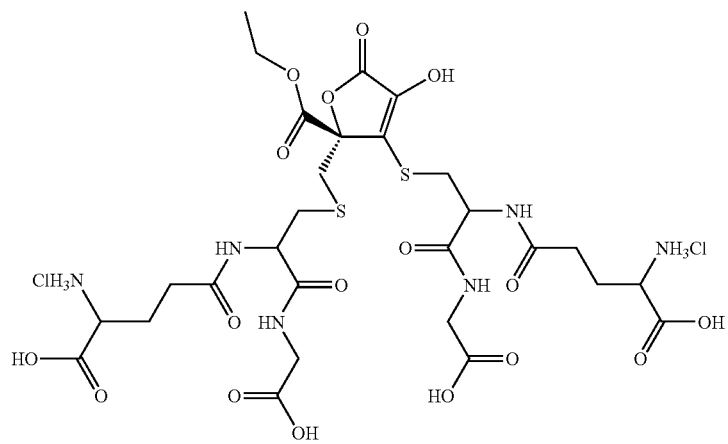

Isomer #2

By following the procedures described in Examples 12 and 20, the HCl salts of both isomer #1 and isomer #2 were prepared (as white sticky solids).

For isomer #1: $^1$H-NMR (300 MHz, D$_2$O) δ (ppm) 4.48 (dd, J=8.5, 5.1 Hz, 2H), 4.40 (dd, J=8.5, 5.1 Hz, 2H), 4.18-4.09 (m, 2H), 3.96-3.90 (m, 2H), 3.86 (brs, 4H), 3.58 (dd, J=14.2, 5.2 Hz, 1H), 3.35-3.13 (m, 3H), 3.03-2.96 (dd, J=14.2, 5.2 Hz, 1H), 2.82-2.75 (dd, J=14.1, 8.7 Hz, 1H), 2.47-2.41 (m, 4H), 2.13-2.04 (m, 4H), 1.13 (t, J=7.2 Hz, 3H). MS-ESI (M+H$^+$) m/z 797.

For isomer #2: $^1$H-NMR (300 MHz, D$_2$O) δ (ppm) 4.46-4.39 (m, 2H), 4.20-4.13 (m, 2H), 3.95-3.90 (m, 4H), 3.86 (pseudo-d, 2H), 3.67 (dd, J=14.2, 4.2 Hz, 1H), 3.37-3.05 (m, 3H), 2.98-2.92 (dd, J=14.2, 5.2 Hz, 1H). 2.87-2.80 (dd, J=14.1, 8.7 Hz, 1H), 2.47-2.39 (m, 4H), 2.13-2.04 (m, 4H), 1.14 (t, J=7.1 Hz, 3H). MS-ESI (M+H$^+$) m/z 797.

Example 23

Preparation of 3-[3-(2-Carboxy-pyrrolidin-1-yl)-2-methyl-3-oxo-propylsulfanyl]-2-[3-(2-carboxy-pyrrolidin-1-yl)-2-methyl-3-oxo-propylsulfanylmethyl]-4-hydroxy-5-oxo-2,5-dihydro-furan-2-carboxylic acid ethyl ester

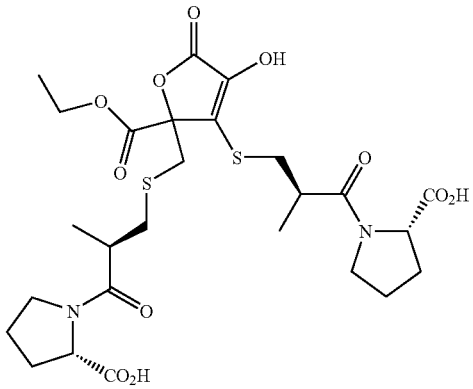

A solution of captopril (293 mg, 1.35 mmol) and ethyl bromopyruvate (0.176 mL, 1.40 mmol) in water (1 mL) and acetonitrile (1 mL) was stirred at 20° C. for 16 hours under argon. The pH of the solution was adjusted to about 7.2 using sodium bicarbonate aqueous solution and stirred at 20° C. for additional 3 hours. The pH of the solution was then adjusted to about 4 using hydrogen bromide aqueous solution (48%). The solution was washed with methylene chloride three times. The organic phase was discarded and aqueous phase was freeze-dried. The residue was dissolved in a solution of methylene chloride-methanol (90:10). The clear solution was collected after centrifugation. Evaporation gave the title furanone product (295 mg). $^1$H-NMR (300 MHz, D$_2$O) δ (ppm) 4.35-4.20 (m, 4H), 3.75-2.70 (m, 12H), 2.25-1.85 (m, 8H), 1.30-1.05 (m, 9H). MS (API-ESI) m/z 617 (M+H$^+$, 31), 639 (M+Na$^+$, 100).

Example 24

Preparation of 4-Hydroxy-5-oxo-3-(pyridin-4-ylsulfanyl)-2-(pyridin-4-ylsulfanylmethyl)-2,5-dihydro-furan-2-carboxylic acid ethyl ester

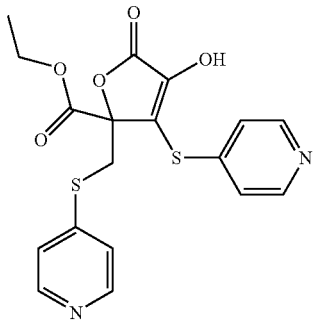

A solution of 4-mercaptopyridine (222 mg, 2.0 mmol) and ethyl bromopyruvate (0.264 mL, 2.1 mmol) in ethanol (5 mL) was stirred at 20° C. for 3 hours under argon. The pH of the solution was adjusted to about 7.2 using sodium bicarbonate aqueous solution. After evaporation to dryness, the residue was dissolved in ethyl acetate and washed with sodium bicarbonate aqueous solution, water, and dried over magnesium sulfate. Evaporation and chromatography (silica gel, methylene chloride-methanol from 90:10 to 80:20) gave the title furanone product (240 mg). $^1$H-NMR (300 MHz, D$_3$COD) δ (ppm) 8.35-8.25 (m, 2H), 8.25-8.20 (m, 2H), 7.40-7.35 (m, 2H), 7.25-7.15 (m, 2H), 4.00-3.80 (m, 3H), 3.70 (d, J=14.5 Hz, 1H), 1.02 (t, J=7.1 Hz, 3H). MS (API-ESI) m/z 203, 405 (M+H$^+$).

Example 25

Preparation of 5,8-Dichloro-3-hydroxy-2-oxo-2H-1-oxo-4,9-dithia-benzo[f]azulene-10a-carboxylic acid ethyl ester

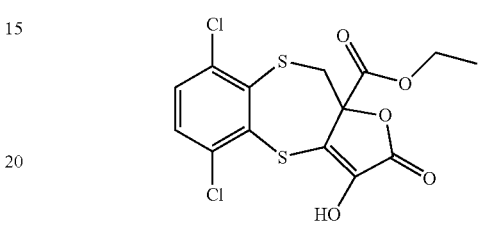

A solution of 3,6-dichloro-1,2-benzenedithiol (211 mg, 1.0 mmol), ethyl bromopyruvate (0.528 mL, 4.2 mmol) and triethylamine (0.1 mL) in acetonitrile (2 mL) and acetone (4 mL) was stirred at 20° C. for 16 hours under argon. After evaporation to dryness, the residue was dissolved in ethyl acetate, washed with diluted aqueous HCl solution and dried over anhydrous magnesium sulfate. Evaporation and multiple chromatographies using two different eluate systems [(silica gel, methylene chloride-methanol from 99:1 to 98:2) and (silica gel, hexane-ethyl acetate 4:1)] in sequence repeatedly gave the title furanone product (20 mg). $^1$H-NMR (300 MHz, D$_3$COD) δ (ppm) 7.33 (s, 2H), 4.30-4.05 (m, 3H), 2.88 (d, J=14.3 Hz, 1H), 1.29 (t, J=7.1 Hz, 3H). MS (API-ESI) m/z 393 (M+H$^+$, 100).

Example 26

Preparation of 3-(1H-Benzoimidazol-2-ylsulfanyl)-2-(1H-benzoimidazol-2-ylsulfanylmethyl)-4-hydroxy-5-oxo-2,5-dihydro-furan-2-carboxylic acid

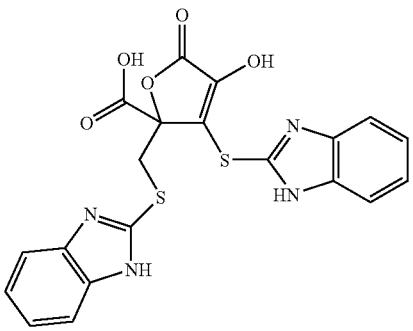

3-(1H-benzoimidazol-2-ylsulfanyl)-2-(1H-benzoimidazol-2-ylsulfanylmethyl)-4-hydroxy-5-oxo-2,5-dihydro-furan-2-carboxylic acid ethyl ester (32 g) prepared as described in Example 1 was suspended in water (400 mL) and ethanol (300 mL). The suspension was stirred continuously and aqueous sodium bicarbonate solution (23 g in 350 mL of water) was added dropwise during about 5 hours to maintain pH of around 7.5 to 8. The resulting mixture was stirred at 20° C. for 2 days. The milky mixture was put on a rotary evaporator to remove ethanol at a temperature below 40° C. under reduced pressure. The suspension became a clear solution soon after the evaporation started. During the evaporation process 400 mL of water were added to ensure complete removal of ethanol. The solution was adjusted to pH8 and allowed to stir at 40° C. for 18 hours. The product was precipitated out by acidifying the solution to pH 5-6 using acetic acid water solution (12 mL of acetic acid in 230 mL of water). The solid was filtered, washed with water (40 mL) and acetonitrile (40 mL), and dried under vacuum, giving 3-(1H-benzoimidazol-2-ylsulfanyl)-2-(1H-benzoimidazol-2-ylsulfanylmethyl)-4-hydroxy-5-oxo-2,5-dihydro-furan-2-carboxylic acid as a pale grey solid (16.5 g). $^1$HNMR (300 MHz, $D_2O$) δ=7.10-6.70 (m, 8H), 3.80 (d, 1H), 3.60 (d, 1H) ppm. $^{13}$CNMR (75 MHz, $D_2O$) δ=173.7, 173.2, 160.5, 156.6, 149.8, 149.3, 137.9, 122.2, 122.0, 113.7, 113.4, 104.5, 87.5, 37.4 ppm.

Example 27

Preparation of 3-(Benzothiazol-2-ylsulfanyl)-2-(benzothiazol-2-ylsulfanylmethyl)-4-hydroxy-5-oxo-2,5-dihydro-furan-2-carboxylic acid (2-hydroxy-ethyl)-amide

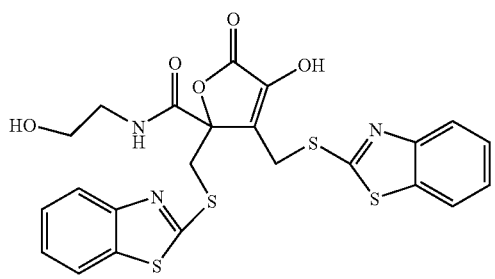

A mixture of 2,3-bis-(benzothiazol-2-ylsulfanylmethyl)-4-hydroxy-5-oxo-2,5-dihydro-furan-2-carboxylic acid (200 mg, 0.41 mmol), N-hydroxy succinimide (55 mg), dimethylaminopyridine (20 mg), and 1-(3-dimethylaminopropyl)-3-ethylcarbodiimide hydrochloride (85 mg) in methylenechloride (20 mL) was stirred at room temperature for 2 h. Ethanolamine (0.03 mL) was added followed by diisopropylethylamine (0.1 mL, and the mixture was stirred overnight at room temperature, and poured into water. The organic layer was separated, dried, and concentrated. The residue was purified by silica gel column eluting with 10% methanol in dichloromethane to give 50 mg of 3-(benzothiazol-2-ylsulfanyl)-2-(benzothiazol-2-ylsulfanylmethyl)-4-hydroxy-5-oxo-2,5-dihydro-furan-2-carboxylic acid (2-hydroxy-ethyl)-amide as a brown solid. $^1$HNMR (CDCl$_3$—CD$_3$OD, 300 MHz): δ: 7.80-7.60 (m, 4H), 7.38-7.20 (m, 4H), 4.20 (AB, J=7 Hz, 2H), 3.55 (m, 2H), 3.20 (m, 2H), ppm. $^{13}$CNMR (CDCl$_3$—CD$_3$OD, 75 MHz): δ: 168.20, 166.28, 152.77, 152.40, 135.26, 126.27, 124.70, 121.43, 121.18, 121.00, 87.21, 60.56, 42.21, 39.61 ppm. MS: 532 (M+H$^+$).

Example 28

Preparation of 3-(Benzothiazol-2-ylsulfanyl)-4-hydroxy-5-oxo-2,5-dihydro-furan-2-carboxylic acid

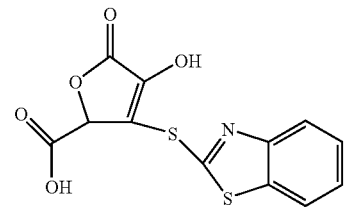

To a solution of glyoxylic acid monohydrate (98 mg, 1.03 mmol) in 6 mL methylenechloride/methanol (5:1) was added triethylamine (418 µL, 3.0 mmol) and stirred vigorously. 3-(benzothiazol-2-ylsulfanyl)-2-oxo-propionic acid ethyl ester (281 mg, 1.06 mmol) in 6 mL methylenechloride/methanol (5:1) was added dropwise over a period of 3 hours and the reaction was stirred overnight (15 hrs) at room temperature. The reaction mixture was then neutralized with NaH$_2$PO$_4$ and washed with ethylacetate. The resulting very polar product remained in the aqueous layer and was purified by reverse-phase HPLC. The pure fractions were pooled and concentrated under reduced pressure. Upon evaporation of solvent, 3-(benzothiazol-2-ylsulfanyl)-4-hydroxy-5-oxo-2,5-dihydro-furan-2-carboxylic acid precipitated out (70 mg) as a white solid which was filtered and washed with water. The filtrate was collected and lyophilized to afford a pale yellow solid which was determined to be the triethylamine salt of the desired product. $^1$H-NMR (MeOD, 300 MHz) δ (ppm): 7.92-7.87 (m, 2H), 7.51-7.38 (m, 2H), 5.68 (s, 1H). MS (ESI) m/z: 310 (M+H$^+$).

Example 29

Preparation of 4-(Furan-2-ylmethylsulfanyl)-5-(furan-2-ylmethylsulfanylmethyl)-3-hydroxy-5-hydroxymethyl-5H-furan-2-one

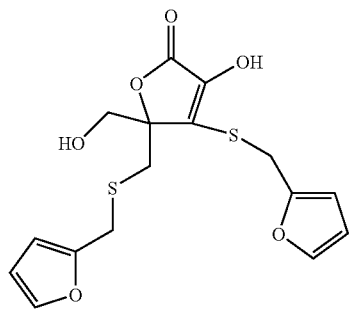

To a solution of 4-hydroxy-5-oxo-3-(2-furanylmethyl sulfanyl)-2-[(2-furanylmethyl sulfanyl)-methyl]-2,5-dihydrofuran-2-carboxylic acid ethyl ester (0.5 g, 1.219 mmol) in anhydrous tetrahydrofuran (THF, 30 mL) was added a THF solution of LiBH$_4$ (2 mL, 4 mmol) at 0-5° C. under argon atmosphere. The mixture was stirred overnight at room temperature and water (1 mL) was slowly added. The mixture was stirred for 5 min and concentrated hydrochloric acid (1 mL) was added. The solution was mixed with water (150 mL) and extracted with methylene chloride (2×100 mL). The combined organic solution was washed with water (50 mL), dried and evaporated. The residue was purified by column chromatography, eluted with a mixed solvent of hexane and ethyl acetate (3:1 to 2:1, v/v) affording 55.6 mg of 4-(furan-2-ylmethylsulfanyl)-5-(furan-2-ylmethylsulfanyl methyl)-3-hydroxy-5-hydroxymethyl-5H-furan-2-one as a cream oil. $^1$H NMR (CD$_3$OD, 300.16 MHz) δ (ppm): 7.45-7.42 (m, 2H), 6.35-6.22 (m, 4H), 4.50-3.71 (m, 5H), 3.48 (d, J=12.2 Hz, 1H), 2.97 (d, J=14.8 Hz, 1H) and 2.64 (d, J=14.8 Hz, 1H). $^{13}$C NMR (CD$_3$OD, 75.48 MHz) δ (ppm): 167.70, 151.21, 150.45, 143.03, 142.38, 142.19, 125.61, 110.33, 110.00, 108.44, 107.81, 88.79, 64.19, 34.07, 28.87 and 26.83. MS (ESI, rel. int.) m/z: 369 (M+H$^+$, 3), 391 (M+Na$^+$, 100).

Example 30

Preparation of 4-(2,2-Dimethyl-Propionyloxy)-3-(furan-2-ylmethylsulfanyl)-2-(furan-2-ylmethylsulfanyl methyl)-5-oxo-2,5-dihydro-furan-2-carboxylic acid ethyl ester

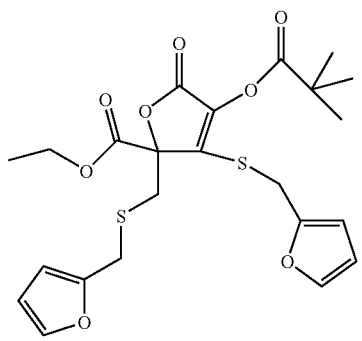

To a solution of 4-hydroxy-5-oxo-3-(2-furanylmethylsulfanyl)-2-[(2-furanylmethyl sulfanyl)-methyl]-2,5-dihydrofuran-2-carboxylic acid ethyl ester (0.3 g, 0.73 mmol) in methylene chloride (25 mL) were added pyridine (0.19 mL, 2.36 mmol) and trimethylacetyl chloride (0.22 mL, 1.77 mmol, 2.4 eq) under argon atmosphere. The mixture was gently refluxed overnight under argon and then evaporated. The residue was purified by column chromatography eluted with a mixed solvent of hexane and ethyl acetate (4:1, v/v) affording 0.3181 g of 4-(2,2-dimethyl-propionyloxy)-3-(furan-2-ylmethylsulfanyl)-2-(furan-2-ylmethylsulfanylmethyl)-5-oxo-2,5-dihydro-furan-2-carboxylic acid ethyl ester as light yellow oil. $^1$H NMR (CDCl$_3$, 300.16 MHz) δ (ppm): 7.40-7.37 (m, 2H), 6.35-6.25 (m, 4H), 4.35 (s, 2H), 4.33-4.22 (m, 2H), 3.90 (d, J=14.7 Hz, 1H), 3.80 (d, J=14.7 Hz, 1H), 3.29 (d, J=15.1 Hz, 1H), 2.97 (d, J=15.1 Hz, 1H), 1.37 (s, 9H) and 1.29 (t, J=7.1 Hz, 3H). $^{13}$C NMR (CDCl$_3$, 75.48 MHz) δ (ppm): 174.35, 166.32, 163.84, 150.29, 148.27, 144.72, 143.10, 142.64, 136.15, 111.00, 110.47, 109.44, 108.98, 87.64, 63.40, 39.30, 36.15, 29.62, 28.02, 26.99 and 14.04. MS (ESI, rel. int.) m/z: 495 (M+H$^+$, 25), 517 (M+Na$^+$, 100).

Example 31

Preparation of 3-(Furan-2-ylmethanesulfonyl)-2-(furan-2-ylmethanesulfonylmethyl)-4-hydroxy-5-oxo-2,5-dihydro-furan-2-carboxylic acid ethyl ester

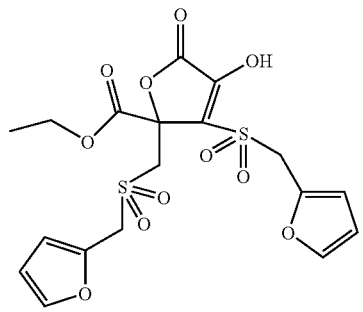

To a solution of 4-hydroxy-5-oxo-3-(2-furanylmethylsulfanyl)-2-[(2-furanylmethyl sulfanyl)-methyl]-2,5-dihydrofuran-2-carboxylic acid ethyl ester (0.5 g, 1.219 mmol) in methylene chloride (25 mL) at −78° C. was added m-chloroperoxybenzoic acid (1.216 g, 77% purity, 4.45 eq). The mixture was stirred overnight and the temperature was left to increase naturally to room temperature. The mixture was evaporated to dryness and the residue was mixed with water (25 mL). After filtration, the aqueous filtrate was evaporated and the residue was purified by column chromatography eluted with ethyl acetate affording 0.1387 g solid with 80% purity. This material was further purified by MPLC with a gradient mobile phase of 95% H2O/5% MeCN (0 min) to 20% H$_2$O/80% MeCN (210 min) giving 67 mg of 3-(furan-2-ylmethanesulfonyl)-2-(furan-2-ylmethanesulfonylmethyl)-4-hydroxy-5-oxo-2,5-dihydro-furan-2-carboxylic acid ethyl ester as a yellow solid. $^1$H NMR (CD$_3$OD, 300.16 MHz) δ (ppm): 7.62-7.55 (m, 2H), 6.59-6.45 (m, 4H), 4.77 (d, J=14.9 Hz, 1H), 4.70 (d, J=14.9 Hz, 1H), 4.61 (s, 2H), 4.38-4.26 (m, 3H), 3.65 (d, J=15.5 Hz, 1H) and 1.32 (t, J=7.1 Hz, 3H). $^{13}$C NMR (CD$_3$OD, 75.48 MHz) δ (ppm): 165.45, 150.21, 144.33, 142.31, 141.41, 112.81, 112.51, 111.03, 80.92, 63.71, 54.77, 54.06, 53.06 and 12.81. MS (ESI, rel. int.) m/z: 492 (M+H$_2$O, 100), 497 (M+Na$^+$, 65).

Example 32

Preparation of Dimethylamino-acetic acid 3-(1H-benzoimidazol-2-ylsulfanyl)-2-(1H-benzoimidazol-2-ylsulfanylmethyl)-4-hydroxy-5-oxo-2,5-dihydro-furan-2-ylmethyl ester

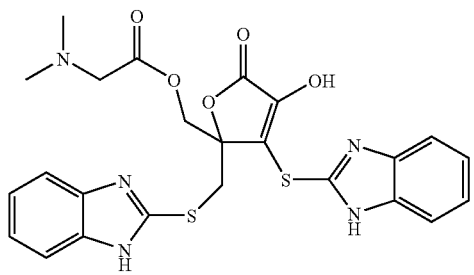

A solution of 4-(1H-benzoimidazol-2-ylsulfanyl)-5-(1H-benzoimidazol-2-ylsulfanylmethyl)-3-hydroxy-5-hydroxymethyl-5H-furan-2-one (220 mg, 0.50 mmol), dimethylaminoacetyl chloride hydrochloride (174 mg, 1.10 mmol) and triethylamine (0.280 mL, 2.00 mmol) in DMF (15 mL) was stirred for 22 h. The reaction mixture was then passed through a plug of $SiO_2$, which was then washed with hexane to remove excess DMF, and subsequently with a 1:1 mixture of EtOAc and MeOH to collect dimethylamino-acetic acid 3-(1H-benzoimidazol-2-ylsulfanyl)-2-(1H-benzoimidazol-2-ylsulfanylmethyl)-4-hydroxy-5-oxo-2,5-dihydro-furan-2-ylmethyl ester. Upon evaporation of solvent, the residue was subjected to column chromatography ($SiO_2$: $CH_2Cl_2$:MeOH:Acetic Acid, 87:10:3 v/v/v) which yielded an off-white solid which was dissolved in 0.5 M HCl and lyophilized (73 mg, 26%, GLI-1007817b). $^1H$ NMR ($D_2O$, 300.16 MHz) δ: 7.20-7.38 (m, 8H), 4.67 (q, J=12.0 Hz, 2H), 3.9104.18 (m, 4H), 2.86-2.96 (m, 6H).). $^{13}C$ NMR ($D_2O$, 75.04 MHz) δ: 167.4, 165.4, 155.7, 147.2, 145.3, 131.5, 130.9, 126.2, 126.1, 113.1, 112.7, 102.0, 85.2, 65.8, 56.6, 43.7, 36.4. MS (ESI-Pos) m/z: 526.2 (M+H$^+$).

Example 33

By following the procedures in the preceding examples and as described in Schemes 1 and 2, the following compounds of Formula I were prepared:

4-(1H-Benzoimidazol-2-ylsulfanyl)-5-(1H-benzoimidazol-2-ylsulfanylmethyl)-3-hydroxy-5-thiazol-2-yl-5H-furan-2-one; $^1$HNMR (DMSO, 300 MHZ) δ (ppm): 7.83 (bs, 2H), 7.46-7.04 (m, 8H), 5.78 (s, 1H), 4.55 (bs, 2H); MS 494.1 (M+H$^+$).

3-(Benzothiazol-2-ylsulfanyl)-2-(benzothiazol-2-ylsulfanylmethyl)-4-hydroxy-5-oxo-2,5-dihydro-furan-2-carboxylic acid; $^1$HNMR (CDCl$_3$—CD$_3$OD, 300 MHz): δ: 7.80-7.60 (m, 4H), 7.38-7.20 (m, 4H), 4.50 (d, J=14.7 Hz, 1H), 4.21(d, J=14.7 Hz, 1H) ppm. $^{13}$CNMR (CDCl$_3$—CD$_3$OD, 75 MHz): δ: 172.09, 169.74, 169.32, 168.22, 156.33, 156.29, 153.87, 139.36, 139.22, 130.45, 130.14, 129.10, 128.65, 125.47, 125.34, 125.03, 124.89, 118.69, 89.43, 41.45 ppm. MS: 489 (M+H$^+$)

3-(2-Chloro-4-fluoro-phenylsulfanyl)-2-(2-chloro-4-fluoro-phenylsulfanylmethyl)-4-hydroxy-5-oxo-2,5-dihydro-furan-2-carboxylic acid ethyl ester; $^1$H NMR ((CD$_3$)$_2$CO, 300.16 MHz) δ (ppm): 7.73-7.80 (m, 1H), 7.49-7.55 (m, 1H), 7.41-7.48 (m, 2H), 7.19-7.31 (m, 2H), 4.11 (q, J=7.1 Hz, 2H), 4.00 (d, J=14.8 Hz, 1H), 3.90 (d, J=14.8 Hz, 1H), 1.25 (t, J=7.1 Hz, 3H). $^{13}$C NMR (CD$_3$)$_2$CO, 75.04 MHz) δ: 167.6, 164.3, 161.0, 137.5, 137.4, 135.6, 135.5, 133.8, 133.6, 130.7, 118.3, 117.9, 116.0, 115.8, 87.0, 63.7, 39.5, 14.2. MS (ESI-Pos) m/z: 507.0(M+H$^+$).

Dimethylamino-acetic acid 3-(benzothiazol-2-ylsulfanyl)-2-(benzothiazol-2-ylsulfanylmethyl)-4-hydroxy-5-oxo-2,5-dihydro-furan-2-ylmethyl ester; $^1$H NMR (CD$_3$OD, 300 MHz) δ (ppm): 7.85-7.80 (m, 4H), 7.36 (m, 4H), 4.81 (s, 2H), 4.35-4.10 (m, 4H), and 2.92 (s, 6H). MS (ESI) m/z: 560 (M+H$^+$, 100)

4-(Benzooxazol-2-ylsulfanyl)-5-(benzooxazol-2-ylsulfanylmethyl)-3-hydroxy-5-hydroxymethyl-5H-furan-2-one; $^1$H NMR (CD$_3$OD, 300.16 MHz) δ (ppm): 3-7.50 (m, 4H), 7.32-7.27 (m, 4H) and 4.12-3.89 (m, 4H). $^{13}$C NMR (CD$_3$OD, 75.48 MHz) δ (ppm): 164.11, 151.90, 151.37, 141.05, 140.67, 124.84, 124.74, 124.22, 118.16, 117.90, 110.85, 110.01, 109.73, 88.09, 63.23 and 34.49. MS (ESI, rel. int.) m/z: 443 (M+H$^+$).

4-(5-Chloro-benzothiazol-2-ylsulfanyl)-5-(5-chloro-benzothiazol-2-ylsulfanylmethyl)-3-hydroxy-5-hydroxymethyl-5H-furan-2-one; $^1$HNMR (300 MHz, Cl$_3$CD-CD$_3$OD) δ=7.77-7.55 (m, 4H), 7.30-7.20 (m, 2H), 4.14 (d, J=14.3 Hz, 1H), 4.00 (d, J=12.2 Hz, 1H), 3.94 (d, J=12.2 Hz, 1H), 3.90 (d, J=14.3 Hz, 1H) ppm. $^{13}$CNMR (75 MHz, Cl$_3$CD-CD$_3$OD) δ=168.5, 153.1, 152.9, 133.5, 132.5, 125.2, 124.8, 121.9, 121.8, 121.0, 120.9, 88.9, 63.8, 35.9 ppm. MS (API-ES) m/z 547 (30), 543 (M+H$^+$).

4-(Benzothiazol-2-ylsulfanyl)-5-(benzothiazol-2-ylsulfanylmethyl)-3-hydroxy-5-hydroxymethyl-5H-furan-2-one; $^1$H NMR (CD$_3$OD, 300.16 MHz) δ (ppm): 7.76-7.62 (m, 4H), 7.39-7.21 (m, 4H), 4.05 (d, J=14.3 Hz, 1H), 3.92 (d, J=14.3 Hz, 1H) and 3.90 (s, 2H). $^{13}$C NMR (CD$_3$OD, 75.48 MHz) δ (ppm): 166.55, 152.52, 152.43, 135.28, 135.19, 126.15, 126.04, 124.59, 124.42, 121.08, 120.97, 120.63, 88.72, 63.91 and 36.01. MS (ESI, rel. int.) m/z: 475 (M+H$^+$).

3-(2-Chloro-6-fluoro-benzylsulfanyl)-2-(2-chloro-6-fluoro-benzylsulfanylmethyl)-4-hydroxy-5-oxo-2,5-dihydro-furan-2-carboxylic acid ethyl ester; $^1$H NMR ((CD$_3$)$_2$CO, 300.16 MHz) δ (ppm): 7.22-7.39 (m, 4H), 7.05-7.18 (m, 2H), 4.61 (d, J=12.4 Hz, 1H), 4.48 (d, J=12.4 Hz, 1H), 4.17 (q, J=7.1 Hz, 2H), 3.90-4.05 (m, 2H), 3.43 (d, J=14.8 Hz, 1H), 3.13 (d, J=14.8 Hz, 1H), 1.23 (t, J=7.1 Hz, 3H). $^{13}$C NMR ((CD$_3$)$_2$CO, 75.04 MHz) δ: 166.9, 166.0, 163.0, 162.8, 159.7, 159.5, 144.1, 135.2, 135.0, 130.4, 130.3, 129.7, 129.6, 125.7, 124.9, 124.7, 123.9, 123.5, 114.7, 114.6, 114.4, 114.3, 62.7, 37.0, 26.8, 20.2, 13.6. MS (ESI-Pos) m/z: 535.0 (M+H$^+$)

3-(5,6-Dichloro-1H-benzoimidazol-2-ylsulfanyl)-2-(5,6-dichloro-1H-benzoimidazol-2-ylsulfanylmethyl)-4-hydroxy-5-oxo-2,5-dihydro-furan-2-carboxylic acid ethyl ester; $^1$H NMR ((CD$_3$)$_2$SO, 300.16 MHz) δ (ppm): 7.58-7.64 (m, 4H), 4.21 (d, J=14.1 Hz, 1H), 4.14 (d, J=140.0 Hz, 1H), 3.90-4.02 (m, 2H), 0.98 (t, J=7.1 Hz, 3H). $^{13}$C NMR ((CD$_3$)$_2$SO, 75.04 MHz) δ: 169.2, 168.4, 156.4, 154.6, 153.1, 124.3, 124.2, 115.6, 84.5, 62.5, 31.2, 14.1. MS (ESI-Pos) m/z: 621.0 (M+H$^+$)

4-Hydroxy-3-(5-methoxy-benzothiazol-2-ylsulfanyl)-2-(5-methoxy-benzothiazol-2-ylsulfanylmethyl)-5-oxo-2,5-dihydro-furan-2-carboxylic acid ethyl ester; $^1$H NMR ((CD$_3$)$_2$CO, 300.16 MHz) δ (ppm): 7.65-7.73 (m, 2H), 7.31-7.38 (m, 2H), 6.90-6.98 (m, 2H), 4.44 (d, J=14.2 Hz, 1H), 4.20 (d, J=14.8 Hz, 1H), 3.94-4.05 (m, 2H), 3.90 (s, 3H), 3.83 (s, 3H), 1.02 (t, J=7.1 Hz, 3H). $^{13}$C NMR ((CD$_3$)$_2$CO, 75.04 MHz) δ: 167.2, 166.2, 159.2, 159.1, 154.2, 127.4, 127.0, 121.6, 114.2, 104.7, 104.6, 86.6, 62.4, 55.2, 55.1, 38.3, 13.3. MS (ESI-Pos) m/z: 577.1(M+H$^+$).

3-(2,4-Dichloro-benzylsulfanyl)-2-(2,4-dichloro-benzylsulfanylmethyl)-4-hydroxy-5-oxo-2,5-dihydro-furan-2-carboxylic acid ethyl ester; $^1$H NMR (CDCl$_3$, 300.16 MHz) δ (ppm): 7.09-7.31 (m, 6H), 4.27-4.50 (m, 2H), 3.98-4.21 (m, 2H), 3.65-3.83 (m, 2H), 3.18 (d, J=15.1 Hz, 1H), 2.83 (d, J=15.0 Hz, H) 1.22 (t, J=7.0 Hz, 3H). $^{13}$C NMR (CDCl$_3$, 75.04 MHz) δ (ppm): 167.5, 166.7, 141.2, 135.0, 134.8, 134.3, 134.0, 133.8, 133.3, 132.0, 131.9, 129.7, 129.6, 127.4, 127.2, 126.9, 87.7, 63.3, 36.6, 34.9, 32.2, 14.0. MS (ESI-Pos) m/z: 569.0 (M+H$^+$).

2-(Benzothiazole-2-sulfinylmethyl)-3-(benzothiazol-2-ylsulfanyl)-4-hydroxy-5-oxo-2,5-dihydro-furan-2-carboxylic acid ethyl ester; $^1$H NMR (CD$_3$OD, 300.16 MHz) δ (ppm): 8.17-8.06 (m, 2H), 7.91-7.83 (m, 2H), 7.64-7.57 (m, 2H), 7.47-7.38 (m, 2H), 4.28 (d, J=14.1

Hz, 1H), 4.22 (d, J=14.1 Hz, 1H), 4.08-3.95 (m, 2H) and 1.12 (t, J=7.1 Hz, 3H). $^{13}$C NMR (CD$_3$OD, 75.48 MHz) δ (ppm): 175.39, 165.88, 164.63, 163.25, 157.15, 153.55, 152.96, 136.17, 135.75, 127.09, 126.54, 126.44, 125.14, 123.80, 122.37, 121.56, 121.23, 113.12, 83.15, 63.31, 59.53 and 12.67. MS (ESI, rel. int.) m/z: 533 (M+H$^+$).

4-(Furan-2-ylmethylsulfanyl)-5-(furan-2-ylmethylsulfanylmethyl)-3-hydroxy-5-hydroxymethyl-5H-furan-2-one; $^1$H NMR (CD$_3$OD, 300.16 MHz) δ (ppm): 7.45-7.42 (m, 2H), 6.35-6.22 (m, 4H), 4.50-3.71 (m, 5H), 3.48 (d, J=12.2 Hz, 1H), 2.97 (d, J=14.8 Hz, 1H) and 2.64 (d, J=14.8 Hz, 1H). $^{13}$C NMR (CD$_3$OD, 75.48 MHz) δ (ppm): 167.70, 151.21, 150.45, 143.03, 142.38, 142.19, 125.61, 110.33, 110.00, 108.44, 107.81, 88.79, 64.19, 34.07, 28.87 and 26.83. MS (ESI, rel. int.) m/z: 369 (M+H$^+$, 3), 391 (M+Na$^+$, 100).

4-Hydroxy-3-(6-nitro-benzothiazol-2-ylsulfanyl)-2-(6-nitro-benzothiazol-2-ylsulfanylmethyl)-5-oxo-2,5-dihydro-furan-2-carboxylic acid ethyl ester; $^1$H NMR ((CD$_3$)$_2$CO, 300.16 MHz) δ: 8.86 (d, J=2.3 Hz, 1H), 8.81 (d, J=2.3 Hz, 1H), 8.24-8.28 (m, 2H), 7.98 (d, J=9.0 Hz, 1H), 7.92 (d, J=9.0 Hz, 1H), 4.80 (d, J=14.7 Hz, 1H), 4.41 (d, J=14.7 Hz, 1H), 4.23 (q, J=7.1 Hz, 2H), 1.23 (t, J=7.1 Hz, 3H). MS (ESI-Pos) m/z: 607.0 (M+H$^+$).

2-(1H-Benzoimidazol-2-ylsulfanylmethyl)-4-ethoxy-3-(1-ethyl-1H-benzoimidazol-2-ylsulfanyl)-5-oxo-2,5-dihydro-furan-2-carboxylic acid ethyl ester; $^1$H NMR (CD$_3$OD, 300.16 MHz) δ (ppm): 7.72-7.66 (m, 4H), 7.57-7.53 (m, 2H), 7.49-7.37 (m, 2H), 4.53-4.29 (m, 6H), 4.0 (q, J=7.1 Hz, 2H), 1.48 (t, J=7.2 Hz, 3H), 1.18 (t, J=7.1 Hz, 3H) and 0.97 (t, J=7.1 Hz, 3H). $^{13}$C NMR (CD$_3$OD, 75.48 MHz) δ (ppm): 165.97, 163.47, 148.88, 147.86, 143.07, 140.42, 134.93, 133.37, 126.18, 124.93, 124.33, 120.70, 117.75, 113.48, 111.12, 85.10, 68.09, 63.94, 40.60, 37.83, 14.20, 14.07 and 13.10. MS (ESI) m/z: 539 (M+H$^+$, 389).

3-(Furan-2-ylmethanesulfinyl)-2-(furan-2-ylmethanesulfinylmethyl)-4-hydroxy-5-oxo-2,5-dihydro-furan-2-carboxylic acid ethyl ester; $^1$H NMR (CD$_3$OD, 300.16 MHz) δ (ppm): 7.62-7.59 (m, 2H), 6.56-6.47 (m, 4H), 4.74 (d, J=14.2 Hz, 1H), 4.58 (d, J=14.2 Hz, 1H), 4.44-4.26 (m, 4H), 4.09 (d, J=14.4 Hz, 1H), 3.23 (d, J=14.4 Hz, 1H) and 1.32 (t, J=7.1 Hz, 3H). $^{13}$C NMR (CD$_3$OD, 75.48 MHz) δ (ppm): 165.89, 163.88, 161.85, 144.19, 144.08, 144.03, 143.84, 126.15, 112.33, 111.91, 111.11, 110.89, 82.27, 63.61, 56.31, 50.87, 50.69 and 12.83. MS (ESI, rel. int.) m/z: 443 (M+H$^+$), 465 (M+Na$^+$, 97).

2-(Furan-2-ylmethanesulfinylmethyl)-3-(furan-2-ylmethanesulfonyl)-4-hydroxy-5-oxo-2,5-dihydro-furan-2-carboxylic acid ethyl ester; $^1$HNMR (CD$_3$OD, 300.16 MHz) δ (ppm): 7.62-7.59 (m, 2H), 6.58-6.48 (m, 4H), 4.82 (d, J=14.8 Hz, 1H), 4.72 (d, J=14.8 Hz, 1H), 4.43-4.26 (m, 4H), 4.45 (d, J=14.5 Hz, 1H), 3.16 (d, J=14.5 Hz, 1H) and 1.32 (t, J=7.1 Hz, 3H). $^{13}$C NMR (CD$_3$OD, 75.48 MHz) δ (ppm): 165.74, 152.38, 149.50, 144.35, 144.09, 143.94, 141.26, 121.88, 112.98, 111.92, 111.07, 110.88, 82.19, 63.68, 55.95, 54.21, 50.74 and 12.82. MS (ESI, rel. int.) m/z: 459 (M+H$^+$).

2-(Furan-2-ylmethanesulfinylmethyl)-3-(furan-2-ylmethanesulfonyl)-4-hydroxy-5-oxo-2,5-dihydro-furan-2-carboxylic acid ethyl ester (single isomer) $^1$H NMR (CD$_3$OD, 300.16 MHz) δ (ppm): 7.59-7.57 (m, 2H), 6.55-6.46 (m, 4H), 4.83 (d, J=15.0 Hz, 1H), 4.70 (d, J=15.0 Hz, 1H), 4.32 (d, J=9.1 Hz, 1H), 4.30 (q, J=7.1 Hz, 2H), 4.20 (d, J=14.2 Hz, 1H), 3.70 (d, J=14.3 Hz, 1H), 3.60 (d, J=14.3 Hz, 1H) and 1.32 (t, J=7.1 Hz, 3H). $^{13}$C NMR (CD$_3$OD, 75.48 MHz) δ (ppm): 165.66, 150.20, 144.27, 143.96, 143.74, 141.52, 112.81, 111.85, 111.08, 110.85, 82.76, 63.64, 54.19, 54.10, 50.66 and 12.83. MS (ESI, rel. int.) m/z: 459 (M+H$^+$).

4-Hydroxy-3-methylsulfanyl-2-methylsulfanylmethyl-5-oxo-2,5-dihydro-furan-2-carboxylic acid ethyl ester; $^1$H-NMR (CDCl$_3$, 300 MHz) δ (ppm): 4.28 (q, J=7.2 Hz, 2H), 3.3 (d, J=14.9 Hz, 1H), 3.14 (d, J=14.9 Hz, 1H), 2.66 (s, 3H), 2.20 (s, 3H), 1.13 (t, J=7.2 Hz, 3H). $^{13}$C-NMR δ (ppm): 168.1, 167.0, 139.8, 129.3, 87.8, 63.1, 40.1, 18.1, 14.3, 14.1. MS (ESI) m/z: 279 (M+H$^+$).

3-(5-Amino-[1,3,4]thiadiazol-2-ylsulfanyl)-2-(5-amino-[1,3,4]thiadiazol-2-ylsulfanylmethyl)-4-hydroxy-5-oxo-2,5-dihydro-furan-2-carboxylic acid; $^1$HNMR (300 MHz, D$_3$COD) δ=3.40 (d, 1H), 3.60 (d, 1H) ppm. $^{13}$CNMR (75 MHz, D$_3$COD) δ=173.3, 172.9, 172.1, 171.1, 159.0, 158.0, 155.4, 104.8, 87.5, 41.5 ppm. MS (ESI) m/z 421 (M+H$^+$).

3-(Benzooxazol-2-ylsulfanyl)-2-(benzothiazol-2-ylsulfanylmethyl)-4-hydroxy-5-oxo-2,5-dihydro-furan-2-carboxylic acid methyl ester; $^1$HNMR (300 MHz, D$_3$COD) δ (ppm): 7.87-7.73 (m, 4H), 7.31-7.45 (m, 4H) 4.39 (d, J=14.4 Hz, 1H), 4.29 (d, J=14.4 Hz, 1H), 3.58 (s, 3H). $^1$HNMR (300 MHz, D$_3$COD) δ (ppm): 7.87-7.73 (m, 4H), 7.31-7.45 (m, 4H) 4.39 (d, J=14.4 Hz, 1H), 4.29 (d, J=14.4 Hz, 1H), 3.58 (s, 3H). $^1$HNMR (300 MHz, D$_3$COD) δ (ppm): 7.87-7.73 (m, 4H), 7.31-7.45 (m, 4H) 4.39 (d, J=14.4 Hz, 1H), 4.29 (d, J=14.4 Hz, 1H), 3.58 (s, 3H).

4-Hydroxy-3-[4-(2-methoxycarbonyl-vinyl)-phenylsulfanyl]-2-[4-(2-methoxycarbonyl-vinyl)-phenylsulfanylmethyl]-5-oxo-2,5-dihydro-furan-2-carboxylic acid ethyl ester; $^1$H NMR ((CD$_3$)$_2$CO, 300.16 MHz) δ (ppm): 7.60-7.66 (m, 6H), 7.47 (d, J=8.4 Hz, 2H), 7.40 (d, J=8.4 Hz, 2H), 6.57 (d, J=2.7 Hz, 1H), 6.51 (d, J=2.7 Hz, 1H), 3.81-4.03 (m, 4H), 3.76 (s, 6H), 1.14 (t, J=7.1 Hz, 3H). MS (ESI-Neg) m/z: 569.1[M−H]$^-$.

3-Hydroxy-5,6-dimethyl-2-oxo-5,6-dihydro-2H-1-oxa-4,7-dithia-azulene-8a-carboxylic acid ethyl ester; $^1$H NMR ((CD$_3$)$_2$CO, 300.16 MHz) δ (ppm): 4.23 (q, J=6.3 Hz, 2H), 3.72-3.89 (m, 1H), 2.94-3.53 (m, 3H), 1.62 (d, J=6.9 Hz, 0.4H), 1.51 (d, J=6.8 Hz, 0.4H), 1.41 (d, J=6.8 Hz, 2.6H), 1.23 (d, J=7.2 Hz, 2.6H), 1.25 (t, J=7.1 Hz, 3H). MS (ESI-Pos) m/z: 305.1 (M+H$^+$).

3-(Furan-2-ylmethylsulfanyl)-2-(furan-2-ylmethylsulfanylmethyl)-4-isobutyryloxy-5-oxo-2,5-dihydro-furan-2-carboxylic acid ethyl ester; $^1$H NMR (CDCl$_3$, 300.16 MHz) δ (ppm): 7.39-7.36 (m, 2H), 6.35-6.25 (m, 4H), 4.35 (s, 2H), 4.33-4.24 (m, 2H), 3.90 (d, J=14.7 Hz, 1H), 3.29 (d, J=15.2 Hz, 1H), 2.97 (d, J=15.2 Hz, 1H), 2.82 (septet, J=7.0 Hz, 1H), and 1.41-1.27 (m, 9H). $^{13}$C NMR (CDCl$_3$, 75.48 MHz) δ (ppm): 172.70, 166.28, 163.89, 150.27, 148.36, 144.90, 143.09, 142.65, 135.96, 111.01, 110.47, 109.43, 108.99, 87.65, 63.41, 36.18, 33.90, 29.62, 28.07, 18.75, 18.69 and 14.04. MS (ESI, rel. int.) m/z: 481 (M+H$^+$, 25), 503 (M+Na$^+$, 100).

4-(2,2-Dimethyl-propionyloxy)-3-ethoxycarbonylmethylsulfanyl-2-ethoxycarbonylmethylsulfanylmethyl-5-oxo-2,5-dihydro-furan-2-carboxylic acid ethyl ester; $^1$H NMR (CDCl$_3$, 300.16 MHz) δ (ppm) 4.40-4.30 (m, 2H), 4.27-4.19 (m, 4H), 3.96 (d, J=16.2 Hz, 1H), 3.85 (d, J=16.2 Hz, 1H), 3.61 (d, J=15.2 Hz, 1H), 3.44 (d, J=15.3 Hz, 1H), 3.37 (d, J=15.3 Hz, 1H), 3.34 (d, J=15.2 Hz, 1H), 1.38 (s, 9H) and 1.27 (t, J=7.1 Hz, 3H). $^{13}$C NMR (CDCl$_3$, 75.48 MHz) δ (ppm): 174.35, 170.11, 166.98, 166.18, 163.48, 143.55, 136.14, 87.18, 63.58, 62.60, 61.64, 39.31, 37.68, 34.85, 32.75, 26.94, 14.21, 14.14 and 14.06. MS (ESI) m/z: 507 (M+H$^+$, 12) and 529 (M+Na$^+$, 100).

4-Hydroxy-5-oxo-3-(4-phenyl-thiazol-2-ylsulfanyl)-2-(4-phenyl-thiazol-2-ylsulfanylmethyl)-2,5-dihydro-furan-2-carboxylic acid ethyl ester; $^1$H-NMR (CDCl$_3$, 300 MHz) δ (ppm): 7.84-7.82 (d, 2H), 7.69-7.66 (d, 2H), 7.42-7.28 (m, 6H), 7.19 (s, 2H) 4.49-4.11 (m, 4H), 1.78-1.23 (t, 3H). MS (ESI) m/z: 569 (M+H$^+$).

3-(2-Dimethylamino-ethylsulfanyl)-2-(2-dimethylamino-ethylsulfanylmethyl)-4-hydroxy-5-oxo-2,5-dihydro-furan-2-carboxylic acid; $^1$H NMR (D$_2$O, 300.16 MHz) δ (ppm) 3.42-3.21 (m, 7H), 3.06 (d, J=14.9 Hz, 1H), 2.90-2.82 (m, 2H) and 2.76-2.74 (m, 12H). $^{13}$C NMR (D$_2$O, 75.48 MHz) δ (ppm) 170.72, 167.76, 141.79, 125.21, 88.01, 56.95, 56.30, 42.93, 42.80, 42.77, 42.59, 27.26 and 24.75. MS (ESI) m/z=321, (M+H—CO$_2$, 47), 365 (M+H$^+$).

3-(Furan-2-ylmethylsulfanyl)-2-(furan-2-ylmethylsulfanylmethyl)-4-hydroxy-5-oxo-2,5-dihydro-furan-2-carboxylic acid ethyl ester; $^1$H NMR (CD$_3$OD, 300.16 MHz) δ (ppm): 7.39-7.33 (m, 2H), 6.33-6.30 (m, 2H), 6.24-6.22 (m, 2H), 4.47 (d, J=14.4 Hz, 1H), 4.31 (d, J=14.4 Hz, 1H), 4.29-4.19 (m, 2H), 3.84 (d, J=14.7 Hz, 1H), 3.74 (d, J=14.7 Hz, 1H), 3.25 (d, J=15.1 Hz, 1H), 2.80 (d, J=15.1 Hz, 1H) and 1.29 (t, J=7.1 Hz, 3H). $^{13}$C NMR (CD$_3$OD, 75.48 MHz) δ (ppm): 167.14, 166.59, 150.46, 149.63, 142.77, 142.61, 140.55, 126.29, 110.80, 110.43, 109.10, 108.73, 87.94, 63.14, 35.95, 29.63, 27.70 and 14.07. MS (ESI) m/z: 411 (M+H$^+$, 5) and 433 (M+Na$^+$, 100).

4-Hydroxy-3-(1-methyl-1H-imidazol-2-ylsulfanyl)-2-(1-methyl-1H-imidazol-2-ylsulfanylmethyl)-5-oxo-2,5-dihydro-furan-2-carboxylic acid ethyl ester; $^1$H-NMR (MeOD, 300 MHz) δ (ppm): 7.70-7.46 (4 d, 4H combined), 4.17-4.11 (m, 2.8H), 4.01 (s, 0.76H), 3.92-3.89 (d, 6H), 3.83-3.78 (2 s, 1H), 1.34-1.24 (t, 3H). MS (ESI) m/z: 411 (M+H$^+$).

3-Cyclopentylsulfanyl-2-cyclopentylsulfanylmethyl-4-hydroxy-5-oxo-2,5-dihydro-furan-2-carboxylic acid ethyl ester; $^1$H-NMR (CDCl$_3$, 300 MHz) δ (ppm): 4.31-4.25 (q, J=7.13 Hz, 2H), 3.36-3.16 (dd, J=14.7 Hz, 2H), 2.11-1.98 (m, 2H), 1.75-1.55 (m, 16H), 1.32 (t, J=7.15 Hz). MS (ESI) m/z: 387 (M+H$^+$, 35), 409 (M+Na$^+$, 100).

3-Butylsulfanyl-2-butylsulfanylmethyl-4-hydroxy-5-oxo-2,5-dihydro-furan-2-carboxylic acid ethyl ester; $^1$H-NMR (CDCl$_3$, 300 MHz) δ (ppm): 4.28-4.26 (q, J=7.16 Hz, 2H), 3.33-3.14 (dd, J=14.8 Hz, 2H), 3.18-3.29 (m, 2H), 2.61 (t, J=7.27 Hz, 2H), 1.64-1.29 (m, 11H), 0.95-0.88 (tt, 6H). MS (ESI) m/z: 363 (M+H$^+$, 75), 385 (M+Na$^+$, 100).

4-Hydroxy-3-isobutylsulfanyl-2-isobutylsulfanylmethyl-5-oxo-2,5-dihydro-furan-2-carboxylic acid ethyl ester; $^1$H-NMR (CDCl$_3$, 300 MHz) δ (ppm): 4.33-4.14 (m, 2H), 3.33-3.14 (dd, J=14.8 Hz, 2H), 3.10 (m, 2H), 2.51 (d, J=6.9 Hz, 2H), 1.89-1.75 (m, 2H), 1.31 (t, J=7.1 Hz, 3H), 1.03-0.95 (m, 12H). MS (ESI) m/z: 385 (M+Na$^+$, 100).

4-Hydroxy-3-(naphthalen-2-ylsulfanyl)-2-(naphthalen-2-ylsulfanylmethyl)-5-oxo-2,5-dihydro-furan-2-carboxylic acid ethyl ester; $^1$H-NMR (CDCl$_3$, 300 MHz) δ (ppm): 7.91-7.54 (m, 8H), 7.55-7.48 (m, 6H), 4.00 (m, 2H), 1.15 (t, 3H). MS (ESI) m/z: 503 (M+H$^+$, 100) and 525 (M+Na$^+$, 70).

4-Hydroxy-5-oxo-3-(1-phenyl-1H-tetrazol-5-ylsulfanyl)-2-(1-phenyl-1H-tetrazol-5-ylsulfanylmethyl)-2,5-dihydro-furan-2-carboxylic acid ethyl ester; $^1$H NMR (DMSO-d$_6$, 300.16 MHz) δ (ppm): 7.71-7.59 (m, 10H), 4.25 (d, J=13.8 Hz, 1H), 4.07-3.84 (m, 3H) and 1.01 (t, J=7.1 Hz, 3H). $^{13}$C NMR (DMSO-d$_6$, 75.48 MHz) δ (ppm): 170.11, 168.99, 160.98, 155.44, 154.61, 133.84, 133.46, 131.27, 130.97, 130.60, 130.57, 125.28, 124.85, 83.94, 62.16 and 14.17. MS (ESI) m/z: 539 (M+H$^+$, 100).

4-Hydroxy-5-oxo-3-(5-phenyl-2H-[1,2,4]triazol-3-ylsulfanyl)-2-(5-phenyl-2H-[1,2,4]triazol-3-ylsulfanylmethyl)-2,5-dihydro-furan-2-carboxylic acid ethyl ester; $^1$H NMR (CD$_3$OD, 300.16 MHz) δ (ppm) 7.94-7.87 (m, 4H), 7.47-7.40 (m, 6H), 4.20-4.08 (m, 2H), 4.03-3.90 (m, 2H) and 1.05 (t, J=7.1 Hz, 3H). $^{13}$C NMR (CD$_3$OD, 75.48 MHz) δ (ppm) 168.26, 158.45, 129.99, 129.71, 128.67, 128.56, 126.16, 126.06, 86.84, 62.19, 37.53 and 12.75. MS (ESI) m/z: 537 (M+H$^+$, 100).

4-Hydroxy-3-(4-methoxy-benzylsulfanyl)-2-(4-methoxy-benzylsulfanylmethyl)-5-oxo-2,5-dihydro-furan-2-carboxylic acid ethyl ester; $^1$H-NMR (CDCl$_3$, 300 MHz) δ (ppm): 7.29-7.22 (m, 4H), 6.88-6.83 (m, 4H), 4.38 (q, J=12.7 Hz, 2H), 4.23-4.12 (m, 2H), 3.81 (s, 3H), 3.79 (s, 3H), 3.76-3.71 (m, 2H), 3.17 (d, J=15.0 Hz, 1H), 2.79 (d, J=15.0 Hz, 1H), 1.26 (t, J=6.5 Hz, 3H). $^{13}$C-NMR δ (ppm): 168.1, 167.1, 159.5, 159.1, 140.9, 130.74, 130.69, 129.8, 129.0, 128.5, 114.5, 114.4, 88.4, 63.4, 55.7, 37.4, 36.3, 35.3, 14.6, 14.4.

4-Hydroxy-5-oxo-3-(thiazol-2-ylsulfanyl)-2-(thiazol-2-ylsulfanylmethyl)-2,5-dihydro-furan-2-carboxylic acid ethyl ester; $^1$H-NMR (D$_2$O, 300 MHz) δ (ppm): 7.65-7.59 (m, 2H), 7.20-7.11 (m, 2H), 4.07 (d, J=14.3 Hz, 1H), 3.92-3.78 (m, 4H), 3.07 (q, J=7.2 Hz, 1.0H), 1.21 (t, J=7.2 Hz, 1.7H), 1.03 (t, J=7.1 Hz, 3H). MS (ESI) m/z: 417 (M+H$^+$).

3-Benzylsulfanyl-2-benzylsulfanylmethyl-4-hydroxy-5-oxo-2,5-dihydro-furan-2-carboxylic acid ethyl ester; $^1$H-NMR (CDCl$_3$, 300 MHz) δ (ppm): 7.38-7.23 (m, 10H), 4.48-4.37 (m, 2H), 4.26-4.12 (m, 2H), 3.81 (d, J=3.4 Hz, 2H), 3.17 (d, J=15.0 Hz, 1H), 2.72 (d, J=15.0 Hz, 1H), 1.27 (t, J=6.5 Hz, 3H). $^{13}$C-NMR δ (ppm): 167.9, 166.7, 140.8, 137.6, 136.9, 129.3, 129.1, 128.8, 128.7, 127.9, 127.8, 127.3, 88.1, 63.1, 37.6, 35.9, 35.3, 14.1.

4-Hydroxy-3-(4-methoxy-phenylsulfanyl)-2-(4-methoxy-phenylsulfanylmethyl)-5-oxo-2,5-dihydro-furan-2-carboxylic acid ethyl ester; $^1$H NMR (CD$_3$OD, 300.16 MHz) δ (ppm): 7.36 (d, J=8.8 Hz, 2H), 7.32 (d, J=8.9 Hz, 2H), 6.87 (d, J=8.8 Hz, 4H), 3.93-3.81 (m, 2H), 3.79 (s, 3H), 3.78 (s, 3H), 3.55 (s, 2H) and 1.12 (t, J=7.1 Hz, 3H). $^{13}$C NMR (CD$_3$OD, 75.48 MHz) δ (ppm): 167.32, 167.04, 160.22, 159.76, 146.03, 134.30, 133.88, 125.88, 122.44, 121.01, 114.41, 114.39, 86.29, 62.46, 54.60, 54.52, 41.09 and 12.81. MS (ESI) m/z: 463 (M+H$^+$, 100) and 485 (M+Na$^+$, 85).

3-(2-Chloro-phenylsulfanyl)-2-(2-chloro-phenylsulfanylmethyl)-4-hydroxy-5-oxo-2,5-dihydro-furan-2-carboxylic acid ethyl ester; $^1$H NMR (CD$_3$OD, 300.16 MHz) δ (ppm): 7.54-7.51 (m, 1H), 7.45-7.39 (m, 2H), 7.32-7.18 (m, 5H), 3.96-3.75 (m, 4H) and 1.07 (t, J=7.1 Hz, 3H). $^{13}$C NMR (CD$_3$OD, 75.48 MHz) δ (ppm): 167.00, 166.22, 149.19, 135.37, 133.96, 133.16, 132.37, 130.96, 130.02, 129.72, 129.65, 128.30, 128.11, 127.28, 127.16, 86.22, 62.71, 37.82 and 12.68. MS (ESI) m/z: 471 (M+H$^+$ 100) and 493 (M+Na, 98).

3-(Benzothiazol-2-ylsulfanyl)-2-(benzothiazol-2-ylsulfanylmethyl)-4-hydroxy-5-oxo-2,5-dihydro-furan-2-carboxylic acid ethyl ester; $^1$H NMR (CD$_3$OD, 300.16 MHz) δ (ppm): 7.90-7.78 (m, 4H), 7.49-7.42 (m, 2H), 7.37-7.31 (m, 2H), 4.50 (d, J=14.7 Hz, 1H), 4.29 (d, J=14.7 Hz, 1H), 4.12-3.97 (m, 2H) and 1.09 (t, J=7.1 Hz, 3H). $^{13}$C NMR (CD$_3$OD, 75.48 MHz) δ (ppm): 167.07, 165.68, 153.35, 152.80, 135.86, 135.71, 126.63, 126.48, 125.21, 124.98, 121.65, 121.56, 121.39, 85.78, 63.28, 37.27 and 13.07. MS (ESI) m/z: 517 (M+H$^+$).

3-(Benzooxazol-2-ylsulfanyl)-2-(benzooxazol-2-ylsulfanylmethyl)-4-hydroxy-5-oxo-2,5-dihydro-furan-2-carboxylic acid ethyl ester; $^1$H NMR (CD$_3$OD, 300.16 MHz) δ (ppm): 7.60-7.48 (m, 4H), 7.36-7.25 (m, 4H), 4.38 (d, J=14.8 Hz, 1H), 4.33 (d, J=14.8 Hz, 1H), 4.14-4.05 (m, 2H) and 1.16 (t, J=7.1 Hz, 3H). $^{13}$C NMR (CD$_3$OD, 75.48 MHz) δ (ppm): 166.73, 165.39, 163.72, 160.13, 152.29, 152.20, 151.52, 141.54, 141.43, 125.19, 125.08, 124.83, 124.72, 118.76, 118.40, 110.71, 110.27, 110.12, 85.46, 63.42, 36.28 and 13.09. MS (ESI) m/z: 485 (M+H$^+$).

4-Hydroxy-5-oxo-3-(4-trifluoromethyl-pyrimidin-2-ylsulfanyl)-2-(4-trifluoromethyl-pyrimidin-2-ylsulfanylmethyl)-2,5-dihydro-furan-2-carboxylic acid ethyl ester; $^1$H NMR (CD$_3$OD, 300.16 MHz) δ (ppm): 8.90 (d, J=4.9 Hz, 1H), 8.82 (d, J=4.9 Hz, 1H), 7.54 (d, J=4.9 Hz, 1H), 7.52 (d, J=4.9 Hz, 1H), 4.26 (d, J=14.4 Hz, 1H), 4.15 (d, J=14.4 Hz, 1H), 4.15-3.95 (m, 2H) and 1.11 (t, J=7.1 Hz, 3H). $^{13}$C NMR (CD$_3$OD, 75.48 MHz) δ (ppm): 173.33, 172.43, 171.76, 168.57, 160.22, 160.10, 158.01, 155.51 (q, J=36.2 Hz), 155.20 (q, J=36.5 Hz), 120.35, (q, J=274.8 Hz), 120.30, (q, J=274.7 Hz), 112.58, 112.37, 101.11, 85.90, 61.86, 35.32 and 12.75. MS (ESI) m/z: 543 (M+H$^+$, 26) and 565 (M+Na$^+$, 100).

4-Hydroxy-3-(4-methyl-pyrimidin-2-ylsulfanyl)-2-(4-methyl-pyrimidin-2-ylsulfanylmethyl)-5-oxo-2,5-dihydro-furan-2-carboxylic acid ethyl ester; $^1$H NMR (CD$_3$OD, 300.16 MHz) δ (ppm): 8.62 (d, J=4.9 Hz, 2H), 8.55 (d, J=4.9 Hz, 2H), 7.23 (t, J=4.9 Hz, 1H), 7.22 (t, J=4.9 Hz, 1H), 4.24 (d, 1H), 4.09 (d, 1H), 4.10-3.85 (m, 2H) and 1.07 (t, J=7.1 Hz, 3H). $^{13}$C NMR (CD$_3$OD, 75.48 MHz) δ (ppm): 171.87, 171.56, 170.56, 168.78, 157.63, 157.38, 117.50, 117.22, 103.01, 85.95, 61.95, 35.05 and 12.81. MS (ESI) m/z: 407 (M+H$^+$).

4-(1H-Benzoimidazol-2-ylsulfanyl)-5-(1H-benzoimidazol-2-ylsulfanylmethyl)-3-hydroxy-5-hydroxymethyl-5H-furan-2-one; $^1$H NMR (CD$_3$OD, 300.16 MHz) δ (ppm): 7.45-7.40 (m, 2H), 7.38-7.33 (m, 2H), 7.20-7.10 (m, 4H), 3.90 (s, 2H), 3.88 (d, J=14.3 Hz, 1H) and 3.79 (d, J=14.3 Hz, 1H). $^{13C}$ NMR (CD3OD, 75.48 MHz) δ (ppm) 172.73, 158.01, 151.24, 149.97, 139.29, 138.92, 122.38, 122.29, 113.96, 113.76, 89.04, 63.38 and 36.58. MS (ESI) m/z: 441 (M+H$^+$).

4-Hydroxy-3-(4-methyl-pyrimidin-2-ylsulfanyl)-2-(4-methyl-pyrimidin-2-ylsulfanylmethyl)-5-oxo-2,5-dihydro-furan-2-carboxylic acid ethyl ester; $^1$H NMR (CD$_3$OD, 300.16 MHz) δ (ppm): 8.42 (d, J=5.1 Hz, 1H), 8.37 (d, J=5.1 Hz, 1H), 7.08 (d, J=5.1 Hz, 1H), 7.06 (d, J=5.1 Hz, 1H), 4.20 (s, 2H), 4.12-4.02 (m, 1H), 4.00-3.90 (m, 1H), 2.49 (s, 3H), 2.46 (s, 3H) and 1.09 (t, J=7.1 Hz, 3H). $^{13}$C NMR (CD3OD, 75.48 MHz) δ (ppm): 170.05, 169.73, 168.60, 168.15, 168.04, 167.24, 157.04, 156.72, 117.10, 116.67, 86.03, 61.98, 34.71, 22.50, 22.49 and 12.74. MS (ESI, negative) m/z: 435 (M+H$^+$).

4-Hydroxy-5-oxo-3-(pyrimidin-2-ylsulfanyl)-2-(pyrimidin-2-ylsulfanylmethyl)-2,5-dihydro-furan-2-carboxylic acid ethyl ester; $^1$H NMR (CD$_3$OD, 300.16 MHz) δ (ppm) 8.62 (d, J=4.9 Hz, 1H), 8.55 (d, J=4.9 Hz, 1H), 7.23 (t, J=4.9 Hz, 1H), 7.22 (t, J=4.9 Hz, 1H), 4.24 (d, 1H), 4.09 (d, 1H), 4.10-3.85 (m, 2H) and 1.07 (t, J=7.1 Hz, 3H). $^{13}$C NMR (CD$_3$OD, 75.48 MHz) δ (ppm) 171.87, 171.56, 170.56, 168.78, 157.63, 157.38, 117.50, 117.22, 103.01, 85.95, 61.95, 35.05 and 12.81. MS (ESI) m/z: 407 (M+H$^+$, 12) and 429 (M+Na$^+$, 100).

4-Hydroxy-5-oxo-3-(2-sulfo-ethylsulfanyl)-2-(2-sulfo-ethylsulfanylmethyl)-2,5-dihydro-furan-2-carboxylic acid ethyl ester; $^1$H NMR (D$_2$O, 300.16 MHz) δ (ppm) 4.22 (q, J=7.1 Hz, 2H), 3.43 (d, J=14.9 Hz, 1H), 3.22-2.86 (m, 9H) and 1.22 (t, J=7.1 Hz, 3H). $^{13}$C NMR (D$_2$O, 75.48 MHz) δ (ppm) 170.38, 169.75, 149.25, 117.51, 87.18, 64.13, 51.37, 51.12, 36.82, 27.57, 26.58 and 13.16. MS (ESI, negative) m/z: 232 (M$^2$–/2, 100), 465 (M$^2$–+H, 22) and 487 (M$^2$–+Na+, 39).

4-Hydroxy-5-oxo-3-(7-trifluoromethyl-quinolin-4-ylsulfanyl)-2-(7-trifluoromethyl-quinolin-4-ylsulfanylmethyl)-2,5-dihydro-furan-2-carboxylic acid ethyl ester; $^1$H NMR (DMSO-d6, 300.16 MHz) δ (ppm) 8.90 (d, 2H), 8.36-8.29 (m, 4H), 7.96-7.88 (m, 3H), 7.38 (s, 1H), 4.23 (d, 1H), 4.12 (d, 1H), 3.89 (broad m, 2H) and 0.93 (t, J=6.3 Hz, 3H). $^{13}$C NMR (DMSO-d6, 75.48 MHz) δ (ppm) 167.44, 166.76, 151.63, 146.89, 146.49, 145.90, 130.47 (q, J=32.1 Hz), 130.42 (q, J=32.2 Hz), 128.23, 127.88, 127.69, 126.09, 126.01, 122.58, 120.88, 85.74, 63.07, 35.91 and 13.92. MS (ESI) m/z: 641 (M+H$^+$).

4-Hydroxy-5-oxo-3-(7-trifluoromethyl-quinolin-4-ylsulfanyl)-2-(7-trifluoromethyl-quinolin-4-ylsulfanylmethyl)-2,5-dihydro-furan-2-carboxylic acid ethyl ester; $^1$H-NMR (CDCl$_3$, 300 MHz) δ (ppm): 7.81-7.58 (m, 4H), 7.44-7.08 (m, 4H), 4.23 (d, J=13.3 Hz, 2H), 3.91 (m, 2H), 0.94 (m, 3H). MS (ESI) m/z: 613 (M+H$^+$).

4-Hydroxy-5-oxo-3-(5-sulfonic acid-1H-benzoimidazol-2-ylsulfanyl)-2-(5-sulfonic acid-1H-benzoimidazol-2-ylsulfanylmethyl)-2,5-dihydro-furan-2-carboxylic acid ethyl ester; $^1$H NMR (D$_2$O, 300.16 MHz) δ (ppm) 7.86 (s, 1H), 7.81 (s, 1H), 7.56 (td, J=8.5 & 1.3 Hz, 2H), 7.41 (d, J=8.5 Hz, 2H), 4.11 (d, J=14.9 Hz, 1H), 4.01 (d, J=14.9 Hz, 1H), 3.70-3.60 (m, 1H), 3.48-3.38 (m, 1H) and 0.69 (t, J=7.1 Hz, 3H). $^{13}$C NMR (D2O, 75.48 MHz) δ (ppm) 171.44, 169.44, 159.68, 153.04, 151.84, 136.72, 120.04, 119.93, 113.81, 112.11, 111.55, 99.01, 85.50, 63.67, 37.48 and 12.38. MS (ESI, negative) m/z: 641 (M–H$^+$)

4-Hydroxy-5-oxo-3-(pyrrolidine-1-carbothioylsulfanyl)-2-(pyrrolidine-1-carbothioylsulfanylmethyl)-2,5-dihydro-furan-2-carboxylic acid ethyl ester; $^1$H NMR (CD$_3$OD, 300.16 MHz) δ (ppm) 4.34 (d, J=14.1 Hz, 1H), 4.11 (d, J=14.1 Hz, 1H), 4.10 (q, J=7.1 Hz, 2H), 3.87-3.79 (m, 6H), 3.66 (t, J=6.4 Hz, 2H), 2.16-2.05 (m, 4H), 2.03-1.92 (m, 4H) and 1.24 (t, J=7.1 Hz, 3H). $^{13}$C NMR (CD$_3$OD, 75.48 MHz) δ (ppm) 192.30, 191.83, 173.94, 169.76, 159.38, 106.58, 87.36, 63.77, 56.76, 52.41, 51.95, 43.44, 27.60, 27.14, 25.48, 25.30 and 14.39. MS (ESI) m/z: 477 (M+H$^+$).

3-Cyclohexylsulfanyl-2-cyclohexylsulfanylmethyl-4-hydroxy-5-oxo-2,5-dihydro-furan-2-carboxylic acid ethyl ester; $^1$H-NMR (CDCl$_3$, 300 MHz) δ (ppm): 4.28 (q, J=7.14 Hz, 2H), 3.90 (m, 1H), 3.19 (dd, J=14.7 Hz, 2H), 2.81 (m, 1H), 2.09-1.31 (m, 23H). MS (ESI) m/z: 415 (M+H$^+$, 60).

3-(2-Dimethylamino-ethylsulfanyl)-2-(2-dimethylamino-ethylsulfanylmethyl)-4-hydroxy-5-oxo-2,5-dihydro-furan-2-carboxylic acid ethyl ester, hydrochloride salt; $^1$H NMR (D$_2$O, 300.16 MHz): 4.20 (qd, J=7.1 & 1.3 Hz, 2H), 3.50-3.21 (m, 8H), 2.90 (q, J=7.6 Hz, 2H), 2.81-2.79 (m, 12H) and 1.17 (t, J=7.1 Hz, 3H) ppm. $^{13C}$ NMR (CDCl$_3$, 75.48 MHz): 168.13, 167.17, 142.16, 124.07, 87.07, 64.53, 56.97, 56.33, 43.07, 42.79, 42.72, 36.59, 27.25, 24.78 and 13.24 ppm. MS: m/z=393 (M+H$^+$).

Example 34

By following the procedures in the preceding examples and as described in reaction Scheme 3, the following compounds of Formula III were prepared:

4-(Benzothiazol-2-ylsulfanyl)-5-benzoyl-3-hydroxy-5H-furan-2-one; $^1$H NMR ((CD$_3$)$_2$SO, 300.16 MHz) δ (ppm): 7.95-8.04 (m, 3H), 7.35-7.70 (m, 6H), 7.12 (s, 1H). $^{13}$C NMR ((CD$_3$)$_2$SO, 75.04 MHz) δ: 192.6, 167.0, 163.0, 153.2, 147.1, 135.7, 135.1, 129.6, 129.4, 127.0, 125.5, 122.5, 122.0, 115.0, 78.7. MS (ESI-Pos) m/z: 370.0 (M+H$^+$).

3-(1H-Benzoimidazol-2-ylsulfanyl)-4-hydroxy-5-oxo-5H-furan-2,2-dicarboxylic acid diethyl ester; $^1$HNMR (300 MHz, d$_6$-DMSO-D$_2$O) δ=7.50-7.45 (m, 2H), 7.20-7.15 (m, 2H), 4.20-4.05 (m, 4H), 1.15-1.00 (m, 6H) ppm. $^{13}$C NMR (75 MHz, d$_6$-DMSO-D$_2$O) δ=165.9, 164.5, 150.3, 147.2, 138.7, 123.0, 114.6, 109.1, 84.4, 63.8, 14.0 ppm. MS (API-ES) m/z 393 (M+H$^+$).

5-Acetyl-4-(benzothiazol-2-ylsulfanyl)-3-hydroxy-5H-furan-2-one $^1$H-NMR (CDCl$_3$, 300 MHz) δ (ppm): 7.88-7.78 (m, 2H), 7.53-7.34 (m, 2.3H), 5.10 (s, 1H), 2.25 (s, 3H). $^1$C-NMR δ (ppm): 202.8, 134.6, 127.5, 126.2, 121.6, 121.4, 81.5, and 25.2. MS (ESI): 308 (M+H$^+$), 525.

3-Benzylsulfanyl-4-hydroxy-5-oxo-2,5-dihydro-furan-2-carboxylic acid ethyl ester; $^1$H-NMR (CDCl$_3$, 300 MHz) δ (ppm): 7.32 (m, 5H), 5.13 (s, 1H), 4.41-4.24 (q, 2H), 4.24-4.16 (m, 2H), 1.28 (t, 3H). MS (ESI) m/z: 295 (M+H$^+$, 100), 317, (M+Na$^+$, 70).

4-Hydroxy-3-(5-methyl-1H-benzoimidazol-2-ylsulfanyl)-5-oxo-2,5-dihydro-furan-2-carboxylic acid 2-isopropyl-5-methyl-cyclohexyl ester; $^1$H-NMR (CDCl3, 300 MHz) δ (ppm): 7.42 (d, J=8.2 Hz, 1H), 7.33 (s, 1H), 6.94 (d, J=8.2 Hz, 1H), 5.31 (m, 1H), 4.75 (m, 1H), 2.40 (s, 3H), 1.86-1.60 (m, 4H), 1.40-1.36 (m, 2H), 0.96-0.63 (m, 12H). MS (ESI) m/z: 445 (M+H$^+$).

Example 35

Neuronal Ischemia Stress Assay

A. Isolation and Culture of Primary Hippocampal Neuronal Cells.

Materials
- Neurobasal/B27: Neurobasal medium (Invitrogen, Carlsbad, Calif.) with 1× B27 supplement (Invitrogen Life Technologies), 0.5 µM L-glutamine, 25 µM L-glutamic acid, and 1× Penicillin/Streptomycin.
- Hank's Basic Salt Solution (HBSS, Ca/Mg-free) was prepared by preparing 1× Hanks CMF (Gibco) supplemented with HEPES (10 mM, pH 7.3), sodium bicarbonate (0.35%), 1× Penicillin/Streptomycin, and 1 mM pyruvate.
- Poly-D-lysine (Sigma, St. Louis, Mo.), 50 µg/ml solution filtered through 0.2 µm filter tubes.
- Sigmacote (Sigma, St. Louis, Mo.).
- Plastic Culture Flasks (T75 cm$^2$) or 12-well cell culture plates treated with Poly-D-Lysine (Sigma, St. Louis, Mo.).

Preparation of Primary Hippocampal Neuronal Cells

A pregnant female mouse (E18-E19) was euthanized with CO$_2$ prior to removal of the uterus, which was then placed in a sterile plastic petri dish. The embryos were removed from the sac, and the embryonic brains were removed and immersed in cold (4° C.) Buffered Salt Solution (HBSS; Ca/Mg free; Invitrogen Life Technologies) in a small petri dish. Hippocampi were then removed from the brains under a dissecting microscope and were placed on a paraffin-covered dish. The meninges were stripped away and the dissected hippocampi were collected in a small petri dish in HBSS. The hippocampi were transferred to a 15-ml centrifuge tube (normally 10-12 brains)filled with HBSS. The tube containing the brains was centrifuged at 1000 rpm for 2 min in a tabletop centrifuge. The supernatant was removed, 2 ml of HBSS was added to the hippocampi in the tube, and the resulting suspension was triturated 2 times each with long-tipped siliconized glass pipettes having progressively smaller apertures, starting with a pipette with a standard size opening (approximately 1.0 mm diameter), following with one having an aperture of half standard size (approximately 0.5 mm diameter), then with one having an aperture about one-half that size (0.25 mm diameter). The suspension was then centrifuged again at 1000 rpm for 2 min in a tabletop centrifuge, the supernatant was discarded, and 2 ml of Neurobasal/B27i (with antibiotics) was added to the tube. The trituration procedure described above was then repeated on this suspension.

The density of cells was determined on a small aliquot of cells using standard counting procedures and correcting for cell viability by trypan blue stain exclusion. Using this procedure, the expected yield is 3×10$^5$-6×10$^5$ cells/brain. Cells were then added to PDL-coated 24-well plates, flasks or MetTek dishes in Neurobasal/B27I at a density of about 1.5× 10$^6$ cells (T75 flask) or about 70,000 cells/well of a 24-well plate. Plated cells were incubated at 37 degrees in an atmosphere of 5% CO$_2$/95% O$_2$. Media was renewed after 3-4 days by replacing half of it with fresh Neurobasal/B27m medium, containing 5 µM cytosine arabinoside (AraC). Seven to eight days from the initial culture, the media was renewed again, by removing one-half or it and replacing with an equal amount of fresh Neurobasal/B27m medium (without Ara-C).

B. Hippocampal Anoxia-Reoxygenation Cell Death Assay.

This assay was used to induce ischemia by anoxia-reoxygenation in cultured hippocampal neuronal cells. Test compounds were added to assess potency and efficacy against ischemia-induced neuronal cell injury and cell death.

Materials.
- Neurobasal media, NoG neurobasal media, B27 supplement and B27 Supplement minus AO were obtained from Invitrogen Life Technologies.
- Neurobasal/B27 medium was prepared with 2× B27 minus AO supplement, 0.5 mM L-glutamine and 0.25× penicillin/streptomycin.
- Cell Tracker Green was obtained from Molecular Probes and a fresh 5 µM solution was prepared from 10 mM stock just before use.
- LoG-Neurobasal contains NoG neurobasal medium plus 1 mM glucose, 0.5 mM L-glutamine, 0.25× Penicillin/Streptomycin, and 10 mM Hepes (pH 7.4).
- Primary hippocampal neuronal cells were prepared according to the methods described above and were cultured in poly-D-lysine coated 24-well plates for 10-11 days prior to use.
- Deoxygenated LoG-Neurobasal medium (100 ml) was prepared by pre-equilibrating the medium in a T150 cm$^2$ flask in a hypoxic chamber overnight. Following pre-incubation under hypoxic conditions, the LoG-Neurobasal media was lightly bubbled with 100% N$_2$ for 30 min to completely deoxygenate the media. An additional 20 ml LoG-Neurobasal was pre-equilibrated in a T75 cm$^2$ flask and was incubated in a normal incubator (5% CO$_2$) overnight. Reoxygenated medium was prepared by placing Neurobasa/B27 media overnight in the culture incubator (5% CO$_2$/95% O$_2$).

10-11 Days after plating the hippocampal neurons, existing culture medium (Neurobasal/B27m) was removed from the cells by aspiration. Cells were washed once with 600 µl/well (24-well culture plates) of glucose free-BSS. Neurons were replenished with deoxygenated LoG-Neurobasal (400 µl per well for each well of a 24-well plate). Test compounds were added directly to each well (usually 3 concentrations of the compound plus positive control, each in triplicate). Most test compounds were dissolved in 100% DMSO; however, concentrations were adjusted such that the final concentration of DMSO in the cell media never exceeded 0.5%. Plates containing cells with test compounds were placed in a hypoxic chamber for 4-5 hr with plate lids ajar. For normoxia controls, pre-equilibrated normoxic LoG-Neurobasal medium was added to each well of cells, and the plate was replaced in the normal culture incubator for 4-5 hr. After 4-5 hr of hypoxia, the existing media was carefully aspirated off, and 400 µL of new, reoxygenated (pre-equilibrated) Neurobasal/B27 was added to each well. The same test compounds (in the same the concentrations) were added back into the corresponding wells. Plates were placed in the cell culture incubator (5% $CO_2$/95% $O_2$) and reoxygenated for 20-24 hr. After reoxygenation for 20-24 hr, live neurons were quantitated using the cell tracker green fluorescence method, described below.

To test for cell viability, existing culture medium was aspirated from each well of the 24 well plates, and neurons were washed once with 1 mL of HBSS (pH 7.4, pre-warmed to 30-37° C.). To each well was added 500 µL of 5 µM Cell Tracker Green fluorescent dye dissolved in HBSS. Plates were placed in the dark at room temperature for 15 minutes, then were washed with 1 mL of HBSS. 500 µL of HBSS was then added to each well, and fluorescent cells were counted using a fluorescent microscope. Significantly increased cell viability compared to control cells is indicative of a protective compound.

Compounds of the present invention when tested as described above provide protection against stressor-induced cell death in at least about 20% of the cells tested, at concentrations ranging from about 1 to 1000 µM.

When tested as described above, compounds of the present invention, such as
4-(Benzothiazol-2-ylsulfanyl)-5-(benzothiazol-2-ylsulfanylmethyl)-3-hydroxy-5-hydroxymethyl-5H-furan-2-one;
1,4-Dihydroxy-4-methyl-3a,4-dihydro-3-oxa-10-thia-4a,9-diaza-cyclopenta[b]fluoren-2-one;
3-(2,4-Dichloro-benzylsulfanyl)-2-(2,4-dichloro-benzylsulfanylmethyl)-4-hydroxy-5-oxo-2,5-dihydro-furan-2-carboxylic acid ethyl ester;
3-(1H-Benzoimidazol-2-ylsulfanyl)-4-hydroxy-5-oxo-5H-furan-2,2-dicarboxylic acid diethyl ester;
4-(Furan-2-ylmethylsulfanyl)-5-(furan-2-ylmethylsulfanylmethyl)-3-hydroxy-5-hydroxymethyl-5H-furan-2-one;
5-Acetyl-4-(benzothiazol-2-ylsulfanyl)-3-hydroxy-5H-furan-2-one;
2-(Furan-2-ylmethanesulfinylmethyl)-3-(furan-2-ylmethanesulfonyl)-4-hydroxy-5-oxo-2,5-dihydro-furan-2-carboxylic acid ethyl ester;
4-Hydroxy-5-oxo-3-(4-phenyl-thiazol-2-ylsulfanyl)-2,5-dihydro-furan-2-carboxylic acid;
3-(Furan-2-ylmethanesulfonyl)-2-(furan-2-ylmethanesulfonylmethyl)-4-hydroxy-5-oxo-2,5-dihydro-furan-2-carboxylic acid ethyl ester;
3-Benzylsulfanyl-4-hydroxy-5-oxo-2,5-dihydro-furan-2-carboxylic acid ethyl ester;
3-[4-(2-Carboxy-vinyl)-phenylsulfanyl]-2-[4-(2-carboxy-vinyl)-phenylsulfanylmethyl]-4-hydroxy-5-oxo-2,5-dihydro-furan-2-carboxylic acid ethyl ester;
3-(5-Amino-[1,3,4]thiadiazol-2-ylsulfanyl)-2-(5-amino-[1,3,4]thiadiazol-2-ylsulfanylmethyl)-4-hydroxy-5-oxo-2,5-dihydro-furan-2-carboxylic acid;
3-(Benzothiazol-2-ylsulfanyl)-4-hydroxy-5-oxo-2,5-dihydro-furan-2-carboxylic acid;
3-Hydroxy-5,6-dimethyl-2-oxo-5,6-dihydro-2H-1-oxa-4,7-dithia-azulene-8a-carboxylic acid ethyl ester;
4-(2,2-Dimethyl-propionyloxy)-3-(furan-2-ylmethylsulfanyl)-2-(furan-2-ylmethylsulfanylmethyl)-5-oxo-2,5-dihydro-furan-2-carboxylic acid ethyl ester;
4-(2,2-Dimethyl-propionyloxy)-3-ethoxycarbonylmethylsulfanyl-2-ethoxycarbonylmethylsulfanyl-methyl-5-oxo-2,5-dihydro-furan-2-carboxylic acid ethyl ester;
4-Hydroxy-3-(5-methyl-1H-benzoimidazol-2-ylsulfanyl)-5-oxo-2,5-dihydro-furan-2-carboxylic acid 2-isopropyl-5-methyl-cyclohexyl ester;
3-Cyclopentylsulfanyl-2-cyclopentylsulfanylmethyl-4-hydroxy-5-oxo-2,5-dihydro-furan-2-carboxylic acid ethyl ester;
3-Butylsulfanyl-2-butylsulfanylmethyl-4-hydroxy-5-oxo-2,5-dihydro-furan-2-carboxylic acid ethyl ester;
4-Hydroxy-5-oxo-3-(9H-purin-6-ylsulfanyl)-2-(9H-purin-6-ylsulfanylmethyl)-2,5-dihydro-furan-2-carboxylic acid ethyl ester;
4-Hydroxy-5-oxo-3-(1-phenyl-1H-tetrazol-5-ylsulfanyl)-2-(1-phenyl-1H-tetrazol-5-ylsulfanylmethyl)-2,5-dihydro-furan-2-carboxylic acid ethyl ester;
4-Hydroxy-3-(4-methoxy-benzylsulfanyl)-2-(4-methoxy-benzylsulfanylmethyl)-5-oxo-2,5-dihydro-furan-2-carboxylic acid ethyl ester;
4-Hydroxy-3-(4-methoxy-phenylsulfanyl)-2-(4-methoxy-phenylsulfanylmethyl)-5-oxo-2,5-dihydro-furan-2-carboxylic acid ethyl ester;
4-(1H-Benzoimidazol-2-ylsulfanyl)-5-(1H-benzoimidazol-2-ylsulfanylmethyl)-3-hydroxy-5-(4-methyl-piperazine-1-carbonyl)-5H-furan-2-one;
3-(Benzothiazol-2-ylsulfanyl)-2-(benzothiazol-2-ylsulfanylmethyl)-4-hydroxy-5-oxo-2,5-dihydro-furan-2-carboxylic acid ethyl ester;
3-(Benzooxazol-2-ylsulfanyl)-2-(benzooxazol-2-ylsulfanylmethyl)-4-hydroxy-5-oxo-2,5-dihydro-furan-2-carboxylic acid ethyl ester;
4-(1H-Benzoimidazol-2-ylsulfanyl)-5-(1H-benzoimidazol-2-ylsulfanylmethyl)-3-hydroxy-5-hydroxymethyl-5H-furan-2-one;
4-Hydroxy-3-(1H-imidazol-2-ylsulfanyl)-2-(1H-imidazol-2-ylsulfanylmethyl)-5-oxo-2,5-dihydro-furan-2-carboxylic acid ethyl ester;
4-Hydroxy-5-oxo-3-(pyrimidin-2-ylsulfanyl)-2-(pyrimidin-2-ylsulfanylmethyl)-2,5-dihydro-furan-2-carboxylic acid ethyl ester;
4-Hydroxy-5-oxo-3-(7-trifluoromethyl-quinolin-4-ylsulfanyl)-2-(7-trifluoromethyl-quinolin-4-ylsulfanylmethyl)-2,5-dihydro-furan-2-carboxylic acid ethyl ester;
3-(Benzoselenazol-2-ylsulfanyl)-2-(benzoselenazol-2-ylsulfanylmethyl)-4-hydroxy-5-oxo-2,5-dihydro-furan-2-carboxylic acid ethyl ester;
3-(2-Diethylamino-ethylsulfanyl)-2-(2-diethylamino-ethylsulfanylmethyl)-4-hydroxy-5-oxo-2,5-dihydro-furan-2-carboxylic acid ethyl ester;
4-Hydroxy-5-oxo-3-(5-sulfo-1H-benzoimidazol-2-ylsulfanyl)-2-(5-sulfo-1H-benzoimidazol-2-ylsulfanylmethyl)-2,5-dihydro-furan-2-carboxylic acid ethyl ester;
3-(1H-Benzoimidazol-2-ylsulfanyl)-2-(1H-benzoimidazol-2-ylsulfanylmethyl)-4-hydroxy-5-oxo-2,5-dihydro-furan-2-carboxylic acid;

3-(1H-Benzoimidazol-2-ylsulfanyl)-2-(1H-benzoimidazol-2-ylsulfanylmethyl)-4-hydroxy-5-oxo-2,5-dihydro-furan-2-carboxylic acid methyl ester;

3-Cyclohexylsulfanyl-2-cyclohexylsulfanylmethyl-4-hydroxy-5-oxo-2,5-dihydro-furan-2-carboxylic acid ethyl ester;

3-(2-Dimethylamino-ethylsulfanyl)-2-(2-dimethylamino-ethylsulfanylmethyl)-4-hydroxy-5-oxo-2,5-dihydro-furan-2-carboxylic acid ethyl ester, hydrochloride salt;

4-Hydroxy-3-(2-methoxycarbonyl-ethylsulfanyl)-2-(2-methoxycarbonyl-ethylsulfanylmethyl)-5-oxo-2,5-dihydro-furan-2-carboxylic acid ethyl ester;

4-Hydroxy-3-methoxycarbonylmethylsulfanyl-2-methoxycarbonylmethylsulfanylmethyl-5-oxo-2,5-dihydro-furan-2-carboxylic acid ethyl ester;

4-Hydroxy-5-oxo-3-(pyridin-4-ylsulfanyl)-2-(pyridin-4-ylsulfanylmethyl)-2,5-dihydro-furan-2-carboxylic acid ethyl ester;

5,8-Dichloro-3-hydroxy-2-oxo-2H-1-oxa-4,9-dithia-benzo[f]azulene-10a-carboxylic acid ethyl ester;

3-(5-Chloro-benzothiazol-2-ylsulfanyl)-2-(5-chloro-benzothiazol-2-ylsulfanylmethyl)-4-hydroxy-5-oxo-2,5-dihydro-furan-2-carboxylic acid ethyl ester;

3-(5-Amino-2H-[1,2,4]triazol-3-ylsulfanyl)-2-(5-amino-2H-[1,2,4]triazol-3-ylsulfanylmethyl)-4-hydroxy-5-oxo-2,5-dihydro-furan-2-carboxylic acid ethyl ester;

4-Hydroxy-5-oxo-3-p-tolylsulfanyl-2-p-tolylsulfanylmethyl-2,5-dihydro-furan-2-carboxylic acid ethyl ester;

3-(5-Amino-[1,3,4]thiadiazol-2-ylsulfanyl)-2-(5-amino-[1,3,4]thiadiazol-2-ylsulfanylmethyl)-4-hydroxy-5-oxo-2,5-dihydro-furan-2-carboxylic acid ethyl ester;

3-(5-Amino-[1,3,4]thiadiazol-2-ylsulfanyl)-2-(5-amino-[1,3,4]thiadiazol-2-ylsulfanylmethyl)-4-hydroxy-5-oxo-2,5-dihydro-furan-2-carboxylic acid ethyl ester;

provided protection against stressor-induced cell death in at least about 40% of the cells tested, at concentrations ranging from 1 to 100 micromolar.

Example 36

Myocyte Calcium-Contractility Assay

A. Isolation and Culture of Primary Neonate Myocytes.
Materials
  10× Heart Dissection Solution (HDS) contains the following components (g/l) in cell culture grade water: NaCl, 68; HEPES, 47.6; NaH$_2$PO$_4$, 2; Glucose, 10; KCl, 4; MgSO$_4$, 1, pH adjusted to 7.4. Prior to filter sterilization of diluted (1× HDS) solution, 10 mg phenol red was added to each 500 milliliters of medium.
  Transferrin and Bovine Insulin were obtained from Invitrogen Life Technologies (Carlsbad, Calif.), and resuspended at a concentration of 4 mg/ml in tissue culture grade water.
  DMEM-F12-DMEM-F12, powder, 1:1 containing glutamine and pyridoxine hydrochloride was purchased from Invitrogen Life Technologies. To one liter equivalent of the powder was added 2.43 g of sodium bicarbonate and 10 ml of 100× Penicillin/Streptomycin in 950 ml of tissue culture grade water with stirring. The pH was adjusted to 7.2 with 1 M HCl and volume was adjusted to 1 liter. The solution was filter sterilized then 2.5 ml of 4 mg/ml Transferrin, 250 µl 4 mg/ml Insulin and 30.7 mg of bromodeoxyuridine were added.
  DMEM-F12 was also prepared with 4% fetal bovine serum (FBS) for pre-coating the tissue culture plates and initial suspension of the cardiomyocyte pellet.
  Collagenase solution-49 mg of collagenase was resuspended in 120 ml 1× HDS.
  Fetal Bovine Serum (FBS) from Invitrogen Life Technologies Preparation of Primary Neonatal Myocyte Cultures Tissue culture ware was pre-coated with DMEM-F12-4% FBS by incubating 50 µl per well of a 96-well plate and 0.25 ml per 12-well plate at 37° C.

Two-day old rat pups were removed from their mothers and placed in a sterile container. Pups were dipped quickly into 70% alcohol, then decapitated and the body was placed in an empty sterile tissue culture dish. An incision was made starting at the neck and progressing towards the belly, cutting through the sternum. The heart was removed and placed in a tissue culture dishes containing 1× HDS. The atria were trimmed, and the remaining ventricles were placed into a separate tissue culture dish containing 1× HDS, where they were sectioned into 3-4 pieces each. Ventricles were then transferred to a sterile 250 ml glass flask and the 1× HDS was removed. Twenty milliliters of pre-warmed collagenase solution were added to the ventricles, followed by incubation at 37° C. with shaking. After 30 minutes, the collagenase solution was removed and replaced with 20 ml fresh pre-warmed collagenase. Incubation was continued for an additional 30 minutes. At the end of the incubation, any tissue chunks were allowed to settle prior to removing the collagenase (containing the isolated cardiomyocytes) from the disrupted tissue pieces. The isolated myocytes were added to a 50 ml Falcon tube containing 2 ml Fetal Bovine Serum (FBS). The remaining tissue pieces were subjected to a second digestion by adding 20 ml fresh pre-warmed collagenase and incubating as above for 30 minutes. This second digest was then centrifuged at 1000 rpm for 10 minutes (tabletop centrifuge). The resulting supernatant was discarded, and the cell pellet was suspended with 4 ml FBS. The resulting cell suspension was placed in the incubator at 37° C. This step was repeated several additional times to harvest additional material.

Percoll gradients were prepared by adding 2.5 ml of 10× HDS to 22.5 ml of Percoll (Invitrogen Life Technologies) with mixing (Percoll Stock). Top Gradient solution (11 ml Percoll Stock and 14 ml 1× HDS) and Bottom Gradient solution (13 ml Percoll Stock and 7 ml 1× HDS) were prepared. Four milliliters of the Top Gradient solution were transferred into 6×15 ml sterile Falcon tubes. Three milliliters of the Bottom Gradient solution were placed in each tube by inserting a serological pipette to the bottom of the tube and slowly adding the liquid.

All the digests (5) were pooled in one 50 ml Falcon tube and centrifuged on a tabletop centrifuge at 1000 rpm for 10 minutes. The supernatant was discarded, and the cell pellet was resuspended in 12 ml of 1× HDS. Two milliliters of the cell suspension was added to the top of each gradient. The gradient tubes were then centrifuged at 3000 rpm for 30 minutes without braking in a Beckman Allegra 6 centrifuge (GH 3.8A rotor). Following centrifugation, the cells segregated into two sharp bands at the two interfaces. The lower band of the two bands was enriched for cardiomyocytes; there was also a cardiomyocyte pellet at the bottom of the tube. The upper band was enriched for fibroblasts and other non-cardiomyocytes. The upper portion of the gradient was aspirated down to just above the cardiomyocyte layer. The cardiomyocyte layer was then carefully removed along with the pellet, and the two fractions were pooled in a sterile 50 ml Falcon tube, along with corresponding fractions from additional gradient tube; then 1× HDS was added to a total volume of about 50 ml. The tube was centrifuged at 1000 rpm for 7 minutes. The supernatant was discarded and resuspended in 25 ml 1×

HDS. A further 25 ml of 1×HDS was added and the centrifugation step was repeated. The cell pellet was resuspended carefully but thoroughly in 40-50 of DMEM/F12-4% FBS.

A small aliquot of the cell suspension was counted in a hemocytometer. The DMEM/F12-FBS coating medium was aspirated from the tissue culture dishes. The cardiomyocytes were added to the dishes at a plating density of $7.5 \times 10^4$/well per 96-well in 200 μL and $1.5 \times 10^5$/well per 12-well in 3 ml. The cultures were incubated at 37° C. with 5% $CO_2$ overnight. The original medium was removed, and add fresh DMEM/F12-5% FBS was added to each culture, prior to incubation at 37° C. with 5% $CO_2$ for a further 48 hours, before use.

B. Contractility Assay

Materials

Complete DMEM-F12: DMEM/F12, powder, 1:1 containing glutamine and pyridoxine hydrochloride was purchased from Invitrogen Life Technologies (Carlsbad, Calif.). Powder sufficient to prepare one liter of buffer and 2.43 g of sodium bicarbonate was mixed into 950 ml of tissue culture grade water. The pH was adjusted to 7.2 with 1 M HCl and the remaining water was added to make 1 liter. Following filter sterilization, 10 ml of 100× Penicillin/Streptomycin, 2.5 ml of 4 mg/ml Transferrin, 250 μl 4 mg/ml Insulin and 30.7 mg of bromodeoxyuridine were added, and the mixture was incubated at 37° C. prior to use.

1 mM glucose in DMEM was made from DMEM without L-glutamine, without glucose, without sodium pyruvate, purchased from Invitrogen Life Technologies.

20 μM Fluo-4: Cell permanent AM ester of Fluo-4 was obtained from Molecular Probes (Eugene, Oreg.) as a dry powder to be stored at −20° C. This fluorescent dye is light sensitive and should be made up fresh at 1 mM in DMSO prior to use to prevent light degradation.

10 mM $CaCl_2$ solution was made fresh each day in 1× HBSS and incubated at 37° C. prior to use.

Neonatal cardiomyocytes were isolated as described above. The cardiomyocytes were plated in 96-well format (black clear-bottomed plates) at a density of $7.5 \times 10^4$ per well and grown for 2 days in the presence of 5% FBS prior to use in the assay.

Physiological ischemia was simulated by placing the cardiomyocytes in an anaerobic chamber (0% $O_2$, 85% $N_2$, 5% $CO_2$ & 10% $H_2$) in DMEM containing 1 mM glucose. Positive control cells are treated with DMEM-F12 containing 25 mM Glucose, which protects against the anoxia.

The test compounds were made up in DMEM-1 mM glucose in 96 deep-well mother plates and appropriately diluted for use in the assay. The media was removed from the cells and replaced with 200 μl of either DMEM-F12 or 1 mM DMEM with or without test compounds. The plates were then placed inside the 37° C. incubator in the anaerobic chamber and incubated for 16 hours. The plates were then removed and reoxygenated by the addition of DMEM-F12. The DMEM with or without test compounds is carefully removed from the cells and replaced with pre-warmed DMEM-F12 containing 5% FBS. Since the anoxic treatment may damage and/or kill the cells, causing them to dislodge from the bottom of the wells gentle aspiration of media is required at this step. The cells were then placed in a normal incubator at 37° C. and incubated for two hours to allow the cells to reoxygenate.

A working solution of 20 μM Fluo-4 was added to pre-warmed 1× HBSS. The cells were loaded with Fluo-4 by first removing media from the cells and replacing with 100 μl of 20 μM Fluo-4. Unloaded control cells were treated in parallel with 1× HBSS alone. All cells were then incubated at 37° C. for 30 minutes. Before fluorescence measurements were made, the cells were washed in indicator-free medium (HBSS) to remove any dye that is non-specifically associated with the cell surface. Cells were then incubated for an additional 20 minutes at room temperature. Basal Fluo-4 fluorescence was measured using the 485 nm excitation and 538 nm emission filter pair on a microplate flourometer (Fluorskan™, Thermo Labsystems Oy, Helsinki, Finland). Each well was read for 160 ms to obtain a baseline reading, then stimulated to contract by addition of 10 mM $CaCl_2$. Following incubation at 37° C. for 30 minutes, a stimulated fluorescence reading was taken after 90 minutes.

Compounds of the present invention when tested as described above such as:

3-[3-(2-carboxy-pyrrolidin-1-yl)-2-methyl-3-oxo-propylsulfanyl]-2-[3-(2-carboxy-pyrrolidin-1-yl)2-methyl-3-oxo-propylsulfanylmethyl]-4-hydroxy-5-oxo-2,5-dihydro-furan-2-carboxylic acid ethyl ester;

4-Hydroxy-3-(5-methoxy-1H-benzoimidazol-2-ylsulfanyl)-2-(5-methoxy-1H-benzoimidazol-2-ylsulfanylmethyl)-5-oxo-2,5-dihydro-furan-2-carboxylic acid ethyl ester;

3-(5-Chloro-benzothiazol-2-ylsulfanyl)-2-(5-chloro-benzothiazol-2-ylsulfanylmethyl)-4-hydroxy-5-oxo-2,5-dihydro-furan-2-carboxylic acid ethyl ester;

4-Hydroxy-3-(5-nitro-1H-benzoimidazol-2-ylsulfanyl)-2-(5-nitro-1H-benzoimidazol-2-ylsulfanylmethyl)-5-oxo-2,5-dihydro-furan-2-carboxylic acid ethyl ester;

3-(5-Amino-2H-[1,2,4]triazol-3-ylsulfanyl)-2-(5-amino-2H-[1,2,4]triazol-3-ylsulfanylmethyl)-4-hydroxy-5-oxo-2,5-dihydro-furan-2-carboxylic acid ethyl ester;

3-(5-Amino-[1,3,4]thiadiazol-2-ylsulfanyl)-2-(5-amino-[1,3,4]thiadiazol-2-ylsulfanylmethyl)-4-hydroxy-5-oxo-2,5-dihydro-furan-2-carboxylic acid ethyl ester;

3-(1H-Benzoimidazol-2-ylsulfanyl)-2-(1H-benzoimidazol-2-ylsulfanylmethyl)-4-hydroxy-5-oxo-2,5-dihydro-furan-2-carboxylic acid ethyl ester;

showed the presence of calcium transients in amounts (about 30% or more) indicative of ability guard against ischemic damage and allow the cells to maintain their contractile function.

Example 37

Rat Middle Cerebral Artery Occlusion (MCAO) Model of Cerebral Ischemia

A. Animal Preparation

Male Wistar rats (Harlan, Ind.) weighing 300-350 g are commonly used in these experiments. Animals are allowed free access to water and commercial rodent diet under standard laboratory conditions. Room temperature is maintained at 20-23° C. and room illumination is on a 12/12-hour light/dark cycle. Animals are acclimatized to the laboratory environment 5 to 7 days prior to the study, and fasted (with free access to water) overnight before surgery.

B. Middle Cerebral Artery Occlusion (MCAO)

Anesthesia is maintained by inhalation of 3.0% isoflurane (Aerrane, Front Dodge, Iowa) in 0.8% oxygen. The animal's neck was shaved and sterilized before operation. Body temperatures were controlled and maintained at 37.5° C.+/−1 degree via external heating and cooling devices. To lower the body temperature, animals are placed in a cooling chamber, which uses ice to cool circulating air. Throughout the study the body temperature is recorded using a temperature transponder (BMDS Inc., Seaford, Del.) implanted subcutaneously at the time of MCAO between the rat shoulder blades that allows the user to read the body temperature via a pocket scanner (BMDS Inc., Seaford, Del.). The body temperature may also be taken by inserting the temperature probe into the animal's rectum. Body temperature is recorded every hour for 6 hours post-occlusion; however, body temperatures were taken more frequently so that they could be maintained at the normothermic temperature.

Animals were subjected to two hours MCAO using a modified intraluminal filament technique, as follows: A midline incision on the ventral part of the neck is made to expose external and internal carotid arteries. The right external and common carotid arteries are ligated by a suture (silk 5/0, Carlisle Laboratories, Farmers Branch, Tex.) and the right internal artery is temporarily ligated using a microvascular clip (Fine Science Tool Inc., Foster City, Calif.). A small incision was made in the common carotid artery. A nylon filament, its tip rounded by heating, is prepared from a fishing line (Stren Fishing Lines, Wilmington, Del.) and is inserted from the right common carotid artery. The filament is advanced into the internal carotid artery 18-20 mm from the point of bifurcation of internal and external arteries and a suture is tightly ligated around the filament. Two hours post occlusion, animals are re-anesthetized to allow reperfusion for the remaining of the experiment by removal of the filament.

C. Drug Administration

Test compounds may be administered by any of a number of routes, such as those described below. Compounds can be administered before, during or after occlusion, as appropriate to the protocol.

a) Intracerebroventricular (ICV) Infusion

The anesthetized animal is placed on a stereotaxic apparatus (Harvard Apparatus, S. Natick, Mass.). Anesthesia is maintained by inhalation of 3.0% isoflurane (Aerrane, Front Dodge, Iowa) in 0.8% oxygen throughout the entire procedure. The scalp is shaved and sterilized prior to surgery. A midline sagittal incision about 3 cm long is made slightly behind the eyes to expose the skull. The skull is scraped with a rounded end spatula to remove periosteal connective tissue. A bur hole is placed 1.5 mm lateral, 1 mm posterior to the left of the bregma to mark the left lateral ventricle. A brain infusion cannula (ALZET Co., Palo Alto, Calif.) is inserted 4 mm deep into the hole. The desired depth is adjusted by attaching spacers to the cannula. The cannula attached to a 4-cm silastic catheter (Helix Medical Inc., Carpinteria, Calif.) fixed in place with dental cement (Ketac-cement, Norristown, Pa.). The catheter is either attached to a primed osmotic pump placed subcutaneously between the shoulder blades for permanent infusion or to a syringe for a short infusion.

b) Intravenous (IV) Osmotic Pump Implantation into the Jugular Vein

Anesthesia is maintained by inhalation of 3.0% isoflurane (Aerrane, Front Dodge, Iowa) in 0.8% oxygen throughout the entire procedure. The animal's neck will be shaved and sterilized before operation. A midline incision is made on the ventral part of the neck to exposes the jugular vein. The vein is isolated and ligated with a suture (silk 5/0, Carlisle Laboratories, Farmers Branch, Tex.) rostral to the point of the incision and a microvascular clip (Fine Science Tool Inc., Foster City, Calif.) close to the heart. A small incision is made between two ligations. A 2-cm silastic catheter (Helix Medical Inc.) attached to a PE-60 tube (Becton. Dickinson and Co. Sparks, Md.) connected to an ALZET (ALZET CO. Palo Alto, Calif.) pump is introduced and advanced 2 mm into the jugular vein toward the heart. The microvascular clip is removed and the catheter is secured in place with a suture (silk 5/0, Carlisle Laboratories, Farmers Branch, Tex.). The pump is placed into a pocket made subcutaneously between the shoulder blades, allowing the catheter to reach over neck to the jugular vein with sufficient slack to permit free movement of neck and head.

c) IV Infusion Via Femoral Vein

Anesthesia is maintained by inhalation of 3.0% isoflurane (Aerrane, Front Dodge, Iowa) in 0.8% oxygen throughout the entire procedure. The exterior site of the right femoral vein is shaved and sterilized prior to surgery. A 3-cm incision is made in the right groin region and the femoral vein is isolated. A small incision is made on the femoral vein temporarily ligated with a microvascular clip to introduce and advance a polyethylene (PE-50) catheter (Becton Dickinson and Co. Sparks, Md.). The catheter is secured in place with suture (silk 5/0, Carlisle Laboratories, Farmers Branch, Tex.). The other end of the catheter is attached to a syringe filled with the heparinized saline for the bolus injection. Using a hemostat, a pocket is made subcutaneously on the back of the animal so the PE catheter can be brought up to the exteriorization point at the nape of the neck for either a bolus injection or a continuous injection by an osmotic pump.

d) Intraperitoneal (IP) Injection

An awake rat is held in a standard hand hold position, a 23¾G needle is injected into the lower right quarter of the abdomen pass the peritoneum, slightly off the midline. To avoid organ injection, the plunger of the syringe is slightly pulled back. If no fluid is withdrawn, the content of the syringe is delivered into the abdominal cavity.

e) Gavage Feeding

A standard rat gavage tube (Popper & Sons Inc., NY) is attached to a 3-cc hypodermic syringe. The animal is held by the shoulder in a vertical position. The feeding tube is placed into the mouth then advanced until it reaches the stomach (the approximate insertion length of the tube was measured prior to the feeding). The content of the syringe is slowly delivered, and then the tube is withdrawn.

D. Behavioral Assessment

One hour after MCAO, the animal was gently held by its tail and observed for forelimb flexion. Then the animal is placed on the floor to be observed for walking pattern; only the animals that score 3 on Bederson grading system (Table 1) are included in the study.

TABLE 1

Bederson Grading System for Neurological Evaluation

| Neurological deficit | Grading | Behavioral observation |
|---|---|---|
| Normal | grade 0: | No observable deficit |
| Moderate | grade 1: | forelimb flexion |
| Severe | grade 2: | forelimb flexion, decreased resistance to lateral push |
|  | grade 3: | forelimb flexion, decreased resistance to lateral push, circle to paretic side |

E. Evaluation of Ischemic Damage

Twenty-four hours post-MCAO, or longer, in some experiments, animals were sacrificed by $CO_2$ asphyxiation (dry ice). The brain was quickly removed from the skull, using standard procedures, rinsed in chilled saline solution, and placed on a rat brain tissue slicer (ASI instrument, MI). Seven 2-mm thick coronal slices are cut from each brain using razor blades. The slices were immersed in 0.9% saline containing 1.0% 2,3,5-triphenyltetrazolume chloride (TTC) (Sigma Chemical Co., St. Louis, Mo.) and incubated in a 37° C. water bath for 30 minutes.

After staining, each 2-mm slice is photographed with a TMC-7 camera (JH Technologies, Ca) which is directly connected to a desktop PC to capture and save the image of each brain slice. This image is used for the measurements of the regions of interest using a computer-based image processing system (Metamorph).

To measure each area, the region of interest is selected using a freehand selection tool, the area is automatically computed by selecting the measure command. The measurements for primary regions of interest are right hemisphere, left hemisphere, total infarct, subcortical infarct, total penumbra and subcortical penumbra. After all regions of interest are measured for all seven slices of the brain, they are sorted by slice number and the corresponding regions of interest using a custom made Excel™ macro. This macro calculates the cortical penumbra, cortical infarct and total ischemic damage for each slice; the corresponding areas of each rat brain will be added together to produce a single measurement for each area. Since the ipsilateral hemisphere is swollen following MCAO, edema volume is calculated and reported as the volumetric differences between the right and left hemispheres of each brain slice. Using the % of hemispheric swelling all the volumes will be corrected for the edema.

The volume of the damage is determined using the calculations below for each rat's brain.

Example 38

Model of Myocardial Infarction: Left Coronary Ligation (Rat)

Male Sprague-Dawley weighing 250-320 g are allowed free access to water and commercial rodent diet under standard laboratory conditions. Room temperature is maintained at 20-23° C. and room illumination is on a 12/12-hour light/dark cycle. Animals are acclimatized to the laboratory environment 5 to 7 days prior to the study and are fasted overnight prior to surgery.

Surgical Procedure for Acute Studies:

Rats are anaesthetized with Urethane (1.2-1.5 gm/kg). Core body temperature is maintained at 37° C. by using a heating blanket. The surgical area is shaved, and a ventral midline incision is made to expose the trachea and jugular area. A catheter (PE50) is placed in the jugular for administration of compound and maintenance anesthesia. The trachea is incised and a 14-16-gauge modified intravenous catheter is inserted and tied in place as an endotracheal tube. The animal is placed in right lateral recumbency and initially placed on a Harvard ventilator with a tidal volume of 5-10 ml/kg. 100%

| Measurement | Equation | Corrected Value(s) |
|---|---|---|
| Cortical Penumbra (C.P.) | Total Penumbra-Subcortical Penumbra | Total Penumbra (T.P.$_{corr.}$) = (T.P. × % H.S./100) <br> C.P.$_{corr.}$ = C.P. − (C.P. × % H.S./100) <br> S.P.$_{corr.}$ = S.P. − (S.P. × % H.S./100) |
| Cortical Infarct | Total Infarct-Subcortical Infarct | T.I.$_{corr.}$ = T.I. − (T.I. × % H.S./100) <br> S.I.$_{corr}$ = S.I. − (S.I. × % H.S./100) <br> C.I.$_{corr.}$ = C.I. − (C.I. × % H.S./100) |
| Total Ischemic Damage (T.I.D.) | Total Penumbra + Total Infarct | T.I.D.$_{corrected}$ = T.I.D. − (T.I.D. × % H.S./100) |
| Total Volume (mm$^3$) | Each value is multiplied by 2 (the thickness of the tissue). | |
| Edema Volume | The volumetric differences between the sum of right and left hemispheres determines the edema volume. | |
| % Hemispheric swelling (H.S.) | Edema × 100/left hemisphere | |

F. Statistical Analysis

Sample size is chosen to achieve a 90% probability of significant results. The measurements, which represented the same region of interest in seven slices of each rat's brain are added together to yield a single measurement for total infarct, subcortical infarct, cortical infarct, total penumbra, subcortical penumbra, cortical penumbra, total ischemic damage and edema in each animal. Group data are presented as means+/−SEM. Differences at the level of $p<0.05$ are considered statistically significant. Between groups comparison of each region of interest are carried out by unpaired student t test (between two groups) or one way ANOVA followed by post hoc Bonferroni's multiple comparisons or by the nonparametric Dunnett's test (between control and the drug treated groups).

Certain compounds of the present invention when tested as described above provided a reduction in total infarct volume of at least about 40% at doses in the range of about 10 μg/kg to about 40 mg/kg.

$O_2$ is delivered to the animals by the ventilator. ECG electrodes are placed to record a standard Lead II ECG. The surgical site is cleaned with alcohol swab, and a skin incision is made over the rib cage over the $4^{th}$-$5^{th}$ intercostal space. The underlying muscles are dissected with care to avoid the lateral thoracic vein, to expose the intercostal muscles. The chest cavity is entered through the $4^{th}$-$5^{th}$ intercostal space, and the incision expanded to allow visualization of the heart. The pericardium is opened to expose the heart. A 6-0 silk suture with a taper needle is passed around the left coronary artery near its origin, which lies in contact with the left margin of the pulmonary cone, at about 1 mm from the insertion of the left auricular appendage. A piece of tubing is placed over the suture to form an occluder. The coronary artery is occluded for 30 minutes by sliding the tube towards the heart until resistance is felt and holding it in place with a vascular clamp. The ECG is monitored for S-T changes indicative of ischemia. After 30 minutes, the occluder is removed, leaving the suture in place. The ECG is monitored for the first 10 minutes of reperfusion. The rat is transferred to the pressure control ventilator for the remainder of the protocol. The rats are ventilated by a small animal ventilator with a peak inspiratory pressure of 10-15 cm $H_2O$ and respiratory rate 60-110 breaths/min. The heart is allowed to reperfuse for 90 minutes.

Surgical Procedure for 24 Hour Study:

Rats are anaesthetized with Ketamine/Xylazine IP (95 and 5 mg/kg) and intubated with a 14-16-gauge modified intravenous catheter. Anesthesia level is checked every 15 minutes by toe pinch. Core body temperature is maintained at 37° C. by using a heating blanket. The surgical area is shaved and scrubbed. A ventral midline incision is made to expose the jugular vein. A catheter (PE50) is placed in the jugular for administration of compound and maintenance anesthesia. The animal is placed in right lateral recumbency and initially placed on a ventilator with a tidal volume of 5-10 ml/kg $H_2O$ or a pressure controlled ventilator with a peak inspiratory pressure of 8-15 cm $H_2O$ and respiratory rate 60-110 breaths/min. 100% $O_2$ is delivered to the animals by the ventilator. ECG electrodes are placed to record a standard Lead II ECG. The surgical site is cleaned with surgical scrub and alcohol. A skin incision is made over the rib cage over the $4^{th}$-5th intercostal space. The underlying muscles are dissected with care to avoid the lateral thoracic vein, to expose the intercostal muscles. The chest cavity is entered through $4^{th}$-5th intercostal space, and the incision expanded to allow visualization of the heart. The pericardium is opened to expose the heart. A 6-0 silk suture with a taper needle is passed around the left coronary artery near its origin, which lies in contact with the left margin of the pulmonary cone, at about 1 mm from the insertion of the left auricular appendage. A piece of tubing is placed over the suture to form an occluder. The coronary artery is occluded for 30 minutes by sliding the tube towards the heart until resistance is felt and holding it in place with a vascular clamp. The ECG is monitored for S-T changes indicative of ischemia. After 30 minutes, the occluder is removed, leaving the suture in place. The ECG is monitored for the first 10 minutes of reperfusion. The incision is closed in three layers. The IV catheter is removed or tunneled under the skin and exteriorized between the shoulder blades to allow for blood withdrawal or further drug therapy. The rat is ventilated until able to ventilate on its own. The rats are extubated and recovered on a heating pad. Once awake, they are returned to their cage(s). Animals may receive Buprenorphine (0.01-0.05 mg/kg SQ) for post-operative analgesia. After the designated reperfusion time (24 hours) the animals are anesthetized and the hearts removed under deep anesthesia.

Treatment Protocols

Diet

Animals are fed a custom diet prior to or after coronary ligation. The length of treatment varies with the study. Doses are calculated based on the average consumption of 15 gms of feed per day for a 300 gm rat. Rat weights are monitored during the study. Feed not consumed is weighed to estimate consumption rates.

Gavage

Animals are dosed orally by gavage. Length and frequency of treatment vary with the study. A standard rat gavage tube (Popper & Sons Inc, NY) is attached to a 3-cc hypodermic syringe. The animal is held by the shoulder in a vertical position. The feeding tube is placed into the mouth then advanced until it reaches the stomach (the approximate insertion length of the tube is measured prior to the feeding). The content of the syringe is slowly delivered, and then the tube is withdrawn.

IV Treatment

A ventral incision is made to expose the jugular area. A catheter (PE50) is placed in the jugular vein for administration of compound. Animals are dosed by bolus injection and/or continuous infusion. The time and duration of treatment varies with the protocol.

Tissue Processing

After reperfusion, each animal receives 200 units of heparin IV under general anesthesia and the heart is removed and placed in cold saline. After removal the coronary artery is ligated with the suture that is already in place. The heart is placed on a perfusion apparatus and Evans Blue dye is infused to delineate the area at risk. The heart is then cut into five 2-mm thick transverse slices from apex to base. The slices are incubated in 1% triphenyltetrazolium chloride (TTC) (Aldrich, Milwaukee, Wis.) in 0.9% saline for 20 minutes at 37° C. Tetrazolium reacts with NADH in the presence of dehydrogenase enzymes causing viable tissue to stain a deep red color and that is easily distinguished from the infarcted pale-unstained necrotic tissue. The slices are placed apex side down in the lid of a small petri dish for the staining procedure. The bottom of the dish is placed over the slices to keep them flat. The slices are photographed in order from apex to base, with the base side up. The areas of infarcted tissue, area at risk and the whole left ventricle are determined using a computerized image analysis system. The total area for each region is added together to give a total for the entire heart. Infarct size is expressed both as a percentage of the total ventricle and the area at risk.

Statistical Analysis

Group data is represented as means+/−SEM. Comparisons between treatment groups are made using ANOVA with $p<0.05$ considered significant. Post hoc comparisons may be made using either Dunnett's test or Tukey's test.

The compounds of the present invention showed activity when tested by this method.

Example 39

Evaluations of Sensorimotor Behavior

A. Fore and Hindlimb Grip Strength Test in Rats

Animals with cerebral infarction induced by transient or permanent unilateral occlusion of the middle cerebral artery (MCA) and sham-operated rats are tested for grip strength, a standard model of neuromuscular function and sensorimotor integration, using a Computerized Grip Strength Meter for Rats (Dual Stand Model, Columbus Instruments, Columbus, Ohio).

Animals are moved into the testing room for 30 minutes before testing. Prior to testing, each gauge is calibrated with a set of known weights and the apparatus is adjusted for the size of animal, according to manufacturer's instructions. The forelimb measurements are carried out with the meter in the tension peak mode to freeze the reading as the subject is pulled away from the grip bar. The hindlimb measurements are carried out with the meter in the compression peak mode to freeze the reading as the subject's hindlimbs are pulled over the bar toward the meter. Each animal is hand-held by the investigator as pulled past the grip bars, using a consistent technique, leaving the fore and hind limbs free to grasp the grip bars.

Testing is carried out on postoperative day 2 and repeated, in a blind-randomized fashion, twice weekly for a defined interval. Typically, three successive readings are taken for each animal with an intertrial interval long enough to record the data and zero both meters for the next trail.

B. Rota-Rod Test in Rats

Apparatus: Rota-Rod Treadmill for Rats (7750 Accelerating Model, from UGO BASILE, COMERIO-ITALY).

Procedure: Animals with cerebral infarction induced by transient or permanent unilateral occlusion of the middle cerebral artery (MCA) and sham-operated rats are tested in this study, using a Rota-Rod Treadmill for Rats (7750 Accelerating Model, UGO Basile, Comerio, Italy). The animals are moved into the testing room 30 minutes before testing. Every rat receives 2-3 training runs of 1-2 minutes at intervals of 2-3 hours before testing.

The cylinder on the apparatus is set in motion before placing the rats in position. The motor is set at a constant selected speed in 7700 on RESET mode, and the rats are placed, one by one, in their sections.

Testing is carried out on postoperative day 2 and repeated, in a blind-randomized fashion, twice weekly for a defined interval. Typically, three successive readings are taken for each animal with an intertrial interval long enough to record the data and zero both meters for the next trail.

The compounds of the present invention can be tested by this method.

Example 40

Model of Congestive Heart Failure

Experimental Preparation 225-275 g male Sprague-Dawley rats are anaesthetized with ketamine/xylazine (95 mg/kg and 5 mg/kg) and intubated with a 14-16-gauge modified intravenous catheter. Core body temperature is maintained at 37° C. by using a heating blanket. The surgical area is clipped and scrubbed, and the animal is placed in right lateral recumbency and initially placed on a ventilator with a peak inspiratory pressure of 10-15 cm $H_2O$ and respiratory rate 60-110 breaths/min. 100% $O_2$ is delivered to the animals by the ventilator. ECG electrodes are positioned to record a standard Lead II ECG. An incision is made over rib cage over the 4th-5th intercostal space. The underlying muscles are dissected with care to avoid the lateral thoracic vein, to expose the intercostal muscles. The chest cavity is entered through 4th-5th intercostal space, and the incision expanded to allow visualization of the heart. The pericardium is opened to expose the heart.

A 6-0 silk suture with a taper needle is passed around the left coronary artery near its origin, about 1 mm from the insertion of the left auricular appendage. The coronary artery is occluded by tying the suture around the artery. The ECG is monitored for S-T changes indicative of ischemia. If the animal develops ventricular fibrillation, gentle cardiac massage is used to convert the animal to a normal rhythm. Sham operated controls are subjected to the same procedure, but the suture is not tied off. The incision is closed in three layers. Infected or moribund animals are eliminated from the study.

Four weeks after surgery, the animals are anesthetized, and a catheter is placed in the right carotid artery and advanced into the left ventricle for hemodynamic measurements. Pressure traces are recorded and analyzed for heart rate, left ventricular systolic and diastolic pressure, left ventricular developed pressure, and dP/dt max and min. After measurements are taken, 2 ml blood is removed and placed in serum and plasma tubes. The heart is removed and placed on a Langendorff apparatus as follows:

Langendorff Procedure

Buffer preparation Krebs-Henseleit (KH) buffer solution containing NaCl 118 mmol/L, KCl 4.7 mmol/L, MgSO4 1.2 mmol/L, KHPO4 1.2 mmol/L, Glucose 11 mmol/L, NaHCO3 25 mmol/L and CaCl2 2.5 mmol/L (Sigma) was made up fresh each day using Nanopure pyrogen-free water.

The animal receives 200 units of heparin, the thorax is opened and the heart is rapidly excised and placed in ice-cold KH buffer solution. After the contractile activity of the heart completely ceases, the heart is trimmed and the ascending aorta freed from the connective tissue. The heart is quickly weighed, then the aorta is cannulated, and the heart mounted on a non-recirculation Langendorff perfusion apparatus (Radnoti Glass Technology, Inc., Monrovia, Calif.). The heart is perfused in a retrograde fashion via the aorta with KH buffer solution oxygenated with 95% $O_2$ and 5% $CO_2$ to maintain pH 7.4 at 37° C. To assess contractile function, a latex balloon is inserted into the left ventricle through the mitral orifice and connected to a pressure transducer by rigid polyethylene tubing. The balloon is inflated with water to a left ventricular end-diastolic pressure (LVEDP) of 1 to 10 mm Hg. Flow is initiated at 12 ml/min and adjusted during the first 15 minutes of baseline to obtain a perfusion pressure between 65 and 75 mmHg. Target parameters for baseline are as follows:

Perfusion pressure 65-75 mmHg
LVEDP 10 mmHg

The heart is allowed to stabilize for 15 minutes. After this time functional measurements are taken, after which a pressure volume curve is generated by adjusting the volume in the balloon in 0.05 ml increments and recording ventricular pressures. The left ventricular systolic pressure (LVSP), left ventricular end diastolic pressure (LVEDP), left ventricular developed pressure (LVDP), first derivative of the rise and fall in the left ventricular pressure (dp/dt max, dp/dt min), perfusion pressure and heart rate are automatically recorded using a computerized data acquisition system.

Other Measurements

After removal, the heart, lungs and liver are weighed. The lungs and liver are weighed and dried overnight for determination of wet to dry ratios.

After completing the Langendorff procedure, the heart is placed in cold saline to stop the beating, then cut into five 2-mm thick transverse slices from apex to base. Slice #3 will be incubated in 1% triphenyltetrazolium chloride (TTC) in 0.9% saline for 20 minutes at 37° C. Tetrazolium reacts with NADH in the presence of dehydrogenase enzymes causing viable tissue to stain a deep red color and that is easily distinguished from the infarcted pale-unstained necrotic tissue. The slice is placed apex side down in the lid of a small petri dish for the staining procedure. The bottom of the dish is placed over the slice to keep it flat. The slice is then photographed and the areas of infarcted tissue, left and right ventricle are determined using a computerized image analysis system. Infarct size is expressed as a percentage of the total ventricle. Total area of the left and right ventricle is measured. The remaining sections are divided into right and left ventricle and frozen for thiobarbituric reactive substances (TBARS) and glutathione assays.

Treatment Protocol

No treatment is given to the sham operated and control groups.

Measurements for CHF Study

In vivo measurements are made of heart rate (HR), left ventricular systolic pressure (LVSP), left ventricular end diastolic pressure (LVEDP), dP/dt min and max, right ventricular systolic pressure (RVSP), right ventricular diastolic pressure (RVDP), and right ventricular end diastolic pressure (RVEDP), as well as total body weight. Ex vivo measurements are made of HR, LVSP, LVEDP, dP/dt min and max, and pressure volume curve. Also measured ex vivo are heart weight, infarct size, Glutathione perosidase (GPX), catalase, thiobarbituric reactive substances (TBARS), glutathione ratio (GSH/GSSG), lung and liver wet to dry weight ratios, serum isoprostane and interleukin-6 (IL-6).

The compounds of the present invention can be tested by this method.

Example 41

Interleukin-1.Beta. Microglial Cell Assay

Materials and Equipment
A. Materials for Cell Preparation and Experiment
 Mouse microgial cell line
 DMEM High Glucose media (Gibco Catalog #11965-092)
 FBS (Hyclone Catalog #SH30070.03)
 100× Penicillin/Streptomycin (Gibco Catalog #15140-122).
 LPS (Sigma Catalog #L2537)
 Interferon-gamma (Sigma Catalog #I4777)
 Cell Tracker Green (Molecular Probes Catalog #C2925)
 HBSS buffer (950 ml Pyrogen-free water, 2.44 g/L MgCl2.6H20, 3.73 g/L KCl, 59.58 g/L Hepes, 58.44 g/L NaCl, 1.36 g/L KH2PO4, 1.91 g/L CaCl2 .2H2O and pH to 4.5 with HCl)
 Sterile 96-well plates precoated with poly-D-lysine (Corning Catalog #3665)
 96-well deep well mother plate, DyNA Block 1000 (VWR Catalog #40002-008)
B. Materials for Il-1 Beta ELISA
 Mouse IL-1 beta Duo Set (R & D Systems Catalog #DY401)
 Substrate Solution (R & D Systems Catalog #DY 999)
 Bovine Serum Albumin fraction V (BSA V) (Sigma Catalog #A4503)
 96-well Costar EIA high binding plates (VWR Catalog #29442-302)
 Plate seal (VWR Catalog #29442-310)
 PBS (Irvine Scientific Catalog #9240)
 Cell Culture Grade Water (Irvine Scientific Catalog #9312)
 Tween 20 (Sigma Catalog #P 1379)
 Sucrose (Sigma Catalog #S7903)
 Sodium Azide (Sigma Catalog #S 8032)
 $H_2SO_4$ 5N (VWR Catalog #JT 5691-2)
Experimental Preparation and Procedure:
 LPS Activation:
 Mouse microglial cells were seeded in poly-D-lysine coated 96-well plates at a density of 10,000 cells/well and allowed to attach for 24 hours. Cells were stimulated by addition of LPS (10 μg/ml) and IFN gamma (10 ng/ml) in the presence or absence of test article. The cells were then incubated for 24 hours at 37° C., after which time the media was removed and used for cytokine determination as described below.
 Cell Viability:
 Viability of mouse microglial cells after exposure to the test article was determined using a fluorescent viability dye, Cell Tracker Green. Cell Tracker Green was used at a working concentration of 5 μM in 1× HBSS. Cells were washed once with HBSS (200 μl/well) and 100 μl Cell Tracker Green was added to each well. Cells were then incubated at 37° C. for 30 minutes, after which time the Cell Tracker was removed and the cells were washed once with HBSS (200 μl/well). 100 μl fresh HBSS was added to each well and the plate was read on a Fluoroskan plate reader using an excitation wavelength of 485 nm and an emission wavelength of 538 nm.
Mouse IL-1Beta Elisa:
Solutions:
Wash Buffer: PBS 1L+500 μl Tween 20 (final 0.05%) pH 7.2-7.4.
Blocking Buffer: 500 ml PBS+5 g BSA V (1%)+25 g Sucrose (5%)+0.25 g Sodium Azide (0.05%).
Reagent Diluent: 500 ml PBS+5 g BSA V (1%) pH 7.2-7.4 and filter sterilize through 0.2 μm.
Stop Solution: 2N sulfuric acid.
 Duo Set Preparations:
1. The IL-1.beta. capture antibody was reconstituted in 1 ml of PBS to give a final concentration of 720 μg/ml, and the working concentration was 4 μg/ml. For coating one 96-well plate (at 100 μl/well) 56 μl of the 720 μg/ml stock was diluted into 10 ml of PBS.
2. The IL-1.beta. standards were reconstituted in 0.5 ml of Reagent Diluent (70 ng/ml). For a high standard of 1 ng/ml (2 wells at 100 μl each+enough for series dilution) 7.1 μl of the 70 ng/ml standard were diluted into 0.5 ml of Reagent Diluent
3. The IL-1.beta. detection antibody was reconstituted in 1 ml of Reagent Diluent to give a final concentration of 18 μg/ml and the working concentration is 100 ng/ml. For one 96-well plate (at 100 μl/well) 56 μl of the 18 μg/ml stock was diluted into 10 ml of Reagent Diluent.
 IL-1.Beta ELISA Procedure:
Plate Preparation:
1. The Costar EIA Hi-binding plate was coated with capture antibody at 4 μg/ml. Each well was coated with 100 μl, and the plate was sealed and incubated overnight at room temperature.
2. Each well was aspirated and washed 3× with Wash Buffer. Each well was filled to the top, dispensed, and any remaining buffer was removed by inverting the plate and gently blotting against clean paper towels.
3. Non-specific binding sites were blocked by adding 300 μl of Blocking Buffer to each well, and after sealing incubating for at least 1 hour at room temperature.
4. After washing the plate was now ready for the samples.
Assay Procedure:
5. 100 μl of either standard or sample were added in each well of the capture-coated and pre-blocked plate. The plate was sealed and incubated for 2 hours at room temperature, followed with washing as in step 2.
6. 100 μl of the detection antibody (100 g/ml) were added to each well.
7. The plate was sealed and incubated at room temperature for 2 hours, followed with washing as in step 2.
8. 100 μl of the working dilution of Streptavidin-HRP was added, and the plate was sealed and incubated in the dark for 20 minutes at room temperature, followed with washing as in Step 2.
9. The fresh Substrate Solution was prepared by mixing Color Reagent A ($H_2O_2$) and Color Reagent B (Tetramethylbenzidine) in a 1:1 ratio. 100 μl of this Substrate Solution mixture was added to each well and the plate was incubated in the dark for 20 minutes at room temperature.
10. 50 μl of Stop Solution was added to each well, mixing was ensured by gently tapping.
11. Each plate was read with the Spectramax once at 450 nm.
Results
 When tested as described above, compounds of the present invention, such as:
3-(2-chloro-4-fluoro-phenylsulfanyl)-2-(2-chloro-4-fluoro-phenylsulfanylmethyl)-4-hydroxy-5-oxo-2,5-dihydro-furan-2-carboxylic acid ethyl ester;
3-(4-fluoro-benzylsulfanyl)-4-hydroxy-5-oxo-5H-furan-2,2-dicarboxylic acid diethyl ester;
4-(benzooxazol-2-ylsulfanyl)-5-(benzooxazol-2-ylsulfanylmethyl)-3-hydroxy-5-hydroxymethyl-5H-furan-2-one;
3-(2-chloro-6-fluoro-benzylsulfanyl)-2-(2-chloro-6-fluoro-benzylsulfanylmethyl)-4-hydroxy-5-oxo-2,5-dihydro-furan-2-carboxylic acid ethyl ester;

4-hydroxy-3-(5-methoxy-benzothiazol-2-ylsulfanyl)-2-(5-methoxy-benzothiazol-2-ylsulfanylmethyl)-5-oxo-2,5-dihydro-furan-2-carboxylic acid ethyl ester;

3-(2,4-dichloro-benzylsulfanyl)-2-(2,4-dichloro-benzylsulfanylmethyl)-4-hydroxy-5-oxo-2,5-dihydro-furan-2-carboxylic acid ethyl ester;

2-(benzothiazole-2-sulfinylmethyl)-3-(benzothiazol-2-ylsulfanyl)-4-hydroxy-5-oxo-2,5-dihydro-furan-2-carboxylic acid ethyl ester;

4-hydroxy-3-(6-nitro-benzothiazol-2-ylsulfanyl)-2-(6-nitro-benzothiazol-2-ylsulfanylmethyl)-5-oxo-2,5-dihydro-furan-2-carboxylic acid ethyl ester;

3-(furan-2-ylmethanesulfinyl)-2-(furan-2-ylmethanesulfinylmethyl)-4-hydroxy-5-oxo-2,5-dihydro-furan-2-carboxylic acid ethyl ester;

3-(benzooxazol-2-ylsulfanyl)-2-(benzothiazol-2-ylsulfanylmethyl)-4-hydroxy-5-oxo-2,5-dihydro-furan-2-carboxylic acid methyl ester;

4-hydroxy-3-[4-(2-methoxycarbonyl-vinyl)-phenylsulfanyl]-2-[4-(2-methoxycarbonyl-vinyl)-phenylsulfanylmethyl]-5-oxo-2,5-dihydro-furan-2-carboxylic acid ethyl ester;

3-(furan-2-ylmethylsulfanyl)-2-(furan-2-ylmethylsulfanylmethyl)-4-isobutyryloxy-5-oxo-2,5-dihydro-furan-2-carboxylic acid ethyl ester;

4-(2,2-dimethyl-propionyloxy)-3-(furan-2-ylmethylsulfanyl)-2-(furan-2-ylmethylsulfanylmethyl)-5-oxo-2,5-dihydro-furan-2-carboxylic acid ethyl ester;

4-(2,2-dimethyl-propionyloxy)-3-ethoxycarbonylmethylsulfanyl-2-ethoxycarbonylmethylsulfanylmethyl-5-oxo-2,5-dihydro-furan-2-carboxylic acid ethyl ester;

4-hydroxy-5-oxo-3-(4-phenyl-thiazol-2-ylsulfanyl)-2-(4-phenyl-thiazol-2-ylsulfanylmethyl)-2,5-dihydro-furan-2-carboxylic acid ethyl ester;

3-(furan-2-ylmethylsulfanyl)-2-(furan-2-ylmethylsulfanylmethyl)-4-hydroxy-5-oxo-2,5-dihydro-furan-2-carboxylic acid ethyl ester;

3-butylsulfanyl-2-butylsulfanylmethyl-4-hydroxy-5-oxo-2,5-dihydro-furan-2-carboxylic acid ethyl ester;

4-hydroxy-3-(4-methoxy-benzylsulfanyl)-2-(4-methoxy-benzylsulfanylmethyl)-5-oxo-2,5-dihydro-furan-2-carboxylic acid ethyl ester;

3-benzylsulfanyl-2-benzylsulfanylmethyl-4-hydroxy-5-oxo-2,5-dihydro-furan-2-carboxylic acid ethyl ester;

2-(1H-benzoimidazol-2-ylsulfanylmethyl)-4-ethoxy-3-(1-ethyl-1H-benzoimidazol-2-ylsulfanyl)-5-oxo-2,5-dihydro-furan-2-carboxylic acid ethyl ester;

3-(benzothiazol-2-ylsulfanyl)-2-(benzothiazol-2-ylsulfanylmethyl)-4-hydroxy-5-oxo-2,5-dihydro-furan-2-carboxylic acid ethyl ester;

4-hydroxy-5-oxo-3-(1-oxy-pyridin-2-ylsulfanyl)-2-(1-oxy-pyridin-2-ylsulfanylmethyl)-2,5-dihydro-furan-2-carboxylic acid ethyl ester;

4-hydroxy-5-oxo-3-(4-trifluoromethyl-pyrimidin-2-ylsulfanyl)-2-(4-trifluoromethyl-pyrimidin-2-ylsulfanylmethyl)-2,5-dihydro-furan-2-carboxylic acid ethyl ester;

4-hydroxy-3-(4-methyl-pyrimidin-2-ylsulfanyl)-2-(4-methyl-pyrimidin-2-ylsulfanylmethyl)-5-oxo-2,5-dihydro-furan-2-carboxylic acid ethyl ester;

3-cyclohexylsulfanyl-2-cyclohexylsulfanylmethyl-4-hydroxy-5-oxo-2,5-dihydro-furan-2-carboxylic acid ethyl ester;

4-Hydroxy-5-oxo-3-(pyrimidin-2-ylsulfanyl)-2-(pyrimidin-2-ylsulfanylmethyl)-2,5-dihydro-furan-2-carboxylic acid ethyl ester;

3-(Benzoselenazol-2-ylsulfanyl)-2-(benzoselenazol-2-ylsulfanylmethyl)-4-hydroxy-5-oxo-2,5-dihydro-furan-2-carboxylic acid ethyl ester;

3-Cyclohexylsulfanyl-2-cyclohexylsulfanylmethyl-4-hydroxy-5-oxo-2,5-dihydro-furan-2-carboxylic acid ethyl ester;

3-(Benzothiazol-2-ylsulfanyl)-2-(benzothiazol-2-ylsulfanylmethyl)-4-hydroxy-5-oxo-2,5-dihydro-furan-2-carboxylic acid isopropyl ester; and 4-Hydroxy-3-(1-methyl-1H-benzoimidazol-2-ylsulfanyl)-2-(1-methyl-1H-benzoimidazol-2-ylsulfanylmethyl)-5-oxo-2,5-dihydro-furan-2-carboxylic acid ethyl ester inhibited the IL-1beta induction with an $EC_{50}$ of 20 μM or less.

Example 42

Rat Paw Edema Assay

Animal Preparation:

Male Sprague-Dawley rats weighing between 175 to 200 g are used in this study. Animals are allowed free access to water and commercial rodent diet under standard laboratory conditions. Room temperature is maintained at 20-23° C. and room illumination is on a 12/12-hour light/dark cycle. Animals are acclimatized to the laboratory environment 5 to 7 days prior to the study.

Experimental Procedure:

Each animal is treated by administration of vehicle, reference or test substance one hour prior to carrageenan injection, as follows:

I.V. Infusion via Femoral Vein: Anesthesia is maintained by inhalation of 3.0% isoflurane (Aerrane, Front Dodge, Iowa) in oxygen throughout the entire procedure. The exterior site of the right femoral vein is shaved and sterilized prior to surgery. A 3-cm incision is made in the right groin region and the femoral vein is isolated. The femoral vein is temporarily ligated with a micro-vascular clip, and a small incision is made on the femoral vein to introduce and advance a polyethylene (PE-50) catheter (Becton. Dickinson and Co., Sparks, Md.). The catheter is secured in place with suture (silk 5/0, Carlisle Laboratories, Farmers Branch, Tex.). The other end of the catheter is attached to a syringe filled with the saline for the bolus injection. Using a hemostat, a pocket is made subcutaneously on the back of the animal so the PE catheter can be brought up to the exteriorization point between the shoulder blade for either a bolus injection or a continuous injection by an osmotic pump.

I.P. Injection: An awake rat is held in a standard hand held position. A 23¾G needle is injected into the lower right quarter of the abdomen pass the peritoneum, slightly off the midline. To avoid organ injection, the plunger of the syringe is slightly pulled back. If no fluid is withdrawn, the content of the syringe is delivered into the abdominal cavity.

Gavage Feeding: A standard rat gavage tube (Popper & Sons Inc, NY) is attached to a 3-cc hypodermic syringe. The animal is held in a vertical position. The feeding tube is placed into the mouth and then gently advanced until it reaches the stomach (the approximate insertion length of the tube should be measured prior to feeding). The content of the syringe is slowly delivered, and then the tube is withdrawn.

One hour post treatment each animal is anesthetized with 3.0% isoflurane (Aerrane, Front Dodge, Iowa) in oxygen and administered 100 μl of 1% Carrageenan Lambda type IV (Sigma Chemical Company, St. Louis, Mo.) suspension in saline, into the intraplantar surface of the right hind paw. Paw edema is measured four hours after carrageenan injection, either by measuring the increase in paw volume using a plethysmometer or the increase in paw weight using a fine scale. Immediately prior to edema measurement, the animals are euthanized via $CO_2$ asphyxiation and 500 μl blood is withdrawn by cardiac puncture for later analysis. Paw volume is determined by the extent to which water is displaced by the paw from a pre-calibrated chamber. The volume of the left hind paw (control) is subtracted from the volume of the right hind paw (carrageenan-treated) to determine the volume of carrageenan-induced edema. To measure the weight difference between paws, both hind paws were removed and weighed separately.

To minimize the variation in the model following steps are taken:
- Carrageenan is made fresh every day prior to the study (2-3 hours before injection).
- The plethysmometer is calibrated each day prior to the study.
- If carrageenan injection causes significant bleeding or a hematoma on the treated foot, the animal is excluded from the study.
- Each paw is marked at the tibio-tarsal joint across the ankle prior to measurements, to ensure each paw is submerged at the same level.
- If reading on the volume needs to be repeated, the paw must be dried off completely.

Statistical Analysis

The difference of the weight or the volume between right and left paw is calculated for each animal for the analysis. Group data are presented as means+/−SEM and $p<0.05$ are considered significant. Inter-group comparisons are carried out by unpaired student t test (between two groups) or one-way ANOVA followed by post hoc Bonferroni's multiple comparisons.

Results

Certain compounds of the present invention showed activity when tested by this method.

Example 43

Mouse Ear Inflammatory Response to Topical Arachidonic Acid

Animals: Balb C Mice 23-28 gms, from Simonsen Labs, Gilroy, Calif.

Materials:
Arachidonic Acid, 99% pure from Porcine Liver (Sigma Aldrich) reconstituted in acetone 2 mg/20 ul (200 mg/ml).
Inhalation anesthesia: Isoflurane 3% (Baxter).
Blood Sample tubes: Microtainer tubes w/ heparin (Becton Dickinson).
TNFa Elisa assay (R&D Science).

Experimental Procedure

Test compounds, positive control (arachidonic acid only) and standard (Dexamethasone @0.1 mg/kg) prepared in solutions of acetone, ethanol or aqueous ethanol, are applied to both sides of the right ear with an Eppendorf repipettor pipette, in a volume of 10 μl each side (20 μl total). 30 Minutes later, 10 μl of arachidonic acid is applied to both sides of the right ear (20 μl total). One hour after the application of arachidonic acid, the mice are deeply anesthetized with isoflurane and a blood sample is taken via the orbital sinuses and placed in Microtainer tubes. The animals are then euthanized by $CO_2$ inhalation and the right ears removed at the base. A uniform plug of ear tissue is obtained using a 8 mm dermal punch. The earplugs are quickly weighed to the nearest 0.1 mg and then flash frozen for TNFα determination.

Statistical Analysis:

Group data are presented as mean+/−SEM and $p<0.05$ is considered significant. Inter-group comparisons are carried out by unpaired student t tests (between two groups) or ANOVA (three or more groups) followed by post hoc Dunnet's test.

Results

The compounds of the present invention, such as:
3-(Benzothiazol-2-ylsulfanyl)-2-(benzothiazol-2-ylsulfanylmethyl)-4-hydroxy-5-oxo-2,5-dihydro-furan-2-carboxylic acid ethyl ester;
4-Hydroxy-5-oxo-3-(5-phenyl-2H-[1,2,4]triazol-3-ylsulfanyl)-2-(5-phenyl-2H-[1,2,4]triazol-3-ylsulfanylmethyl)-2,5-dihydro-furan-2-carboxylic acid ethyl ester;
4-(1H-Benzoimidazol-2-ylsulfanyl)-5-(1H-benzoimidazol-2-ylsulfanylmethyl)-3-hydroxy-5-hydroxymethyl-5H-furan-2-one;
4-Hydroxy-5-oxo-3-(4-trifluoromethyl-pyrimidin-2-ylsulfanyl)-2-(4-trifluoromethyl-pyrimidin-2-ylsulfanylmethyl)-2,5-dihydro-furan-2-carboxylic acid ethyl ester;
4-Hydroxy-5-oxo-3-(pyrimidin-2-ylsulfanyl)-2-(pyrimidin-2-ylsulfanylmethyl)-2,5-dihydro-furan-2-carboxylic acid ethyl ester;
4-Hydroxy-5-oxo-3-(2-sulfo-ethylsulfanyl)-2-(2-sulfo-ethylsulfanylmethyl)-2,5-dihydro-furan-2-carboxylic acid ethyl ester;
4-Hydroxy-5-oxo-3-(7-trifluoromethyl-quinolin-4-ylsulfanyl)-2-(7-trifluoromethyl-quinolin-4-ylsulfanylmethyl)-2,5-dihydro-furan-2-carboxylic acid ethyl ester;
3-(Benzoselenazol-2-ylsulfanyl)-2-(benzoselenazol-2-ylsulfanylmethyl)-4-hydroxy-5-oxo-2,5-dihydro-furan-2-carboxylic acid ethyl ester;
4-Hydroxy-5-oxo-3-(5-sulfonic acid-1H-benzoimidazol-2-ylsulfanyl)-2-(5-sulfonic acid-1H-benzoimidazol-2-ylsulfanylmethyl)-2,5-dihydro-furan-2-carboxylic acid ethyl ester;
3-(1H-Benzoimidazol-2-ylsulfanyl)-2-(1H-benzoimidazol-2-ylsulfanylmethyl)-4-hydroxy-5-oxo-2,5-dihydro-furan-2-carboxylic acid;
4-Hydroxy-5-oxo-3-(pyrrolidine-1-carbothioylsulfanyl)-2-(pyrrolidine-1-carbothioylsulfanylmethyl)-2,5-dihydro-furan-2-carboxylic acid ethyl ester;
3-Cyclohexylsulfanyl-2-cyclohexylsulfanylmethyl-4-hydroxy-5-oxo-2,5-dihydro-furan-2-carboxylic acid ethyl ester;
3-(2-Dimethylamino-ethylsulfanyl)-2-(2-dimethylamino-ethylsulfanylmethyl)-4-hydroxy-5-oxo-2,5-dihydro-furan-2-carboxylic acid ethyl ester, hydrochloride salt;
4-Hydroxy-5-oxo-3-(pyridin-4-ylsulfanyl)-2-(pyridin-4-ylsulfanylmethyl)-2,5-dihydro-furan-2-carboxylic acid ethyl ester;
5,8-Dichloro-3-hydroxy-2-oxo-2H-1-oxa-4,9-dithia-benzo[f]azulene-10a-carboxylic acid ethyl ester;
3-(5-Chloro-benzothiazol-2-ylsulfanyl)-2-(5-chloro-benzothiazol-2-ylsulfanylmethyl)-4-hydroxy-5-oxo-2,5-dihydro-furan-2-carboxylic acid ethyl ester;
3-(5-Amino-[1,3,4]thiadiazol-2-ylsulfanyl)-2-(5-amino-[1,3,4]thiadiazol-2-ylsulfanylmethyl)-4-hydroxy-5-oxo-2,5-dihydro-furan-2-carboxylic acid ethyl ester;
showed significant reduction in edema (10 to 70%, $p<0.05$) when tested by this method.

Example 44

Skin Protection Assay

Cytoprotective activity for skin can be evaluated in cell culture using the Epiderm Skin Model (EPI-100) from the Mattek Corporation of Ashland, Mass. Cell cultures of neonatal foreskin are cultured in accordance with the manufacturer's directions, and are assayed for percent cellular viability by measuring the amount of 3-(4,5-dimethylthazol-2-yl)-2,5-diphenyltetrazolium bromide (MTT) dye taken up by the cells. Viable cells take up this dye and convert it to insoluble formazin crystals that reside in the mitochondria of the cells until extracted with alcohol. The amount of MTT converted to extractable formazin crystals is directly proportional to the viability of the cell culture. MTT is measured spectrophotometrically.

Cells are exposed to UV light at a rate of 1.5 Minimal Erythemal Dose (MED) per hour per square centimeter, for a total dose of about 31.5 mJ/cm$^2$, from a solar simulator (filtered to yield wavelengths in the region of 290-400 nm) in the presence of the cytoprotective compound or mixtures thereof to measure the effect of test compounds to protect the cell culture from the generation of free radicals resulting from the ultraviolet light.

The controls for this study are cell cultures without added test compound (positive control). All cell cultures are also compared to cultures that are not exposed to UV light and do not include the cytoprotective agents or blends in order to determine percent cellular viability (negative control). This latter measurement is assumed to be equal to 100% viability.

Cell cultures treated with certain furanone compounds of the invention show greater survival than do positive control cell cultures, when tested as described above.

Example 45

E-Selectin Cell Inflammation Assay

Endothelial-Leukocyte Adhesion Molecule (ELAM), also known as E-selectin, is expressed on the surface of endothelial cells. In this assay, lipopolysaccharide (LPS) and IL-1β are used to stimulate the expression of ELAM; test agents are tested for their abilities to reduce this expression, in accordance with studies showing that reduction of leukocyte adhesion to endothelial cell surface is associated with decreased cellular damage (e.g., Takada, M., Et al., Transplantation 64: 1520-25, 1997; Steinberg, J. B., et al., J. Heart Lung Trans. 13:306-313, 1994).

Endothelial cells may be selected from any of a number of sources and cultured according to methods known in the art; including, for example, coronary artery endothelial cells, human brain microvascular endothelial cells (HBMEC; Hess, D.C., et al., Neurosci. Left. 213(1): 37-40, 1996), or lung endothelial cells. Cells are conveniently cultured in 96-well plates. Cells are stimulated by adding a solution to each well containing 10 μg/ml LPS and 100 pg/ml IL-1β for 6 hours in the presence of test agent (specific concentrations and time may be adjusted depending on the cell type). Treatment buffer is removed and replaced with pre-warmed Fixing Solution® (100 μl/well) for 25 minutes at room temperature. Cells are then washed 3×, then incubated with Blocking Buffer (PBS+ 2% FBS) for 25 minutes at room temperature. Blocking Buffer containing Monoclonal E-Selectin Antibody (1:750, Sigma Catalog #S-9555) is added to each well. Plates are sealed and stored at 4° overnight. Plates are washed 4× with 160 μL Blocking Buffer per well. Second Antibody-HRP diluted 1:5000 in Blocking Buffer is then added (100 μL/well), and plates are incubated at room temperature (protected from light) for two hours. Plates are then washed 4× with Blocking Buffer before addition of 100 μL of ABTS Substrate solution at room temperature (Zymed, Catalog #00-2024). Wells are allowed to develop for 35 minutes, before measurement at 402 nm in a Fluoroskan® Reader with shake program for 10 seconds. Positive results are recorded as a decrease in ELAM concentration in tested wells, as compared to control wells.

In an ELAM assay, such as the one described herein, the following compounds of the present invention were able to reduce the expression of ELAM at $EC_{50}$ of 30 μM or less:

R-3-[2-(4-Amino-4-carboxy-butyrylamino)-2-(carboxymethyl-carbamoyl)-ethylsulfanyl]-2-[2-(4-amino-4-carboxy-butyrylamino)-2-(carboxymethyl-carbamoyl) ethylsulfanylmethyl]-4-hydroxy-5-oxo-2,5-dihydro-furan-2-carboxylic acid ethyl ester;

3-(5-Chloro-benzothiazol-2-ylsulfanyl)-2-(5-chloro-benzothiazol-2-ylsulfanylmethyl)-4-hydroxy-5-oxo-2,5-dihydro-furan-2-carboxylic acid ethyl ester;

3-Cyclohexylsulfanyl-2-cyclohexylsulfanylmethyl-4-hydroxy-5-oxo-2,5-dihydro-furan-2-carboxylic acid ethyl ester;

4-Hydroxy-5-oxo-3-(pyrrolidine-1-carbothioylsulfanyl)-2-(pyrrolidine-1-carbothioylsulfanylmethyl)-2,5-dihydro-furan-2-carboxylic acid ethyl ester;

3-(Benzoselenazol-2-ylsulfanyl)-2-(benzoselenazol-2-ylsulfanylmethyl)-4-hydroxy-5-oxo-2,5-dihydro-furan-2-carboxylic acid ethyl ester;

4-Hydroxy-5-oxo-3-(7-trifluoromethyl-quinolin-4-ylsulfanyl)-2-(7-trifluoromethyl-quinolin-4-ylsulfanylmethyl)-2,5-dihydro-furan-2-carboxylic acid ethyl ester;

4-Hydroxy-5-oxo-3-(2-sulfo-ethylsulfanyl)-2-(2-sulfo-ethylsulfanylmethyl)-2,5-dihydro-furan-2-carboxylic acid ethyl ester;

4-Hydroxy-5-oxo-3-(4-trifluoromethyl-pyrimidin-2-ylsulfanyl)-2-(4-trifluoromethyl-pyrimidin-2-ylsulfanylmethyl)-2,5-dihydro-furan-2-carboxylic acid ethyl ester;

4-Hydroxy-5-oxo-3-(1-oxy-pyridin-2-ylsulfanyl)-2-(1-oxy-pyridin-2-ylsulfanylmethyl)-2,5-dihydro-furan-2-carboxylic acid ethyl ester;

3-(Benzothiazol-2-ylsulfanyl)-2-(benzothiazol-2-ylsulfanylmethyl)-4-hydroxy-5-oxo-2,5-dihydro-furan-2-carboxylic acid ethyl ester;

3-(2-Chloro-phenylsulfanyl)-2-(2-chloro-phenylsulfanylmethyl)-4-hydroxy-5-oxo-2,5-dihydro-furan-2-carboxylic acid ethyl ester;

3-Hexylsulfanyl-2-hexylsulfanylmethyl-4-hydroxy-5-oxo-2,5-dihydro-furan-2-carboxylic acid ethyl ester;

4-Hydroxy-5-oxo-3-(1-phenyl-1H-tetrazol-5-ylsulfanyl)-2-(1-phenyl-1H-tetrazol-5-ylsulfanylmethyl)-2,5-dihydro-furan-2-carboxylic acid ethyl ester;

4-Hydroxy-3-(naphthalen-2-ylsulfanyl)-2-(naphthalen-2-ylsulfanylmethyl)-5-oxo-2,5-dihydro-furan-2-carboxylic acid ethyl ester;

4-Hydroxy-5-oxo-3-(4-phenyl-thiazol-2-ylsulfanyl)-2-(4-phenyl-thiazol-2-ylsulfanylmethyl)-2,5-dihydro-furan-2-carboxylic acid ethyl ester;

4-(5-sulfo-1H-benzoimidazol-2-ylsulfanyl)-5-(5-sulfo-1H-benzoimidazol-2-ylsulfanylmethyl)-3-hydroxy-5-hydroxymethyl-5H-furan-2-one;

3-(Furan-2-ylmethylsulfanyl)-2-(furan-2-ylmethylsulfanylmethyl)-4-isobutyryloxy-5-oxo-2,5-dihydro-furan-2-carboxylic acid ethyl ester;

4-Hydroxy-3-[4-(2-methoxycarbonyl-vinyl)-phenylsulfanyl]-2-[4-(2-methoxycarbonyl-vinyl)-phenylsulfanylmethyl]-5-oxo-2,5-dihydro-furan-2-carboxylic acid ethyl ester;

4-Hydroxy-3-(6-nitro-benzothiazol-2-ylsulfanyl)-2-(6-nitro-benzothiazol-2-ylsulfanylmethyl)-5-oxo-2,5-dihydro-furan-2-carboxylic acid ethyl ester;

2-(Benzothiazole-2-sulfinylmethyl)-3-(benzothiazol-2-yl-sulfanyl)-4-hydroxy-5-oxo-2,5-dihydro-furan-2-carboxylic acid ethyl ester;
3-(2,4-Dichloro-benzylsulfanyl)-2-(2,4-dichloro-benzylsulfanylmethyl)-4-hydroxy-5-oxo-2,5-dihydro-furan-2-carboxylic acid ethyl ester;
4-Hydroxy-3-(5-methoxy-benzothiazol-2-ylsulfanyl)-2-(5-methoxy-benzothiazol-2-ylsulfanylmethyl)-5-oxo-2,5-dihydro-furan-2-carboxylic acid ethyl ester;
3-(2-Chloro-6-fluoro-benzylsulfanyl)-2-(2-chloro-6-fluoro-benzylsulfanylmethyl)-4-hydroxy-5-oxo-2,5-dihydro-furan-2-carboxylic acid ethyl ester;
Dimethylamino-acetic acid 3-(1H-benzoimidazol-2-ylsulfanyl)-2-(1H-benzoimidazol-2-ylsulfanylmethyl)-4-hydroxy-5-oxo-2,5-dihydro-furan-2-ylmethyl ester;
3-(2-Chloro-4-fluoro-phenylsulfanyl)-2-(2-chloro-4-fluoro-phenylsulfanylmethyl)-4-hydroxy-5-oxo-2,5-dihydro-furan-2-carboxylic acid ethyl ester;
3-(Benzothiazol-2-ylsulfanyl)-2-(benzothiazol-2-ylsulfanylmethyl)-4-hydroxy-5-oxo-2,5-dihydro-furan-2-carboxylic acid;
2-(Furan-2-ylmethanesulfinylmethyl)-3-(furan-2-ylmethanesulfonyl)-4-hydroxy-5-oxo-2,5-dihydro-furan-2-carboxylic acid ethyl ester;
3-(furan-2-ylmethanesulfinyl)-2-(furan-2-ylmethanesulfinylmethyl)-4-hydroxy-5-oxo-2,5-dihydro-furan-2-carboxylic acid ethyl ester;
4-(2,2-dimethyl-propionyloxy)-3-ethoxycarbonylmethylsulfanyl-2-ethoxycarbonylmethylsulfanylmethyl-5-oxo-2,5-dihydro-furan-2-carboxylic acid ethyl ester;
3-(2-Dimethylamino-ethylsulfanyl)-2-(2-dimethylamino-ethylsulfanylmethyl)-4-hydroxy-5-oxo-2,5-dihydro-furan-2-carboxylic acid;
3-(5,6-Dichloro-1H-benzoimidazol-2-ylsulfanyl)-2-(5,6-dichloro-1H-benzoimidazol-2-ylsulfanylmethyl)-4-hydroxy-5-oxo-2,5-dihydro-furan-2-carboxylic acid ethyl ester;
3-Benzylsulfanyl-2-benzylsulfanylmethyl-4-hydroxy-5-oxo-2,5-dihydro-furan-2-carboxylic acid ethyl ester;
3-(1H-Benzoimidazol-2-ylsulfanyl)-4-hydroxy-5-oxo-2,5-dihydro-furan-2-carboxylic acid ethyl ester;
4-Hydroxy-3-(5-methyl-1H-benzoimidazol-2-ylsulfanyl)-5-oxo-2,5-dihydro-furan-2-carboxylic acid 2-isopropyl-5-methyl-cyclohexyl ester;
Di-[2-(4-Hydroxy-5-oxo-2-carboxylic acid methyl ester)]-disulfide;
3-(4-Fluoro-benzylsulfanyl)-4-hydroxy-5-oxo-5H-furan-2,2-dicarboxylic acid diethyl ester;
4-(1H-Benzoimidazol-2-ylsulfanyl)-3-hydroxy-1-oxa-7,9-diaza-spiro[4,5]dec-3-ene-2,6,8,10-tetraone;
3-(Benzothiazol-2-ylsulfanyl)-2-(benzothiazol-2-ylsulfanylmethyl)-4-hydroxy-5-oxo-2,5-dihydro-furan-2-carboxylic acid isopropyl ester;
4-Acetoxy-3-(furan-2-ylmethylsulfanyl)-2-(furan-2-ylmethylsulfanylmethyl)-5-oxo-2,5-dihydro-furan-2-carboxylic acid ethyl ester;
4-Ethoxy-3-(1-ethyl-1H-benzoimidazol-2-ylsulfanyl)-2-(1-ethyl-1H-benzoimidazol-2-ylsulfanylmethyl)-5-oxo-2,5-dihydro-furan-2-carboxylic acid ethyl ester;
2-(1H-Benzoimidazol-2-ylsulfanylmethyl)-4-ethoxy-3-(1-ethyl-1H-benzoimidazol-2-ylsulfanyl)-5-oxo-2,5-dihydro-furan-2-carboxylic acid ethyl ester;
4-Acetoxy-3-benzylsulfanyl-2-benzylsulfanylmethyl-5-oxo-2,5-dihydro-furan-2-carboxylic acid ethyl ester; and
4-Hydroxy-3-(1-methyl-1H-benzoimidazol-2-ylsulfanyl)-2-(1-methyl-1H-benzoimidazol-2-ylsulfanylmethyl)-5-oxo-2,5-dihydro-furan-2-carboxylic acid ethyl ester.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:
1. A method of treatment for a mammal suffering from a dermatologic condition selected from the group consisting of contact dermatitis, acne, rosacea, and psoriasis, comprising administering a therapeutically effective amount of a compound of Formula I:

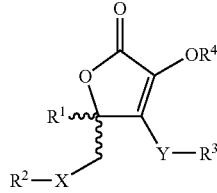

Formula I wherein:
$R^1$ is: C(O)OR'; —C(O)NR'R"; —CH$_2$OR'''; cyano; optionally substituted heterocyclyl; optionally substituted heterocyclyl-alkyl; optionally substituted heteroaryl, or optionally substituted heteroaralkyl;
$R^2$ is: optionally substituted alkyl; optionally substituted cycloalkyl; optionally substituted aryl; optionally substituted aralkyl; optionally substituted heterocyclyl; optionally substituted heteroaryl; optionally substituted heteroaralkyl; an optionally substituted nucleoside; an optionally substituted amino acid; or an optionally substituted di-, tri- or tetra-peptide;
$R^3$ is: optionally substituted alkyl; optionally substituted cycloalkyl; optionally substituted aryl; optionally substituted aralkyl; optionally substituted heterocyclyl; optionally substituted heteroaryl; optionally substituted heteroaralkyl; an optionally substituted nucleoside; an optionally substituted amino acid; or an optionally substituted di-, tri- or tetra-peptide;
$R^4$ is: hydrogen; alkyl; alkylcarbonyl; (poly)alkoxyalkylene; or dialkoxyphosphoryloxy;
X is: —S—; —S(O)—; —S(O)$_2$—; or X taken together with $R^2$ is —P(O)(OR')$_2$;
Y is: —S—; —S(O)—; —S(O)$_2$—; or Y taken together with $R^3$ is —P(O)(OR')$_2$;
or X—$R^2$ taken together with Y—$R^3$ form an optionally substituted aliphatic or aromatic ring;
R' is: hydrogen; alkenyl; optionally substituted alkyl; optionally substituted cycloalkyl; phosphoryl; or optionally substituted aryl;
R" is: hydrogen; alkenyl; optionally substituted alkyl; or optionally substituted aryl;
or R' and R" together with the atom to which they are attached form a 5- to 7-membered aromatic, saturated or unsaturated ring, optionally incorporating one or more additional heteroatoms chosen from N, O, or S, and optionally substituted with one or more substitutents selected from the group consisting of optionally substituted lower alkyl, halo, cyano, alkylthio, lower alkoxy, carboxy, benzyl, and oxo;

R''' is: hydrogen; alkenyl; optionally substituted alkyl; acyl, optionally substituted cycloalkyl; phosphoryl; or optionally substituted aryl;

or a compound of Formula III:

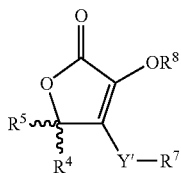

Formula III wherein:

$R^5$ is: —C(O)OR$^a$; —C(O)NR$^a$R$^b$; CH$_2$OR$^d$; —C(O)R$^c$; cyano; optionally substituted heterocyclyl; or optionally substituted heteroaryl;

$R^6$ is: hydrogen; —C(O)OR$^a$; —C(O)NR$^a$R$^b$; CH$_2$OR$^d$; —C(O)R$^c$; cyano; optionally substituted alkyl; optionally substituted heterocyclyl; optionally substituted aryl, or optionally substituted heteroaryl;

or $R^5$ and $R^6$ with the atom to which they are attached form an optionally substituted ring;

$R^7$ is: optionally substituted alkyl; optionally substituted cycloalkyl; optionally substituted aryl; optionally substituted aralkyl; optionally substituted heterocyclyl; optionally substituted heteroaryl; optionally substituted heteroaralkyl; an optionally substituted nucleoside; an optionally substituted amino acid; or an optionally substituted di-, tri- or tetra-peptide; with the proviso that when $R^6$ is alkyl, then $R^7$ is optionally substituted heterocyclyl, optionally substituted heteroaryl, or optionally substituted heteroaralkyl, or $R^5$ and $R^7$ with the atoms to which they are attached form an optionally substituted heterocyclic ring;

$R^8$ is: hydrogen; alkyl; alkylcarbonyl; (poly)alkoxyalkylene; or dialkoxyphosphoryloxy; Y' is: S—;

$R^a$ is: hydrogen; alkenyl; optionally substituted alkyl; optionally substituted cycloalkyl; or optionally substituted aryl;

$R^b$ is: hydrogen; alkenyl; optionally substituted alkyl; or optionally substituted aryl;

or $R^a$ and $R^b$ together with the atom to which they are attached for a 5- to 7-membered aromatic, saturated or unsaturated ring, optionally incorporating one or more additional heteroatom chosen from N, O, or S, and optionally substituted with one or more substituents selected from the group consisting of optionally substituted lower alkyl, halo, cyano, alkylthio, lower alkoxy, carboxy, benzyl, and oxo;

$R^c$ is: optionally substituted alkyl or optionally substituted aryl; and $R^d$ is: hydrogen; alkenyl; optionally substituted alkyl; acyl; optionally substituted cycloalkyl; or optionally substituted aryl; including single tautomers; single stereoisomers and mixtures of tautomers and/or stereoisomers, and the pharmaceutically acceptable salts thereof.

2. The method of claim 1, wherein X and Y are both —S—.

3. A method of treatment for a mammal suffering from a dermatologic condition selected from the group consisting of contact dermatitis, acne, rosacea, and psoriasis comprising administering a therapeutically effective amount of a compound selected from the group consisting of:

R-3-[2-(4-Amino-4-carboxy-butyrylamino)-2-(carboxymethyl-carbamoyl)-ethylsulfanyl]-2-[2-(4-amino-4-carboxy-butyrylamino)-2-(carboxymethyl-carbamoyl-) ethylsulfanylmethyl]-4-hydroxy-5-oxo-2,5-dihydro-furan-2-carboxylic acid ethyl ester;

3-(5-Chloro-benzothiazol-2-ylsulfanyl)-2-(5-chloro-benzothiazol-2-ylsulfanylmethyl)-4-hydroxy-oxo-2,5-dihydro-furan-2-carboxylic acid ethyl ester;

3-Cyclohexylsulfanyl-2-cyclohexylsulfanylmethyl-4-hydroxy-5-oxo-2,5-dihydro-furan-2-carboxylic acid ethyl ester;

4-Hydroxy-5-oxo-3-(pyrrolidine-1-carbothioylsulfanyl)-2-(pyrrolidine-1-carbothioylsulfanylmethyl)-2,5-dihydro-furan-2-carboxylic acid ethyl ester;

3-(Benzoselenazol-2-ylsulfanyl)-2-(benzoselenazol-2-ylsulfanylmethyl)-4-hydroxy-5-oxo-2,5-dihydro-furan-2-carboxylic acid ethyl ester;

4-Hydroxy-5-oxo-3-(7-trifluoromethyl-quinolin-4-ylsulfanyl)-2-(7-trifluoromethyl-quinolin-4-ylsulfanylmethyl)-2,5-dihydro-furan-2-carboxylic acid ethyl ester;

4-Hydroxy-5-oxo-3-(2-sulfo-ethylsulfanyl)-2-(2-sulfo-ethylsulfanylmethyl)-2,5-dihydro-furan-2-carboxylic acid ethyl ester;

Hydroxy-5-oxo-3-(4-trifluoromethyl-pyrimidin-2-ylsulfanyl)-2-(4-trifluoromethyl-pyrimidin-2-ylsulfanylmethyl)-2,5-dihydro-furan-2-carboxylic acid ethyl ester;

4-Hydroxy-5-oxo-3-(1-oxy-pyridin-2-ylsulfanyl)-2-(1-oxy-pyridin-2-ylsulfanylmethyl)-2,5-dihydro-furan-2-carboxylic acid ethyl ester;

3-(Benzothiazol-2-ylsulfanyl)-2-(benzothiazol-2-ylsulfanylmethyl)-4-hydroxy-5-oxo-2,5-dihydro-furan-2-carboxylic acid ethyl ester;

3-(2-Chloro-phenylsulfanyl)-2-(2-chloro-phenylsulfanylmethyl)-4-hydroxy-5-oxo-2,5-dihydro-furan-2-carboxylic acid ethyl ester;

3-Hexylsulfanyl-2-hexylsulfanylmethyl-4-hydroxy-5-oxo-2,5-dihydro-furan-2-carboxylic acid ethyl ester;

4-Hydroxy-5-oxo-3-(1-phenyl-1H-tetrazol-5-ylsulfanyl)-2-(1-phenyl-1H-tetrazol-5-ylsulfanylmethyl)-2,5-dihydro-furan-2-carboxylic acid ethyl ester;

4-Hydroxy-3-(naphthalen-2-ylsulfanyl)-2-(naphthalen-2-ylsulfanylmethyl)-5-oxo-2,5-dihydro-furan-2-carboxylic acid ethyl ester;

4-Hydroxy-5-oxo-3-(4-phenyl-thiazol-2-ylsulfanyl)-2-(4-phenyl-thiazol-2-ylsulfanylmethyl)-2,5-dihydro-furan-2-carboxylic acid ethyl ester;

4-(5-sulfo-1H-benzoimidazol-2-ylsulfanyl)-5-(5-sulfo-1H-benzoimidazol-2-ylsulfanylmethyl)-3-hydroxy-5-hydroxymethyl-5H-furan-2-one;

3-(Furan-2-ylmethysulfanyl)-2-(furan-2-ylmethylsulfanylmethyl)-4-isobutyryloxy-5-oxo-2,5-dihydro-furan-2-carboxylic acid ethyl ester;

4-Hydroxy-3-[4-(2-methoxycarbonyl-vinyl)-phenylsulfanyl]-2-[4-(2-methoxycarbonyl-vinyl)-phenylsulfanylmethyl]-5-oxo-2,5-dihydro-furan-2-carboxylic acid ethyl ester;

4-Hydroxy-3-(6-nitro-benzothiazol-2-ylsulfanyl)-2-(6-nitro-benzothiazol-2-ylsulfanylmethyl)-5-oxo-2,5-dihydro-furan-2-carboxylic acid ethyl ester;

2-(Benzothiazole-2-sulfinylmethyl)-3-(benzothiazol-2-ylsulfanyl)-4-hydroxy-5-oxo-2,5-dihydro-furan-2-carboxylic acid ethyl ester;

3-(2,4-Dichloro-benzylsulfanyl)-2-(2,4-dichloro-benzylsulfanylmethyl)-4-hydroxy-5-oxo-2,5-dihydro-furan-2-carboxylic acid ethyl ester;

4-Hydroxy-3-(5-methoxy-benzothiazol-2-ylsulfanyl)-2-(5-methoxy-benzothiazol-2-ylsulfanymethyl)-5-oxo-2,5-dihydro-furan-2-carboxylic acid ethyl ester;
3-(2-Chloro-6-fluoro-benzylsulfanyl)-2-(2-chloro-6-fluoro-benzylsulfanylmethyl)-4-hydroxy-5-oxo-2,5-dihydro-furan-2-carboxylic acid ethyl ester;
Dimethylamino-acetic acid 3-(1H-benzoimidazol-2-ylsulfanyl)-2-(1H-benzoimidazol-2-ylsulfanylmethyl)-4-hydroxy-5-oxo-2,5-dihydro-furan-2-ylmethyl ester;
3-(2-Chloro-4-fluoro-phenylsulfanyl)-2-(2-chloro-4-fluoro-phenylsulfanylmethyl)-4-hydroxy-5-oxo-2,5-dihydro-furan-2-carboxylic acid ethyl ester;
3-(Benzothiazol-2-ylsulfanyl)-2-(benzothiazol-2-ylsulfanylmethyl)-4-hydroxy-5-oxo-2,5-dihydro-furan-2-carboxylic acid;
2-(Furan-2-ylmethanesulfinylmethyl)-3-(furan-2-ylmethanesulfonyl)-4-hydroxy-5-oxo-2,5-dihydro-furan-2-carboxylic acid ethyl ester;
3-(furan-2-ylmethanesulfinyl)-2-(furan-2-ylmethanesulfinylmethyl)-4-hydroxy-5-oxo-2,5-dihydro-furan-2-carboxylic acid ethyl ester;
4-(2,2-dimethyl-propionyloxy)-3-ethoxycarbonylmethylsulfanyl-2-ethoxycarbonylmethylsulfanylmethyl-5-oxo-2,5-dihydro-furan-2-carboxylic acid ethyl ester;
3-(2-Dimethylamino-ethylsulfanyl)-2-(2-dimethylamino-ethylsulfanylmethyl)-4-hydroxy-5-oxo-2,5-dihydro-furan-2-carboxylic acid;
3-(5,6-Dichloro-1H-benzoimidazol-2-ylsulfanyl)-2-(5,6-dichloro-1H-benzoimidazol-2-ylsulfanylmethyl)-4-hydroxy-5-oxo-2,5-dihydro-furan-2-carboxylic acid ethyl ester;
3-Benzylsulfanyl-2-benzylsulfanylmethyl-4-hydroxy-5-oxo-2,5-dihydro-furan-2-carboxylic acid ethyl ester;
4-(1H-Benzoimidazol-2-ylsulfanyl)-3-hydroxy-1-oxa-7,9-diaza-spiro[4,5]dec-3-ene-2,6,8,10-tetraone;
3-(Benzothiazol-2-ylsulfanyl)-2-(benzothiazol-2-ylsulfanylmethyl)-4-hydroxy-5-oxo-2,5-dihydro-furan-2-carboxylic acid isopropyl ester;
4-Acetoxy-3-(furan-2-ylmethylsulfanyl)-2-(furan-2-ylmethylsulfanylmethyl)-5-oxo-2,5-dihydro-furan-2-carboxylic acid ethyl ester;
4-Ethoxy-3-(1-ethyl-1H-benzoimidazol-2-ylsulfanyl)-2-(1-ethyl-1H-benzoimidazol-2-ylsulfanyl)-5-oxo-2,5-dihydro-furan-2-carboxylic acid ethyl ester;
2-(1H-Benzoimidazol-2-ylsulfanylmethyl)-4-ethoxy-3-(1-ethyl-1H-benzoimidazol-2-ylsulfanyl)-5-oxo-2,5-dihydro-furan-2-carboxylic acid ethyl ester;
4-Acetoxy-3-benzylsulfanyl-2-benzylsulfanylmethyl-5-oxo-2,5-dihydro-furan-2-carboxylic acid ethyl ester;
4-Hydroxy-3-(1-methyl-1H-benzoimida-zol-2-ylsulfanyl)-2-(1-methyl-1H-benzoimidazol-2-ylsulfanylmethyl)-5-oxo-2,5-dihydro-furan-2-carboxylic acid ethyl ester;
3-(1H-Benzothiazol-2-ylsulfanyl)-4-hydroxy-5-oxo-2,5-dihydro-furan-2-carboxylic acid ethyl ester;
4-Hydroxy-3-(5-methyl-1H-benzoimidazol-2-ylsulfanyl)-5-oxo-2,5-dihydro-furan-2-carboxylic acid 2-isopropyl-5-methyl-cyclohexyl ester;
3-(4-Fluoro-benzylsulfanyl)-4-hydroxy-5-oxo-5H-furan-2,2-dicarboxylic acid diethyl ester.

4. A method of treatment for a mammal suffering from a dermatologic condition selected from the group consisting of contact dermatitis, acne, rosacea, and psoriasis comprising administering a therapeutically effective amount of a compound selected from the group consisting of:

3-(5-Chloro-benzothiazol-2-ylsulfanyl)-2-(5-chloro-benzothiazol-2-ylsulfanylmethyl)-4-hydroxy-5-oxo-2,5-dihydro-furan-2-carboxylic acid ethyl ester;
3-Cyclohexylsulfanyl-2-cyclohexylsulfanylmethyl-4-hydroxy-5-oxo-2,5,-dihydro-furan-2-carboxylic acid ethyl ester;
3-(Benzoselenazol-2-ylsulfanyl)-2-(benzoselenazol-2-ylsulfanylmethyl)-4-hydroxy-5-oxo-2,5-dihydro-furan-2-carboxylic acid ethyl ester;
3-(Benzothiazol-2-ylsulfanyl)-2-(benzothiazol-2-ylsulfanylmethyl)-4-hydroxy-5-oxo-2,5-dihydro-furan-2-carboxylic acid ethyl ester;
3-(2-Chloro-phenysulfanyl)-2-(2-chloro-phenylsulfanylmethyl)-4-hydroxy-5-oxo-2,5-dihydro-furan-2-carboxylic acid ethyl ester;
3-Hexylsulfanyl-2-hexylsulfanylmethyl-4-hydroxy-5-oxo-2,5-dihydro-furan-2-carboxylic acid ethyl ester;
4-Hydroxy-3-(naphthalen-2-ylsulfanyl)-2-(naphthalen-2-ylsulfanylmethyl)-5-oxo-2,5-dihydro-furan-2-carboxylic acid ethyl ester;
4-Hydroxy-5-oxo-3-(4-phenyl-thiazol-2-ylsulfanyl)-2-(4-pheny-1-thiazol-2-ylsulfanylmethyl)-2,5-dihydro-furan-2-carboxylic acid ethyl ester;
3-(Furan-2-ylmethylsulfanyl)-2-(furan-2-ylmethylsulfanylmethyl)-4-isobutyryloxy-5-oxo-2,5-dihydro-furan-2-carboxylic acid ethyl ester;
3-(2,4-Dichloro-benzylsulfanyl)-2-(2,4-dichloro-benzylsulfanylmethyl)-4-hydroxy-5-oxo-2,5-dihydro-furan-2-carboxylic acid ethyl ester;
3-(2-chloro-4-fluoro-phenylsulfanyl)-2-(2-chloro-4-fluoro-phenylsulfanylmethyl)-4-hydroxy-5-oxo-2,5-dihydro-furan-2-carboxylic acid ethyl ester;
3-(furan-2-ylmethanesulfinyl)-2-(furan-2-ylmethanesulfinylmethyl)-4-hydroxy-5-oxo-2,5-dihydro-furan-2-carboxylic acid ethyl ester;
4-(2,2-dimethyl-propionyloxy)-3-ethoxycarbonylmethylsulfanyl-2-ethoxycarbonylmethylsulfanylmethyl-5-oxo-2,5-dihydro-furan-2-carboxylic acid ethyl ester;
3-(Benzothiazol-2-ylsulfanyl)-2-(benzothiazol-2-ylsulfanylmethyl)-4-hydroxy-5-oxo-2,5-dihydro-furan-2-carboxylic acid isopropyl ester;
4-Hydroxy-3-(1-methyl-1H-benzoimidazol-2-ylsulfanyl)-2-(1-methyl-1H-benzoimidazol-2-ylsulfanymethyl)-5-oxo-2,5-dihydro-furan-2-carboxylic acid ethyl ester;
3-(1H-Benzoimidazol-2-ylsulfanyl)-4-hydroxy-5-oxo-2,5-dihydro-furan-2-carboxylic acid ethyl ester;
4-Hydroxy-3(5-methyl-1H-benzoimidazol-2-ylsulfanyl)-5-oxo-2,5-dihydro-furan-2-carboxylic acid 2-isopropyl-5-methyl-cyclohexyl ester;
3-(4-Fluoro-benzylsulfanyl)-4-hydroxy-5-oxo-5H-furan-2,2,-dicarboxylic acid diethyl ester.

5. The method of claim 1, comprising topically administering at least one compound of Formula I or of Formula III.

6. The method of claim 3, comprising applying to the area of skin in need of such treatment a composition comprising at least one compound selected from the group consisting of:

R-3-[2-(4-Amino-4-carboxy-butyrylamino)-2-(carboxymethyl-carbamoyl)-ethylsulfanyl]-2-[2-(4-amino-4-carboxy-butyrylamino)-2-(carboxymethyl-carbamoyl)-ethylsulfanylmethyl]-4-hydroxy-5-oxo-2,5-dihydro-furan-2-carboxylic acid ethyl ester;
3-(5-Chloro-benzothiazol-2-ylsulfanyl)-2-(5-chloro-benzothiazol-2-ylsulfanylmethyl)-4-hydroxy-5-oxo-2,5-dihydro-furan-2-carboxylic acid ethyl ester;

3-Cyclohexylsulfanyl-2-cyclohexylsulfanylmethyl-4-hydroxy-5-oxo-2,5-dihydro-furan-2-carboxylic acid ethyl ester;

4-Hydroxy-5-oxo-3-(pyrrolidine-1-carbothioylsulfanyl)-2-(pyrrolidine-1-carbothioylsulfanylmethyl)-2,5-dihydro-furan-2-carboxylic acid ethyl ester;

3-(Benzoselenazol-2-ylsulfanyl)-2-(benzoselenazol-2-ylsulfanylmethyl)-4-hydroxy-5-oxo-2,5-dihydro-furan-2-carboxylic acid ethyl ester;

4-Hydroxy-5-oxo-3-(7-trifluoromethyl-quinolin-4-ylsulfanyl)-2-(7-trifluoromethyl-quinolin-4-ylsulfanylmethyl)-2,5-dihydro-furan-2-carboxylic acid ethyl ester;

4-Hydroxy-5-oxo-3-(2-sulfo-ethylsulfanyl)-2-(2-sulfo-ethylsulfanylmethyl)-2,5-dihydro-furan-2-carboxylic acid ethyl ester;

4-Hydroxy-5-oxo-3-(4-trifluoromethyl-pyrimidin-2-ylsulfanyl)-2-(4-trifluoromethyl-pyrimidin-2-ylsulfanylmethyl)-2,5-dihydro-furan-2-carboxylic acid ethyl ester;

4-Hydroxy-5-oxo-3-(1-oxy-pyridin-2-ylsulfanyl)-2-(1-oxy-pyridin-2-ylsulfanylmethyl)-2,5-dihydro-furan-2-carboxylic acid ethyl ester;

3-(Benzothiazol-2-ylsulfanyl)-2-(benzothiazol-2-ylsulfanylmethyl)-4-hydroxy-5-oxo-2,5-dihydro-furan-2-carboxylic acid ethyl ester;

3-(2-Chloro-phenylsulfanyl)-2-(2-chloro-phenylsulfanylmethyl)-4-hydroxy-5-oxo-2,5-dihydro-furan-2-carboxylic acid ethyl ester;

3-Hexylsulfanyl-2-hexylsulfanylmethyl-4-hydroxy-5-oxo-2,5-dihydro-furan-2-carboxylic acid ethyl ester;

4-Hydroxy-5-oxo-3-(1-phenyl-1H-tetrazol-5t-ylsulfanyl)-2-(1-phenyl-1H-tetrazol-5-ylsulfanylmethyl)-2,5-dihydro-furan-2-carboxylic acid ethyl ester;

4-Hydroxy-3-(naphthalen-2-ylsulfanyl)-2-(naphthalen-2-ylsulfanylmethyl)-5-oxo-2,5-dihydro-furan-2-carboxylic acid ethyl ester;

4-Hydroxy-5-oxo-3-(4-phenyl-thiazol-2-ylsulfanyl)-2-(4-phenyl-thiazol-2-ylsulfanylmethyl)-2,5-dihydro-furan-2-carboxylic acid ethyl ester;

4-(5-sulfo-1H-benzoimidazol-2-ylsulfanyl)-5-(5-sulfo-1H-benzoimidazol-2-ylsulfanylmethyl)-3-hydroxy-5-hydroxymethyl-5H-furan-2-one;

3-(Furan-2-ylmethylsulfanyl)-2-(furan-2-ylmethylsulfanylmethyl)-4-isobutyryloxy-5-oxo-2,5-dihydro-furan-2-carboxylic acid ethyl ester;

4-Hydroxy-3-[4-(2-methoxycarbonyl-vinyl)-phenylsulfanyl]-2-[4-(2-methoxycarbonyl-vinyl)-phenylsulfanylmethyl]-5-oxo-2,5-dihydro-furan-2-carboxylic acid ethyl ester;

4-Hydroxy-3-(6-nitro-benzothiazol-2-ylsulfanyl)-2-(6-nitro-benzothiazol-2-ylsulfanylmethyl)-5-oxo-2,5-dihydro-furan-2-carboxylic acid ethyl ester;

2-(Benzothiazole-2-fulfinylmethyl)-3-(benzothiazol-2-ylsulfanyl)-4-hydroxy-5-oxo-2,5-dihydro-furan-2-carboxylic acid ethyl ester;

3-(2,4-Dichloro-benzylsulfanyl)-2-(2,4,-dichloro-benzylsulfanylmethyl)-4-hydroxy-5-oxo-2,5-dihydro-furan-2-carboxylic acid ethyl ester;

4-Hydroxy-3-(5-methoxy-benzothiazol-2-ylsulfanyl)-2-(5-methoxy-benzothiazol-2-ylsulfanylmethyl)-5-oxo-2,5-dihydro-furan-2-carboxylic acid ethyl ester;

3-(2-Chloro-6-fluoro-benzylsulfanyl)-2-(2-chloro-6-fluoro-benzylsulfanylmethyl)-4-hydroxy-5-oxo-2,5-dihydro-furan-2-carboxylic acid ethyl ester;

Dimethylamino-acetic acid 3-(1H-benzoimidazol-2-ylsulfanyl)-2-(1H-benzoimidazol-2-ylsulfanylmethyl)-4-hydroxy-5-oxo-2,5-dihydro-furan-2-ylmethyl ester;

3-(2-Chloro-4-fluoro-phenylsulfanyl)-2-(2-chloro-4-fluoro-phenyslsulfanylmethyl)-4-hydroxy-5-oxo-2,5-dihydro-furan-2-carboxylic acid ethyl ester;

3-(Benzothiazol-2-ylsulfanyl)-2-(benzothiazol-2-ylsulfanylmethyl)-4-hydroxy-5-oxo-2,5-dihydro-furan-2-carboxylic acid;

2-(Furan-2-ylmethanesulfinylmethyl)-3-(furan-2-ylmethanesulfonyl)-4-hydroxy-5-oxo-2,5-dihydro-furan-2-carboxylic acid ethyl ester;

3-(furan-2-ylmethanesulfinyl)-2-(furan-2-ylmethanesulfinylmethyl-4-hydroxy-5-oxo-2,5-dihydro-furan-2-carboxylic acid ethyl ester;

4-(2,2-dimethyl-propionyloxy)-3-ethoxycarbonylmethylsulfanyl-2-ethoxycarbonylmethylsulfanylmethyl-5-oxo-2,5-dihydro-furan-2-carboxylic acid ethyl ester;

3-(2-Dimethylamino-ethylsulfanyl)-2-(2-dimethylamino-ethylsulfanylmethyl)-4-hydroxy-5-oxo-2,5-dihydro-furan-2-carboxylic acid;

3-(5,6-Dichloro-1H-benzoimidazol-2-ylsulfanyl)-2-(5,6-dichloro-1H-benzoimidazol-2-ylsulfanylmethyl)-4-hydroxy-5-oxo-2,5-dihydro-furan-2-carboxylic acid ethyl ester;

3-Benzylsulfanyl-2-benzylsulfanylmethyl-4-hydroxy-5-oxo-2,5-dihydro-furan-2-carboxylic acid ethyl ester;

4-(1H-Benzoimidazol-2-ylsulfanyl)-3-hydroxy-1-oxa-7,9-diaza-spiro[4,5]dec-3-ene-2,6,8,10-tetraone;

3-(Benzothiazol-2-ylsulfanyl)-2-(benzothiazol-2-ylsulfanylmethyl)-4-hydro-xy-5-oxo-2,5-dihydro-furan-2-carboxylic acid isopropyl ester;

4-Acetoxy-3-(furan-2-ylmethylsulfanyl)-2-(furan-2-ylmethylsulfanylmethyl)-5-oxo-2,5-dihydro-furan-2-carboxylic acid ethyl ester;

4-Ethoxy-3-(1-ethyl-1H-benzoimidazol-2-ylsulfanyl)-2-(1-ethyl-1H-benzoimidazol-2-ylsulfanylmethyl)-5-oxo-2,5-dihydro-furan-2-carboxylic acid ethyl ester;

2-(1H-Benzoimidazol-2-ylsulfanylmethyl)-4-ethoxy-3-1-ethyl-1H-benzoimidazol-2-ylsulfanyl)-5-oxo-2,5-dihydro-furan-2-carboxylic acid ethyl ester;

4-Acetoxy-3-benzylsulfanyl-2-benzylsulfanylmethyl-5-oxo-2,5-dihydro-furan-2-carboxylic acid ethyl ester;

4-Hydroxy-3-(1-methyl-1H-benzoimidazol-2-ylsulfanyl)-2-(1-methyl-1H-benzoimidazol-2-ylsulfanylmethyl)-5-oxo-2,5-dihydro-furan-2-carboxylic acid ethyl ester;

3-(1H-Benzoimidazol-2-ylsulfanyl)-4-hydroxy-5-oxo-2,5-dihydro-furan-2-carboxylic acid ethyl ester;

4-Hydroxy-3-(5-methyl-1H-benzoimidazol-2-ylsulfanyl)-5-oxo-2,5-dihydro-furan-2-carboxylic acid 2-isopropyl-5-methyl-cyclohexyl ester;

3-(4-Fluoro-benzylsulfanyl)-4-hydroxy-5-oxo-5H-furan-2,2-dicarboxylic acid diethyl ester.

7. The method of claim 1, comprising administering a formulation for topical application comprising one or more topical excipients and at least one compound of Formula I or of Formula III.

8. The method of claim 1, additionally comprising an additional benefit agent, selected from the group consisting of sunscreens, retinoid and derivatives thereof, antioxidants, hydroxyacids, botanical extracts, salicylic acid, benzoyl peroxide, antibiotics, antiandrogens, anti-inflammatory agents, vitamins, tocopherol (α-, β-, γ-, δ-) and esters thereof, corticosteroids and mixtures thereof.

9. The method of claim 3, additionally comprising an additional benefit agent, selected from the group consisting of sunscreens, retinoid and derivatives thereof, antioxidants, hydroxyacids, botanical extracts, salicylic acid, benzoyl peroxide, antibiotics, antiandrogens, anti-inflammatory agents, vitamins, tocopherol (α-, β-, γ-, δ-) and esters thereof, corticosteroids and mixtures thereof.

10. The method of claim 3, comprising administering a formulation for topical application comprising one or more topical excipients and at least one compound of Formula I or of Formula III.

11. The method of claim 4, additionally comprising an additional benefit agent, selected from the group consisting of sunscreens, retinoid and derivatives thereof, antioxidants, hydroxyacids, botanical extracts, salicylic acid, benzoyl peroxide, antibiotics, antiandrogens, anti-inflammatory agents, vitamins, tocopherol (α-, β-, γ-, δ-) and esters thereof, corticosteroids and mixtures thereof.

12. The method of claim 4, comprising administering a formulation for topical application comprising one or more topical excipients and at least one compound of Formula I or of Formula III.

* * * * *

UNITED STATES PATENT AND TRADEMARK OFFICE
CERTIFICATE OF CORRECTION

PATENT NO. : 7,985,771 B2  
APPLICATION NO. : 10/630170  
DATED : July 26, 2011  
INVENTOR(S) : Boddupalli et al.

It is certified that error appears in the above-identified patent and that said Letters Patent is hereby corrected as shown below:

In the Claims

Column 107, Claim 1, Line 15, Formula III:

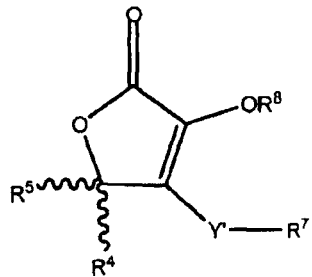

Formula III should read

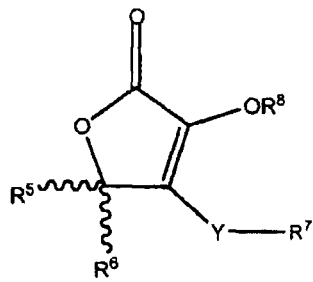

Formula III

Signed and Sealed this  
Second Day of June, 2015

Michelle K. Lee  
*Director of the United States Patent and Trademark Office*